United States Patent
Muller et al.

(10) Patent No.: US 10,363,261 B2
(45) Date of Patent: Jul. 30, 2019

(54) ENOLASE INHIBITORS AND METHODS OF TREATMENT THEREWITH

(71) Applicant: Board of Regents, The University of Texas System, Austin, TX (US)

(72) Inventors: Florian Muller, Houston, TX (US); David S. Maxwell, Pearland, TX (US); William G. Bornmann, Missouri City, TX (US); Yu-Hsi Lin, Houston, TX (US); Basvoju A. Bhanu Prasad, Katy, TX (US); Zhenghong Peng, Missouri City, TX (US); Duoli Sun, Houston, TX (US); Nikunj Satani, Houston, TX (US); M. Emilia Di Francesco, Houston, TX (US); Ronald A. Depinho, Houston, TX (US); Barbara Czako, Houston, TX (US); Federica Pisaneschi, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/557,288

(22) PCT Filed: Mar. 9, 2016

(86) PCT No.: PCT/US2016/021609
§ 371 (c)(1),
(2) Date: Sep. 11, 2017

(87) PCT Pub. No.: WO2016/145113
PCT Pub. Date: Sep. 15, 2016

(65) Prior Publication Data
US 2018/0147219 A1    May 31, 2018

Related U.S. Application Data

(60) Provisional application No. 62/130,431, filed on Mar. 9, 2015.

(51) Int. Cl.
| | | |
|---|---|---|
| C07F 9/553 | (2006.01) |
| C07F 9/572 | (2006.01) |
| C07F 9/59 | (2006.01) |
| A61K 31/662 | (2006.01) |
| A61P 35/00 | (2006.01) |
| A61K 31/675 | (2006.01) |
| A61K 45/06 | (2006.01) |

(52) U.S. Cl.
CPC ........... *A61K 31/675* (2013.01); *A61K 45/06* (2013.01); *A61P 35/00* (2018.01); *C07F 9/5532* (2013.01); *C07F 9/572* (2013.01); *C07F 9/59* (2013.01); *A61K 2300/00* (2013.01); *Y02A 50/414* (2018.01); *Y02A 50/415* (2018.01)

(58) Field of Classification Search
CPC .. C07D 207/26; C07D 211/76; C07D 223/08; C07D 225/02; A61K 31/675; A61P 35/00
USPC ..................... 546/21; 548/111; 540/450, 484
See application file for complete search history.

(56) References Cited

U.S. PATENT DOCUMENTS 9,452,182 B2    9/2016  Muller et al.
2014/0378529 A1  12/2014  Muller et al.

FOREIGN PATENT DOCUMENTS

WO    WO 2013-090732    6/2013

OTHER PUBLICATIONS

Cecil Textbook of Medicine, edited by Bennet, J.C., and Plum F., 20th edition,vol. 1, 1004-1010 1996.*
Freshney et al.,Culture of Animal Cells, A Manual of Basic Technique, Alan R. Liss, Inc., 1983, New York, p. 4.*
Dermeret al., Bio/Technology, 1994, 12:320.*
Golub et al., Science, 286, 531-537, 1999.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
pccompound, 1-2, Create Date May 23, 2011 and Jun. 27, 2011.*
Liu et al. Tetrahedron (2011), 67(12), 2206-2214.*
"An efficient synthesis of antibiotic SF-2312 (3-dihydroxyphosphoryl-1,5-dihydroxy-2-pyrrolidone)," XP002757760, Chemical Abstracts Service, retrieved from STN Database Accession No. 2011:375926, 2011.

(Continued)

*Primary Examiner* — Venkataraman Balasubramanian
(74) *Attorney, Agent, or Firm* — Parker Highlander PLLC

(57) ABSTRACT

Provided herein are compounds of the formula (I) wherein the variables $R_1$, $R_2$, $R_3$, $R_4$, $X_1$, $X_2$, $Y_1$, and $A_1$ are as defined herein. Such compounds may be used, for example, for the inhibition of enolase enzymes, including preferential inhibition of one isoenzyme of over one or more of the other isoenzymes. Methods of treatment using these compounds, as well as pharmaceutical compositions thereof, are also provided.

(I)

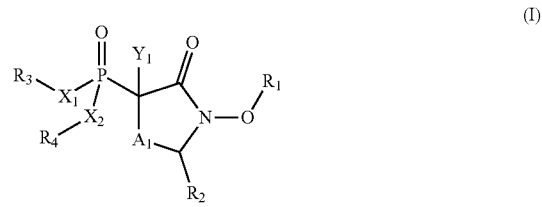

19 Claims, 60 Drawing Sheets

(56) References Cited

OTHER PUBLICATIONS

"Phosphorus-containing antibiotic SF-2312," XP002757761, Chemical Abstracts Service, retrieved from STN Database Accession No. 1986:107918, 1986.
Anderson et al., "Reaction intermediate analogues for enolase," *Biochemistry*, 23(12):2779-2789, 1984.
Bady et al., "DNA fingerprinting of glioma cell lines and considerations on similarity measurements," *Neuro-oncology*, 14:701-711, 2012.
Brewer and Wampler, "A differential scanning calorimetric study of the effects of metal ions, substrate/product, substrate analogues and chaotropic anions on the thermal denaturation of yeast enolase 1," *Int. J. Biol. Macromol.*, 28:213-218, 2001.
Capello et al., "α-enolase: a promising therapeutic and diagnostic tumor target," *FEBS J.*, 278(7):1064-1074, 2011.
Duncan et al., "Integrated genomic analyses identify ERRFI1 and TACC3 as glioblastoma-targeted genes," *Oncotarget*, 1:265-277, 2010.
Hanaya et al., "An efficient synthesis of antibiotic SF-2312 (3-dihydroxyphosphoryl-1,5-dihydroxy-2-pyrrolidone)," *Heterocycles*, 82(2):1675-1683, 2011.
International Preliminary Report on Patentability issued in corresponding PCT Application No. PCT/US2016/021609, dated Sep. 21, 2017.
International Search Report and Written Opinion issued in corresponding PCT Application No. PCT/US2016/021609, dated May 25, 2016.
Jung et al., "A Unique Small Molecule Inhibitor of Enolase Clarifies Its Role in Fundamental Biological Processes," *ACS Chem. Biol.*, 8(6):1271-1282, 2013.
Liu et al., "A new approach to cyclic hydroxamic acids: intramolecular cyclization of N-benzyloxy carbamates with carbon nucleophiles," *Tetrahedron*, 67(12):2206-2214, 2011.
Marangos and Schmechel, "The neurobiology of the brain enolase," *Essays Neurochem. Neuropharmacol.*, 4:211-247, 1980.
Marangos et al., "Functional properties of neuronal and glial isoenzymes of brain enolase," *J. Neurochem.*, 31(3):727-732, 1978.
Marangos et al., "The existence and neurobiological significance of neuronal and glial forms of the glycolytic enzyme enolase," *Biol. Psychiatry*, 17(4):563-579, 1979.
Muller et al., "Passenger deletions generate therapeutic vulnerabilities in cancer," *Nature*, 488(7411):337-342, 2012.
Navarro et al., "Structural flexibility in Trypanosoma brucei enolase revealed by X-ray crystallography and molecular dynamics," *FEBS J.*, 274:5077-5089, 2007.
Owotoki et al., "Synthesis of 1-Hydroxypyrrolidin-2,5-dione Derivatives of the Phosphonic-Hydroxamic Acid Antibiotic SF-2312," *Aus. J. Chem. Sci.*, 59(4):283, 2006.
Poyner et al., "Toward identification of acid/base catalysts in the active site of enolase: comparison of the properties of K345A, E168Q, and E211Q variants," *Biochemistry*, 35(5):1692-1699, 1996.
Qin et al., "Structures of asymmetric complexes of human neuron specific enolase with resolved substrate and product and an analogous complex with two inhibitors indicate subunit interaction and inhibitor cooperativity," *J. Inorg. Biochem.*, 111:187-194, 2012.
Stommel et al., "Coactivation of receptor tyrosine kinases affects the response of tumor cells to targeted therapies," *Science*, 318:287-290, 2007.
Torsvik et al., "U-251 revisited: genetic drift and phenotypic consequences of long-term cultures of glioblastoma cells," *Cancer Med.*, 3:812-824, 2014.
Watanabe et al., "Studies on a new Phosphonic acid antibiotic, SF-2312," *Science Reports of Meiji Seika Kaisha*, 25:12-17, 1986.
Wedekind, et al., "Chelation of serine 39 to $Mg^{2+}$ latches a gate at the active site of enolase: structure of the bis($Mg^{2+}$) complex of yeast enolase and the intermediate analog phosphonoacetohydroxamate at 2.1-A resolution," *Biochemistry*, 33:9333-9342, 1994.
Ying et al., "Oncogenic Kras maintains pancreatic tumors through regulation of anabolic glucose metabolism," *Cell*, 149:656-670, 2012.
Yuan et al., "A positive/negative ion-switching, targeted mass spectrometry-based metabolomics platform for bodily fluids, cells, and fresh and fixed tissue," *Nature Protocols*, 7:872-881, 2012.
Zhang et al., "Catalytic metal ion binding in enolase: the crystal structure of an enolase-$Mn^{2+}$-phosphonoacetohydroxamate complex at 2.4-A resolution," *Biochemistry*, 33:6295-6300, 1994.

\* cited by examiner

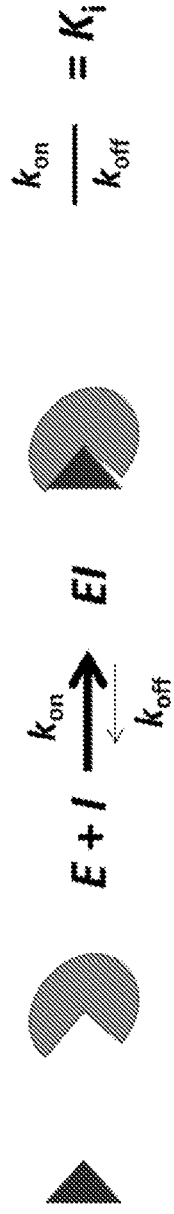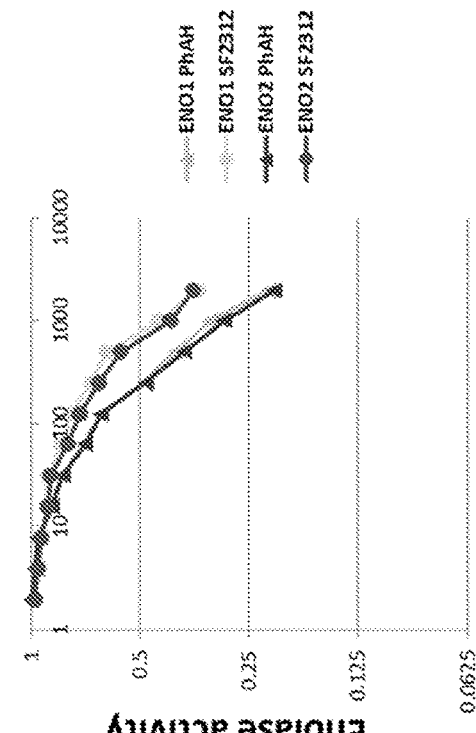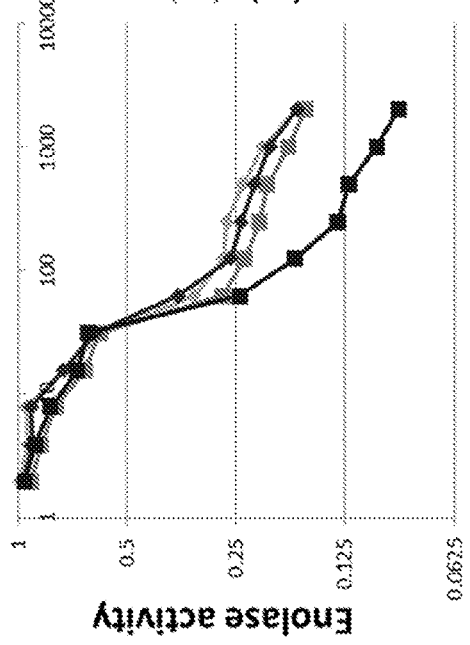
FIGS. 2A & 2B

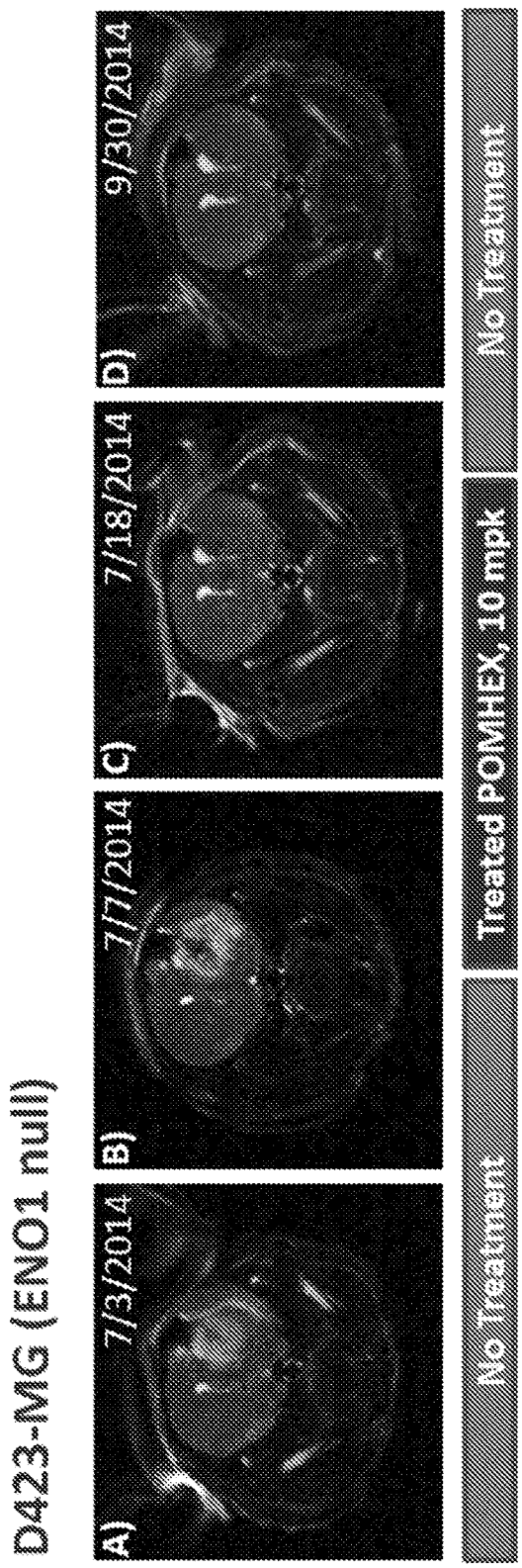
FIGS. 11A-D

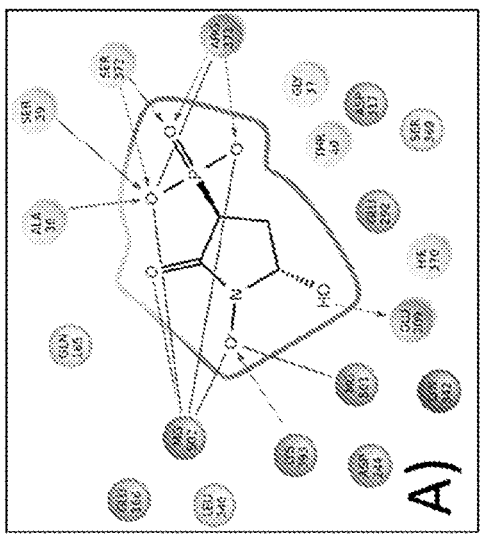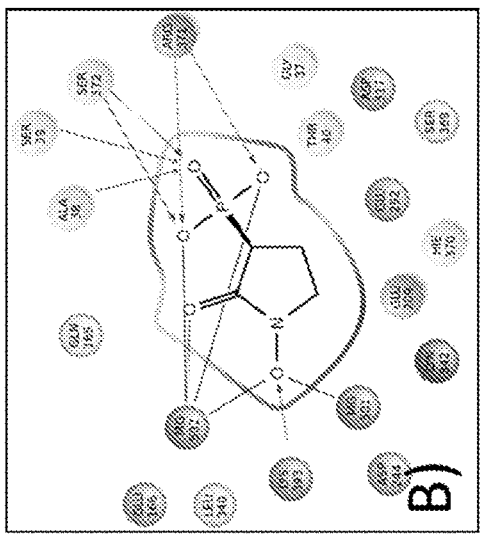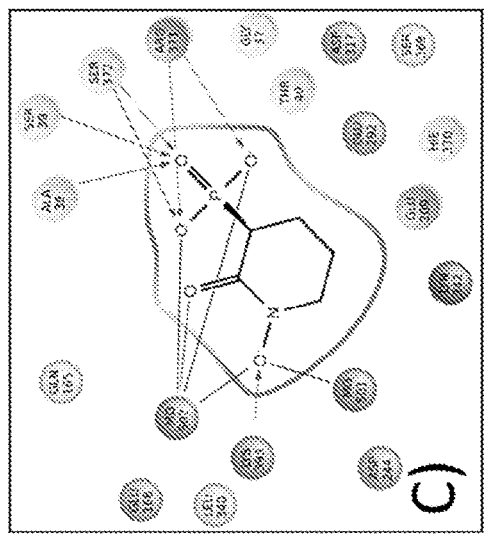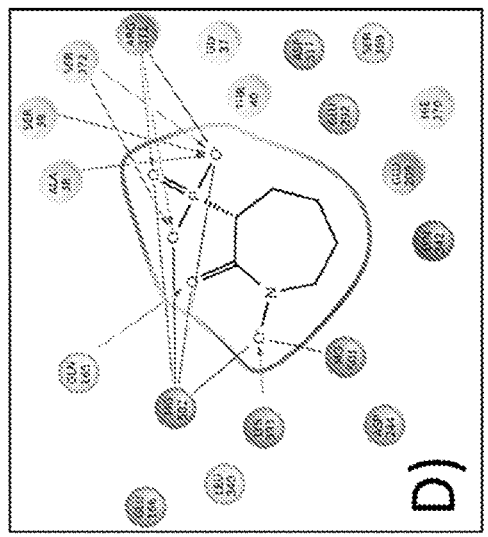
FIGS. 13A-D

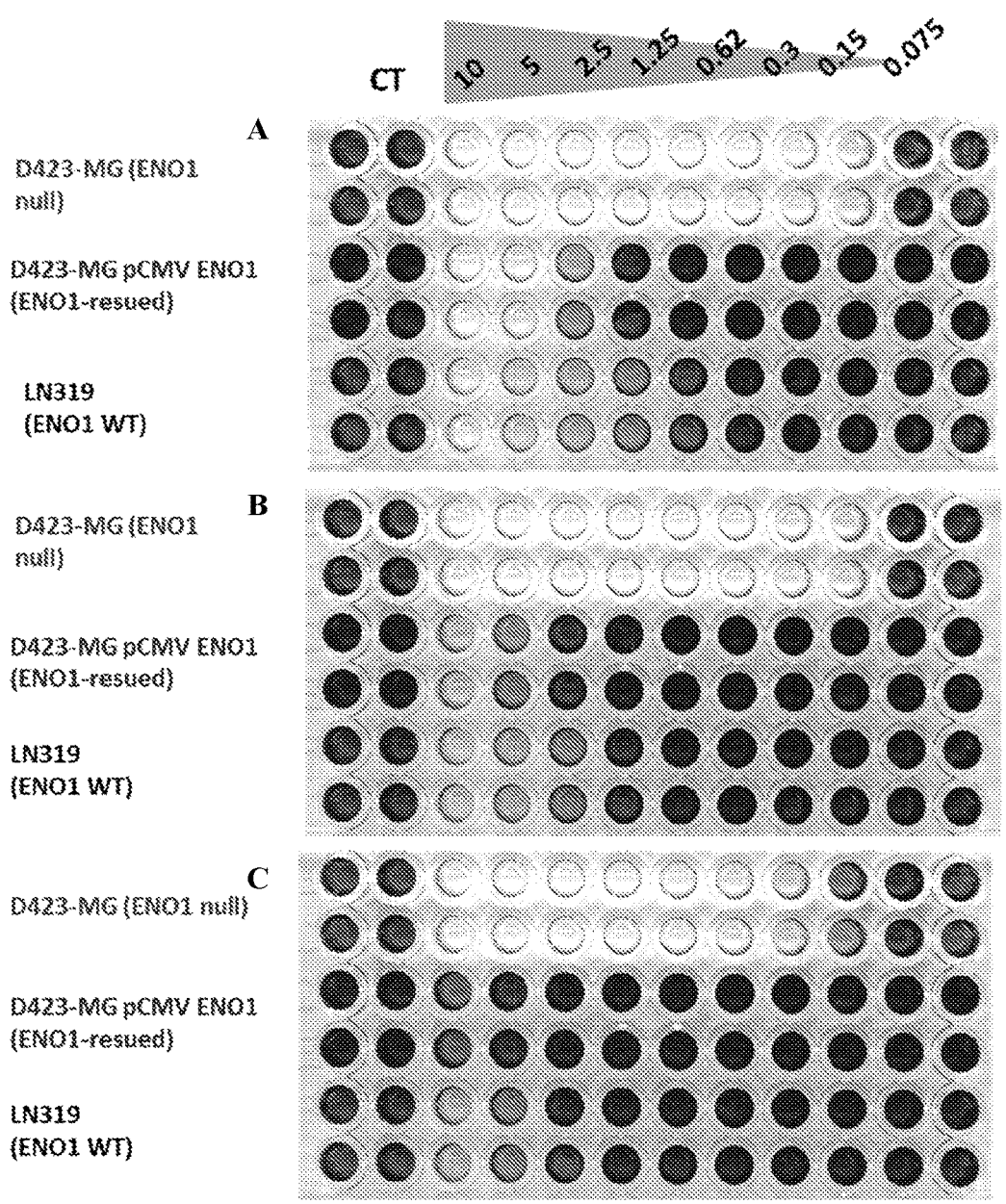
FIGS. 19A-C

Foscarnet
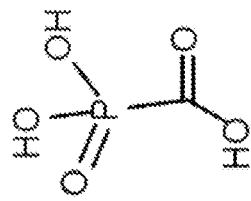
Fosfomycin
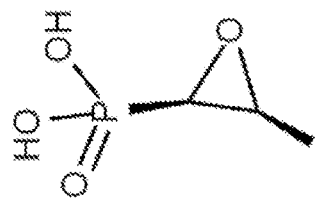
Fosmidomcyin
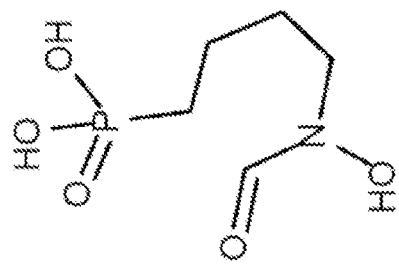
FIG. 29

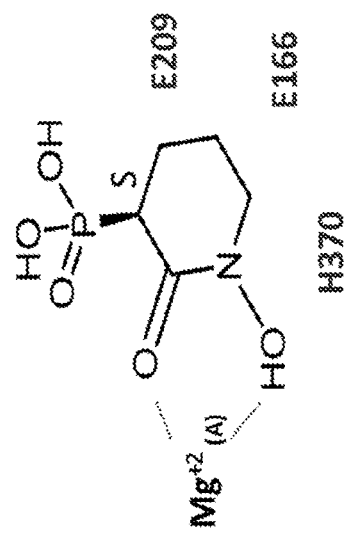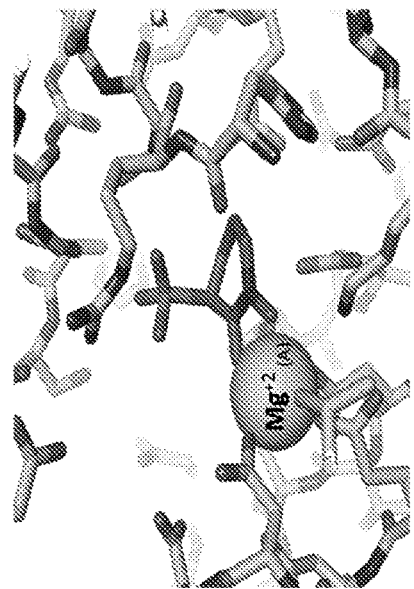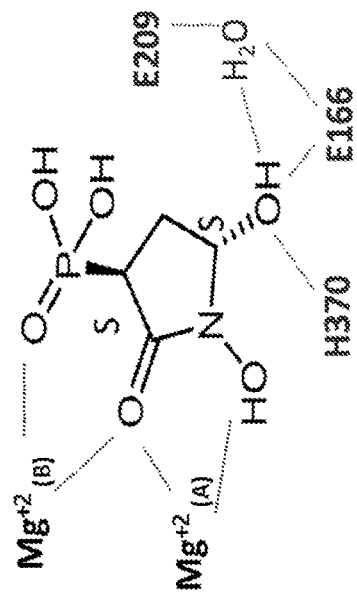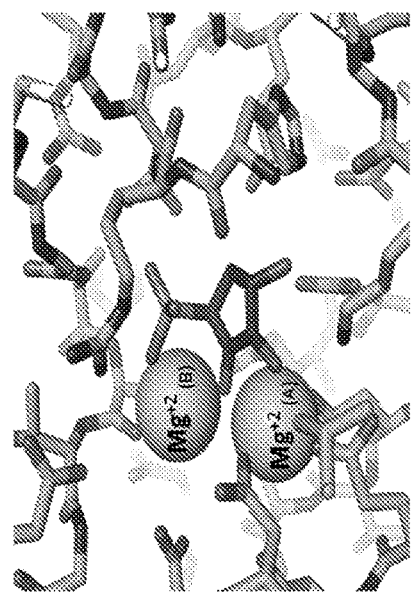
FIG. 48

ENOLASE INHIBITORS AND METHODS OF TREATMENT THEREWITH

The application is a national phase application under 35 U.S.C. § 371 of International Application No. PCT/US2016/021609, filed Mar. 9, 2016, which claims benefit of priority to U.S. Provisional Application Ser. No. 62/130,431, filed Mar. 9, 2015, the entire contents of each of which are hereby incorporated by reference.

This invention was made with government support under Grant Number CA095616 awarded by the National Institutes of Health. The Government has certain rights in the invention.

BACKGROUND OF THE INVENTION

1. Field of the Invention

The present disclosure relates generally to the field of therapeutics, chemotherapeutics, and chemistry. In some embodiments, the present disclosure relates to compounds which may be used as inhibitors of enolase, chemotherapeutic agents or as antibiotics.

2. Description of Related Art

Enolase is the penultimate enzyme in the glycolysis pathway. It converts 2-phosphoglycerate to phosphoenolpyruvate and is therefore very important in the production of ATP. As such, this enzyme has arisen as a target for chemotherapeutic development (Capello, et al., 2011). Three major forms of enolase are known to exist in humans, with enolase 1 (alpha-enolase) being the dominant form present in most tissues. Enolase 2 is present in brain tissue and neurons.

Several cancer subtypes have mutations or deletions in genes that affect the activity of enolase 1 (Muller, et al., 2012; US 2014/0378529; WO 2013/0909732). Compounds and compositions that can exploit these differences may be useful as chemotherapeutic agents. Desirable properties include reduced toxicity to normal cells vis-à-vis cancer cells and/or preferential inhibition of enolase 2. In view of the continuing unmet medical needs related to cancer and other cell-proliferative diseases, new compounds and compositions having such desirable properties as well as other beneficial activity profiles have the potential to hold tremendous promise.

SUMMARY OF THE INVENTION

In some aspects, the present disclosure provides compounds of the formula:

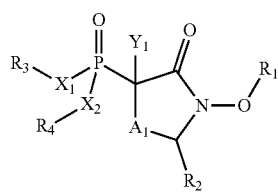

(I)

wherein:
R$_1$ is hydrogen, acyl$_{(C\leq12)}$ or substituted acyl$_{(C\leq12)}$;
R$_2$ is hydrogen, hydroxy, alkoxy$_{(C\leq12)}$, substituted alkoxy$_{(C\leq12)}$, acyloxy$_{(C\leq12)}$, or substituted acyloxy$_{(C\leq12)}$;
X$_1$ and X$_2$ are each independently O, S, or NR$_a$, wherein:
R$_a$ is hydrogen, alkyl$_{(C\leq6)}$, or substituted alkyl$_{(C\leq6)}$;
R$_3$ and R$_4$ are each independently hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of these groups; or a phosphate protecting group; or R$_3$ and R$_4$ are taken together and are alkanediyl$_{(C\leq8)}$ or substituted alkanediyl$_{(C\leq8)}$; or —X$_3$—R$_5$; wherein:
X$_3$ is a covalent bond, alkanediyl$_{(C\leq8)}$, or substituted alkanediyl$_{(C\leq8)}$; and
R$_5$ is acyl$_{(C\leq18)}$, alkoxy$_{(C\leq18)}$, —C(O)-alkoxy$_{(C\leq18)}$, acyloxy$_{(C\leq18)}$, or a substituted version of any of these groups;
A$_1$ is alkanediyl$_{(C\leq8)}$, substituted alkanediyl$_{(C\leq8)}$, alkylaminodiyl$_{(C\leq8)}$, or substituted alkylaminodiyl$_{(C\leq8)}$; and
Y$_1$ is hydrogen, amino, halo, hydroxy, phosphate, alkyl$_{(C\leq12)}$, or substituted alkyl$_{(C\leq12)}$; provided that the compound is not:

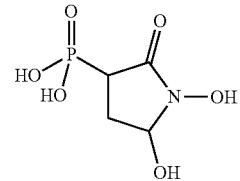 [SMILES: O=C1C(P(=O)(O)O)CC(O)N1O]

or a pharmaceutically acceptable salt or ester thereof. In some embodiments, the compounds is further defined as:

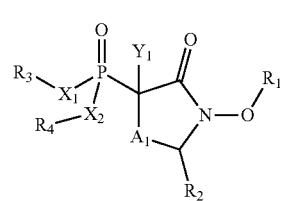

(I)

wherein:
R$_1$ is hydrogen, acyl$_{(C\leq12)}$ or substituted acyl$_{(C\leq12)}$;
R$_2$ is hydrogen, alkoxy$_{(C\leq12)}$, substituted alkoxy$_{(C\leq12)}$, acyloxy$_{(C\leq12)}$, or substituted acyloxy$_{(C\leq12)}$;
X$_1$ and X$_2$ are each independently O, S, or NR$_a$, wherein:
R$_a$ is hydrogen, alkyl$_{(C\leq6)}$, or substituted alkyl$_{(C\leq6)}$;
R$_3$ and R$_4$ are each independently hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of these groups; or a phosphate protecting group; or R$_3$ and R$_4$ are taken together and are alkanediyl$_{(C\leq8)}$ or substituted alkanediyl$_{(C\leq8)}$; or —X$_3$—R$_5$; wherein:
X$_3$ is a covalent bond, alkanediyl$_{(C\leq8)}$, or substituted alkanediyl$_{(C\leq8)}$; and
R$_5$ is acyl$_{(C\leq18)}$, alkoxy$_{(C\leq18)}$, —C(O)-alkoxy$_{(C\leq18)}$, acyloxy$_{(C\leq18)}$, or a substituted version of any of these groups;
A$_1$ is alkanediyl$_{(C\leq8)}$, substituted alkanediyl$_{(C\leq8)}$, alkylaminodiyl$_{(C\leq8)}$, or substituted alkylaminodiyl$_{(C\leq8)}$; and
Y$_1$ is hydrogen, amino, halo, hydroxy, phosphate, alkyl$_{(C\leq12)}$, or substituted alkyl$_{(C\leq12)}$;
or a pharmaceutically acceptable salt or ester thereof. In some embodiments, the compound is further defined as:

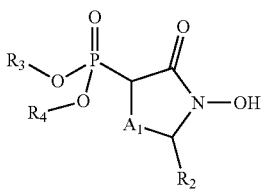

(II)

wherein:
R$_2$ is hydrogen, alkoxy$_{(C≤12)}$, substituted alkoxy$_{(C≤12)}$, acyloxy$_{(C≤12)}$, or substituted acyloxy$_{(C≤12)}$;
R$_3$ and R$_4$ are each independently hydrogen, alkyl$_{(C≤12)}$, substituted alkyl$_{(C≤12)}$, or a phosphate protecting group; and
A$_1$ is alkanediyl$_{(C≤8)}$, substituted alkanediyl$_{(C≤8)}$, alkylaminodiyl$_{(C≤8)}$, or substituted alkylaminodiyl$_{(C≤8)}$; or

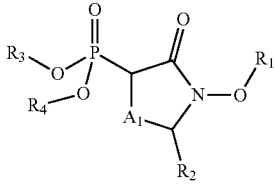

(III)

wherein:
R$_1$ is acyl$_{(C≤12)}$ or substituted acyl$_{(C≤12)}$;
R$_2$ is hydroxy, alkoxy$_{(C≤12)}$, substituted alkoxy$_{(C≤12)}$, acyloxy$_{(C≤12)}$, or substituted acyloxy$_{(C≤12)}$;
R$_3$ is alkyl$_{(C≤12)}$, substituted alkyl$_{(C≤12)}$, or a phosphate protecting group;
R$_4$ is hydrogen, alkyl$_{(C≤12)}$, substituted alkyl$_{(C≤12)}$, or a phosphate protecting group; and
A$_1$ is alkanediyl$_{(C≤8)}$, substituted alkanediyl$_{(C≤8)}$, alkylaminodiyl$_{(C≤8)}$, or substituted alkylaminodiyl$_{(C≤8)}$;
or a pharmaceutically acceptable salt or ester thereof. In other embodiments, the compound is further defined as:

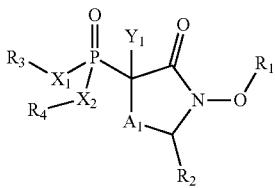

(I)

wherein:
R$_1$ is hydrogen, acyl$_{(C≤12)}$ or substituted acyl$_{(C≤12)}$;
R$_2$ is hydrogen, hydroxy, alkoxy$_{(C≤12)}$, substituted alkoxy$_{(C≤12)}$, acyloxy$_{(C≤12)}$, or substituted acyloxy$_{(C≤12)}$;
X$_1$ and X$_2$ are each independently O, S, or NR$_a$, wherein:
R$_a$ is hydrogen, alkyl$_{(C≤6)}$, or substituted alkyl$_{(C≤6)}$;
R$_3$ and R$_4$ are each independently hydrogen or alkyl$_{(C≤12)}$, aryl$_{(C≤12)}$, aralkyl$_{(C≤12)}$, heteroaryl$_{(C≤12)}$, heteroaralkyl$_{(C≤12)}$, or a substituted version of these groups; or a phosphate protecting group; or R$_3$ and R$_4$ are taken together and are alkanediyl$_{(C≤8)}$ or substituted alkanediyl$_{(C≤8)}$; or —X$_3$—R$_5$; wherein:
X$_3$ is a covalent bond, alkanediyl$_{(C≤8)}$, or substituted alkanediyl$_{(C≤8)}$; and
R$_5$ is acyl$_{(C≤18)}$, alkoxy$_{(C≤18)}$, —C(O)-alkoxy$_{(C≤18)}$, acyloxy$_{(C≤18)}$, or a substituted version of any of these groups;
A$_1$ is alkanediyl$_{(C≤8)}$, substituted alkanediyl$_{(C≤8)}$, alkylaminodiyl$_{(C≤8)}$, or substituted alkylaminodiyl$_{(C≤8)}$; and
Y$_1$ is amino, halo, hydroxy, phosphate, alkyl$_{(C≤12)}$, or substituted alkyl$_{(C≤12)}$;
or a pharmaceutically acceptable salt or ester thereof. In some embodiments, the compound is further defined as:

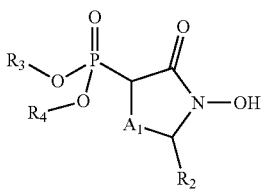

(II)

wherein:
R$_2$ is hydrogen, alkoxy$_{(C≤12)}$, or substituted alkoxy$_{(C≤12)}$;
R$_3$ and R$_4$ are each independently hydrogen, alkyl$_{(C≤12)}$, substituted alkyl$_{(C≤12)}$, or a phosphate protecting group; and
A$_1$ is alkanediyl$_{(C≤8)}$, substituted alkanediyl$_{(C≤8)}$, alkylaminodiyl$_{(C≤8)}$, or substituted alkylaminodiyl$_{(C≤8)}$;
or a pharmaceutically acceptable salt or ester thereof.

In some embodiments, R$_1$ is hydrogen. In other embodiments, R$_1$ is acyl$_{(C≤8)}$ or substituted acyl$_{(C≤8)}$ such as acetyl, ethyl carbonyl (—C(O)CH$_2$CH$_3$), or 2-methylpropyl carbonyl (—C(O)CH$_2$CH(CH$_3$)CH$_3$). In some embodiments, R$_2$ is hydroxy. In other embodiments, R$_2$ is acyloxy$_{(C≤8)}$ or substituted acyloxy$_{(C≤8)}$ such as acetoxy, propionate, or 3-methylbutanoate. In other embodiments, R$_2$ is hydrogen.

In some embodiments, R$_3$ is hydrogen. In other embodiments, R$_3$ is alkyl$_{(C≤12)}$ or substituted alkyl$_{(C≤12)}$ such as methyl carboxymethyl. In other embodiments, R$_3$ is a phosphate protecting group such as a phosphate protecting group of the formula: -alkanediyl$_{(C≤6)}$-acyloxy$_{(C≤12)}$ or substituted -alkanediyl$_{(C≤6)}$-acyloxy$_{(C≤12)}$. In some embodiments, R$_3$ is —CH$_2$-acyloxy$_{(C≤12)}$ such as pivaloyloxymethyl. In other embodiments, R$_3$ is aryl$_{(C≤8)}$ or substituted aryl$_{(C≤8)}$ such as phenyl, 2-methylphenyl, or 4-methylphenyl. In other embodiments, R$_3$ is aralkyl$_{(C≤8)}$ or substituted aralkyl$_{(C≤8)}$ such as benzyl. In other embodiments, R$_3$ is —X$_3$—R$_5$; wherein:
X$_3$ is a covalent bond, alkanediyl$_{(C≤8)}$, or substituted alkanediyl$_{(C≤8)}$; and
R$_5$ is acyl$_{(C≤18)}$, alkoxy$_{(C≤18)}$, —C(O)-alkoxy$_{(C≤18)}$, acyloxy$_{(C≤18)}$, or a substituted version of any of these groups.

In some embodiments, X$_3$ is alkanediyl$_{(C≤8)}$ or substituted alkanediyl$_{(C≤8)}$. In some embodiments, R$_5$ is alkoxy$_{(C≤18)}$ or a substituted alkoxy$_{(C≤18)}$ such as pentadecanoxy. In other embodiments, R$_5$ is —C(O)-alkoxy$_{(C≤18)}$ or substituted —C(O)-alkoxy$_{(C≤18)}$ such as —C(O)OCH(CH$_3$)$_2$.

In some embodiments, X$_1$ is O. In other embodiments, X$_1$ is NH. In some embodiments, X$_2$ is O. In other embodiments, X$_2$ is NH.

In some embodiments, R$_4$ is hydrogen. In other embodiments, R$_4$ is alkyl$_{(C≤12)}$ or substituted alkyl$_{(C≤12)}$ such as methyl carboxymethyl. In other embodiments, R$_4$ is a phosphate protecting group such as a phosphate protecting group of the formula: -alkanediyl$_{(C≤6)}$-acyloxy$_{(C≤12)}$ or substituted -alkanediyl$_{(C≤6)}$-acyloxy$_{(C≤12)}$. In some embodiments, $R_4$ is —CH$_2$-acyloxy$_{(C≤12)}$ such as pivaloyloxymethyl. In other embodiments, $R_4$ is aryl$_{(C≤8)}$ or substituted aryl$_{(C≤8)}$ such as phenyl, 2-methylphenyl, or 4-methylphenyl.

In some embodiments, $A_1$ is alkanediyl$_{(C≤4)}$ or substituted alkanediyl$_{(C≤4)}$ such as —CH$_2$—, —CH$_2$CH$_2$—, or —CH$_2$CH$_2$CH$_2$—. In some embodiments, $Y_1$ is hydrogen. In other embodiments, $Y_1$ is halo such as fluoro. In other embodiments, $Y_1$ is alkyl$_{(C≤6)}$ or substituted alkyl$_{(C≤6)}$ such as methyl.

In some embodiments, the compound is further defined as:

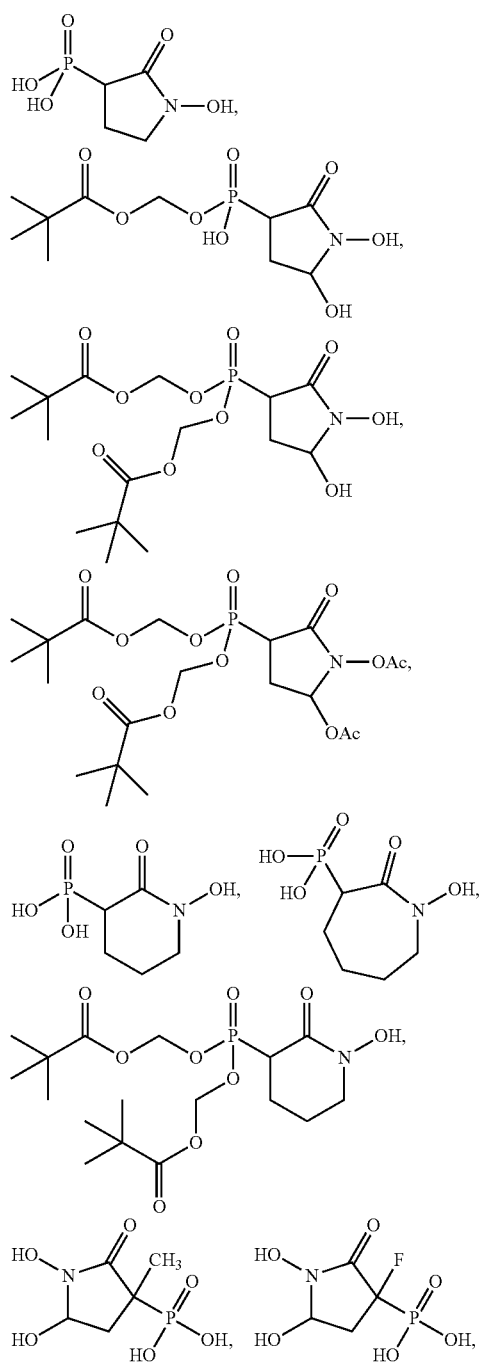

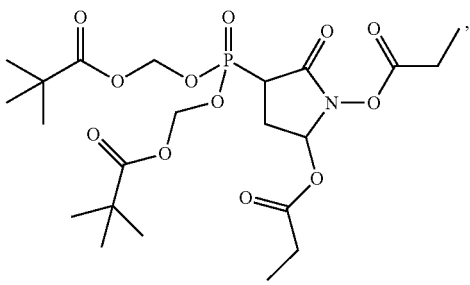

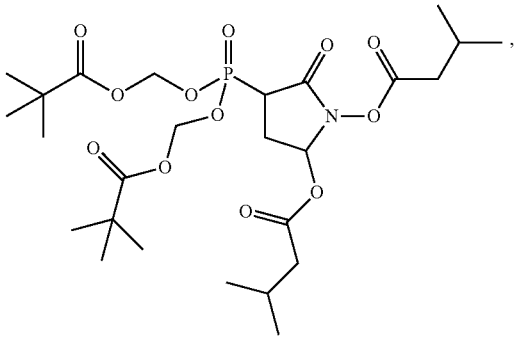

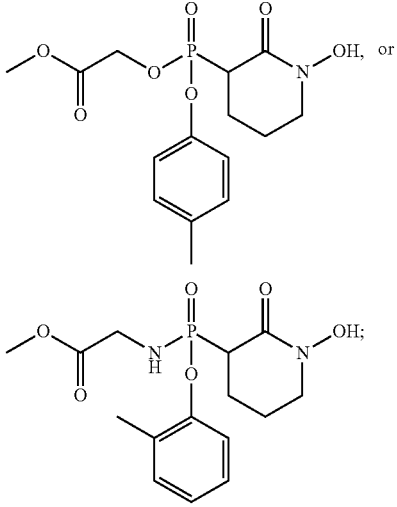

or a pharmaceutically acceptable salt of any of these formulas. In some embodiments, the compound is further defined as:

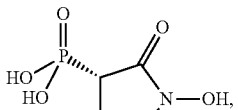

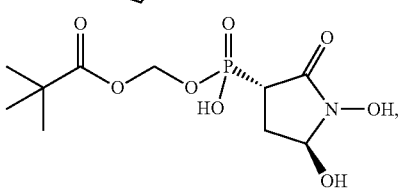

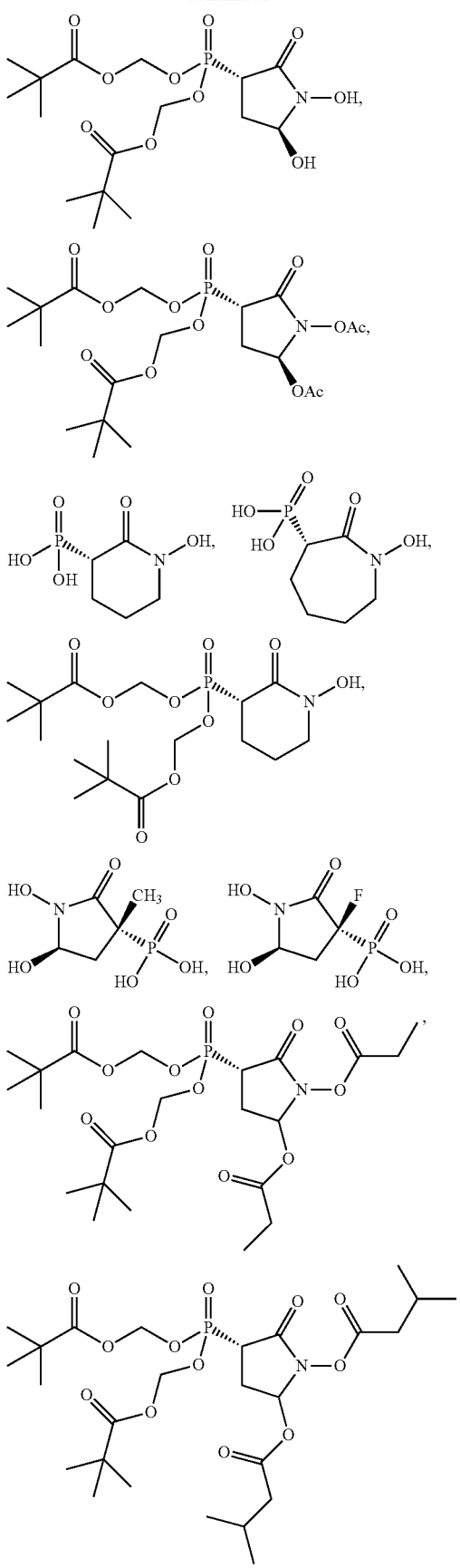
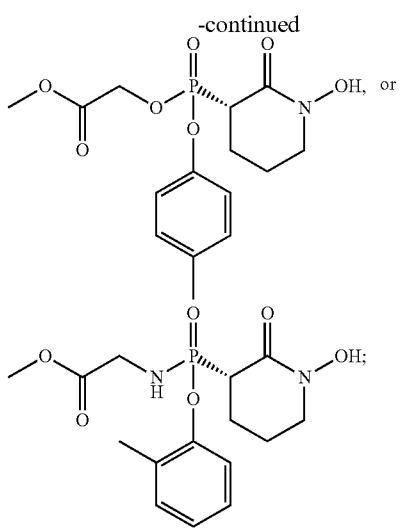

or a pharmaceutically acceptable salt of any of these formulas.

In another aspect, the present disclosure provides pharmaceutical compositions comprising:
(A) a compound of the present disclosure; and
(B) an excipient.

In some embodiments, the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion.

In yet another aspect, the present disclosure provides methods of treating or preventing cancer comprising administering to a patient in need thereof a therapeutically effective amount of a compound of the formula:

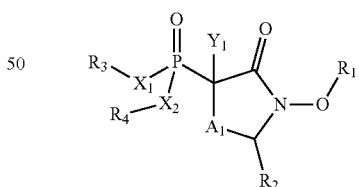

(I)

wherein:
$R_1$ is hydrogen, acyl$_{(C \leq 12)}$ or substituted acyl$_{(C \leq 12)}$;
$R_2$ is hydroxy, hydroxy, alkoxy$_{(C \leq 12)}$, substituted alkoxy$_{(C \leq 12)}$, acyloxy$_{(C \leq 12)}$, or substituted acyloxy$_{(C \leq 12)}$;
$X_1$ and $X_2$ are each independently O, S, or $NR_a$, wherein: $R_a$ is hydrogen, alkyl$_{(C \leq 6)}$, or substituted alkyl$_{(C \leq 6)}$;
$R_3$ and $R_4$ are each independently hydrogen or alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of these groups; or a phosphate protecting group; or $R_3$ and $R_4$ are taken together and are alkanediyl$_{(C≤8)}$ or substituted alkanediyl$_{(C≤8)}$; or —X$_3$—R$_5$; wherein:
  X$_3$ is a covalent bond, alkanediyl$_{(C≤8)}$, or substituted alkanediyl$_{(C≤8)}$; and
  R$_5$ is acyl$_{(C≤18)}$, alkoxy$_{(C≤18)}$, —C(O)-alkoxy$_{(C≤18)}$, acyloxy$_{(C≤18)}$, or a substituted version of any of these groups;
A$_1$ is alkanediyl$_{(C≤8)}$, substituted alkanediyl$_{(C≤8)}$, alkylaminodiyl$_{(C≤8)}$, or substituted alkylaminodiyl$_{(C≤8)}$; and
Y$_1$ is hydrogen, amino, halo, hydroxy, phosphate, alkyl$_{(C≤12)}$, or substituted alkyl$_{(C≤12)}$;
or a pharmaceutically acceptable salt or ester thereof. In some embodiments, the compound is further defined as:

(III)

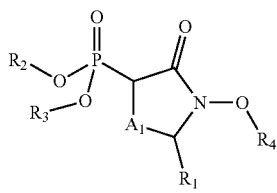

wherein:
  R$_1$ is hydrogen, hydroxy, alkoxy$_{(C≤12)}$, substituted alkoxy$_{(C≤12)}$, acyloxy$_{(C≤12)}$, or substituted acyloxy$_{(C≤12)}$;
  R$_2$ and R$_3$ are each independently hydrogen, alkyl$_{(C≤12)}$, substituted alkyl$_{(C≤12)}$, or a phosphate protecting group;
  R$_4$ is hydrogen, acyl$_{(C≤12)}$, or substituted acyl$_{(C≤12)}$; and
  A$_1$ is alkanediyl$_{(C≤8)}$, substituted alkanediyl$_{(C≤8)}$, alkylaminodiyl$_{(C≤8)}$, or substituted alkylaminodiyl$_{(C≤8)}$;
or a pharmaceutically acceptable salt or ester thereof. In some embodiments, the compound is further defined as:

(IV)

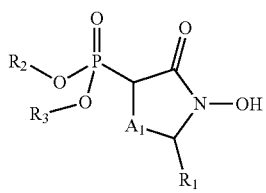

wherein:
  R$_1$ is hydrogen, hydroxy, alkoxy$_{(C≤12)}$, or substituted alkoxy$_{(C≤12)}$;
  R$_2$ and R$_3$ are hydrogen, alkyl$_{(C≤12)}$, substituted alkyl$_{(C≤12)}$, or a phosphate protecting group; and
  A$_1$ is alkanediyl$_{(C≤8)}$, substituted alkanediyl$_{(C≤8)}$, alkylaminodiyl$_{(C≤8)}$, or substituted alkylaminodiyl$_{(C≤8)}$;
or a pharmaceutically acceptable salt or ester thereof. In some embodiments, the compound is further defined as:

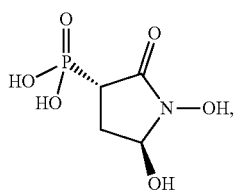 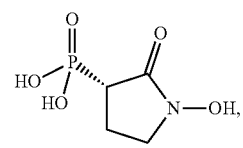

-continued

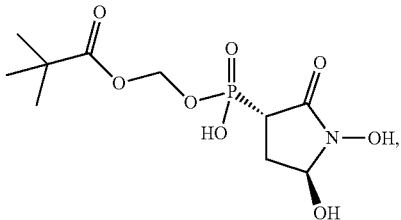

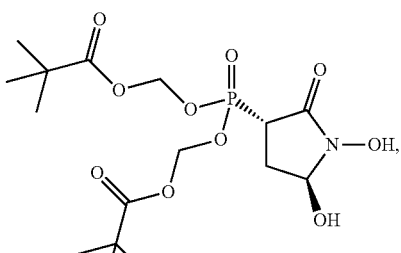

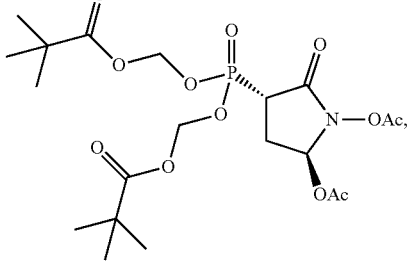

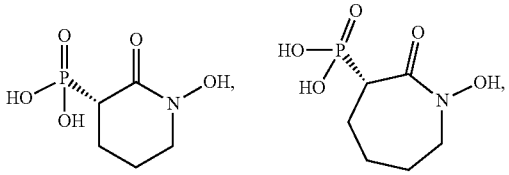

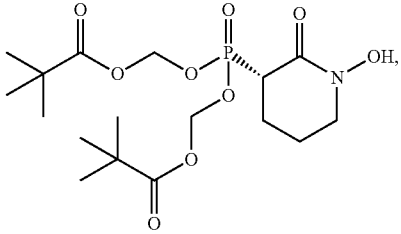

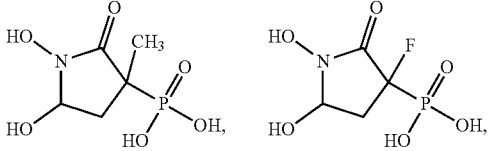

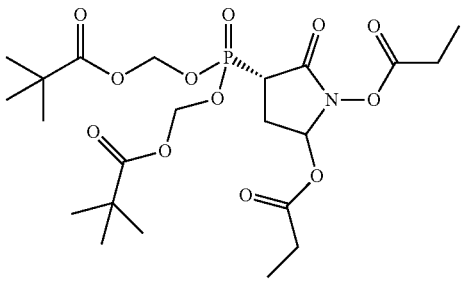

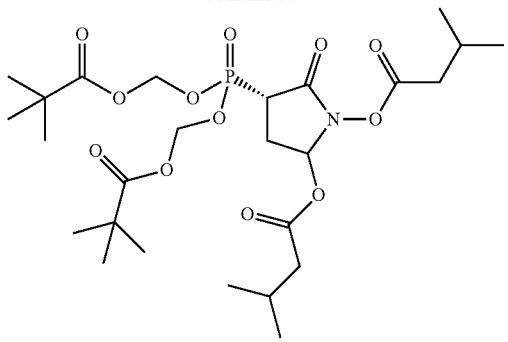

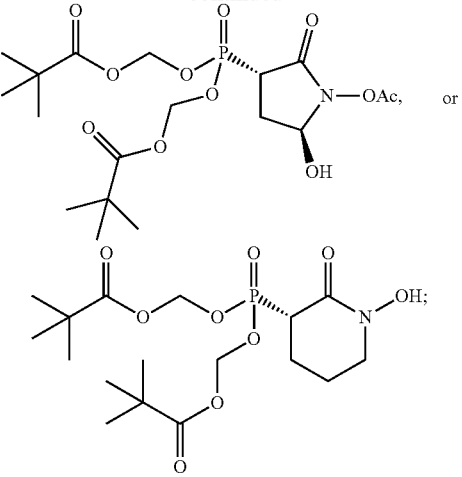

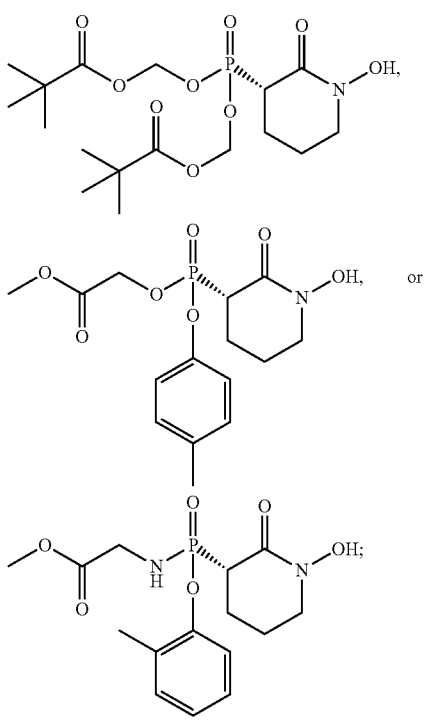

or a pharmaceutically acceptable salt of any of these formulas. In some embodiments, the compound is further defined as:

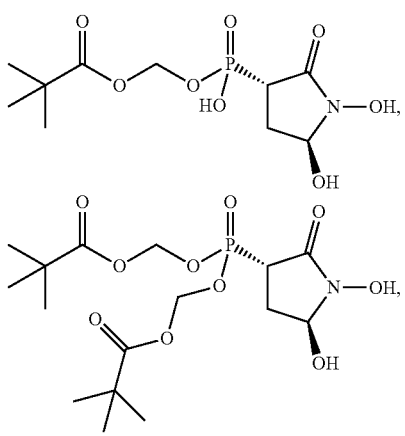

or a pharmaceutically acceptable salt of any of these formulas.

In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer has a deletion of ENO1. In some embodiments, the cancer has an ENO1 homozygous deletion. In some embodiments, the cancer is a glioblastoma, a hepatocellular carcinoma or a cholangiocarcinoma. In some embodiments, the cancer has an ENO1 heterozygous deletion. In some embodiments, the cancer is a neuroblastoma, a gastrointestinal stroma tumor, an ependimoma, or an oligodendroglioma. In some embodiments, the cancer is brain cancer, liver cancer, or kidney cancer. In some embodiments, the brain cancer is glioblastoma multiforme. In some embodiments, the liver cancer is hepatocellular carcinoma. In some embodiments, kidney cancer is a VHL deficient kidney cancer.

In some embodiments, the cancer comprises cells having a mutated ENO1 gene. In some embodiments, the cancer comprises cells having a heterozygous mutation in the ENO1 gene. In some embodiments, the cancer comprises cells having a homozygous mutation in the ENO1 gene. In some embodiments, the mutated ENO1 gene results in an enolase 1 protein which exhibits greater than a 25% decrease in catalytic activity relative to a wild type enolase 1 protein. In some embodiments, the protein exhibits a greater than 50% decrease in catalytic activity. In some embodiments, the cancer comprise cells with a deletion of the ENO1 gene. In some embodiments, the cancer comprise cells with a 1p36 gene deletion. In some embodiments, the deletion of the ENO1 gene results in the cancer cell which exhibits less than 25% of the wild type activity of enolase 1. In some embodiments, the cancer cells exhibit less than 10% of the wild type activity of enolase 1. In some embodiments, the cancer comprises cells with a homozygous deletion of the ENO1 gene. In some embodiments, the cancer comprises cells with a heterozygous deletion of the ENO1 gene. In some embodiments, the cancer is of a cell which overexpresses enolase 2.

In other embodiments, the cancer comprises a cell having a mutation in mitochondrial succinate dehydrogenase or fumarate hydratase. In some embodiments, the cancer comprises cells with a mutation in mitochondrial succinate dehydrogenase. In some embodiments, the cancer comprises cells with a mutation in mitochondrial fumarate hydratase. In some embodiments, the cancer is gastrointestinal stromal tumor, paraganglioma, phaeochromocytoma, leiomyoma, leiomyosarcoma, or renal cell carcinoma.

In some embodiments, the compound administered comprises a phosphate protecting group at $R_2$, $R_3$, or both. In some embodiments, the phosphate protecting group is pivaloyloxymethyl. In some embodiments, the administration of the therapeutically effective amount of the compound results in a reduced risk of hemolytic anemia compared with an administration of a therapeutically effective amount of a different enolase inhibitor. In some embodiments, the compound is a compound of the present disclosure containing at least one pivaloyloxymethyl group.

In some embodiments, the compound is administered in conjunction with a second therapeutic modality. In some embodiments, the second therapeutic modality is a chemotherapeutic agent, surgery, radiotherapy, or immunotherapy. In some embodiments, the patient is a mammal. In some embodiments, the patient is a human.

In still another aspect, the present disclosure provides methods of inhibiting enolase comprising:

(A) obtaining a compound of the formula:

(I)

wherein:
$R_1$ is hydrogen, acyl$_{(C \leq 12)}$ or substituted acyl$_{(C \leq 12)}$;
$R_2$ is hydrogen, hydroxy, alkoxy$_{(C \leq 12)}$, substituted alkoxy$_{(C \leq 12)}$, acyloxy$_{(C \leq 12)}$, or substituted acyloxy$_{(C \leq 12)}$;
$X_1$ and $X_2$ are each independently O, S, or $NR_a$, wherein:
$R_a$ is hydrogen, alkyl$_{(C \leq 6)}$, or substituted alkyl$_{(C \leq 6)}$;
$R_3$ and $R_4$ are each independently hydrogen or alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of these groups; or a phosphate protecting group; or $R_3$ and $R_4$ are taken together and are alkanediyl$_{(C \leq 8)}$ or substituted alkanediyl$_{(C \leq 8)}$; or —$X_3$—$R_5$; wherein:
$X_3$ is a covalent bond, alkanediyl$_{(C \leq 8)}$, or substituted alkanediyl$_{(C \leq 8)}$; and
$R_5$ is acyl$_{(C \leq 18)}$, alkoxy$_{(C \leq 18)}$, —C(O)-alkoxy$_{(C \leq 18)}$, acyloxy$_{(C \leq 18)}$, or a substituted version of any of these groups;
$A_1$ is alkanediyl$_{(C \leq 8)}$, substituted alkanediyl$_{(C \leq 8)}$, alkylaminodiyl$_{(C \leq 8)}$, or substituted alkylaminodiyl$_{(C \leq 8)}$; and
$Y_1$ is hydrogen, amino, halo, hydroxy, phosphate, alkyl$_{(C \leq 12)}$, or substituted alkyl$_{(C \leq 12)}$;
or a pharmaceutically acceptable salt or ester thereof; and (B) contacting enolase with a sufficient amount of the compound to inhibit enolase.

In some embodiments, the compound is further defined as:

(III)

wherein:
$R_1$ is hydrogen, hydroxy, alkoxy$_{(C \leq 12)}$, substituted alkoxy$_{(C \leq 12)}$, acyloxy$_{(C \leq 12)}$, or substituted acyloxy$_{(C \leq 12)}$;
$R_2$ and $R_3$ are each independently hydrogen, alkyl$_{(C \leq 12)}$, substituted alkyl$_{(C \leq 12)}$, or a phosphate protecting group;
$R_4$ is hydrogen, acyl$_{(C \leq 12)}$, or substituted acyl$_{(C \leq 12)}$; and
$A_1$ is alkanediyl$_{(C \leq 8)}$, substituted alkanediyl$_{(C \leq 8)}$, alkylaminodiyl$_{(C \leq 8)}$, or substituted alkylaminodiyl$_{(C \leq 8)}$;
or a pharmaceutically acceptable salt or ester thereof. In some embodiments, the compound is further defined as:

(IV)

wherein:
$R_1$ is hydrogen, hydroxy, alkoxy$_{(C \leq 12)}$, substituted alkoxy$_{(C \leq 12)}$, acyloxy$_{(C \leq 12)}$, or substituted acyloxy$_{(C \leq 12)}$;
$R_2$ and $R_3$ are hydrogen, alkyl$_{(C \leq 12)}$, substituted alkyl$_{(C \leq 12)}$, or a phosphate protecting group; and
$A_1$ is alkanediyl$_{(C \leq 8)}$, substituted alkanediyl$_{(C \leq 8)}$, alkylaminodiyl$_{(C \leq 8)}$, or substituted alkylaminodiyl$_{(C \leq 8)}$;
or a pharmaceutically acceptable salt or ester thereof. In some embodiments, the compound is further defined as:

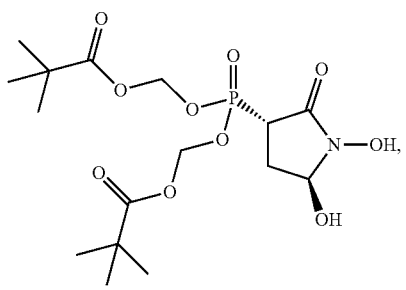

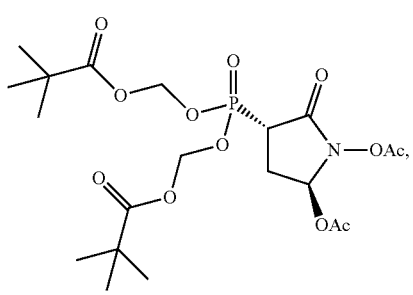

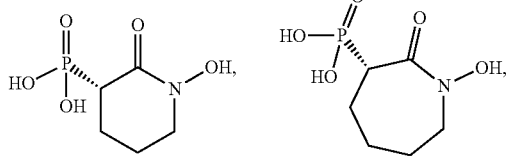

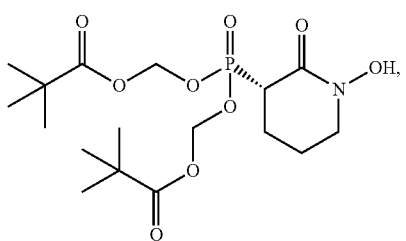

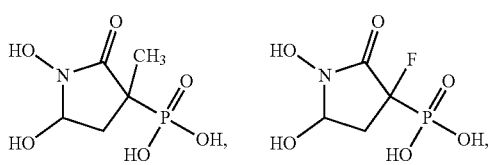

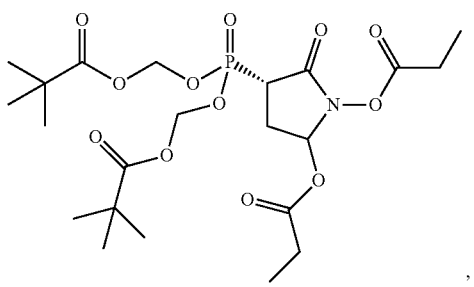

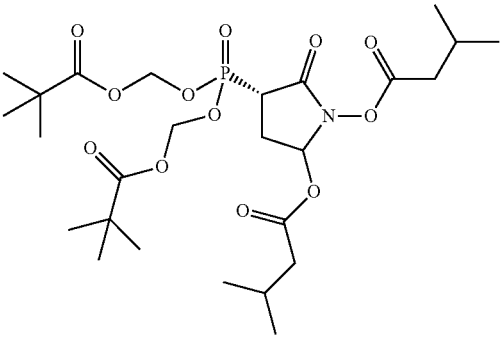

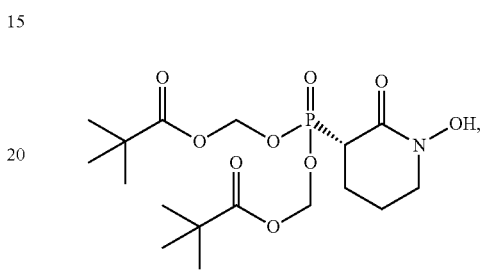

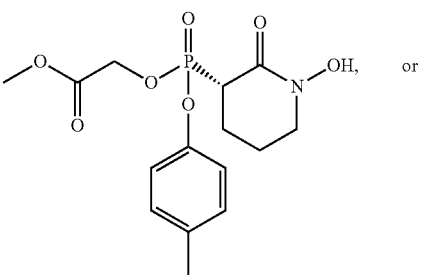

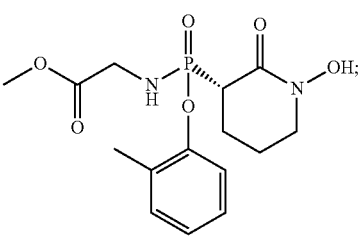

or a pharmaceutically acceptable salt thereof.

In some embodiments, the enolase is enolase 1. In other embodiments, the enolase is enolase 2. In some embodiments, the method comprises inhibiting enolase in vitro. In other embodiments, the method comprises inhibiting enolase in vivo. In some embodiments, the method comprises administering the compound to a patient. In some embodiments, the patient is a mammal. In some embodiments, the patient is a human. In some embodiments, the method of inhibiting enolase is sufficient to block glycolysis. In some embodiments, the method of inhibiting enolase is sufficient to induce apoptosis in a cell.

In yet another aspect, the present disclosure provides methods of treating or preventing an infection comprising administering to a patient in need thereof a therapeutically effective amount of a compound of the formula:

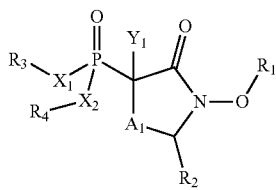

(I)

wherein:
- $R_1$ is hydrogen, acyl$_{(C \leq 12)}$ or substituted acyl$_{(C \leq 12)}$;
- $R_2$ is hydrogen, hydroxy, alkoxy$_{(C \leq 12)}$, substituted alkoxy$_{(C \leq 12)}$, acyloxy$_{(C \leq 12)}$, or substituted acyloxy$_{(C \leq 12)}$;
- $X_1$ and $X_2$ are each independently O, S, or NR$_a$, wherein:
  - $R_a$ is hydrogen, alkyl$_{(C \leq 6)}$, or substituted alkyl$_{(C \leq 6)}$;
- $R_3$ and $R_4$ are each independently alkyl$_{(C \leq 12)}$, aryl$_{(C \leq 12)}$, aralkyl$_{(C \leq 12)}$, or a substituted version of these three groups; or a phosphate protecting group;
- $A_1$ is alkanediyl$_{(C \leq 8)}$, substituted alkanediyl$_{(C \leq 8)}$, alkylaminodiyl$_{(C \leq 8)}$, or substituted alkylaminodiyl$_{(C \leq 8)}$; and
- $Y_1$ is hydrogen, amino, halo, hydroxy, phosphate, alkyl$_{(C \leq 12)}$, or substituted alkyl$_{(C \leq 12)}$;

or a pharmaceutically acceptable salt or ester thereof. In some embodiments, the compound is further defined as:

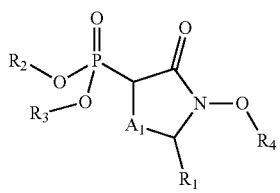

(III)

wherein:
- $R_1$ is hydrogen, hydroxy, alkoxy$_{(C \leq 12)}$, substituted alkoxy$_{(C \leq 12)}$, acyloxy$_{(C \leq 12)}$, or substituted acyloxy$_{(C \leq 12)}$;
- $R_2$ and $R_3$ are each independently hydrogen, alkyl$_{(C \leq 12)}$, substituted alkyl$_{(C \leq 12)}$, or a phosphate protecting group;
- $R_4$ is hydrogen, acyl$_{(C \leq 12)}$, or substituted acyl$_{(C \leq 12)}$; and
- $A_1$ is alkanediyl$_{(C \leq 8)}$, substituted alkanediyl$_{(C \leq 8)}$, alkylaminodiyl$_{(C \leq 8)}$, or substituted alkylaminodiyl$_{(C \leq 8)}$;

or a pharmaceutically acceptable salt or ester thereof. In some embodiments, the compound is further defined as:

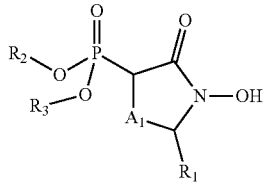

(IV)

wherein:
- $R_1$ is hydrogen, hydroxy, alkoxy$_{(C \leq 12)}$, substituted alkoxy$_{(C \leq 12)}$, acyloxy$_{(C \leq 12)}$, or substituted acyloxy$_{(C \leq 12)}$;
- $R_2$ and $R_3$ are hydrogen, alkyl$_{(C \leq 12)}$, substituted alkyl$_{(C \leq 12)}$, or a phosphate protecting group; and
- $A_1$ is alkanediyl$_{(C \leq 8)}$, substituted alkanediyl$_{(C \leq 8)}$, alkylaminodiyl$_{(C \leq 8)}$, or substituted alkylaminodiyl$_{(C \leq 8)}$;

or a pharmaceutically acceptable salt or ester thereof. In some embodiments, the compound is further defined as:

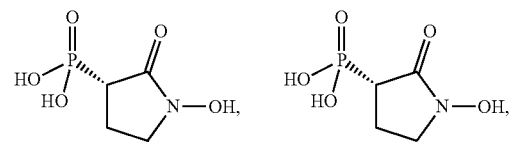

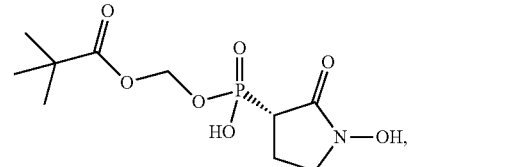

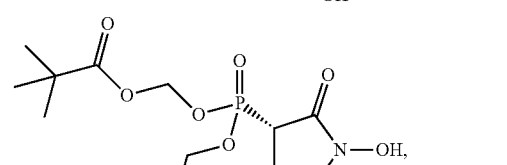

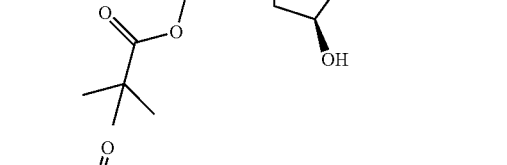

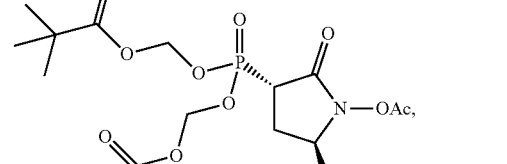

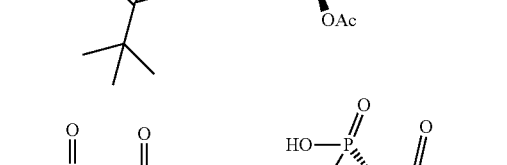

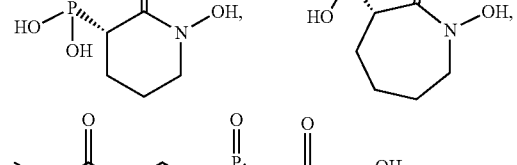

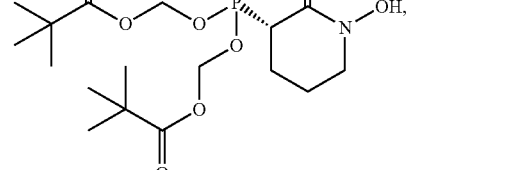

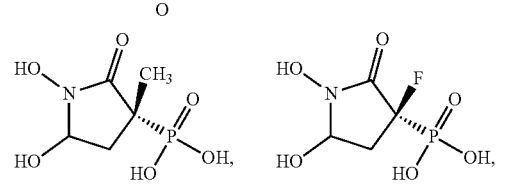

-continued

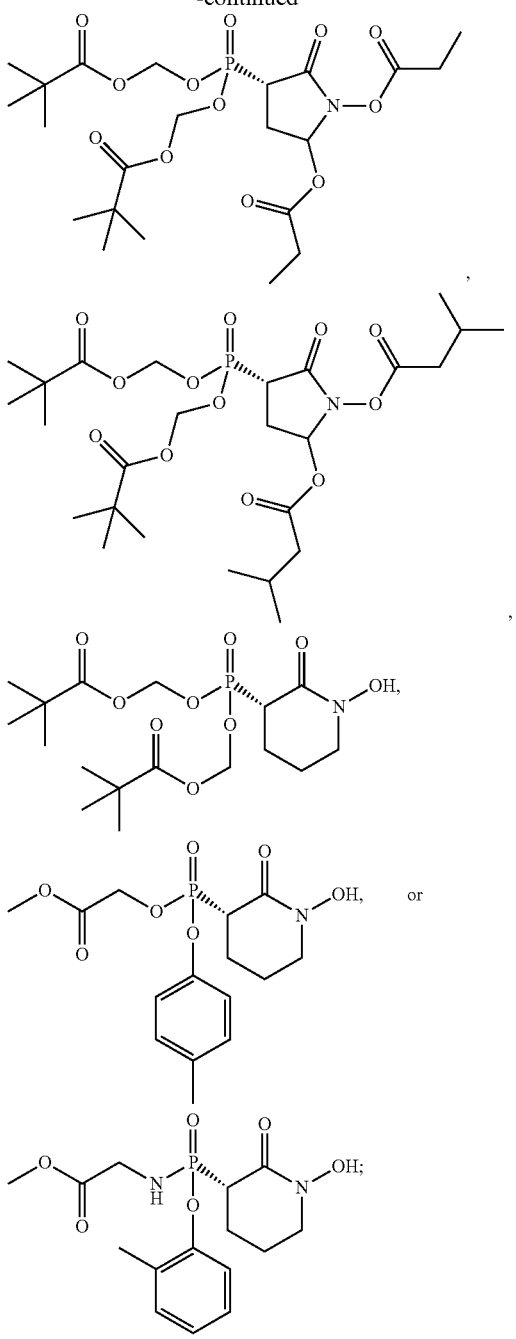

or a pharmaceutically acceptable salt of any of these formulas.

In some embodiments, the compound is not:

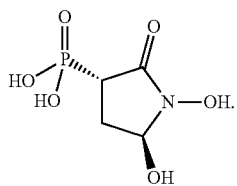

In some embodiments, the compound is not:

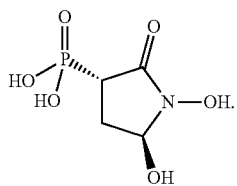

or a pharmaceutically acceptable salt of any of these formulas.

In some embodiments, the infection is a bacterial infection. In some embodiments, the bacterial infection is caused by a bacteria species which is an obligate anaerobe. In some embodiments, bacteria is of a bacterial species selected from *Actinomyces, Bacteroides, Bifidobacterium, Bilophilia, Clostridium, Eubacterium, Fusobacterium, Lactobacillus, Peptostreptococcus, Propionibacterium, Porphyromonas, Prevotella, Sutterella,* and *Veillonella*. In some embodiments, the bacteria is a *Clostridium* species. In some embodiments, the bacteria is *Clostridium difficile*. In some embodiments, the bacterial infection further comprises an infection caused by a second bacteria.

In other embodiments, the infection is a parasitic infection. In some embodiments, the parasitic infection is a *Trypanosoma* parasite. In some embodiments, the parasitic infection is a parasite infection selected from: *Trypanosoma brucei* and *Trypanosoma Cruzi*. In some embodiments, the parasitic infection results in African sleeping sickness and Chagas' disease.

In some embodiments, the compound administered comprises a phosphate protecting group at $R_2$, $R_3$, or both. In some embodiments, the phosphate protecting group is pivaloyloxymethyl. In some embodiments, the administration of the therapeutically effective amount of the compound results in a reduced risk of hemolytic anemia compared with an administration of a therapeutically effective amount of a different enolase inhibitor. In some embodiments, the compound is a compound containing one or more pivaloyloxymethyl groups.

In some embodiments, the method further comprises administering a second therapeutic agent. In some embodiments, the second therapeutic agent is a second antibiotic. In some embodiments, the second therapeutic agent is an anti-parasitic agent. In some embodiments, the patient is a mammal. In some embodiments, the patient is a human.

In still another aspect, the present disclosure provides pharmaceutical compositions comprising a compound of the formula:

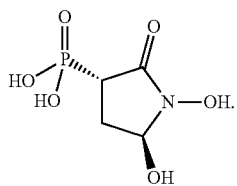

or a pharmaceutically acceptable salt thereof, and an excipient. In some embodiments, the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A & 2B: The inhibition of ENO1 and ENO2 when the enzyme is pre-incubated with the inhibitors, PhAH and SF2312, before the introduction of the substrate is shown in FIG. 2A. Pre-incubation of PhAH (diamonds) or SF2312 (squares) with either human ENO1 or ENO2 before the addition of the substrate 2-PG resulted in profound inhibition of enzymatic activity (IC~20 nM); inhibition of ENO2 with SF2312 was more profound and more durable than ENO1 ($IC_{50}$ for SF2312 is 10-times lower for ENO2 than ENO1) while PhAH caused more or less equal inhibition of ENO1 and ENO2 FIG. 2B shows the inhibition of ENO1 (light gray and gray symbols) and ENO2 (dark gray and black symbols) when the enzyme is treated with both the substrate and the inhibitors, PhAH (triangles) and SF2312 (circles). Concomitant addition of SF2312/PhAH and 2-PG resulted in much weaker inhibition than if the inhibitors were pre-incubated before addition of substrate; this behavior was described previously for PhAH inhibition of yeast enolase (Anderson, et al., 1984), i.e. PhAH acts as a "slow" $k_{on}$ inhibitor. SF2312 was actually less potent than PhAH when assayed under these conditions, indicating that it shows an even slower $k_{on}$ than PhAH.

Several glioma cell lines, including ENO1-deleted D423-MG were tested for sensitivity to Pom-Hex under conventional growth conditions. There was a clear hierarchy of sensitivity, with the normal human astrocytes being highly resistant whereas the ENO1 deleted D423 glioma cells being sensitive to even low nM levels of the inhibitor. Cell lines that were heterozygous for ENO1, which he had previously shown to have intermediate sensitivity to PhAH, also showed intermediate sensitivity to Pom-Hex.

Figure 9:
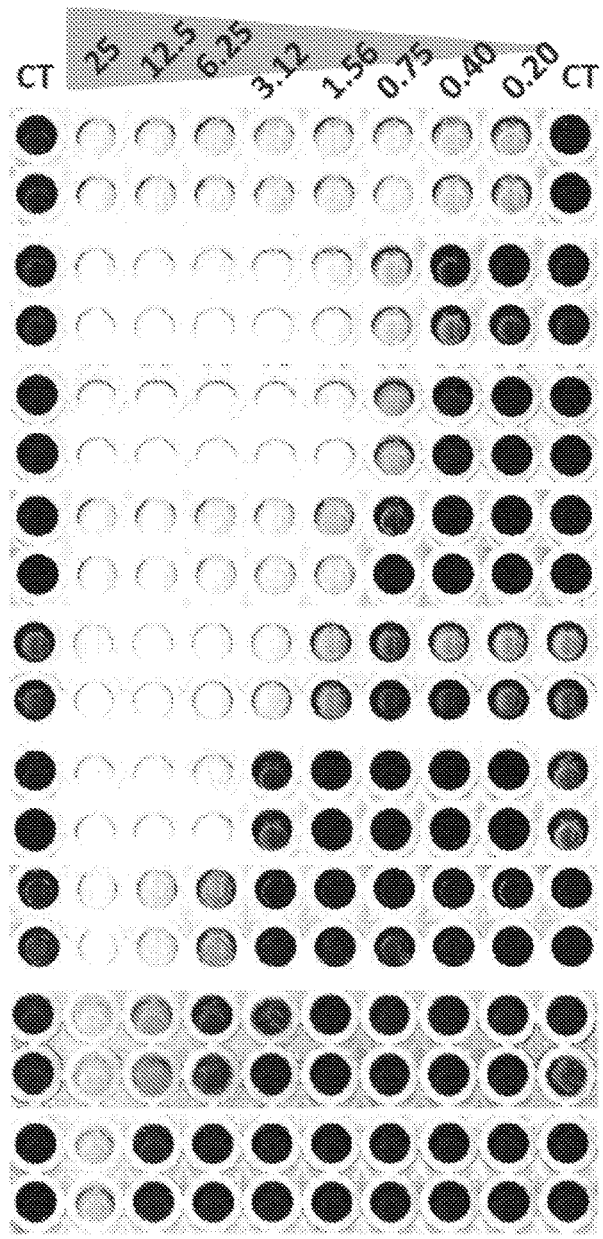

FIG. 9 shows the effect of treating a cell under growth conditions with Pom-Hex after terminal fixation and staining with crystal violet. Several glioma cell lines, including ENO1-deleted D423-MG were tested for sensitivity to Pom-Hex under conventional growth conditions. There was a clear hierarchy of sensitivity, with the normal human astrocytes being highly resistant whereas the ENO1 deleted D423 glioma cells being sensitive to even low nM levels of the inhibitor. Cell lines that were heterozygous for ENO1, which he had previously shown to have intermediate sensitivity to PhAH, also showed intermediate sensitivity to Pom-Hex.

Figure 10A:
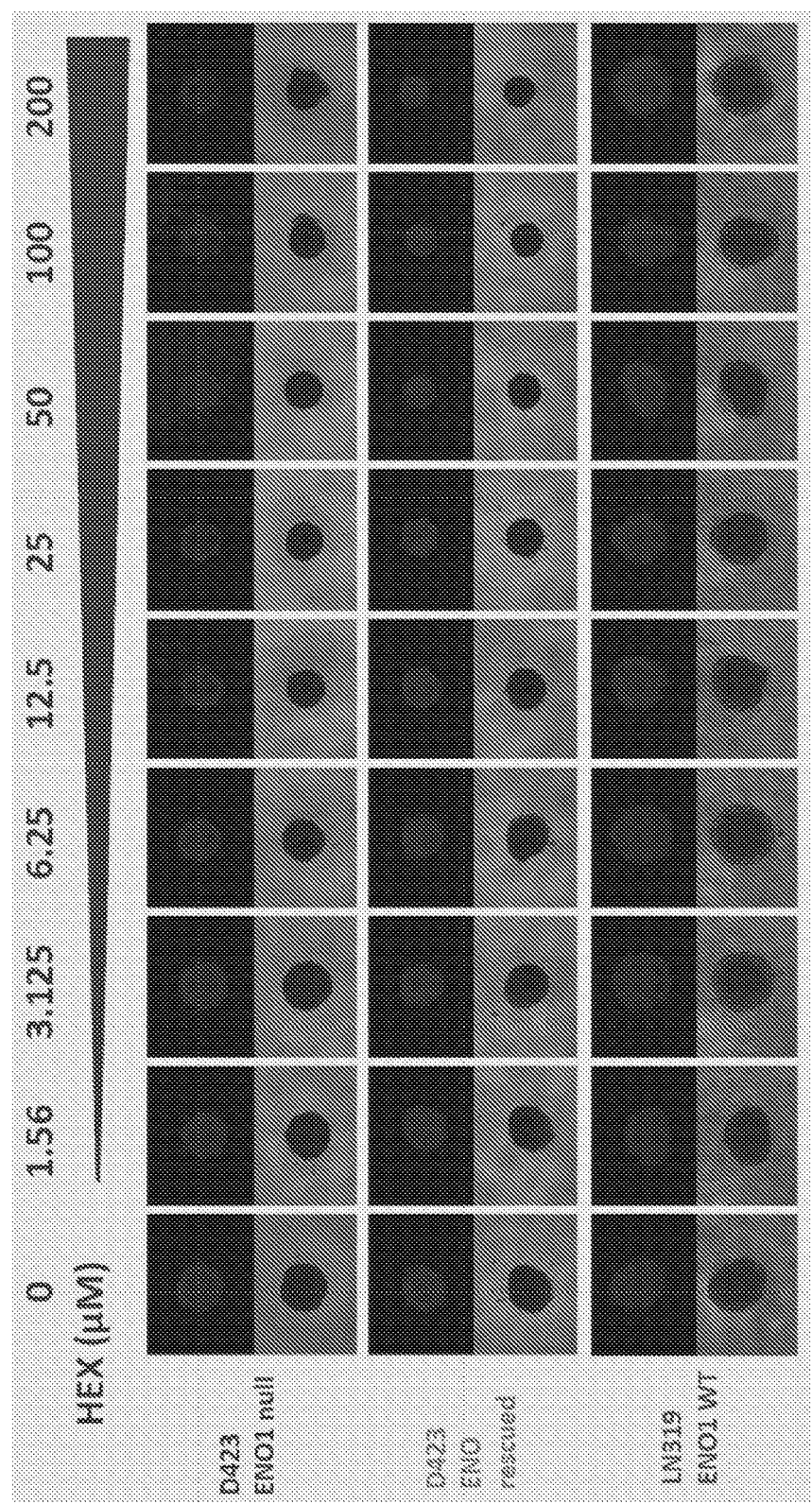
Figure 10B:
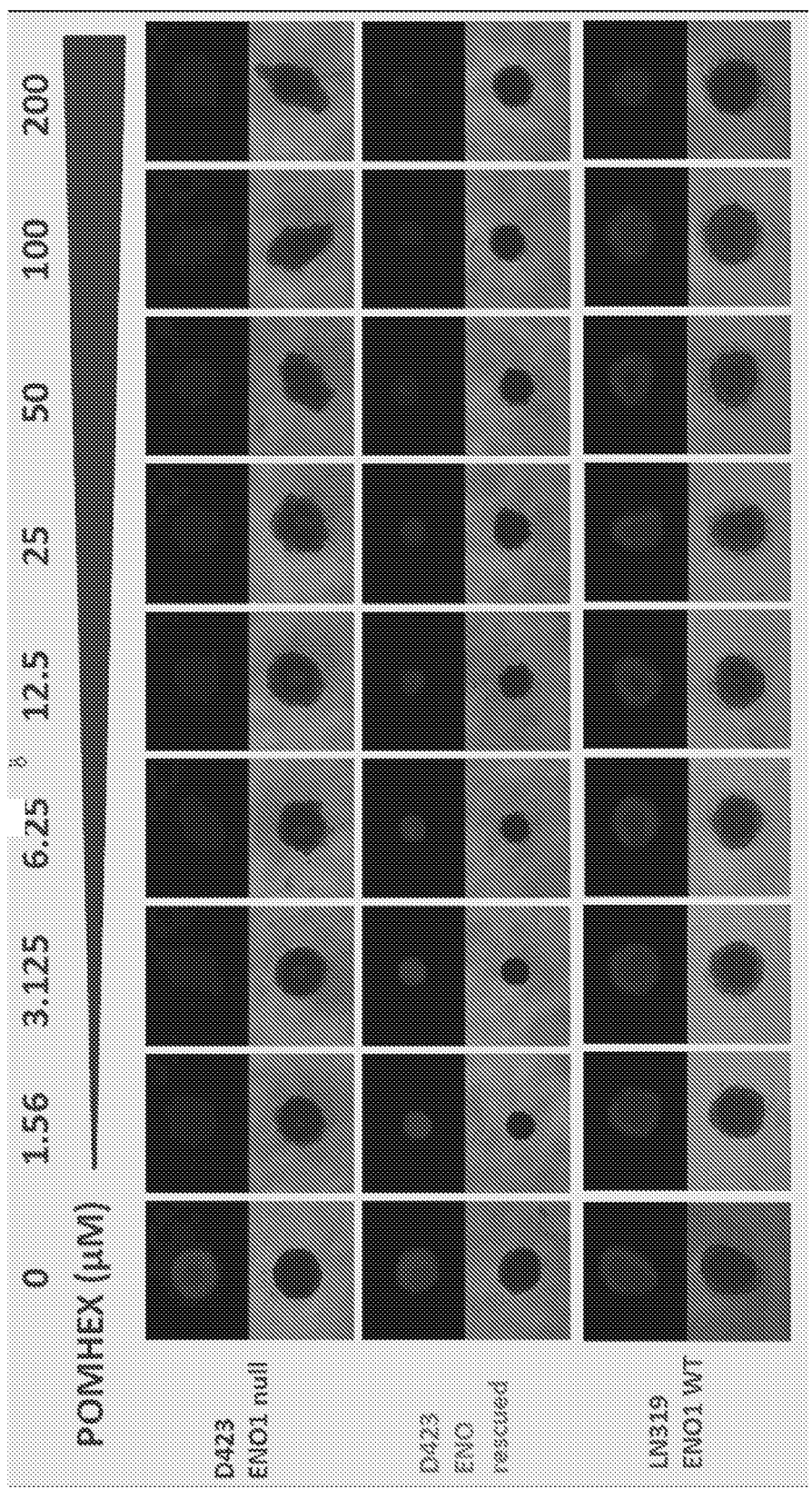

FIGS. 10A & 10B show the effects of Hex (FIG. 10A) and Pom-Hex (FIG. 10B) on 3-dimensional neurosphere glioma cells. To more accurately model tumors, glioma cells were grown in 3 dimensional neurosphere conditions and visualized with 100 nM tetramethylrhodamine, which is actively taken up by live but not dead cells. The surface to volume ratio is considerably smaller than in convention cell culture conditions and as such, compounds with poor cell penetration such as phosphonates have considerably lower efficacy than in conventional cell culture. Thus, under these conditions, even ENO1 deleted cells were only mildly sensitive to the parental free phosphonate, Hex (FIG. 10A). However, under the same conditions, the cell permeable pro-drug, Pomhex, was highly toxic to ENO1 deleted glioma cells (FIG. 10B).

FIGS. 11A-D show the tracking of a glioma tumor via T2 MRI in the absence of treatment with continuous growth (FIGS. 11A & 11B), with IV injection of Pom-Hex at 10 mg/kg which showed the stoppage of tumor growth and completely eradicated the tumor as noted by disappearance of the high contrast area (FIG. 11C), and 3 months after discontinuation of treatment as the animal remained healthy and tumor free (FIG. 11D). Nude mice were injected with D423-MG glioma cells which carry the 1p36 deletion spanning ENO1. Tumors formed around 30 days post injection and growth was tracked non-invasively by T2 MRI. In the absence of treatment, tumors grew continuously, ultimately killing the animal. The tumor area (right side of the brain) is distinguished from the normal mouse brain by high contrast.

Figure 12:
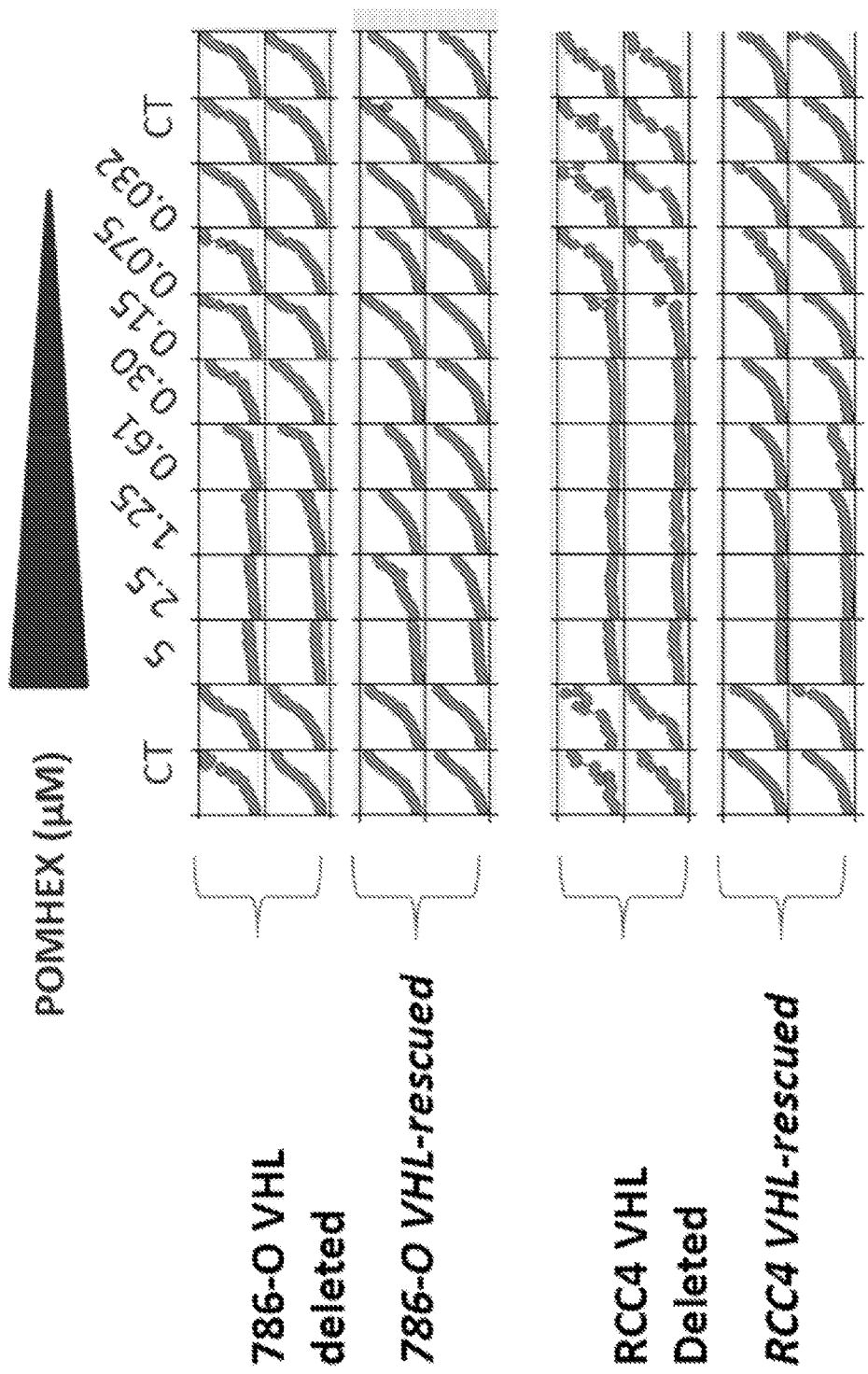

FIG. 12 shows the inhibitory effects of increasing dose of Pom-Hex on VHL deleted kidney cancer cells and VHL rescued kidney cancer cells. In two independent VHL deleted kidney cancer cell lines, RCC4 (bottom pair) and 786-O (top pair), the enolase inhibitor Pom-Hex was 4-8 times more toxic to the VHL deleted (upper panels), compared to isogenic rescued controls, expressing VHL from an ectopic locus (lower panels, italics). The cells were measured by live growth imaging using Incucyte.

FIGS. 13A-D show amino acid residues involved in inhibitor binding based on modeling studies of cyclic backbone-stabilized derivatives of PhAH docked with ENO2. Residues (human ENO2 numbering) that are less than 41 from the docked inhibitors, are shown, with those forming direct interactions pointed out by lines. Most of these residues are highly conserved, consistent with close interaction with the enzyme substrate. The main interactions with the Mg atoms remain essentially the same as with PhAH. Increasing the ring size does not provide additional interactions (FIGS. 13B-D, respectively). Without being bound by theory, the addition of the hydroxy group in SF2312 (FIG. 13A) results in a strong hydrogen bond with a highly conserved residue. Without being bound by theory, it is believe that one stereoisomer of SF2312 and of the other inhibitors was compatible with preferred binding at the active site.

Figure 14:
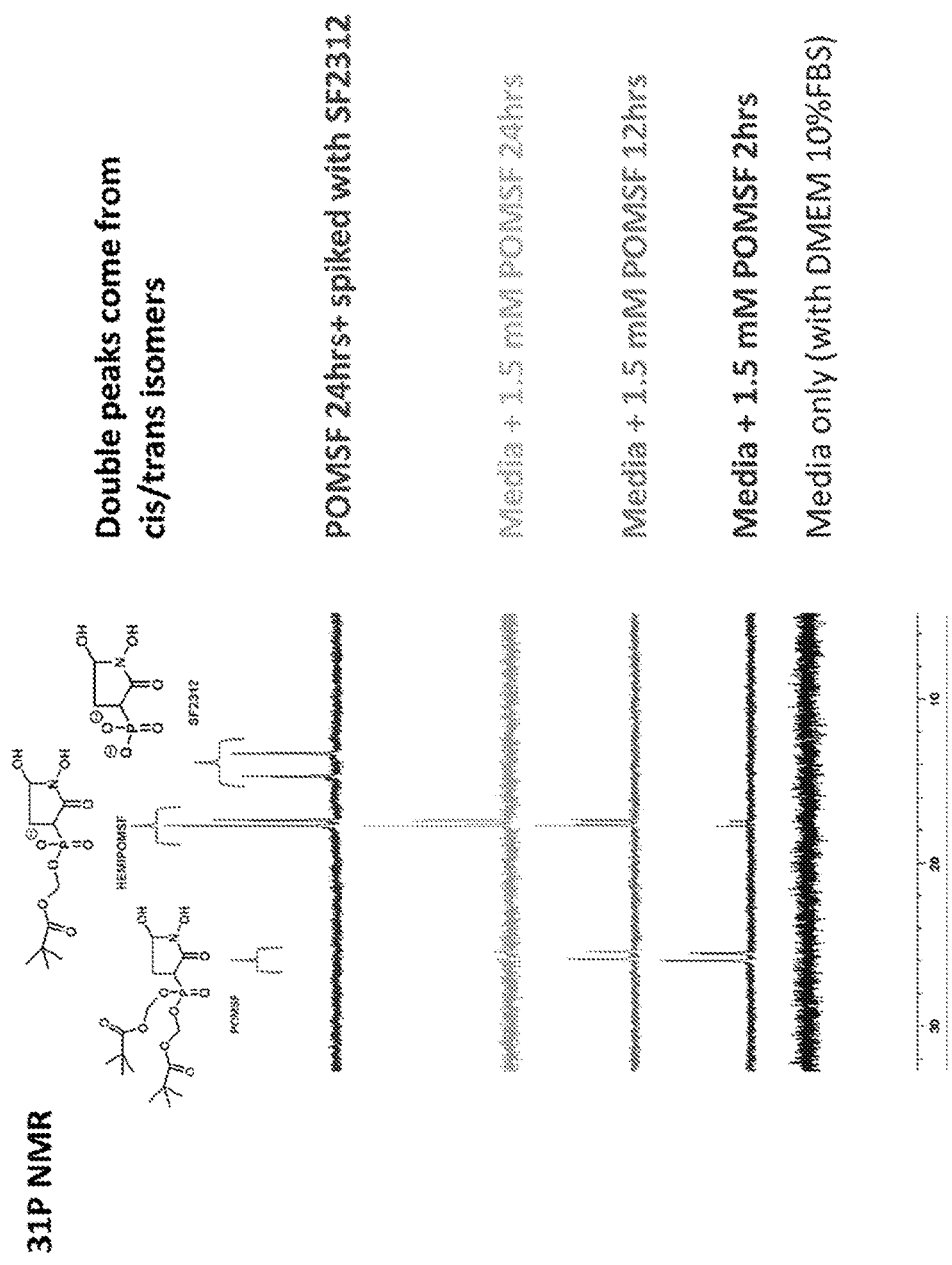

FIG. 14 shows the stability of Pom-SF2312 in cell culture media (DMEM with 10% fetal bovine serum) over time was measured by proton-decoupled $^{31}P$ NMR. Within 12 hours, more than half of Pom-SF2312 hydrolyzed to Hemi-Pom-SF2312. However, Hemi-Pom-SF2312 did not appreciably hydrolyze to SF2312 within 24 hours.

Figures 15A, 15B:
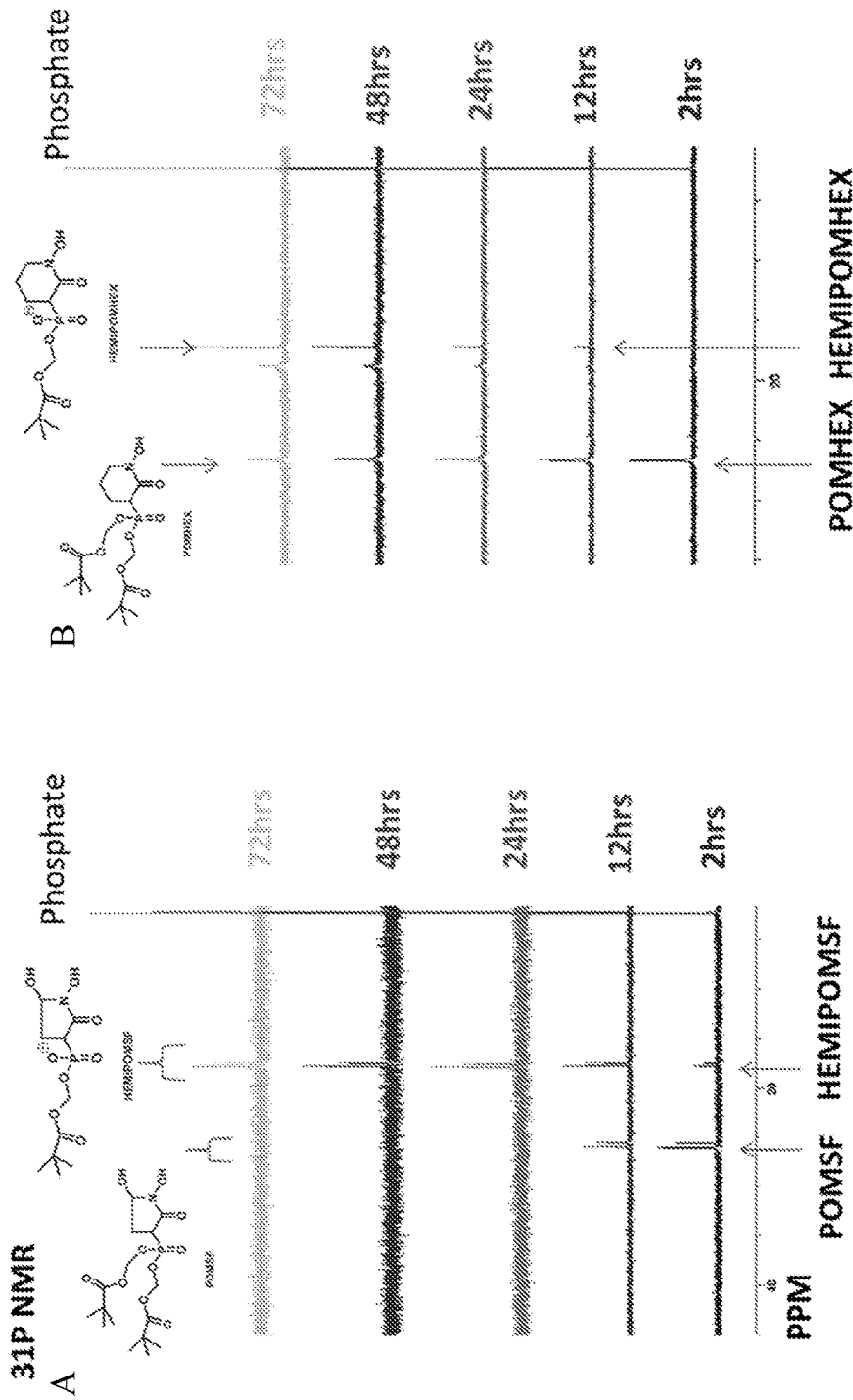

FIGS. 15A & 15B show the increased stability of Pom-Hex (FIG. 15A) shows considerably greater stability than Pom-SF2312 (FIG. 15B) in media. While over half of Pom-SF2312 had hydrolyzed by 12 hours, it took more than 24 hrs for half of the initial Pom-Hex to hydrolyze. Estimated half-lives are 8 hours for Pom-SF2312 and 36 hours for Pom-Hex. The hydrolysis did not proceed further, and neither SF2312, nor Hex, were detectable even after 72 hours of incubation.

Figures 16A, 16B:
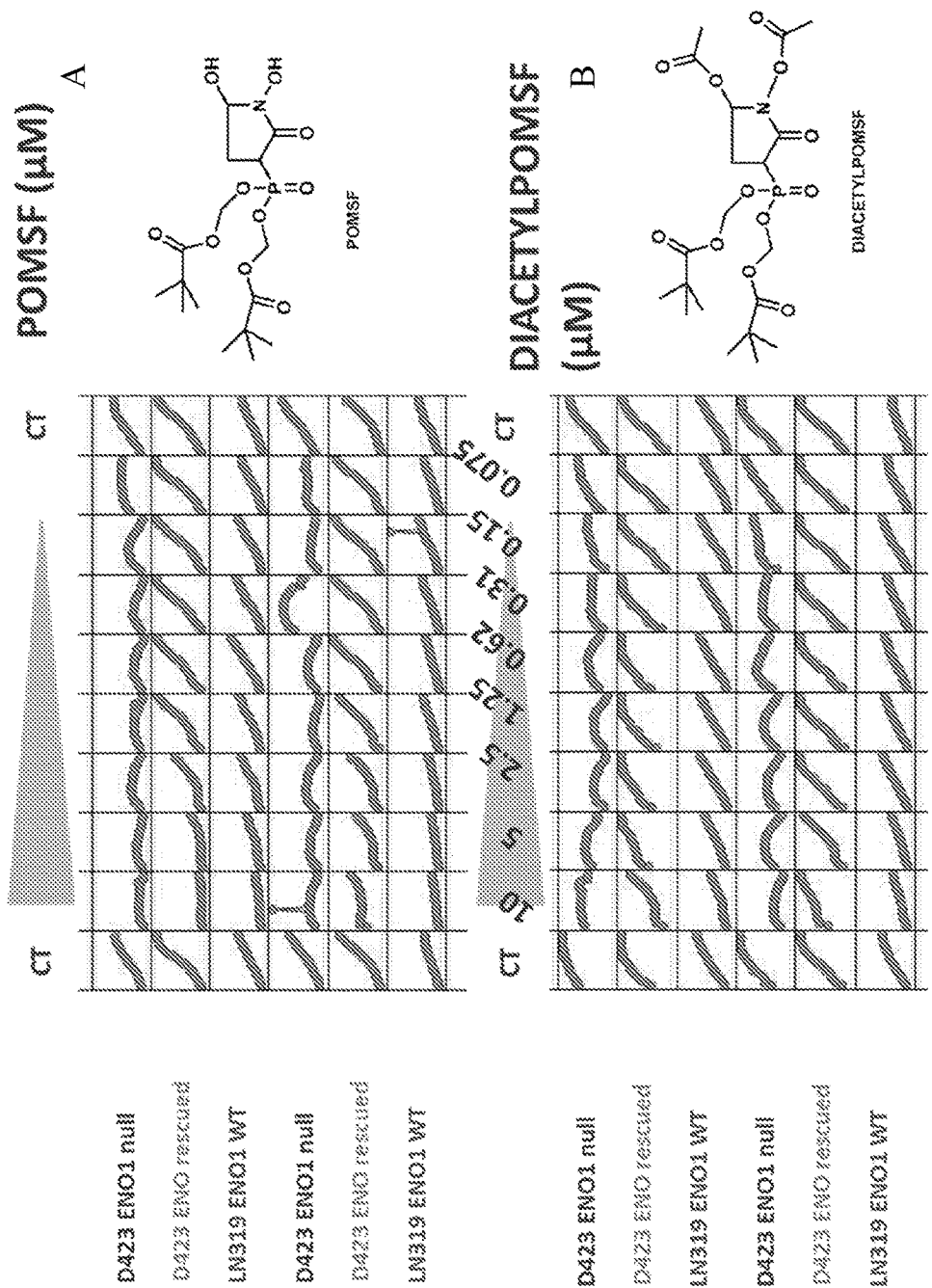

FIGS. 16A & 16B show that Pom-SF2312 (FIG. 16A) and Diacetyl-Pom-SF2312 (FIG. 16B) are selectively toxic to ENO1-deleted glioma cells. Approximate $IC_{50}$'s for growth inhibition of ENO1 null glioma cells are <75 nM for Pom-SF2312 and ~150 nM for Diacetyl-Pom-SF2312, while Pom-Hex has an $IC_{50}$ of around 35 nM.

Figure 17:
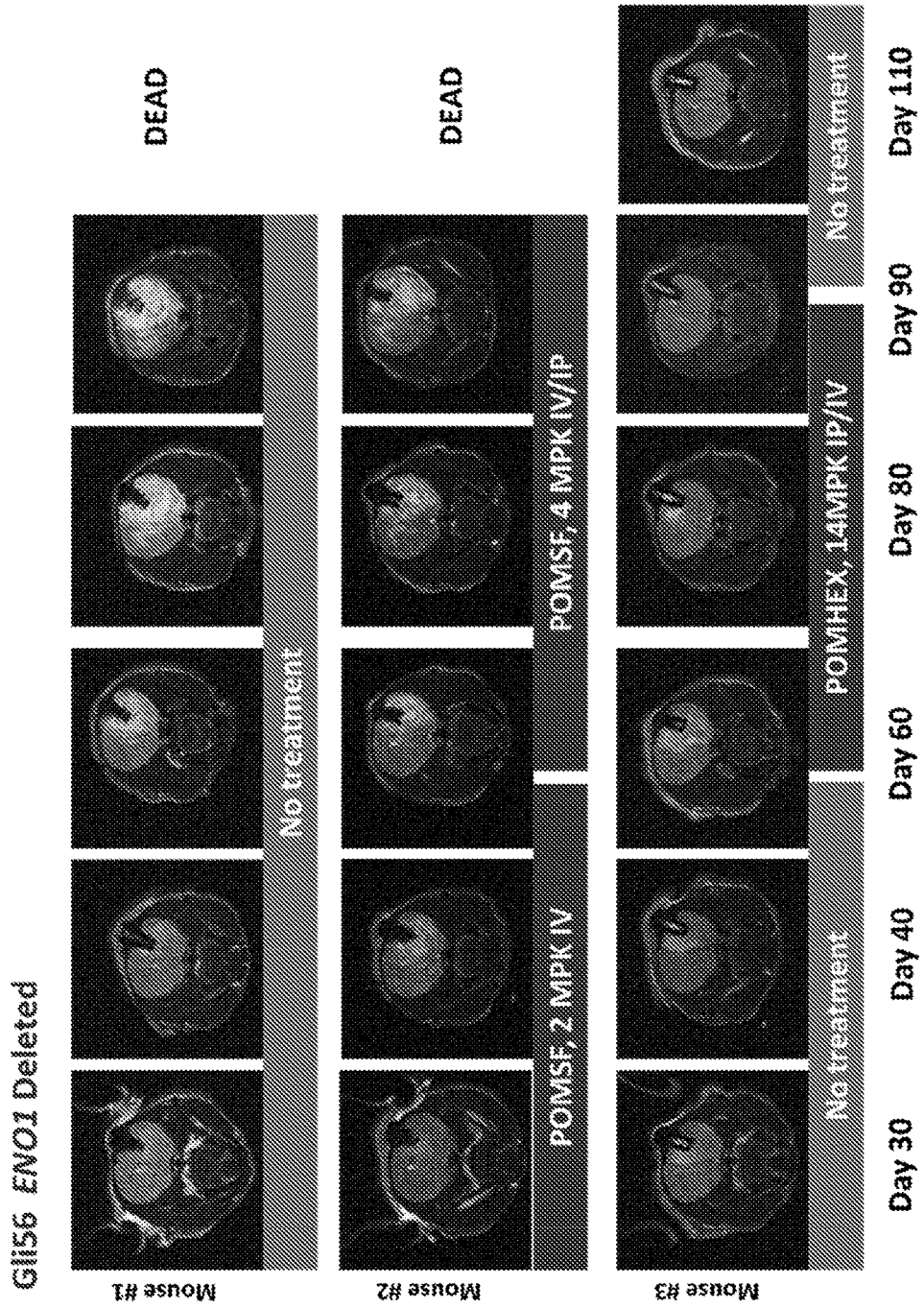
Figure 18A:
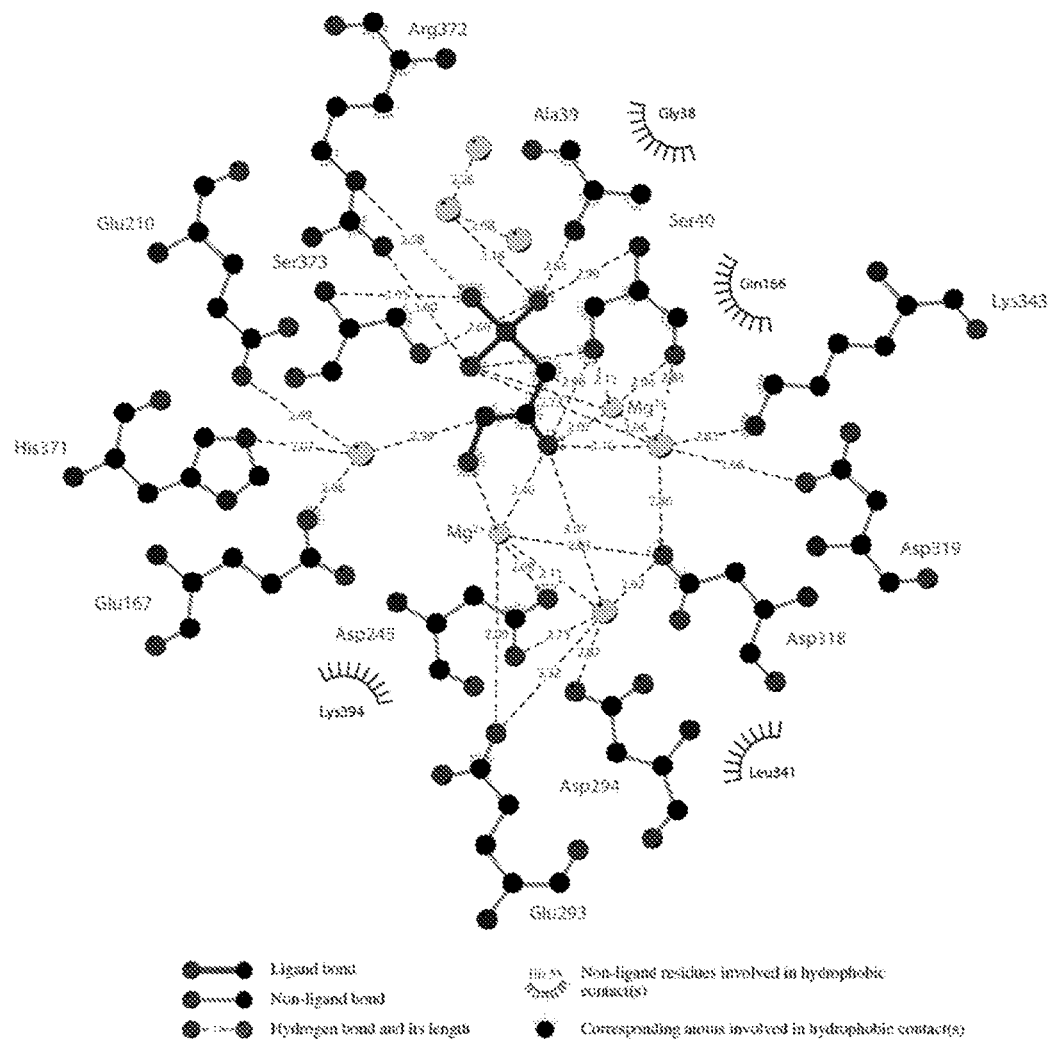
Figure 18B:
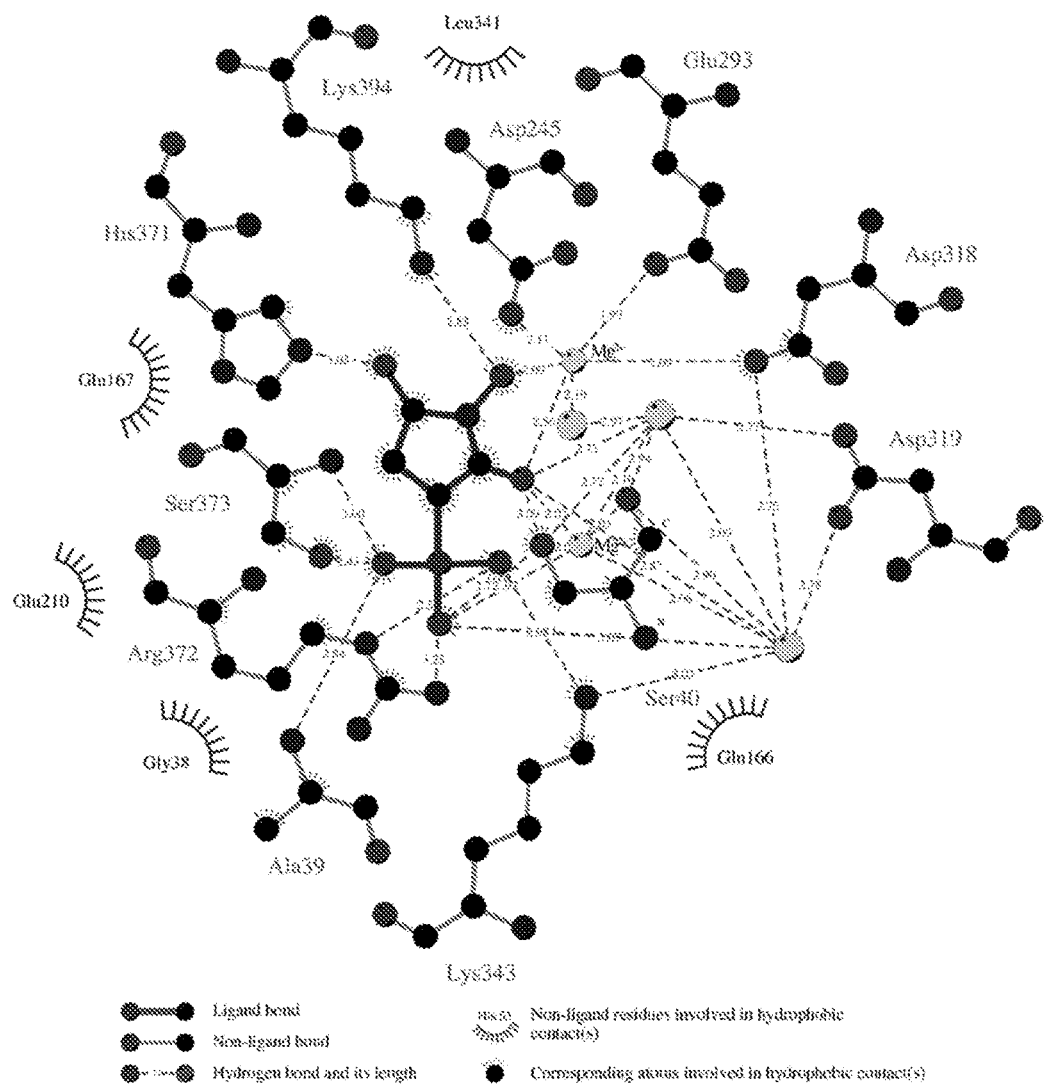
Figure 18C:
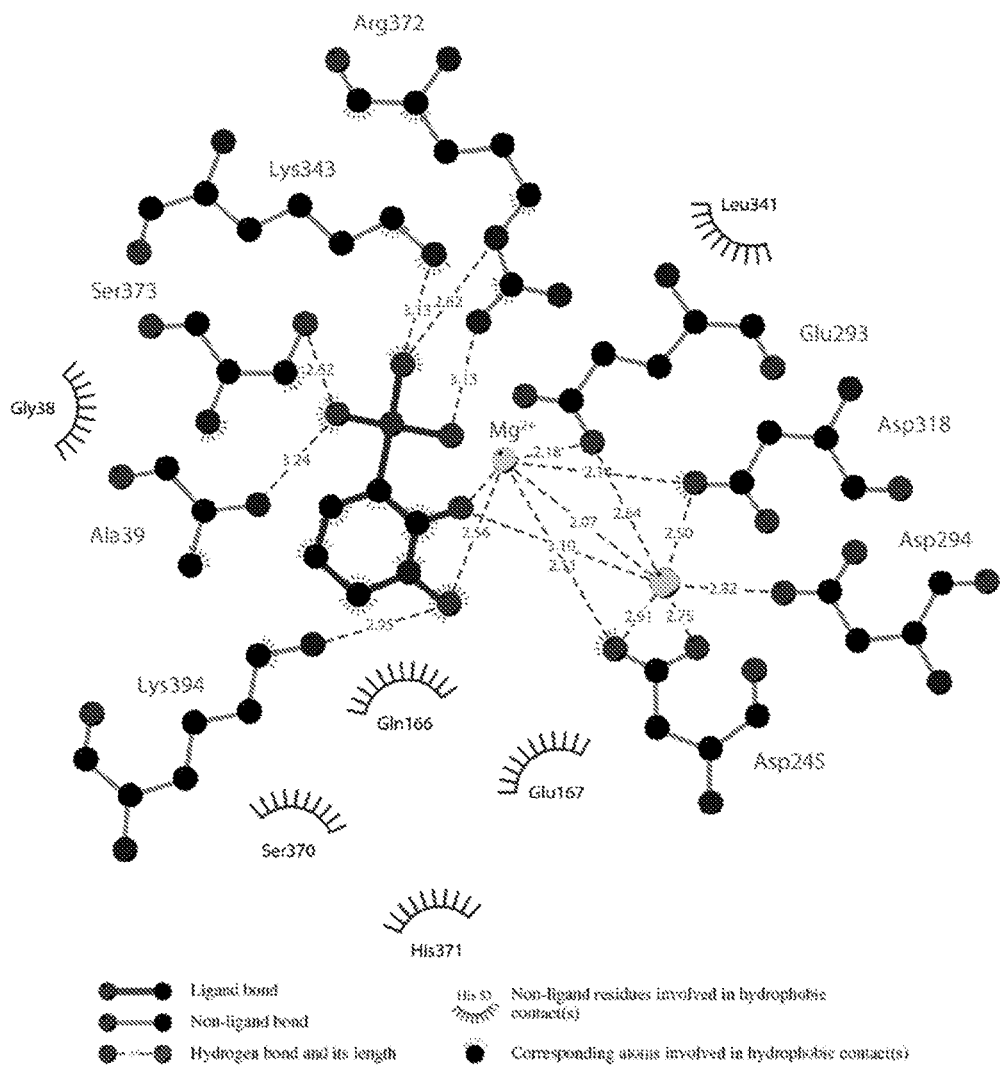
Figure 18D:
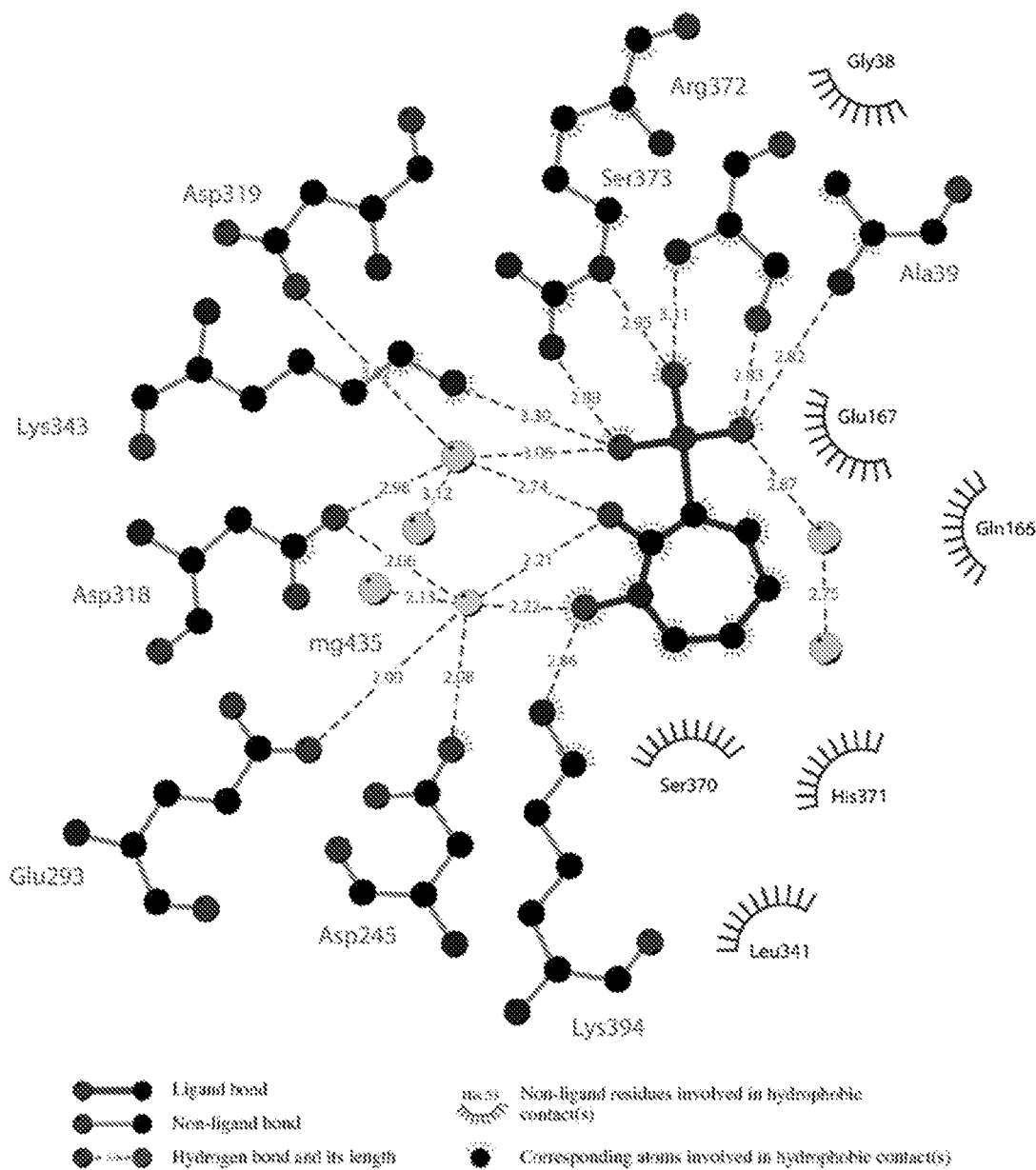
Figure 19D:
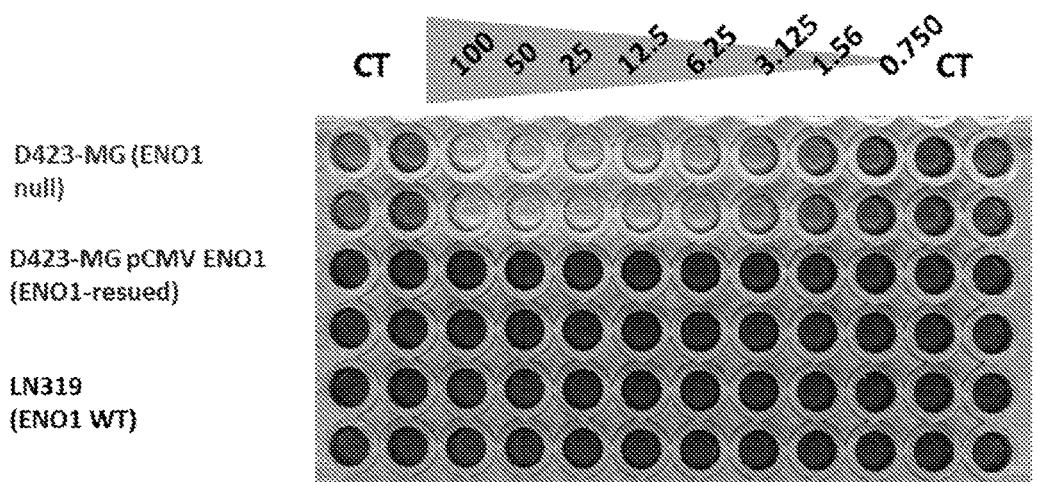
Figure 19E:
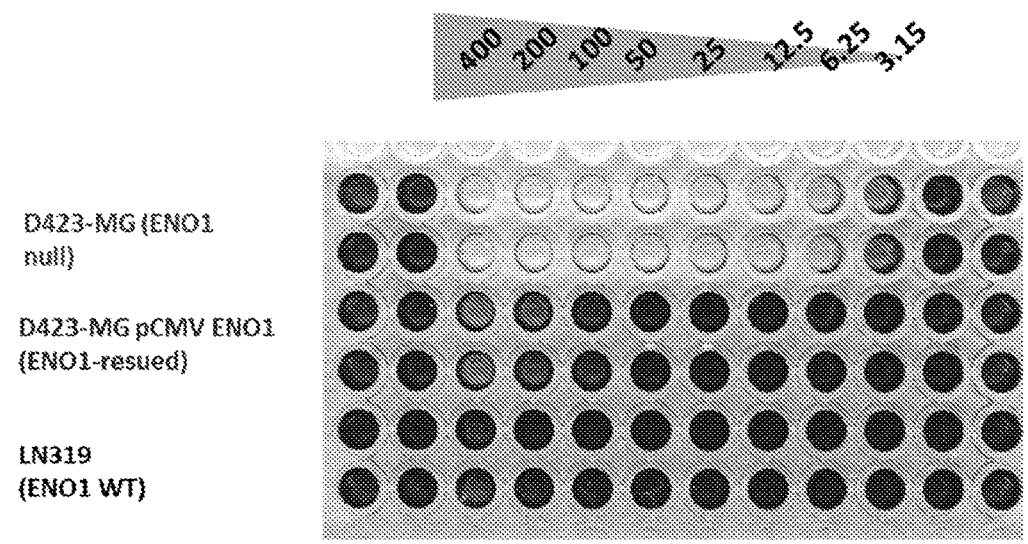
Figure 19F:
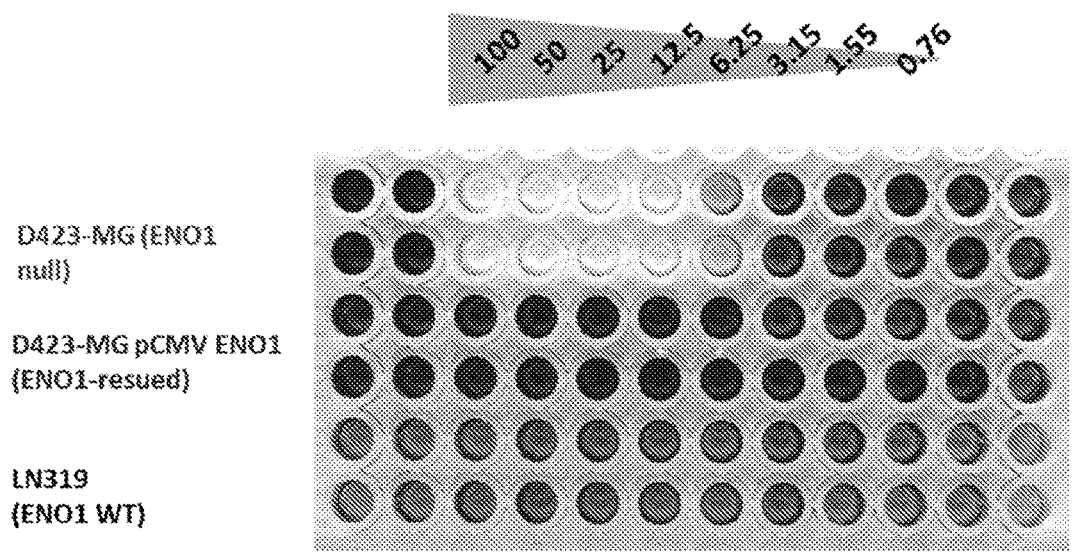

FIG. 17 shows animals (NUDE immunocompromised mice) injected intracranially with the ENO1 deleted Glioblastoma cell line, Gli56. After 30 days, tumors became readily visible by MRI ($T_2$, the white hyperintense regions are tumor on the background grey of the normal brain). In the absence of treatment, Gli56 tumors grow continuously (Mouse #1, and Mouse #3, from Day 30 to Day 40). The treatment with Pom-SF2312 did not significantly slow tumor growth (Mouse #2), even at 4 MPK (mg/kg), which was the maximum tolerated dose. However, Pom-Hex treatment not only stopped tumor growth, but actually led to a profound tumor regression, and eventual disappearance. Tumors have not recurred even after discontinuation of treatment.

FIG. 18A-18D show the crystal structure with PhAh (FIG. 18A), SF2312 (FIG. 18B), Hex (FIG. 18C), and Hepta (FIG. 18D) bound into the active site of the enolase enzyme.

FIG. 19A-19F show the activity in POMHex (FIG. 19A), POMSF (FIG. 19B), Diacetyl POMSF (FIG. 19C), 115-36 (FIG. 19D), MethylSF2312 (FIG. 19E), and FluoroSF2312 (FIG. 19F) for D423-MG (ENO1 null), D423-MG pCMV ENO1 which is ENO1 rescued, and LN319 which is wild type for ENO1

Figure 20:
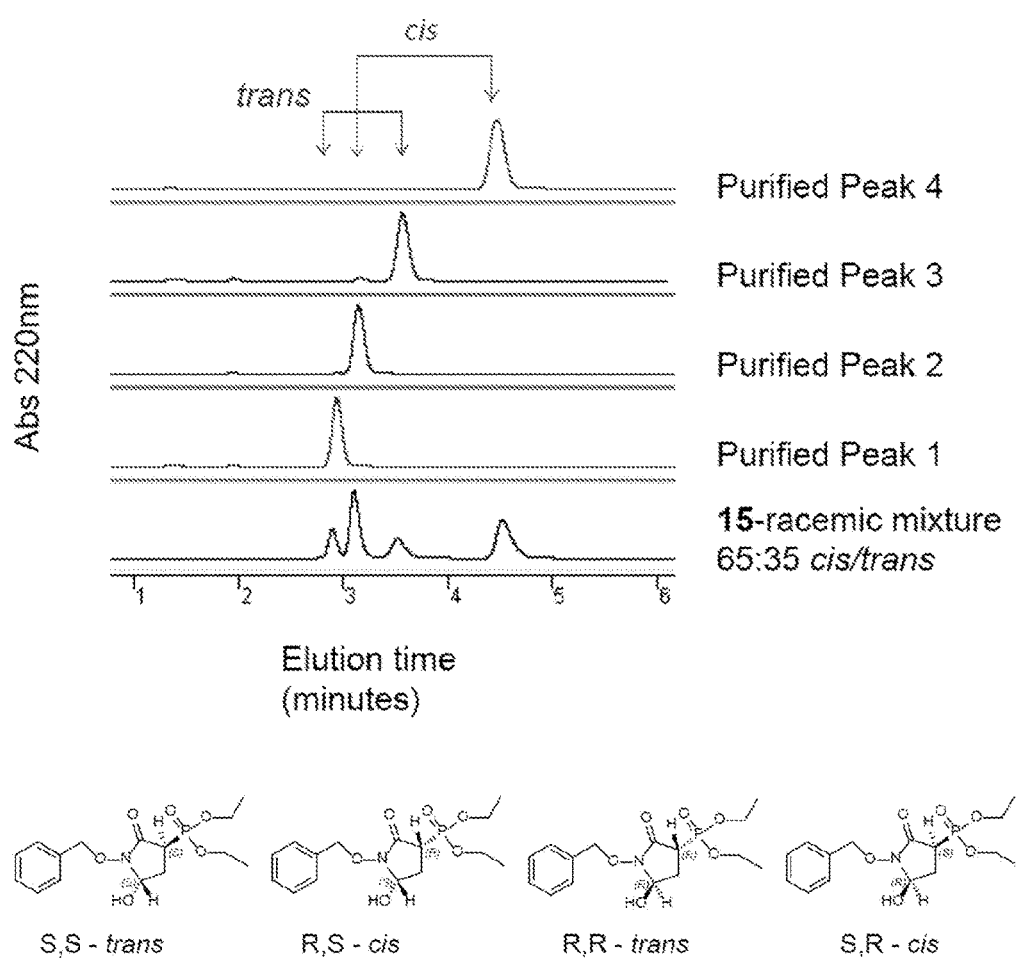

FIG. 20 shows chiral chromatographic separation of intermediate 15. Intermediate 15, consisting of a mixture of cis/trans isomers in a 65:35 ratio, was analyzed by chiral HPLC. The chromatogram showed 4 peaks, two majors and two minors, in a ratio of 65:35. Based on relative abundance, these were assigned to the cis and trans isomers; this was confirmed by NMR (see FIG. 21). The four isomers were separated and each one was re-analyzed on the same chiral HPLC to confirm chiral purity. HPLC conditions were as follow: Mobile phase, Isocratic 76% Hexane, 18% Ethanol, 4% Isopropanol, 2% acetonitrile, 0.1% TFA; flow rate: 20 mL/minute. Column: Normal phase Lux Cell-1 21.2×150 mm (Phenomenex®, Torrence, Calif.).

Figure 21A:
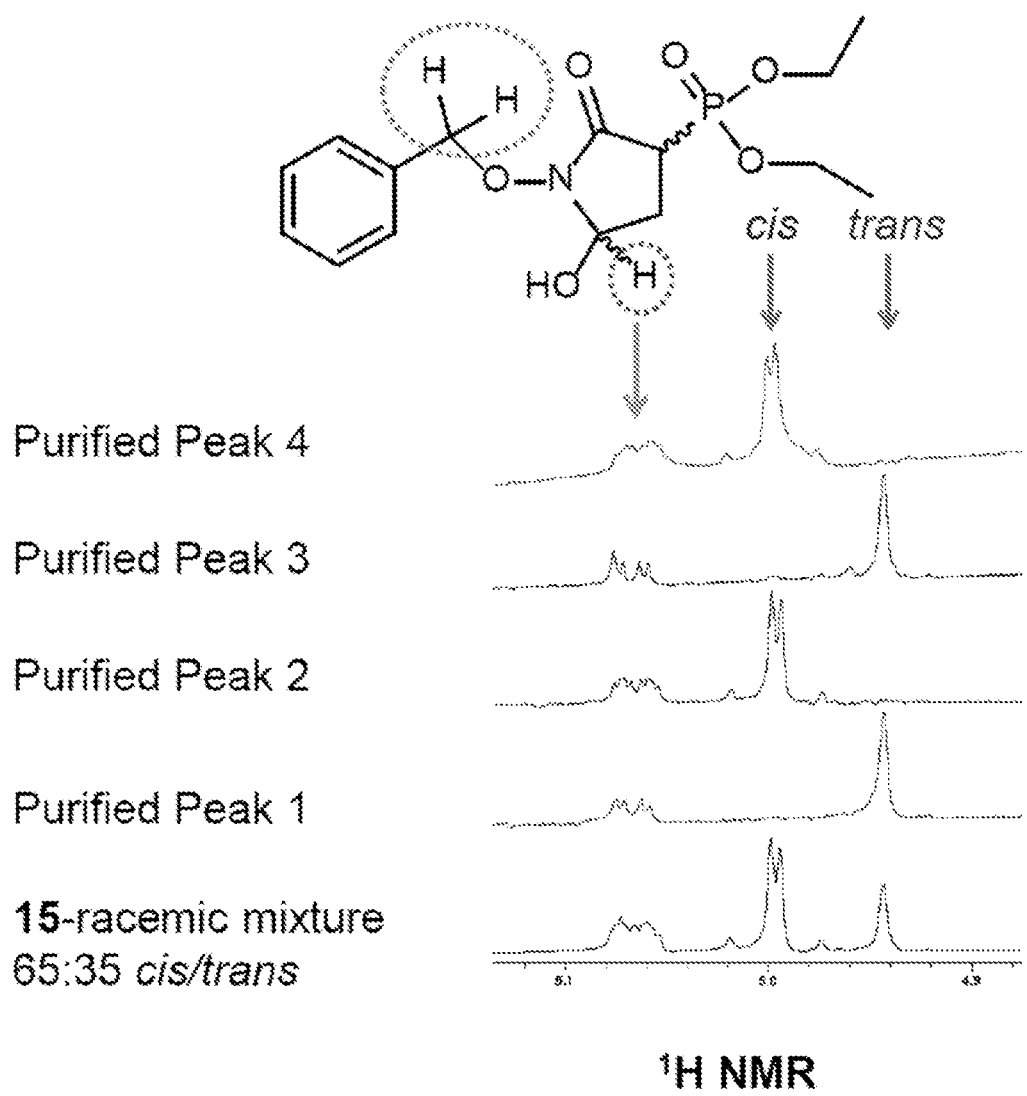
Figure 21B:
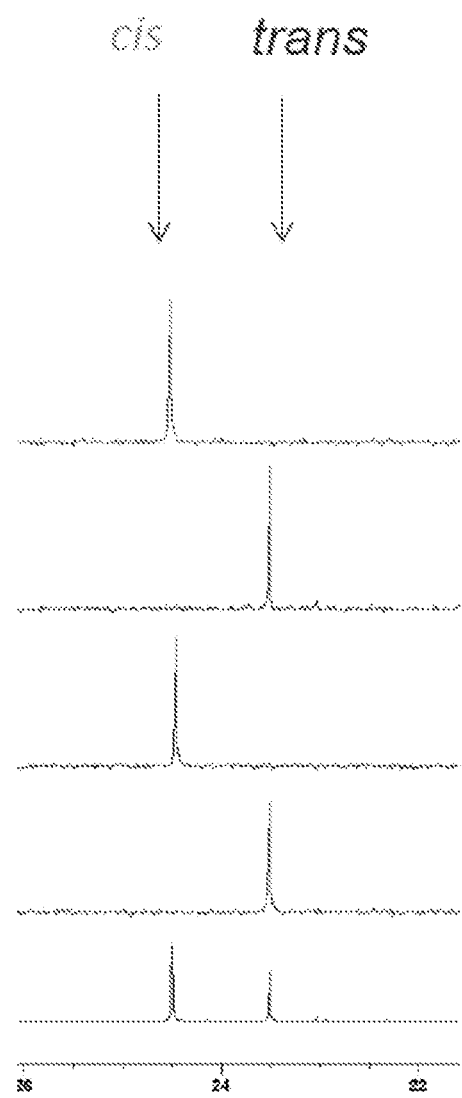

FIGS. 21A & 21B show NMR characterization of chiral chromatography purified entities. NMR on the chiral chromatography purified enantiomers were performed as the enantiomers came off the column. In order to minimize time between purification and NMR recording (to avoid racemization), mobile phase solvents were not evaporate but one equivalent volume of deuterated acetonitrile was added for signal-lock. Because of the presence of solvents from the mobile phase (hexane, ethanol, isopropanol, acetonitrile, TFA), the $^1$H spectrum upfield of 4 ppm is obfuscated. However, the hemiaminal and benzyl protons are readily identifiable (FIG. 21A). The initial intermediate 15, is characterized by two sets of hemiaminal protons (multiplet, 5.08-5.06 ppm) and benzyl methylene (cis: ab-system 4.99 ppm; trans: 4.94) protons in 65:35 ratio in agreement with Hanaya and Itoh (2011). In the $^{31}$P NMR spectrum (FIG. 21B), two peaks are evident, previously identified as the cis and trans isomers (downfield at 24.5 ppm and upfield at 23.5 ppm, respectively as noted in Hanaya and Itoh, 2011), present in 65:35 ratio. Each purified enantiomer showed a single peak on $^{31}$P NMR (trans: 24.5 ppm; cis: 23.5 ppm) as well as one set of hemiaminal and benzyl methylene protons (Hanaya and Itoh, 2011).

Figures 22A, 22B:
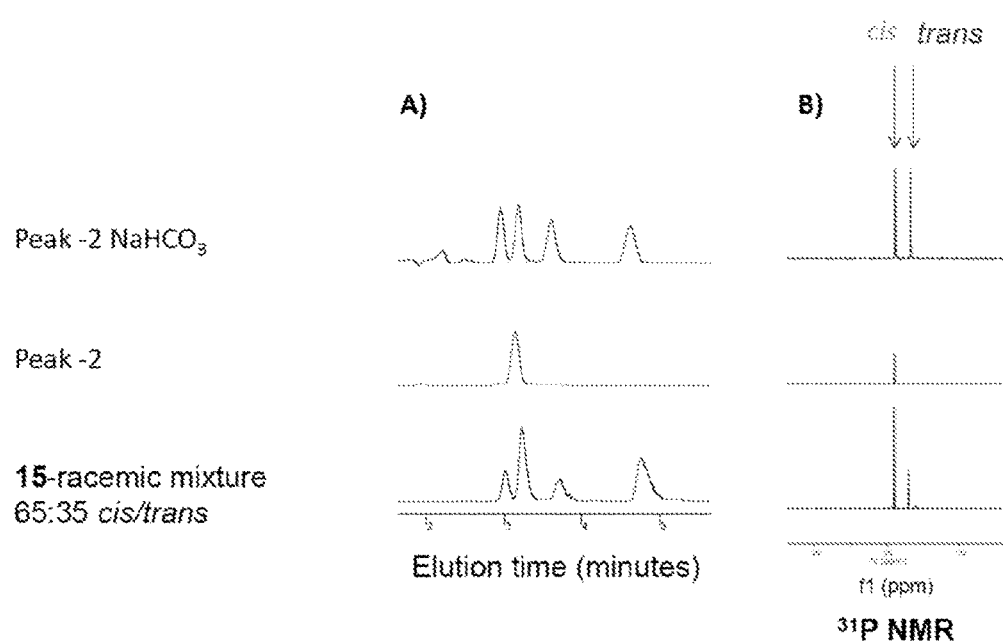

FIGS. 22A & 22B show the loss of enantiopurity upon mild alkaline aqueous treatment. Immediately after chiral chromatography, each enantiomer was washed with saturated NaHCO$_3$ (to neutralize TFA) and extracted with ethyl acetate; the organic phase was dried over MgSO$_4$ and evaporated. Chiral HPLC analysis showed the presence of the initial four distinct peaks, proving chiral instability of this intermediate (top trace in FIG. 22A; the middle trace shows the purified enantiomer peak 2 before racemization, while the bottom trace shows the initial racemic mixture of intermediate 15). Racemization was confirmed by $^{31}$P NMR (FIG. 22B): only one cis-diastereomer is detected in isolated peak 2 (middle trace) while both cis and trans diastereomers are evident after aqueous treatment (top trace). The experiment was repeated with purified peaks 1, 3 and 4, with identical results.

Figure 23:
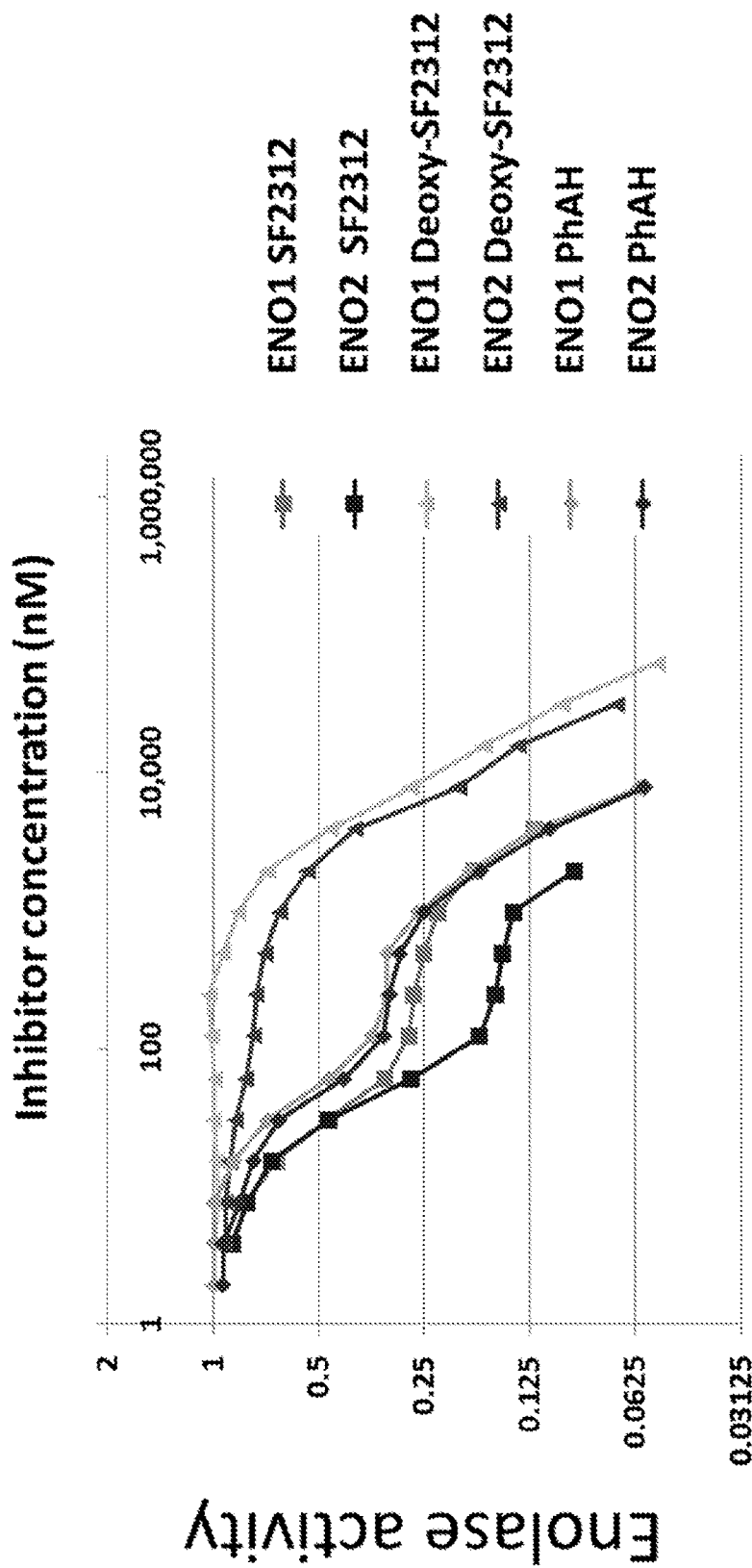

FIG. 23 shows SF2312 is a potent inhibitor of human enolase. Enolase enzymatic activity was measured spectrofluorimetrically in vitro by following the conversion of 2-PGA to PEP. Human ENO1 and ENO2 were overexpressed in the human D423 cell line and lysates thereof were used for enzymatic assays. Inhibitors (PhAH, SF2312 and DeoxySF2312) were incubated with the enzyme prior to addition of 5 mM 2-PGA substrate. Enzymatic activity was normalized to that in the absence of the inhibitor (set to 1, y-axis) and plotted as function of inhibitor concentration (2-fold dilution series, in nM, x-axis). SF2312 was the most potent inhibitor especially against ENO2 (ENO1 inhibition with SF2312, light gray trace with square symbols; ENO2 dark gray trace with black symbols).

Figures 24A, 24B:
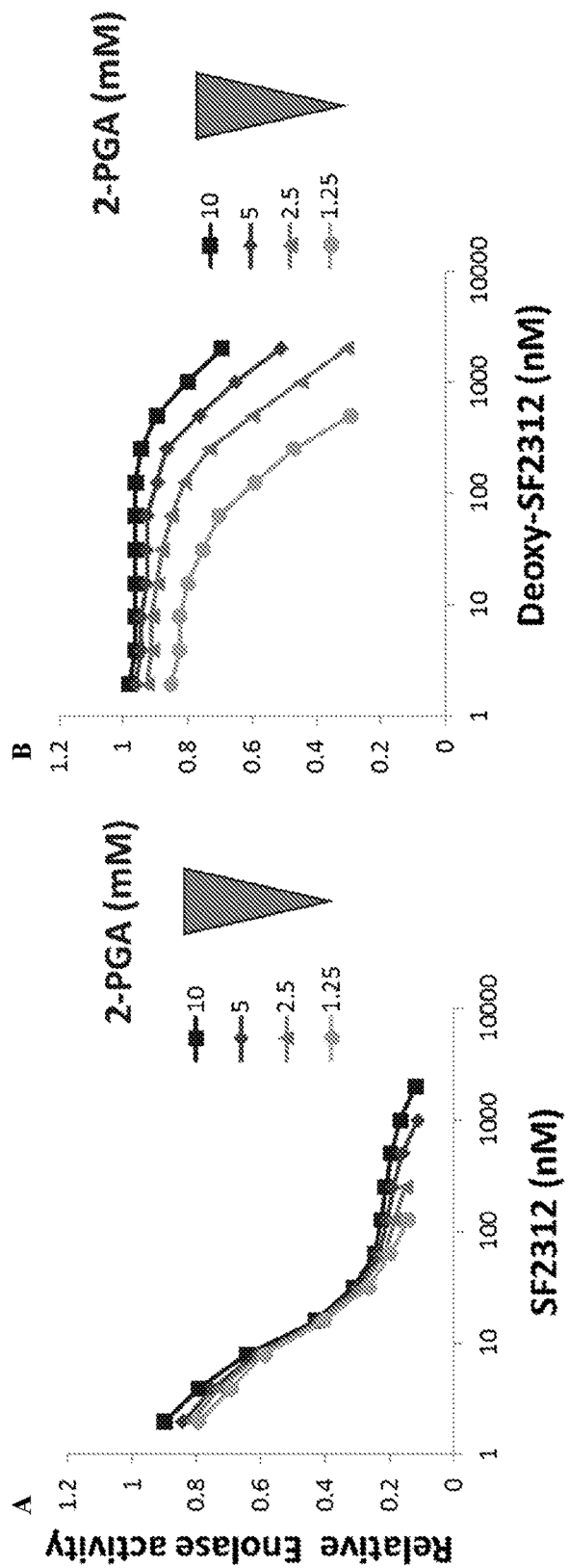

FIGS. 24A & 24B show SF2312 showing mixed competitive and non-competitive kinetics. Enolase activity (lysates of the D423 cell line overexpressing ENO2) was measured as a function of substrate (2-PGA) and inhibitor (SF2312, FIG. 24A, Deoxy-SF2312, FIG. 24B) concentration. SF2312 showed highly unusual mixed substrate-dependence inhibition kinetics. At 50% inhibition (IC$_{50}$) of enolase activity, SF2312 behaved as a classical non-competitive inhibitor, being essentially unaffected by the concentration of substrate (2-PGA). However, at inhibition higher than 75% of initial activity (IC$_{75}$), there was a clear dependence on the concentration of substrate. This mixed inhibition is highly unusual and may be related to the known interactions between the monomers of the enolase dimer, whereby binding of one inhibitor molecule to one dimer, alters the conformation and binding affinity of the other dimer. Deoxy-SF2312 showed typical substrate-competitive kinetics (Qin, et al., 2012).

Figures 25A, 25B:
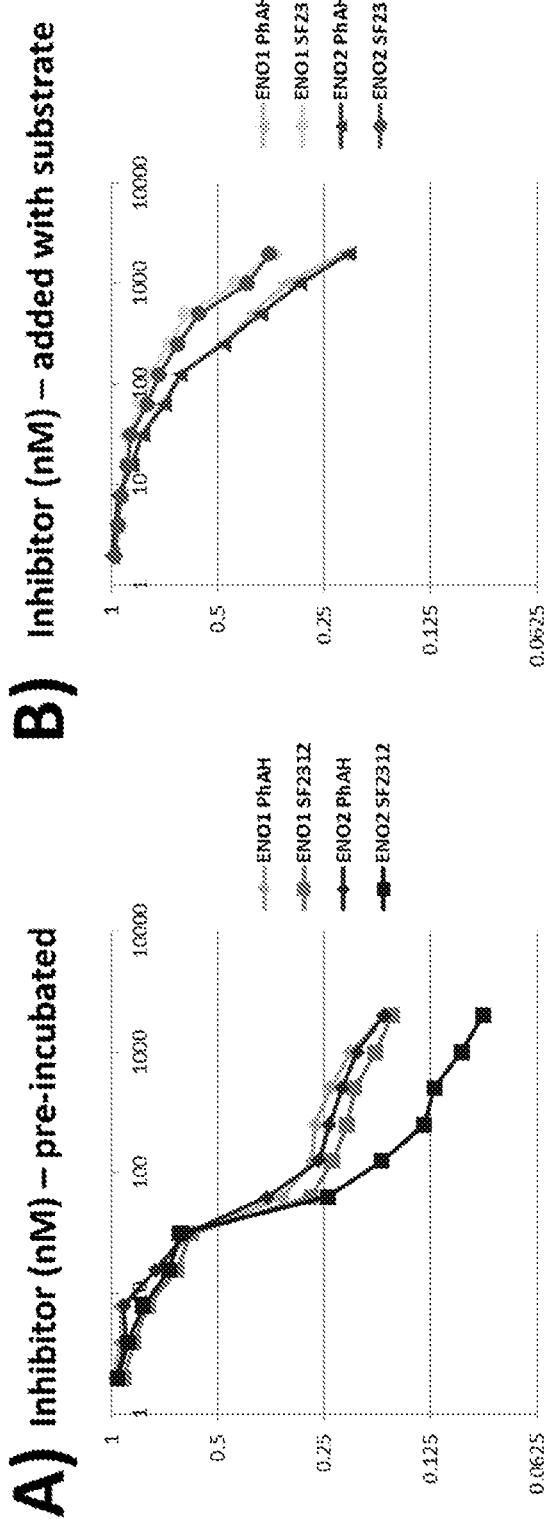

FIGS. 25A & 25B shows SF2312 is a slow binding inhibitor with a lower k$_{off}$ for ENO2 than ENO1. FIG. 25A Pre-incubation of PhAH (diamonds) or SF2312 (squares) with ENO1 (light gray, gray) or ENO2 (dark gray, black) as described in FIG. 23 and FIG. 24 before the addition of the substrate 2-PGA resulted in profound inhibition of enzymatic activity (IC~20 nM); inhibition of ENO2 with SF2312 was more profound and more durable for than ENO1 (IC$_{50}$ for SF2312 is 10-fold lower for ENO2 than ENO1) while PhAH caused more or less equal inhibition of ENO1 and ENO2. FIG. 25B Addition of SF2312/PhAH prior to 2-PGA resulted in much weaker inhibition than if the inhibitors were pre-incubated before addition of substrate; this behavior was described previously for PhAH inhibition of yeast enolase, i.e. PhAH acts as a "slow" k$_{on}$ inhibitor (Anderson, et al., 1984). SF2312 was less potent than PhAH when assayed under these conditions, indicating that it shows an even slower k$_{on}$ than PhAH. Since SF2312 is more potent than PhAH when pre-incubated prior to addition of substrate, this indicates that SF2312 has a much slower k$_{off}$ than PhAH and that the increased inhibitory potency of SF2312 against ENO2 over ENO1 is due to differences in k$_{off}$ rather than k$_{on}$. SF2312, like PhAH, binds the di-Mg form of the enzyme. ENO2 has higher affinity for the second magnesium ion (Mg$_b$) and overall much greater stability than ENO1 (Marangos, et al., 1978; Marangos and Schmechel, 1980; Marangos, et al., 1979). Since the Mg$_b$ must first dissociate before the inhibitor can come out of the active site, without wishing to be bound by any theory, it is believed that the higher affinity of ENO2 for Mg$_b$ may explain the slower k$_{off}$ for SF2312 in ENO2 versus ENO1.

Figures 26A, 26B:
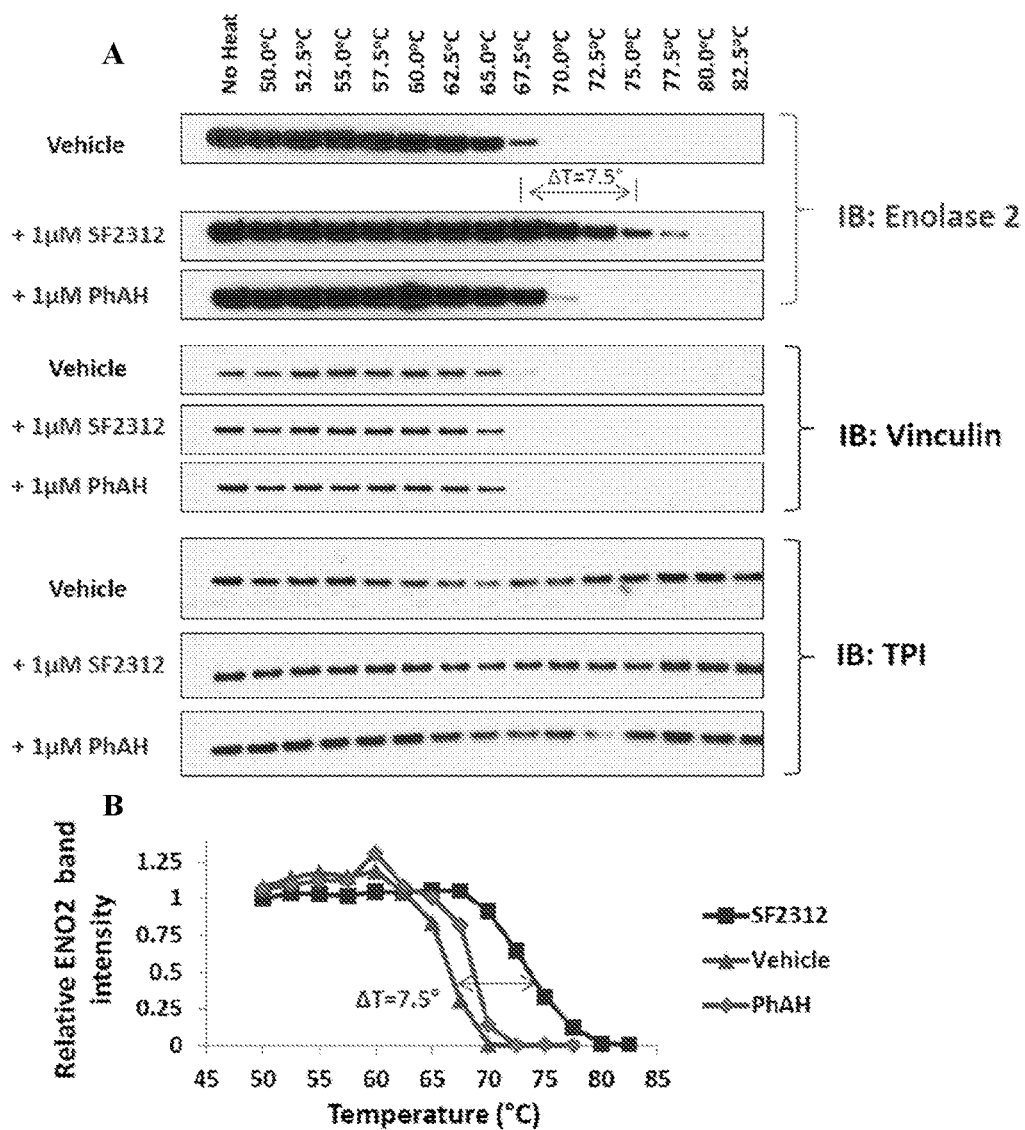

FIGS. 26A & 26B show SF2312 stabilizes enolase 2 against thermal denaturation. Lysates of D423 overexpressing ENO2 cells were incubated with vehicle, PhAH or SF2312. Thermal denaturation was performed with a temperature gradient PCR machine, followed by centrifugation and immunoblotting of the supernatant. Denatured proteins precipitate and are lost from the supernatant. Immunoblotting of the supernatant against ENO2 showed that the addition of 1 µM SF2312 shifted the thermal denaturation curve by 7.5° C. (arrows), while PhAH shifted it by a much more modest 2.5° C. Thermal denaturation of vinculin and triosphosphate isomerase (TPI) was unaffected by either inhibitors. The bottom panel shows the quantification of band intensity (y-axis) versus temperature (x-axis), with the trace in triangles being vehicle, diamonds being PhAH and squares being SF2312 treatment groups.

Figures 27A, 27B:
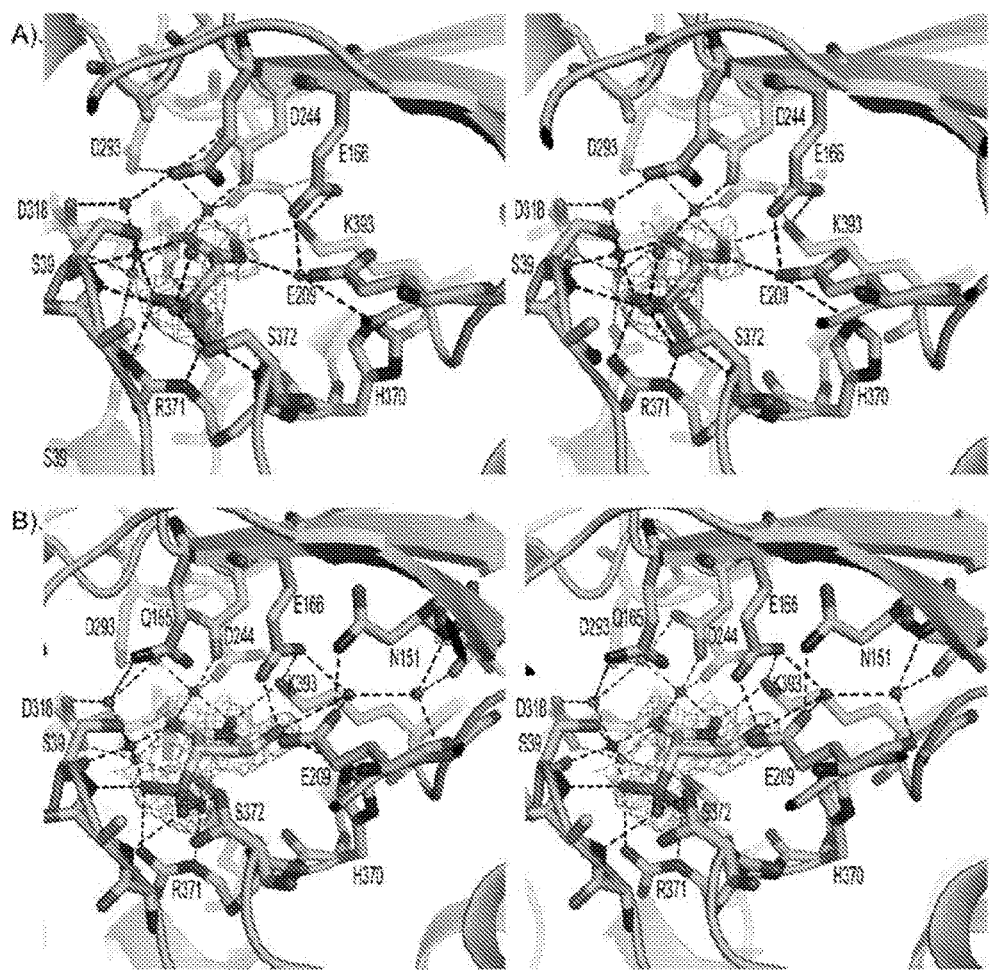

FIGS. 27A & 27B show PhAH and SF2312 interact with ENO2 through a complex network of electrostatic, metal coordination and hydrogen bond interactions. Stereo presentation of PhAH (FIG. 27A) and SF2312 (FIG. 27B) binding in the ENO2 active site. The protein backbone is shown using the cartoon depiction with key amino acids for magnesium or ligand binding highlighted using the stick representation. Magnesium ions and water molecules are shown as spheres respectively. Hydrogen bonds and metal coordination bonds are both represented by black dashed lines. The 2Fo-Fc unbiased omit electron density map for each ligand, cotoured at 1.50, is shown as a grey mesh around the ligand. Coordinates were deposited in PDB (ENO2:PhAH, 4ZA0; ENO2:SF2312, 4ZCW).

Figures 28A, 28B:
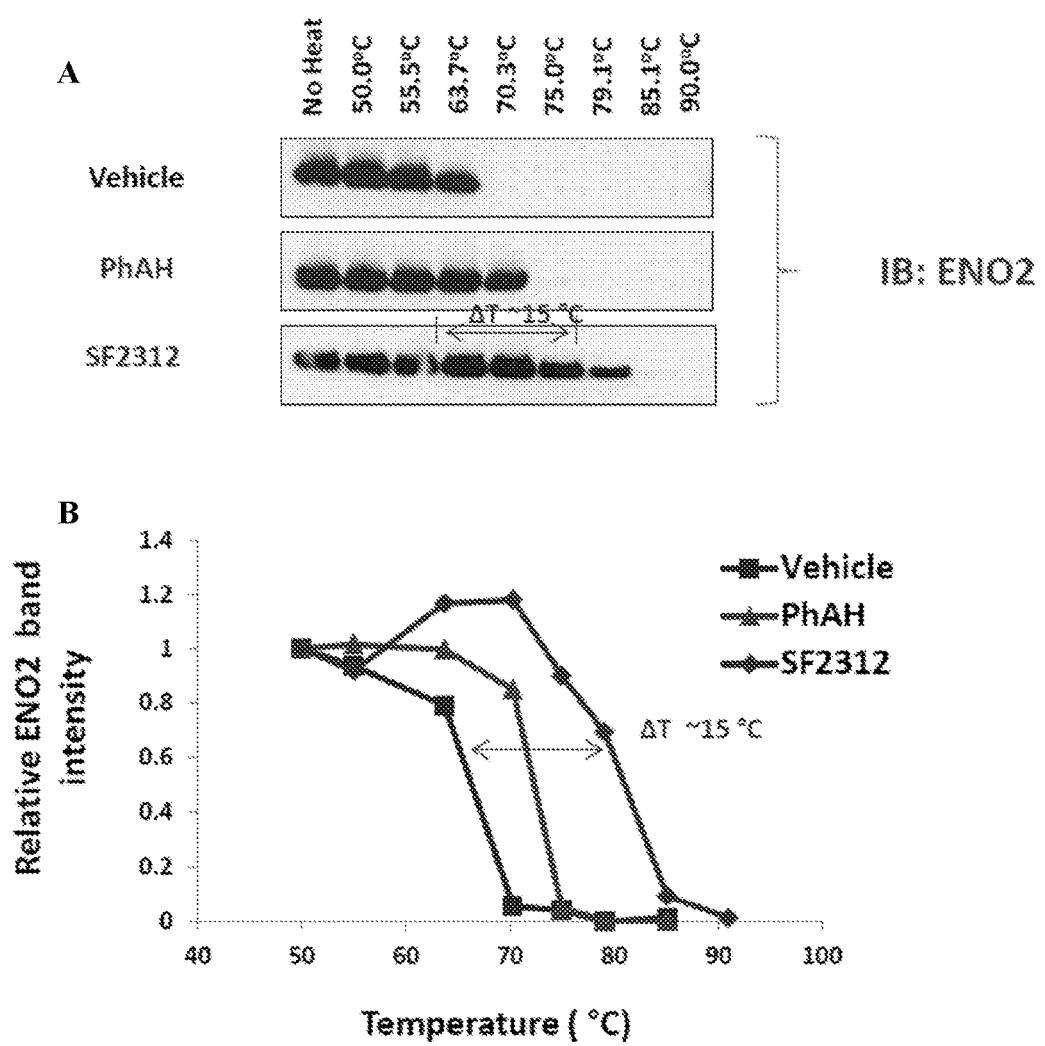
Figures 30A, 30B, 30C, 30D, 30E, 30F:
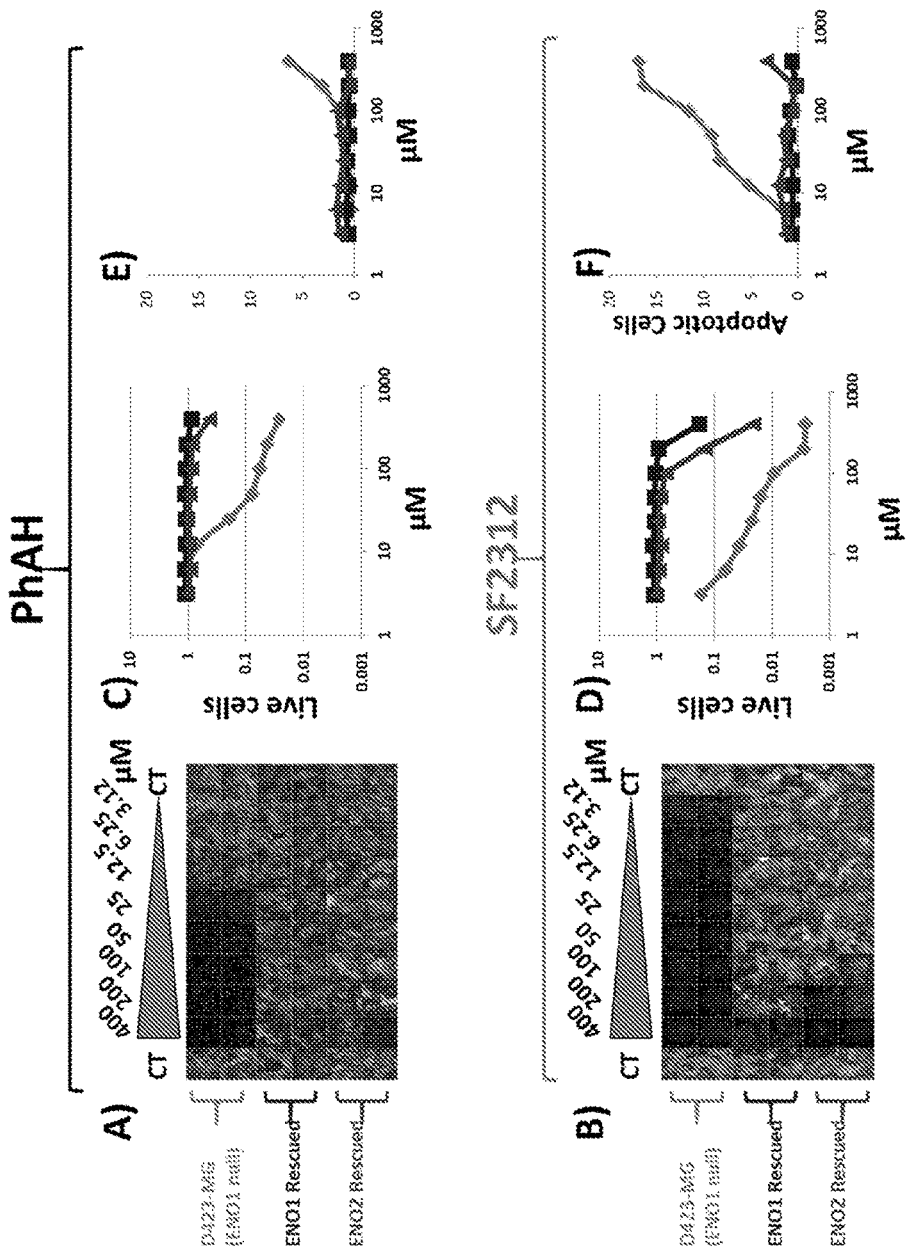

FIGS. 28A & 28B show SF2312 stabilizes recombinant human Enolase 2 against thermal denaturation. Purified *E. coli* expressed ENO2 was incubated with 10 µM SF2312, PhAH or vehicle and subjected to thermal denaturation with the supernatant separated as described in the Examples. The supernatant was immunoblotted against ENO2 (FIG. 28A) and the band intensity plotted as function of temperature (FIG. 28B). SF2312 treatment shifted the thermal denaturation curve by ~15° C., considerably more than that observed with the same concentration of PhAH.

FIG. 29 shows structures of phosphonates with similarity to SF2312 but lacking enolase inhibitory activity. Fosmidomycin, fosfomycin and foscanet where tested for enolase inhibitory activity in lysates of D423 ENO1 and ENO2 expressing cells as described in FIGS. 23 & 24. Despite similarity to SF2312 and deoxy-SF2312, no inhibitory activity was observed as high as 10 mM.

FIGS. 30A-30F show SF2312 is more potent than PhAH against ENO1-deleted glioma cells. SF2312 was compared head-to-head with PhAH for its effect on cell proliferation (total cell number, Hoechst 33342) and apoptosis. D423 ENO1-deleted (light gray), D423 isogenic controls expressing ENO1 (dark gray) or overexpressing ENO2 (light gray) were treated with varying concentrations of inhibitors as indicated in µM, with the first and the last column servicing as vehicle controls. After 2-weeks of treatment, plates were assayed for cell number (total cell number, Hoechst 33342) and apoptosis (YO-PRO®-1 positive cells) using the Operetta® High Content Imaging System. Panels to the left show 96-well plates treated with SF2312 (FIG. 30A) and PhAH (FIG. 30B) stained with Hoechst; the extent of light color indicates cell number. Quantified results for cell number and apoptosis as a function of inhibitor concentration are presented in panels FIGS. 30C & 30D and FIGS. 30E & 30F respectively; each data point represents average of two replicates, expressed as a function of vehicle control (N=4). SF2312 proved considerably more toxic to ENO1-deleted cells than PhAH, especially with regards to its ability to induce apoptosis.

Figures 31A, 31B, 31C, 31D:
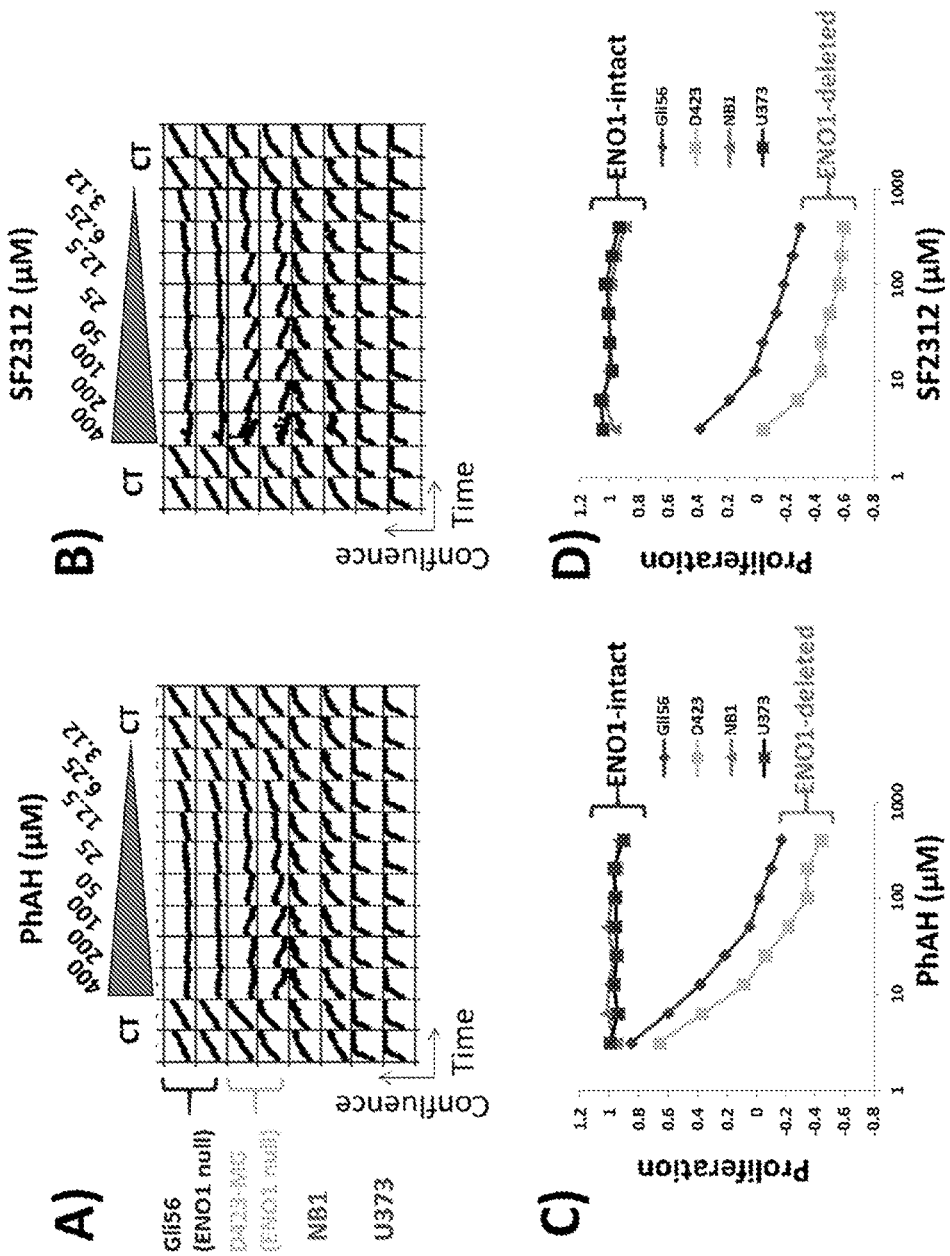

FIGS. 31A-31D show SF2312 selectively inhibits the proliferation of ENO1-deleted glioma cells. Gli56 and D423 ENO1 deleted and non-deleted (U373, NB1) cell lines were treated with varying doses of SF2312 (FIG. 31B) or PhAH (FIG. 31A) for a total of ten days. Cell proliferation was measured using the Incucyte with growth curves shown in dark gray traces (y-axis, cell confluence, x-axis, time). Steep rising curves indicate increases in confluence and proliferation. Flat curves indicate steady confluence and inhibited proliferation, while declining curves indicate cell death. In FIG. 31C (PhAH) and FIG. 31D, for each cell line, proliferation was quantified (N=2 replicates) and expressed relative to vehicle controls (N=4) as a function of inhibitor concentration. While both PhAH and SF2312 showed selective inhibition of proliferation of ENO1-deleted cell lines, SF2312 was more potent than PhAH.

Figure 41:
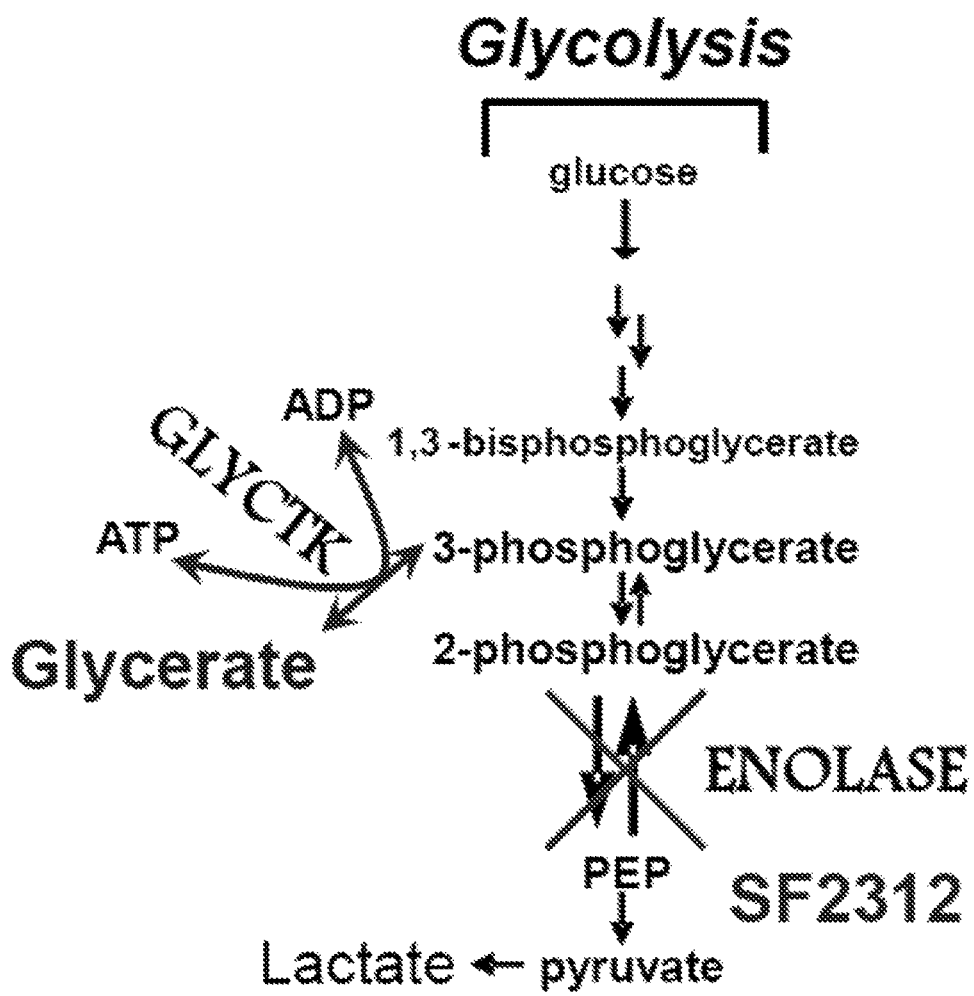

FIGS. 32A-32D shows SF2312 selectively inhibits glycolysis in ENO1-deleted glioma cells. D423 ENO1-deleted and isogenic rescued cells were supplemented with $^{13}C$-1 labeled glucose and treated with 10 µM of SF2312 or PhAH for 72 hours. Conditioned media was extracted with cold 80% methanol and scanned by $^{13}C$ NMR in proton decoupled mode. Peaks at ~97 and 93 ppm correspond to the isomers of glucose, while the peaks at ~20 ppm corresponds to the C3 of lactate, and at 64 ppm corresponds to the C3 of glycerate (FIG. 41). Peaks were quantified by integration (y-axis, integral units). Bars represent individual measurements of independently treated, extracted and measured samples. Statistical significant differences by unpaired, two-tailed, t-test with Bonferroni correction are indicated; for the statistically significant comparisons, the variance was similar. Treatment with SF2312 resulted in a dramatic reduction in $^{13}C3$-lactate, with a concomitant increase in $^{13}C3$-glycerate production, selectively in D423 ENO1-deleted cells and not isogenic rescued cells. PhAH treatment resulted in similar effects, but of a lesser magnitude. The experiment was conducted only once, but the conclusions were confirmed by an independent experiment using $^{13}C$-uniformly labeled glucose (FIG. 34)

Figure 33:
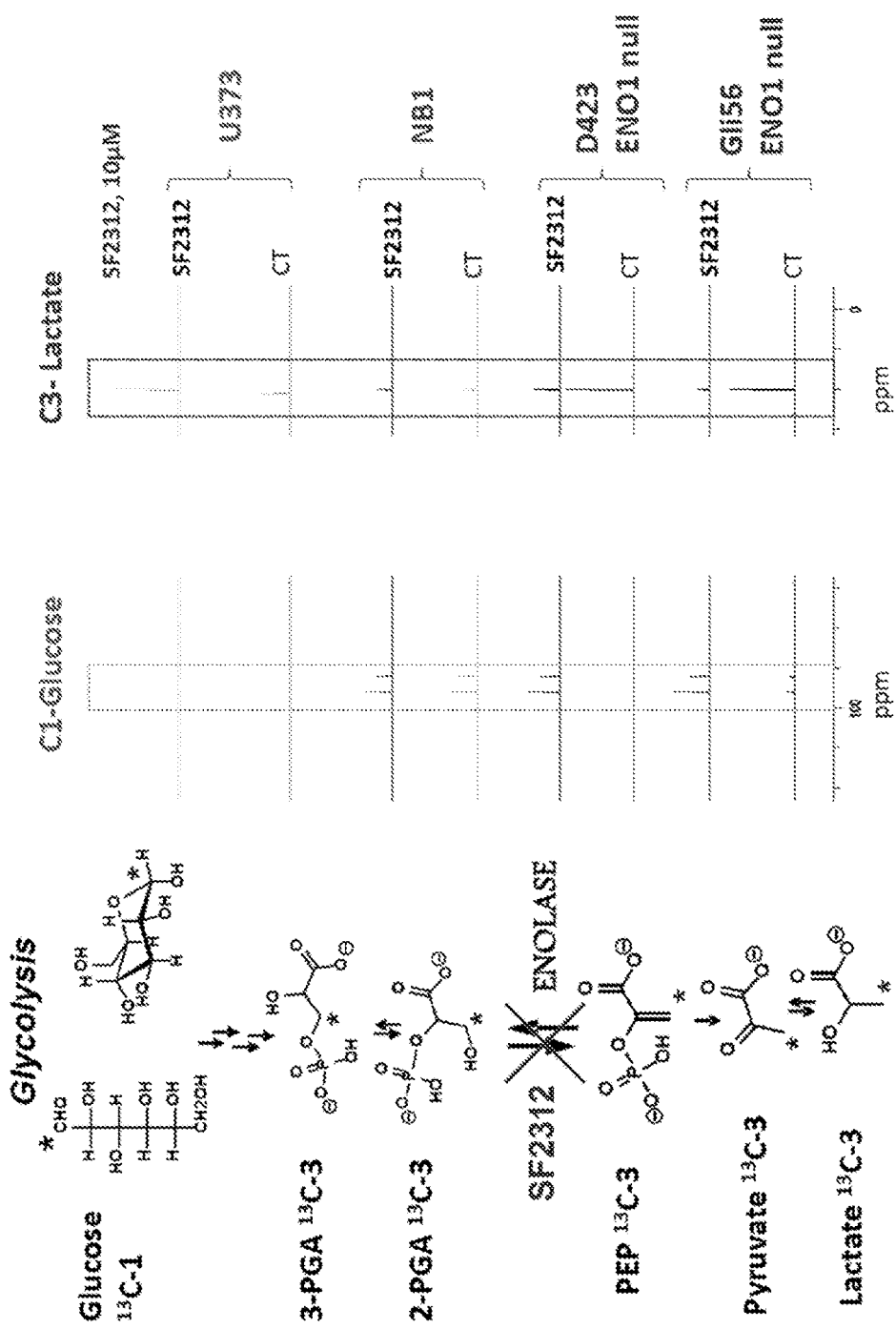

FIG. 33 shows SF2312 selectively inhibits glycolysis in ENO1-deleted glioma cells. Gli56 and D423 ENO1-deleted and non-deleted (U373, NB1) cells were supplemented with $^{13}C$-1 labeled glucose (indicated by asterisk*) treated with 10 µM of SF2312 for four days. Conditioned media was harvested after four days and extracted and scanned by $^{13}C$ NMR in proton decoupled mode. Large peaks at ~97 and 93 ppm correspond to the isomers of glucose and at ~20 ppm to the C3 of lactate. In the absence of treatment, glucose peaks disappeared with concomitant appearance of lactate peaks. Treatment with SF2312 inhibited the disappearance of glucose and the appearance of lactate peaks, but only in the D423 and Gli56 ENO1 deleted cells, indicating selective inhibition of glycolysis in these cell lines.

Figure 34A:
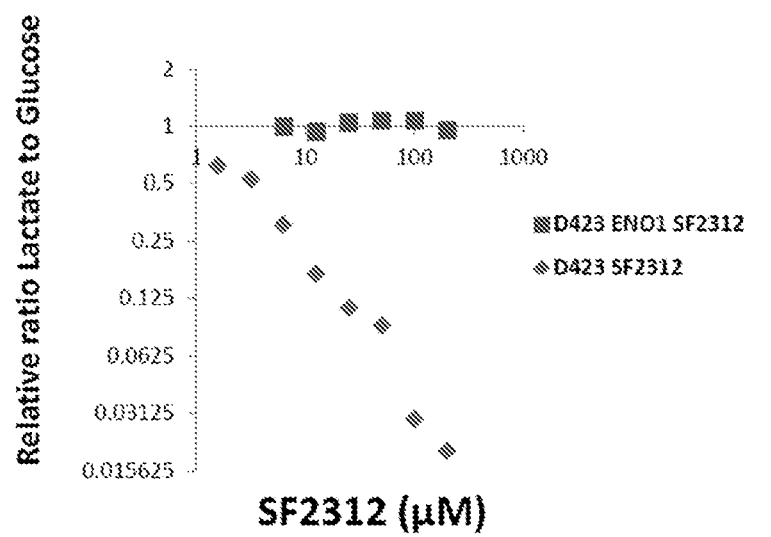
Figure 34B:
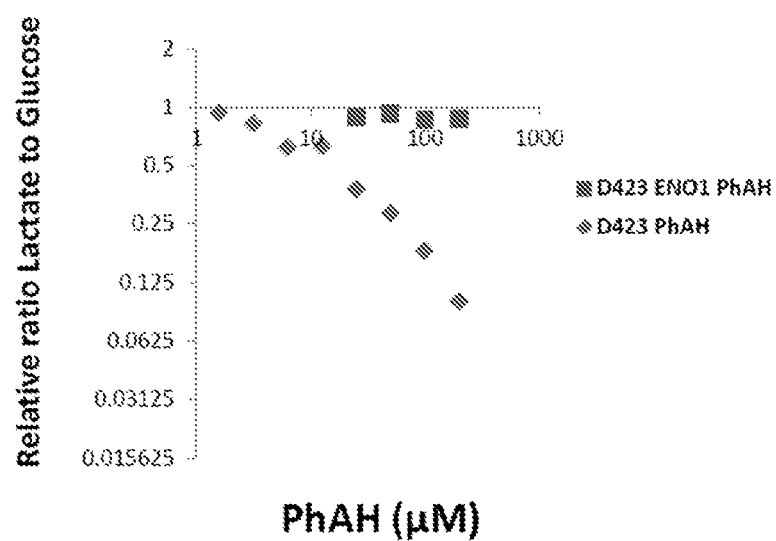
Figure 34C:
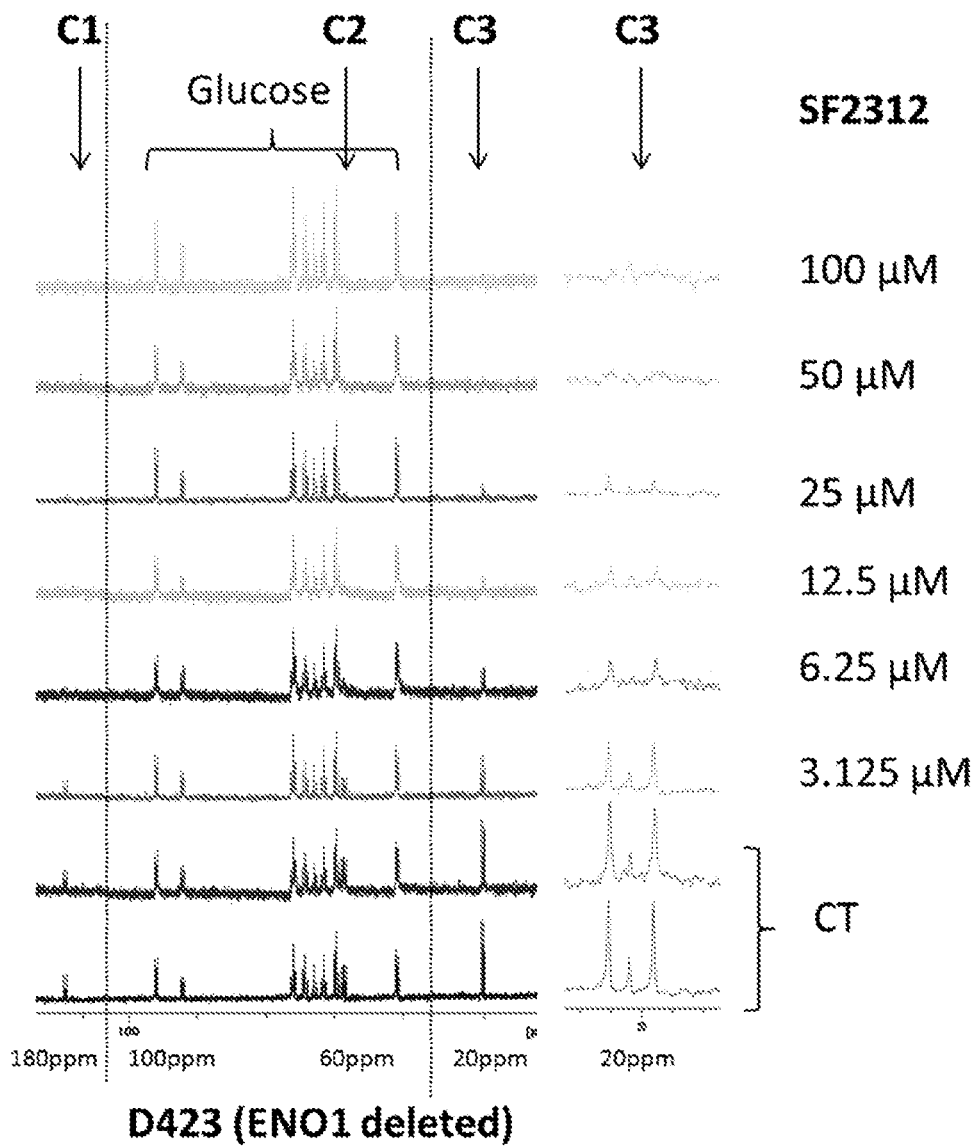

FIGS. 34A-34C show SF2312 selectively inhibits conversion of uniformly labeled $^{13}C$-glucose to $^{13}C$-lactate in ENO1-deleted glioma cells. D423 ENO1-deleted (diamonds) and D423 ectopically rescued cells (D423 ENO1; squares) were treated with varying doses of SF2312 and PhAH in media containing 10 mM $^{13}C$-uniformly labeled glucose. Forty-eight hours later, media was collected and $^{13}C$-NMR scanned. The right panel shows raw traces of media from D423 ENO1-deleted cells treated with different concentrations of SF2312. The peaks corresponding to glucose (from 100 to 50 ppm, FIG. 34C) are bracketed, while the peaks corresponding to the C1, C2, and C3 atoms of lactate are pointed out with black arrows. A zoom in of the C3 lactate peak is shown. The ratio of the integral of lactate to the integral of glucose was determined, normalized with respect to vehicle treated control, and plotted as a function of PhAH or SF2312 concentration (FIGS. 34A & 34B). Concentrations of SF2312 as low as 6.25 µM were sufficient to decrease the ratio of $^{13}C$ Lactate/$^{13}C$ glucose by 70% whilst 50 µM of PhAH were necessary for a similar level of inhibition in ENO1-deleted glioma cells. In contrast, even at 200 µM, neither PhAH nor SF2312 decreased lactate/glucose in D423 ENO1-rescued glioma cells.

Figures 35A, 35B, 35C, 35D, 35E, 35F:
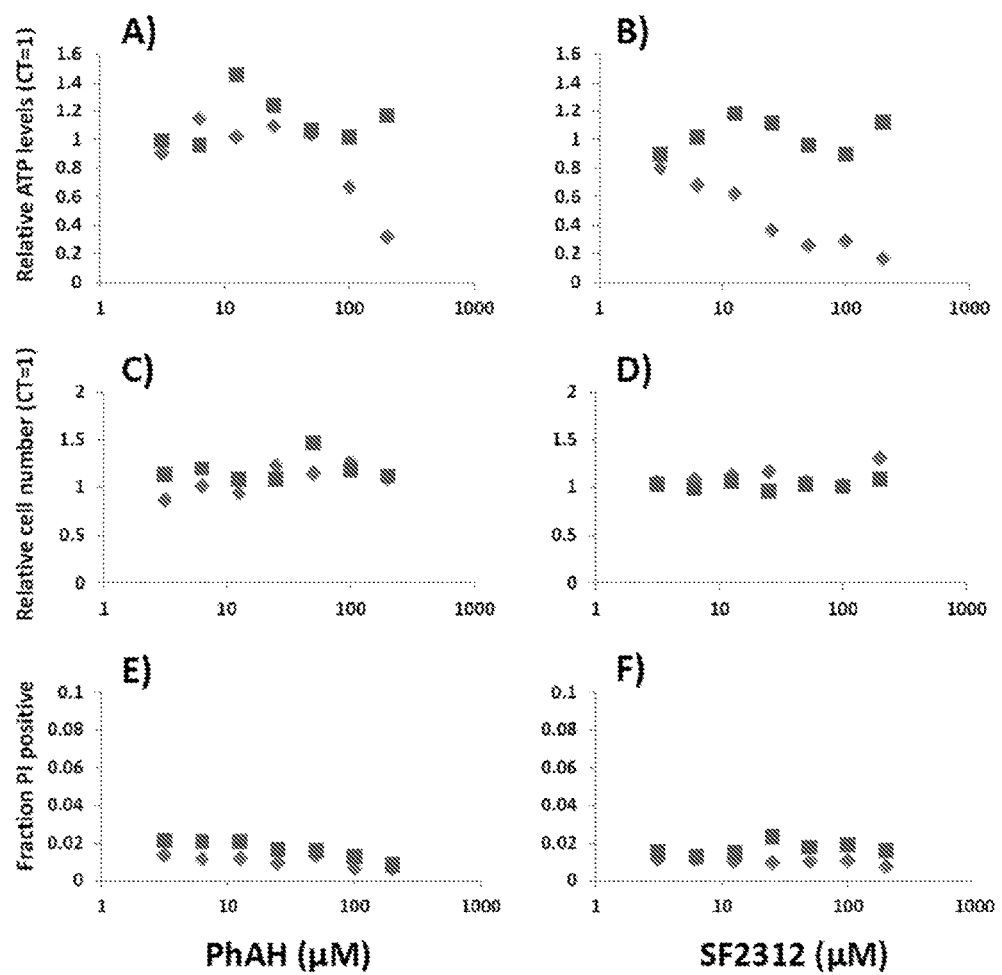
Figures 36A, 36B, 36C, 36D, 36E, 36F, 36G, 36H:
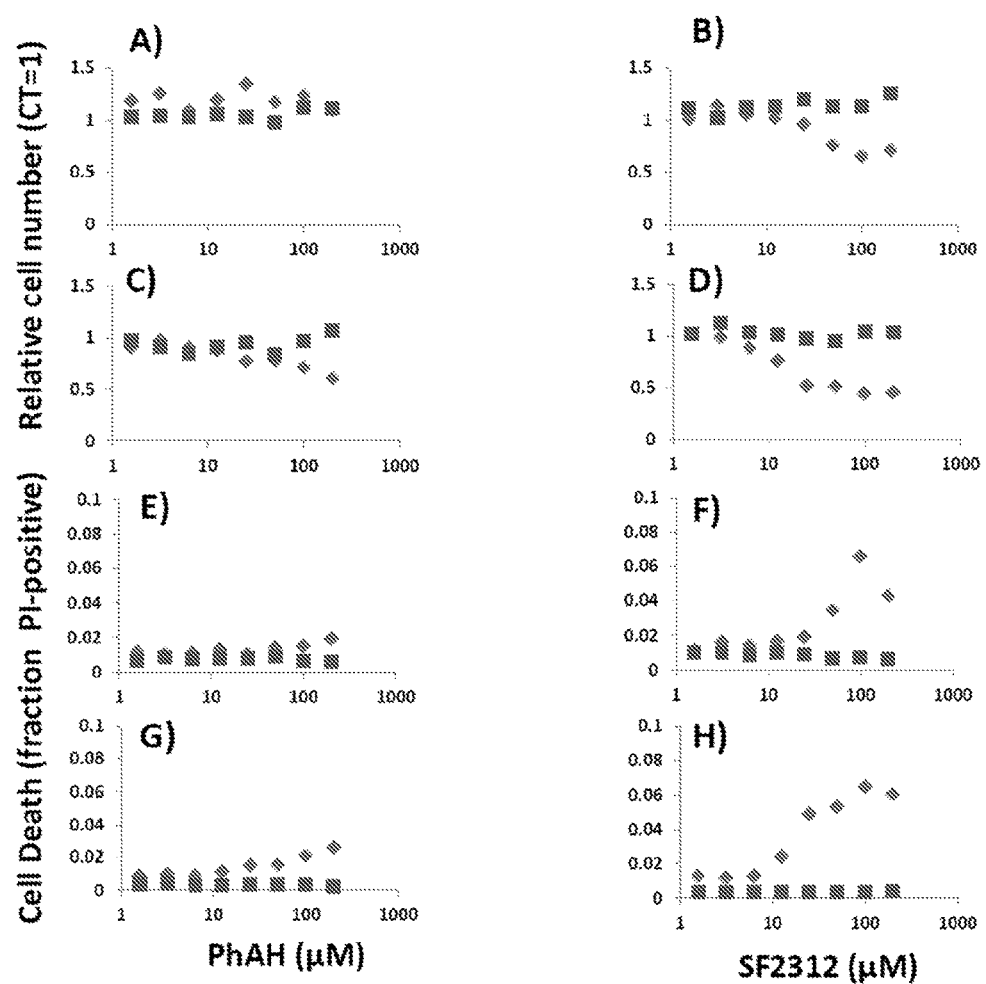

FIGS. 35A-35F shows SF2312 selectively depletes ATP in ENO1-deleted glioma cells. D423 ENO1-deleted (diamonds) and isogenic ENO1-rescued control (squares) glioma cells were treated for 8 hours with PhAH (FIGS. 35A, 35C, & 35F) or SF2312 (FIGS. 35B, 35D, & 35F) at concentrations indicated in the x-axis and the effects on ATP (FIGS. 35A & 35B), cell number (FIGS. 35C & 35D) and cell death (FIGS. 35E & 35F) were determined. ATP was measured using the Cell-Titer Glow assay. Each data point represents the average of two replicated expressed as function of vehicle treated control. Cell number as measured nuclei measured via Hoechst 33342 using the Operetta®. Each datapoint represents the average of two replicate wells with nine fields quantified per well and expressed relative to untreated controls (FIGS. 35C & 35D). The extent of cell death (FIGS. 35E & 35F) was expressed as the fraction of propidium iodide positive nuclei. Each data point represents the average of two replicates of nine observation fields each. At 8 hours of treatment, SF2312 treatment led to a dose dependent depletion of ATP in ENO1-deleted but not rescued glioma cells.

FIGS. 36A-36H shows effect of SF2312 and PhAH on cell death and cell number in ENO1-deleted and isogenic rescued glioma cells. D423 ENO1-deleted (diamonds) and isogenic ENO1-rescued control (squares) glioma cells were treated for 24 hours (FIGS. 36A, 36B, 36E, & 36F) or 48 hours (FIGS. 36C, 36D, 36G, & 36H) with PhAH (FIGS. 36A, 36C, 36E, & 36G) or SF2312 (FIGS. 36B, 36D, 36F, & 36H) at concentrations indicated in the x-axis and the effects on cell number (FIGS. 36A, 36B, 36C, & 36D) and cell death (FIGS. 36E, 36F, 36G, & 36H) were determined. Cell number as measured nuclei measured via Hoechst 33342 using the Operetta®. Each datapoint represents the average of two replicate wells with nine fields quantified per well and expressed relative to untreated controls (FIGS. 36A, 36B, 36C, & 36D). The extent of cell death (FIGS. 36E, 36F, 36G, & 36H) was expressed as the fraction of propidium iodide positive nuclei. Each data point represents the average of two replicates of nine observation fields each. SF2312 treatment led to a time and dose dependent induction of cell death in ENO1-deleted but not rescued cells. Cell death in response to PhAH was considerably weaker.

Figures 37A, 37B:
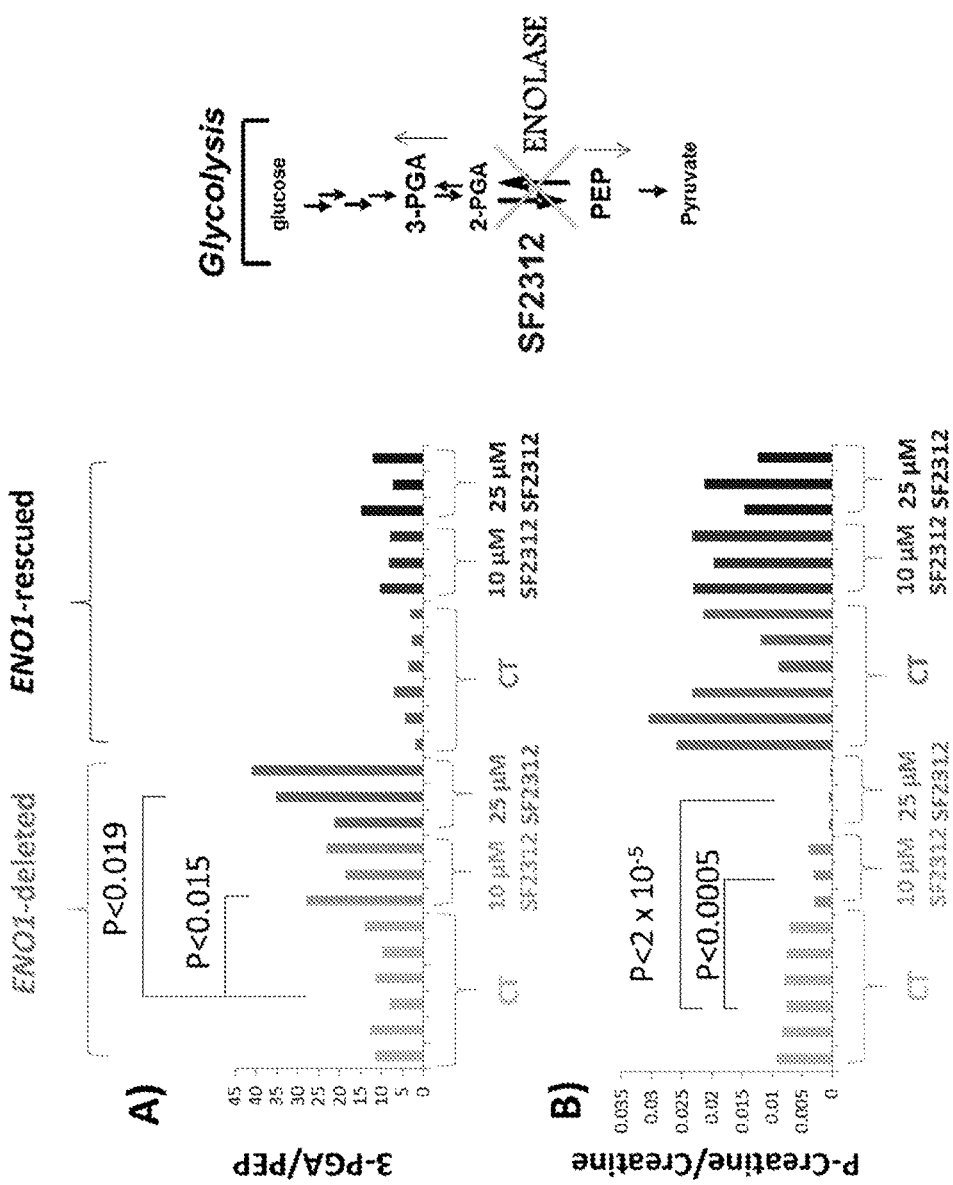

FIGS. 37A & 37B show SF2312 treatment leads to accumulation of metabolites upstream of the enolase reaction and depletion of high energy phosphate. D423 ENO1-deleted and isogenic control glioma cells were treated with vehicle, 10 µM and 25 µM SF2312 for 72 hours. Polar metabolites were extracted and quantified by mass spec as described in the examples. Bars represent individual measurements of independently treated, extracted and measured cells. Light gray bars, D423 ENO1-deleted glioma cells CT (N=6); light medium gray bars, ENO1-deleted cells treated with 10 µM SF2312 (N=3); Medium gray bars, ENO1-deleted with 25 µM SF2312 (N=3); dark gray bars, D423 ENO1-rescued cells CT (N=6); light gray bars, ENO1-rescued treated with 10 µM SF2312 (N=3); gray bars, ENO1-rescued with 25 µM SF2312 treated (N=3), dark gray. Statistically significant comparisons, by unpaired, 2-tailed, t-test with Bonferroni correction are indicated; for the significant comparisons, the variance was similar. In ENO1-deleted glioma cells, treatment with SF2312 led to an increase in the ratio of 3-PGA to PEP (FIG. 37A), metabolites immediately upstream and downstream of the enolase reaction, consistent with inhibition of enolase. A similar trend emerged in ENO1-rescued cells but did not reach statistical significance (P<0.06). SF2312 treatment led to a selective depletion of phospho-creatine in ENO1-deleted but not rescued cells (FIG. 37B).

Figure 38:
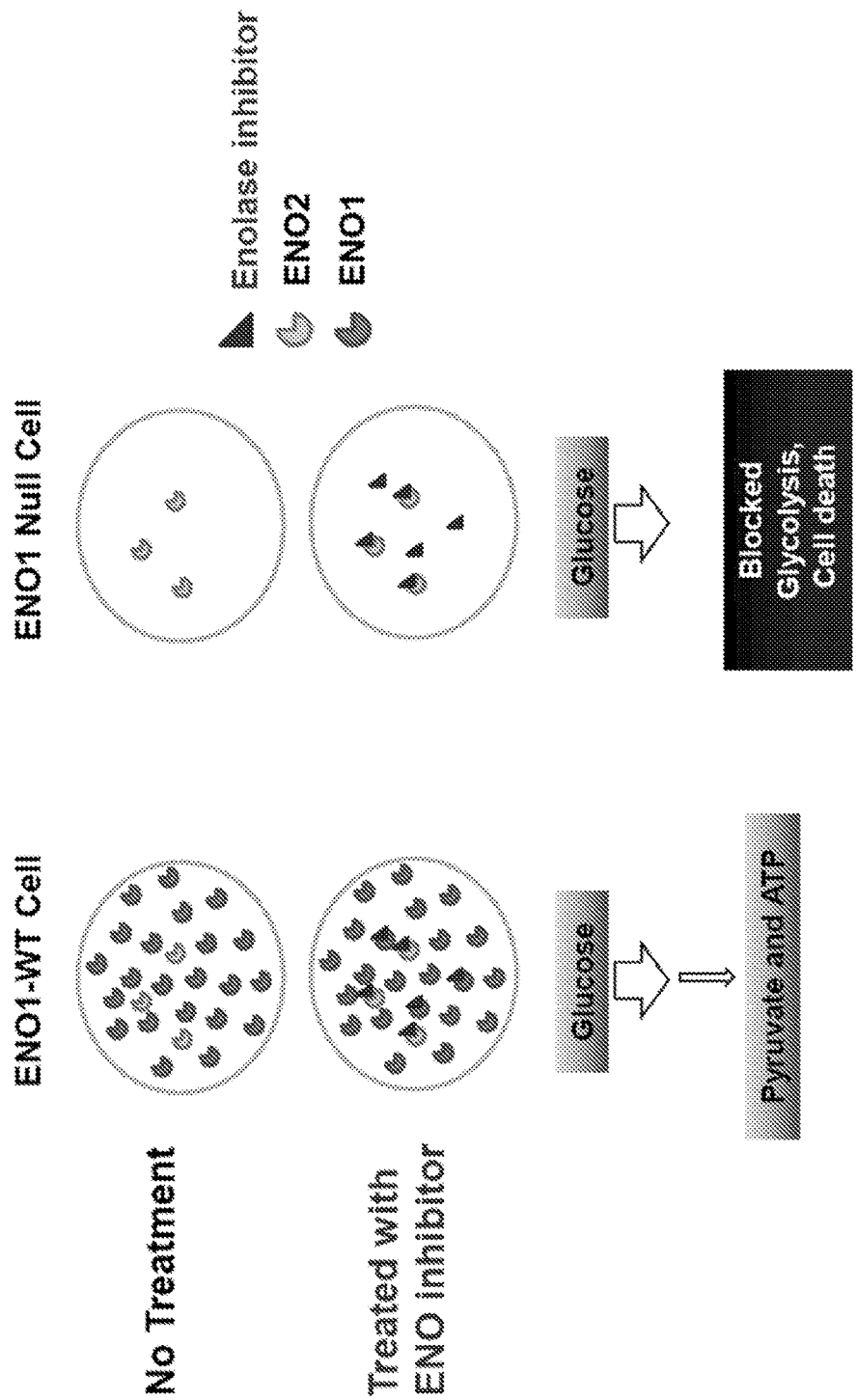

FIG. 38 shows the differential effect of ENO1 wild type and ENO1 null cells when treated with ENO inhibitor on cell survival as a consequence of ENO1 and ENO2 inhibition.

Figure 39A:
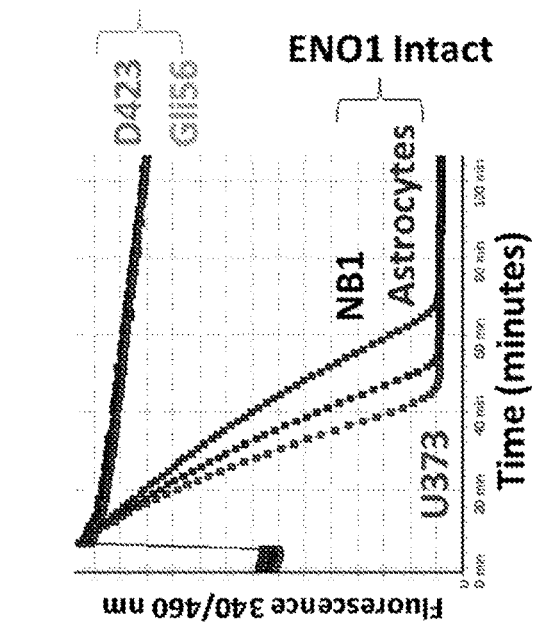
Figure 39B:
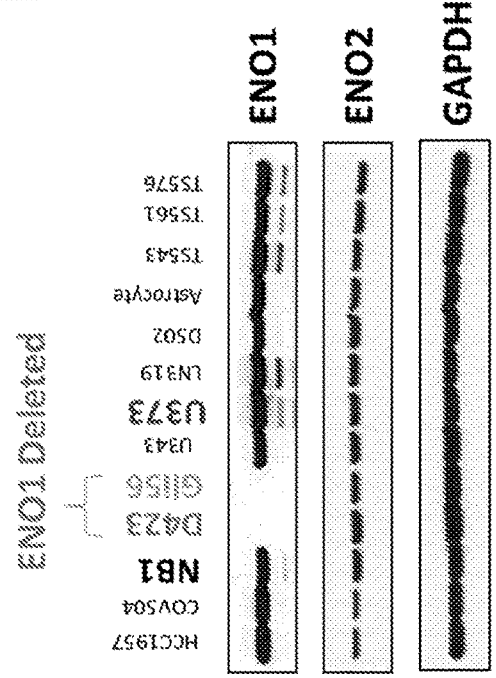

FIGS. 39A & 39B show ENO1-deleted glioma cells have decreased enolase activity. D423 and Gli56 glioma cells carry 1p36 homozygous deletions spanning ENO1 (Muller, et al., 2012). Absence of ENO1 expression in D423 and Gli56 cells was verified by western blot (FIG. 39A); despite complete absence of ENO1, levels of ENO2 remained similar to the other cell lines. As a result, D423 and Gli56 ENO1-deleted cells are profoundly deficient in enolase activity as compared to ENO1 intact cells (FIG. 39B). Native lysates from D423 (light gray) and Gli56 (light gray) ENO1-deleted and ENO1-intact U373 (dark gray) and NB1 (dark gray) glioma cells, as well as normal human astrocytes (dark gray), were equalized for protein and enolase activity was measured using the NADH-linked assay (y-axis, measured fluorescently 340 nm excitation/460 nm emission; see examples). The slope of each trace reflects the level of enolase activity; ENO1-intact NB1, U373 and astrocytes have slopes ~10-steeper than ENO1-deleted D423 and Gli56, confirming that the latter are profoundly deficient in enolase activity.

Figures 40A, 40B:
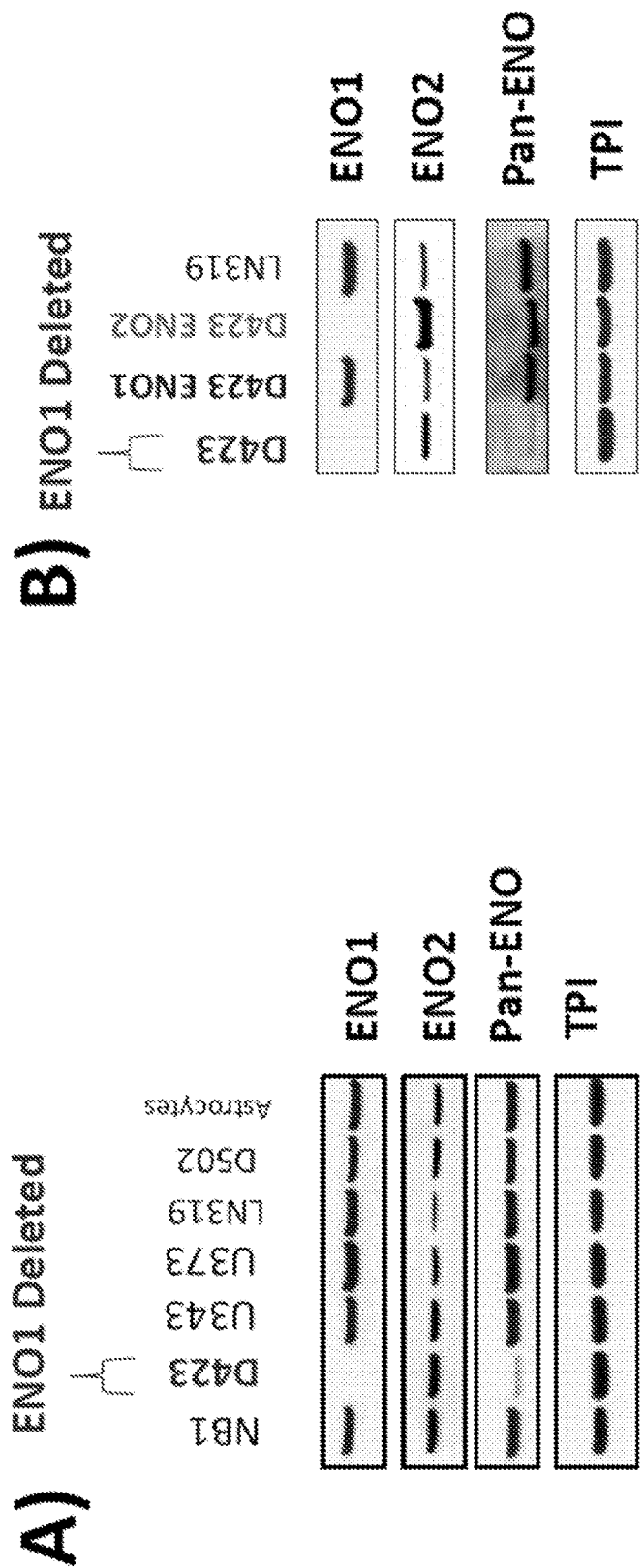

FIGS. 40A & 40B show expression of Enolase in ENO1-deleted, ENO1-rescued and ENO2-rescued glioma cells. The expression of ENO1, ENO2 and total enolase (Pan-ENO) was determined by immunoblotting in a panel of glioma cell lines (FIG. 40A) and in D423 ENO1-deleted, rescued by re-expression of ENO1 (D423 ENO1, dark gray) or overexpression of ENO2 (D423 ENO2, light gray) glioma cells with reference to the ENO1-intact LN319 glioma line (FIG. 40B). TPI was used as a loading control. ENO1 was undetectable in the D423 ENO1-deleted cell line (FIG. 40A), while ENO2 expression was similar to the other cell lines in the panel. Total expression of enolase, as determined by the pan-ENO antibody, was reduced in D423 ENO1-deleted cells. Ectopic expression of ENO1 (D423 ENO1, FIG. 40B) or overexpression of ENO2 (D423 ENO2), restored total enolase expression (Pan-ENO, FIG. 40B) to levels similar to that in the ENO1-intact LN319 glioma cell line.

FIG. 41 shows SF2312 treatment leads to a build-up of intermediates upstream of enolase. ENO1-intact (U373, NB1) and ENO1-deleted (D423, Gli56) glioma cells were grown in $^{13}$C-1 glucose media and treated with 10 µM SF2312. Media was extracted and scanned by proton-decoupled $^{13}$C NMR. In ENO1-deleted but not in ENO1-intact cell lines, SF2312 treatment led to the appearance of a distinct peak at 64 ppm. This peak is consistent with secretion of glycerate into the media, which may form 3-phosphoglycerate by the action of glycerate kinase (GLYCTK) or by spontaneous hydrolysis as a result of accumulation of substrates (phosphoglycerate) upstream of enolase.

Figures 42A, 42B:
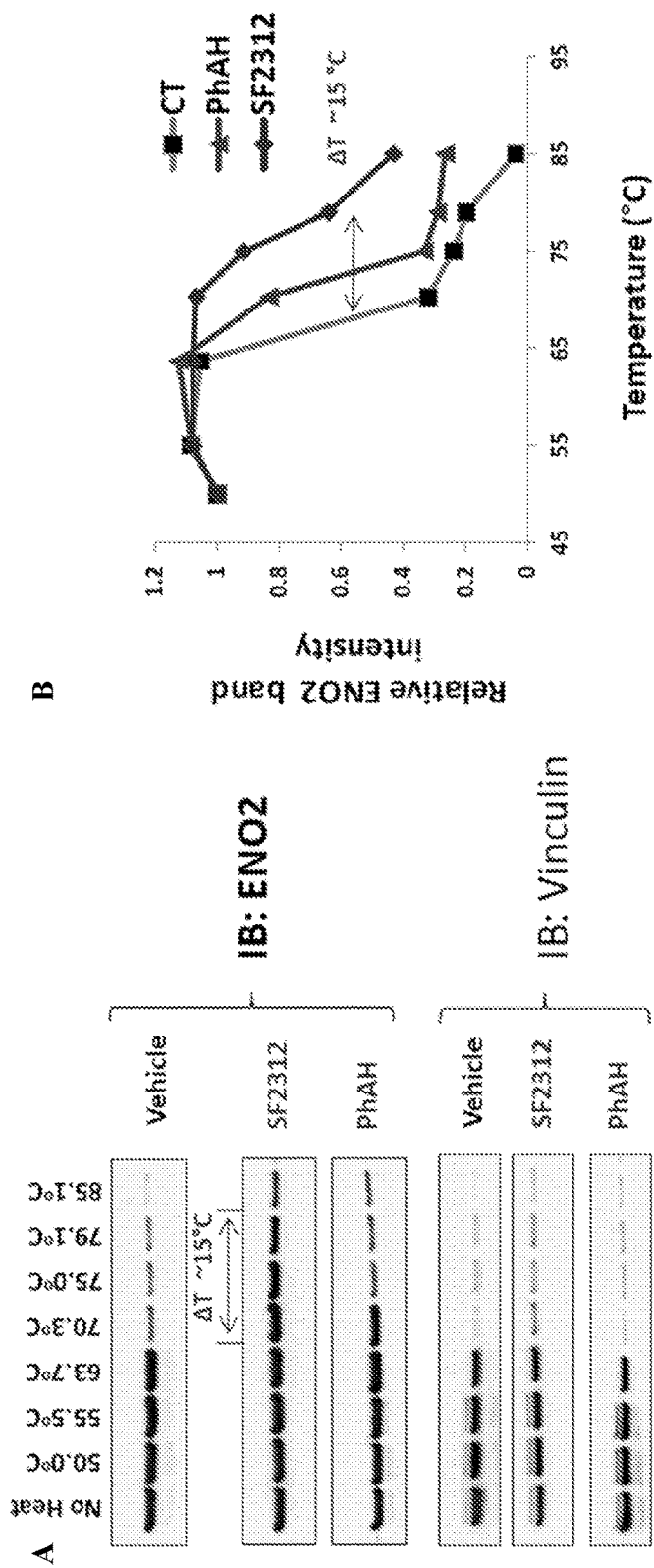

FIGS. 42A & 42B shows thermal stabilization of ENO2 by SF2312 and PhAH in intact glioma cells. Shift Assays (Martinez Molina, et al., 2013) in D423 cells overexpressing ENO2 were performed as detailed in methods. Intact glioma cells were treated with 100 µM PhAH, SF2312 or vehicle and individual aliquots heated between 50 and 90° C. as indicated. Lysates were generated and supernatant was immunoblotted for ENO2 and Vinculin (FIG. 42A). Relative intensity of the ENO2 bands was plotted as a function of temperature (FIG. 42B). Both PhAH and SF2312 resulted in dramatic stabilization of ENO2, with the effect being more dramatic for the later.

Figure 43:
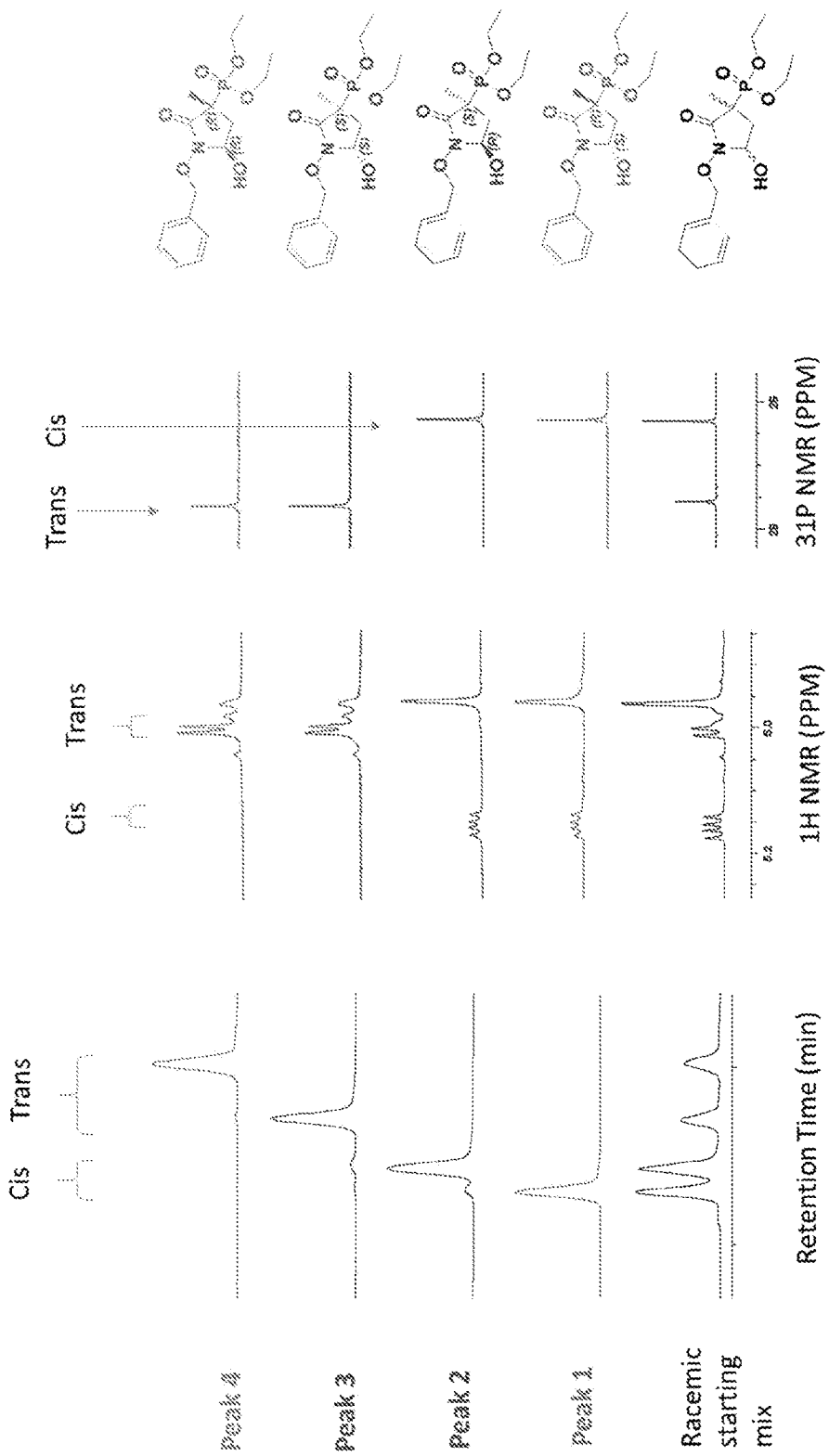

FIG. 43 shows the separation of the different diastereomers of a full protected derivative of Methyl SF2312. The peaks were analyzed and separated using chiral HPLC.

Figure 44:
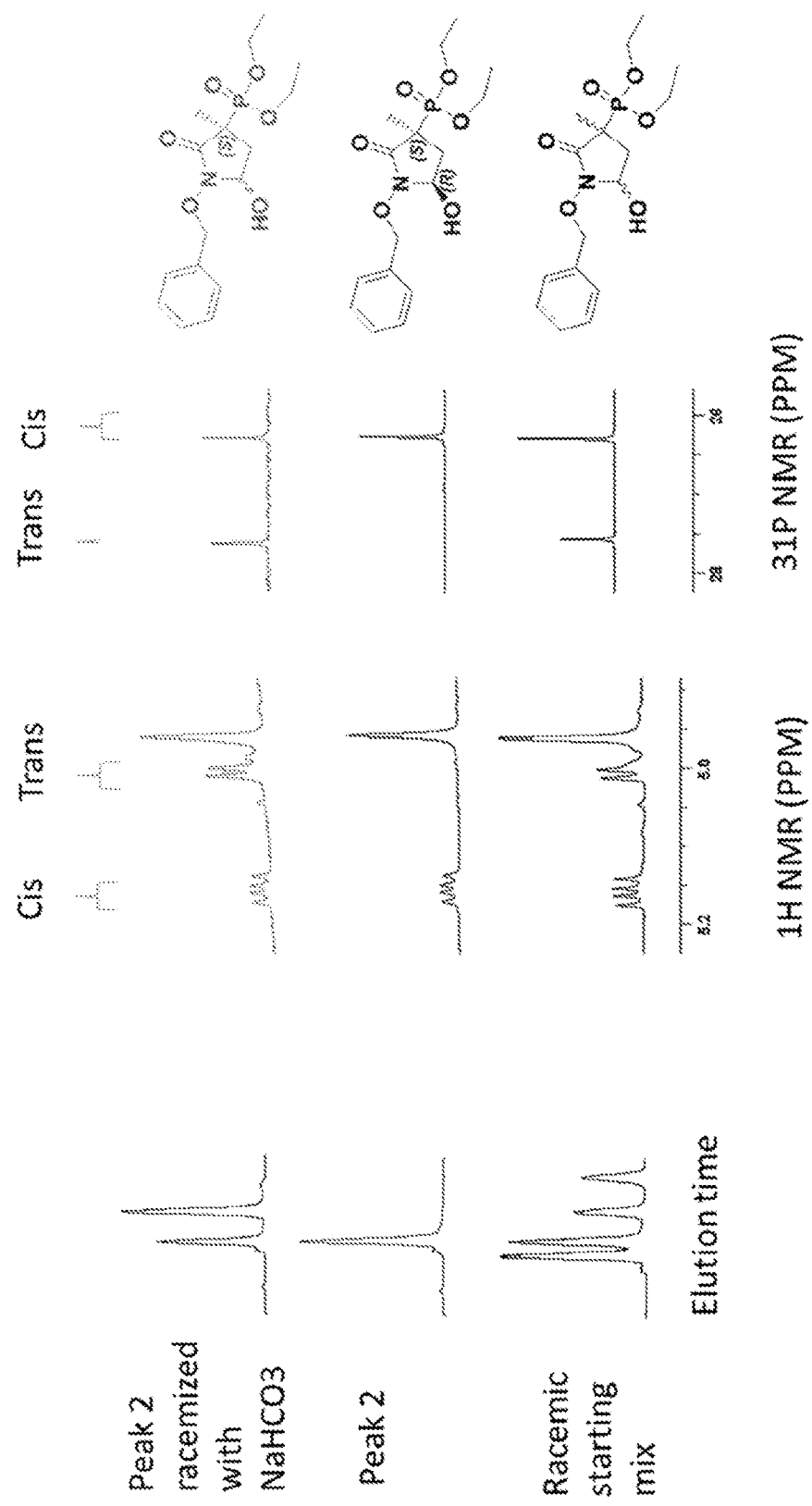

FIG. 44 shows the racemized, enantiopurified, and racemic starting material of Methyl SF2312 and the corresponding blow-up of the $^1$H and $^{31}$P NMR spectra.

Figure 45:
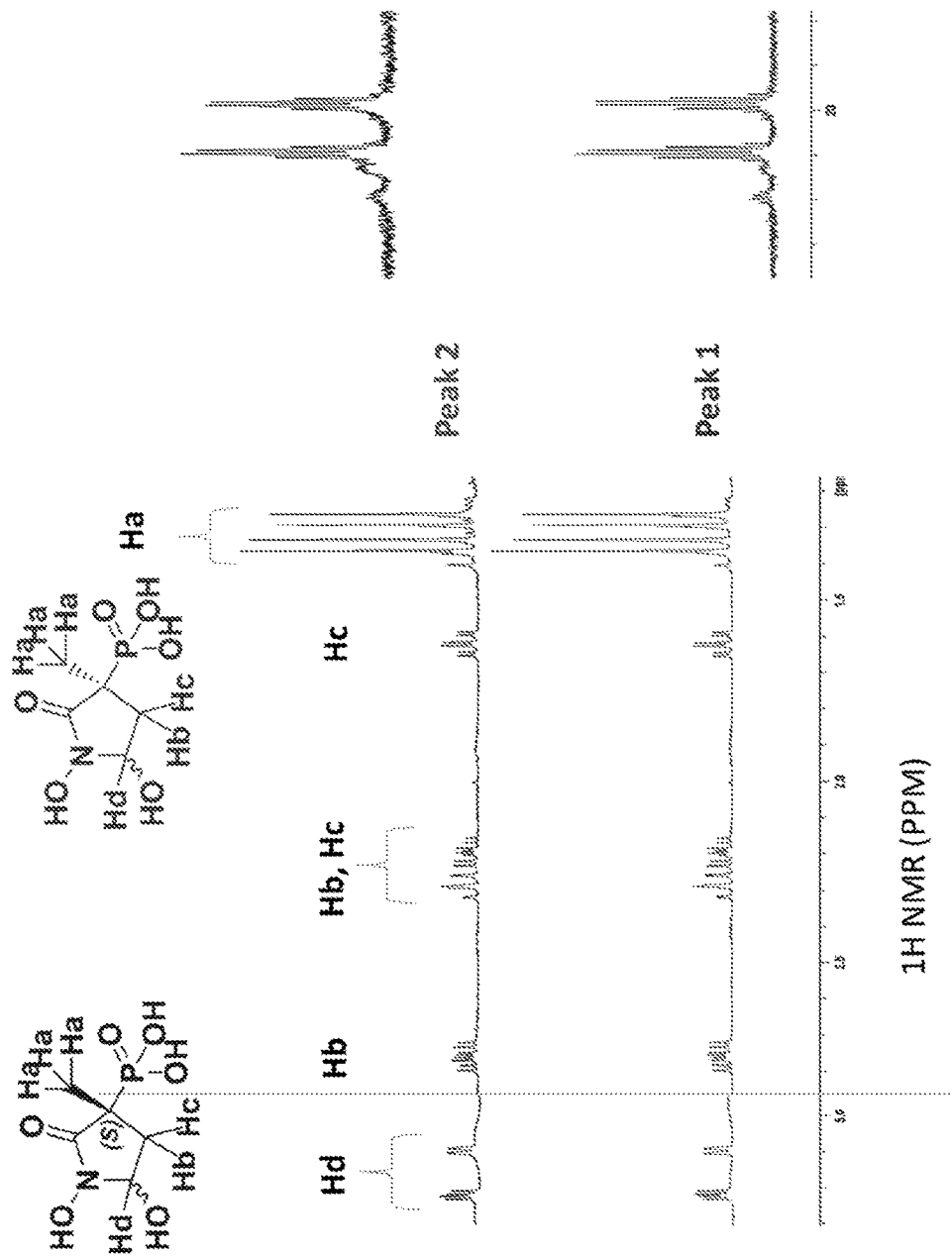

FIG. 45 shows the $^1$NMR spectra and the $^{31}$P NMR spectra of the deprotected and enantiopure Methyl SF2312. Peak 1 represents the right most structure.

Figure 46:
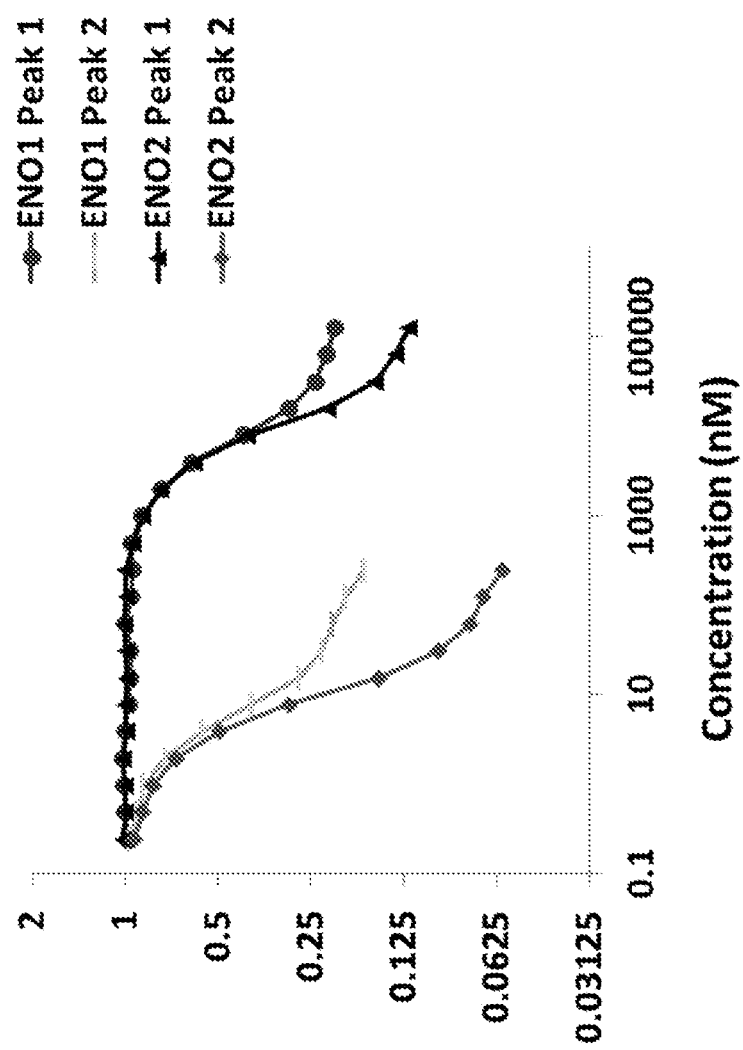

FIG. 46 shows that the compound corresponding to peak 2 of Methyl SF2312 shows 1000 fold higher activity than the compound of peak 1 of Methyl SF2312.

Figure 47:
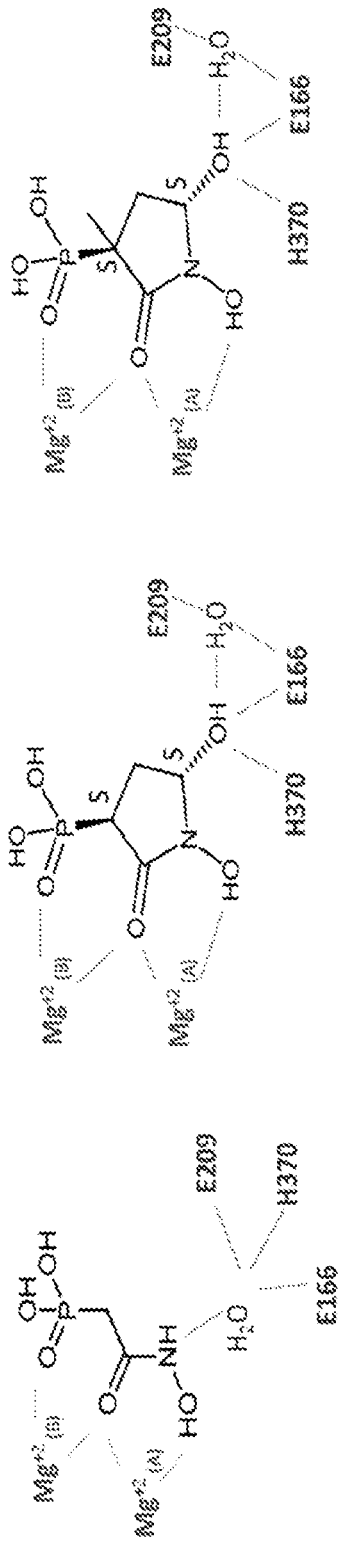

FIG. 47 shows the binding interactions of PhAH, SF2312, and Methyl SF2312 within the active site of the enolase enzyme.

FIG. 48 shows the binding interactions as well as crystal structures for SF2312 and Hex with the active site of the enolase enzyme.

DESCRIPTION OF ILLUSTRATIVE EMBODIMENTS

In some aspects, the present disclosure provides compounds that may be used as enolase inhibitors. The compounds and compositions provided herein may be used, for example, for the treatment of cancer or bacterial infections. In some embodiments, the cancer is deficient in the enolase 1 enzyme. For example, inhibition of enolase may be used to block glycolysis and lead to cellular apoptosis. In some embodiments, the compounds and compositions provided herein preferentially inhibit enolase 2 over enolase 1.

I. Compounds and Synthetic Methods

In some embodiments, the present disclosure provides compounds of the formula:

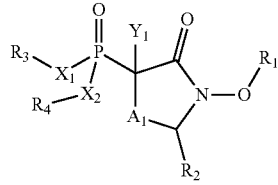

(I)

wherein:
$R_1$ is hydrogen, $acyl_{(C\leq12)}$ or substituted $acyl_{(C\leq12)}$;

$R_2$ is hydrogen, hydroxy, $alkoxy_{(C\leq12)}$, substituted $alkoxy_{(C\leq12)}$, $acyloxy_{(C\leq12)}$, or substituted $acyloxy_{(C\leq12)}$;

$X_1$ and $X_2$ are each independently O, S, or $NR_a$, wherein:
$R_a$ is hydrogen, $alkyl_{(C\leq6)}$, or substituted $alkyl_{(C\leq6)}$;

$R_3$ and $R_4$ are each independently hydrogen or $alkyl_{(C\leq12)}$, $aryl_{(C\leq12)}$, $aralkyl_{(C\leq12)}$, $heteroaryl_{(C\leq12)}$, $heteroaralkyl_{(C\leq12)}$, or a substituted version of these groups; or a phosphate protecting group; or $R_3$ and $R_4$ are taken together and are $alkanediyl_{(C\leq8)}$ or substituted $alkanediyl_{(C\leq8)}$; or —$X_3$—$R_5$; wherein:

$X_3$ is a covalent bond, $alkanediyl_{(C\leq8)}$, or substituted $alkanediyl_{(C\leq8)}$; and $R_5$ is $acyl_{(C\leq18)}$, $alkoxy_{(C\leq18)}$, —C(O)-$alkoxy_{(C\leq18)}$, $acyloxy_{(C\leq18)}$, or a substituted version of any of these groups;

$A_1$ is $alkanediyl_{(C\leq8)}$, substituted $alkanediyl_{(C\leq8)}$, $alkylaminodiyl_{(C\leq8)}$, or substituted $alkylaminodiyl_{(C\leq8)}$; and $Y_1$ is hydrogen, amino, halo, hydroxy, phosphate, $alkyl_{(C\leq12)}$, or substituted $alkyl_{(C\leq12)}$;

provided that the compound is not:

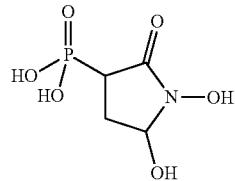 [SMILES: O=C1C(P(=O)(O)O)CC(O)N1O]

or a pharmaceutically acceptable salt or ester thereof.

In some embodiments, the compound is further defined as:

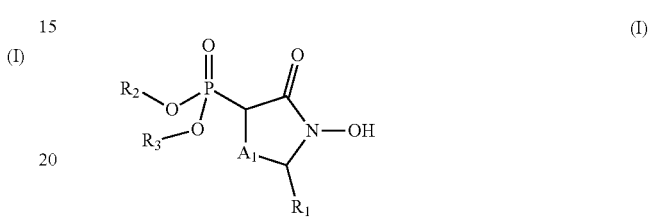

(I)

wherein: $R_1$ is hydrogen, $alkoxy_{(C\leq12)}$, substituted $alkoxy_{(C\leq12)}$, $acyloxy_{(C\leq12)}$, or substituted $acyloxy_{(C\leq12)}$; $R_2$ and $R_3$ are hydrogen, $alkyl_{(C\leq12)}$, substituted $alkyl_{(C\leq12)}$, or a phosphate protecting group; and A is $alkanediyl_{(C\leq8)}$, substituted $alkanediyl_{(C\leq8)}$, $alkylaminodiyl_{(C\leq8)}$, or substituted $alkylaminodiyl_{(C\leq8)}$; or a compound of the formula:

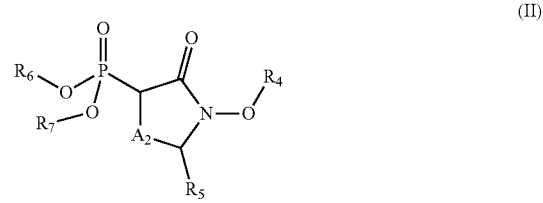

(II)

wherein: $R_4$ is $acyl_{(C\leq12)}$ or substituted $acyl_{(C\leq12)}$; $R_5$ is hydroxy, $alkoxy_{(C\leq12)}$, substituted $alkoxy_{(C\leq12)}$, $acyloxy_{(C\leq12)}$, or substituted $acyloxy_{(C\leq12)}$; $R_6$ is $alkyl_{(C\leq12)}$, substituted $alkyl_{(C\leq12)}$, or a phosphate protecting group; $R_7$ is hydrogen, $alkyl_{(C\leq12)}$, substituted $alkyl_{(C\leq12)}$, or a phosphate protecting group; and $A_2$ is $alkanediyl_{(C\leq8)}$, substituted $alkanediyl_{(C\leq8)}$, $alkylaminodiyl_{(C\leq8)}$, or substituted $alkylaminodiyl_{(C\leq8)}$; or a pharmaceutically acceptable salt or ester thereof. Examples of the compounds provided herein are shown in Table 1 (below), as well as in the Summary of the Invention, Examples, and Claims sections.

TABLE 1

Examples of Compounds Provided Herein

| Compound ID | Structure |
|---|---|
| Deoxy-SF2312 | 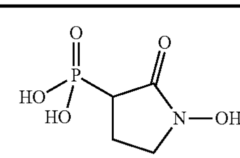 |

TABLE 1-continued

Examples of Compounds Provided Herein

| Compound ID | Structure |
| --- | --- |
| Hex | 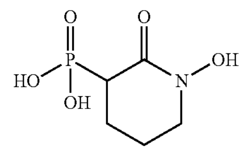 |
| Pom-Hex | 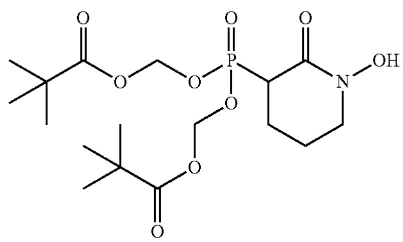 [SMILES: CC(C)(C)C(=O)OCOP(=O)(OCOC(=O)C(C)(C)C)C1CCCN(O)C1=O] |
| Hepta | 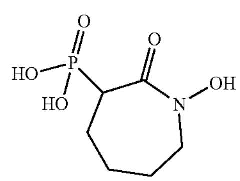 [SMILES: O=C1C(P(=O)(O)O)CCCCN1O] |
| Pom-SF2312 or Pom-SF | 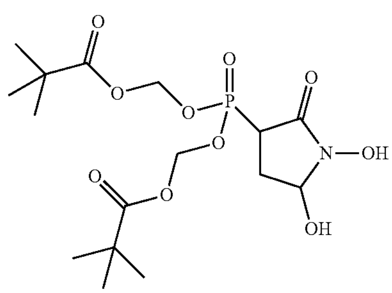 [SMILES: CC(C)(C)C(=O)OCOP(=O)(OCOC(=O)C(C)(C)C)C1CC(O)N(O)C1=O] |
| Hemi-Pom-SF2312 | 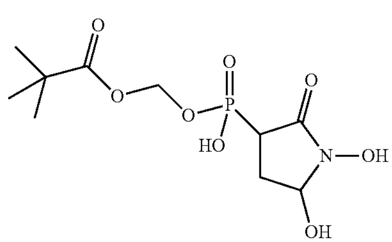 [SMILES: CC(C)(C)C(=O)OCOP(=O)(O)C1CC(O)N(O)C1=O] |
| Diacetyl-POM-SF2312, Diacetyl-POM-SF, or DiAcPOMSF2312 | 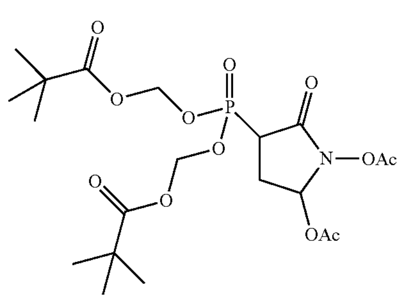 [SMILES: CC(=O)OC1CC(P(=O)(OCOC(=O)C(C)(C)C)OCOC(=O)C(C)(C)C)C(=O)N1OC(C)=O] |

TABLE 1-continued

Examples of Compounds Provided Herein

| Compound ID | Structure |
| --- | --- |
| Methyl-SF2312 | 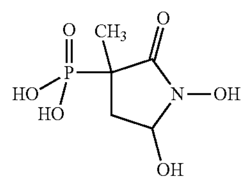 |
| Fluoro-SF2312 | 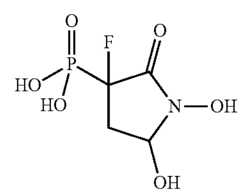 [SMILES: O=C1N(O)C(O)CC1(F)P(=O)(O)O] |
| 115-36 | 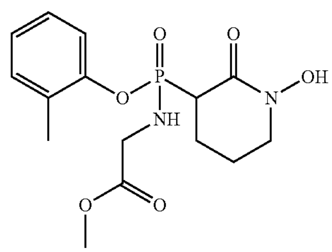 [SMILES: COC(=O)CNP(=O)(Oc1ccccc1C)C1CCCN(O)C1=O] |
| Dipropyl-POM-SF2312, Dipropyl-POM-SF, or DiPrPOMSF2312 | 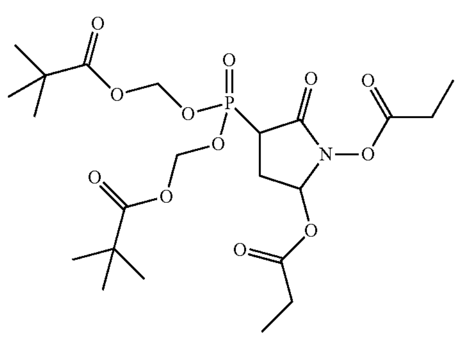 [SMILES: CCC(=O)OC1CC(P(=O)(OCOC(=O)C(C)(C)C)OCOC(=O)C(C)(C)C)C(=O)N1OC(=O)CC] |
| Diisobutyl-POM-SF2312, Diisobutyl-POM-SF, or DiiBuPOMSF2312 | 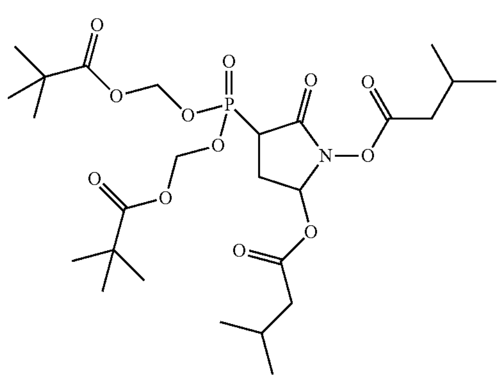 [SMILES: CC(C)CC(=O)OC1CC(P(=O)(OCOC(=O)C(C)(C)C)OCOC(=O)C(C)(C)C)C(=O)N1OC(=O)CC(C)C] |

TABLE 1-continued

Examples of Compounds Provided Herein

| Compound ID | Structure |
|---|---|
| ArAcidHex | (structure) |

The compounds provided herein may be made, for example, using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can each independently have either an S or the R configuration. In view the modeling and X-ray crystallographic results presented in FIGS. 13A-D and FIGS. 27A & 27B, in some embodiments, the S enantiomers of the compounds provided herein may be used to achieve inhibition of enolase at a lower concentration than the corresponding R enantiomers.

In some aspects, the compounds of the present disclosure are present in an enantiomerically pure form. The enantiomeric purity of the compound may be described using enantiomeric excess or ee. Enantiomeric excess is calculated using the formula:

$$ee = \{([R]-[S])/([R]+[S])\} \times 100\%$$

wherein the concentration of each of the optical isomers are measured using methods known in the art such as chiral HPLC or through NMR using chiral shift reagents. In some embodiments, the compound is substantially purified from other optical isomers. In some embodiments, the term "substantially purified" means that the compound is present in an ee of greater than 90%. In some embodiments, the ee is greater than 95%. In some embodiments, the ee is greater than 98%. In some aspects, the compounds described herein can be prepared as a single optical isomer by using asymmetric synthesis techniques including but not limited to using an enantioselective catalyst or a chiral auxiliary, such that one optical isomer is produced in the reaction. In other aspects, mixtures of the optical isomers can be separated utilizing chiral resolution to separate the optical isomers from a racemic mixture through methods known to those of skill in the art. Some non-limiting chiral resolution methods include chiral chromatography, differential precipitation or crystallization, or chiral resolving agents.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, phospho, or carboxy group is bonded to any group that, when the prodrug is administered to a subject, cleaves to form a hydroxy, amino, phosphate, or carboxylic acid, respectively. In some aspects, the present disclosure provides pro-drug forms of the compounds. Also, provided by the present disclosure are pro-drug forms of SF2312 which may be used in the pharmaceutical compositions or methods described herein.

In some aspects, the pro-drug form of the instant compounds comprises protecting the phosphate group with a phosphate protecting group. In some embodiments, the phosphate group is a phosphate protecting group. Some non-limiting examples of phosphate protecting groups include, but are not limited to: alkyl, aryl, aralkyl, acyl, acyloxy, acyloxy-alkanediyl, or substituted version of any of these groups. In some embodiments, the phosphate protecting group is acyl$_{(C \leq 12)}$, acyloxy$_{(C \leq 12)}$, or -alkanediyl$_{(C \leq 6)}$-acyloxy$_{(C \leq 12)}$, or a substituted version of any of these groups. In some embodiments, the phosphate protecting group is -alkanediyl$_{(C \leq 6)}$-acyloxy$_{(C \leq 12)}$ or a substituted -alkanediyl$_{(C \leq 6)}$-acyloxy$_{(C \leq 12)}$. In some embodiments, the phosphate protecting group is a pivaloyloxymethyl (POM) group. The pivaloyloxymethyl group has the structure —CH$_2$OC(O)C(CH$_3$)$_3$. In some embodiments, the phosphate protecting group is cleavable in vivo by an esterase. In other embodiments, the phosphate protecting group is alkyl$_{(C \leq 12)}$, aryl$_{(C \leq 12)}$, or aralkyl$_{(C \leq 12)}$. In some embodiments, the phosphate protecting group is phenyl, benzyl, or a substituted version of either of these groups. Other phosphate protecting groups are taught at least by Wuts, *Greene's Protecting Groups in Organic Synthesis*, 5$^{th}$ Ed., 2014 and Schultz, 2003.

In some embodiments, the pro-drug forms of the compounds of the present invention have decreased hemolytic activity compared to the compounds not in the pro-drug form. For example, SF2312, Hex and PhAH, when administered at 100 mg/kg IV for longer than a week cause a drop in hematocrit from 45% to 29%. Mild hemolytic anemia can be observed at concentrations as low as 50 mg/kg with these compounds. Pom-Hex is at least ~200-fold more potent than Hex, (FIGS. 10A & 10B), so one would anticipate hemolytic anemia at doses above 0.5 mg/kg. In actuality, doses as high as 10 mg/kg IV for up to 1 month, do not cause a statistically significant drop in hematocrit. Thus, despite dramatically enhanced potency against ENO1-deleted glioma cells, there is no commensurate increase in hemolytic anemia toxic side effects. In some embodiments, the pro-drug form of a compound of the present disclosure may be used to reduce the risk of the patient developing hemolytic anemia. Erythrocytes are sensitive to disruptions in the glycolytic cycle as glycolysis is the cell's only source of energy in the form of ATP. For example, when a prodrug is used that protects the phosphate with an ester, since erythrocytes lack esterase enzymes and these cells cannot generate the active form of the compounds. Since the cells cannot form the active form of the compound, decreased hemolytic side effects may be observed.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present invention.

II. Treatment Methods

In one aspect, the present disclosure provides compounds and compositions that may be used as inhibitors of enolase enzymes. Such compounds include those compounds described above as well as SF2312, which as the formula:

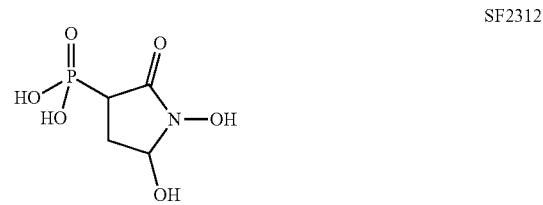 [SMILES: O=C1C(P(=O)(O)O)CC(O)N1O]

SF2312

SF2312 was first described as a new phosphonic acid antibiotic in Watanabe et al., *Science Reports of Meiji Seika Kaisha*, 25:12-17, 1986.

Three enolase subunits (u, 13, and y) are known to assemble as five different enolase isoenzymes. Some non-limiting isoenzymes are enolase 1 (u), enolase 2 (y), and enolase 3 (0). Enolase 2 is expressed at low levels in many cell types, but at high levels in neurons and neural tissues, while enolase 3 is primarily found in muscle tissue, and enolase 1 is expressed at varying levels in all tissue. As noted previously, enolases catalyze the conversion of 2-phosphoglycerate to phosphoenolpyruvate in glycolysis. While the sequence of the enolase enzyme and its subunits are highly conserved, in some embodiments, the inhibitors can preferentially inhibit one or more subunit or isoenzyme of enolase. In some embodiments, the enolase inhibitors provided herein may be used to treat or prevent a wide variety of diseases and disorders, including those discussed below.

A. Bacterial Infections

In another aspect of the present disclosure, the compounds, compositions, and methods disclosed herein may be used to treat bacterial infections. While humans contain numerous different bacteria on and inside their bodies, an imbalance in bacterial levels or the introduction of pathogenic bacteria can cause a symptomatic bacterial infection. Pathogenic bacteria cause a variety of different diseases including but not limited to numerous foodborne illness, typhoid fever, tuberculosis, pneumonia, syphilis, and leprosy.

Additionally, different bacteria have a wide range of interactions with body and those interactions can modulate ability of the bacteria to cause an infection. For example, bacteria can be conditionally pathogenic such that they only cause an infection under specific conditions. For example, *Staphylococcus* and *Streptococcus* bacteria exist in the normal human bacterial biome, but these bacteria when they are allowed to colonize other parts of the body causing a skin infection, pneumonia, or sepsis. Other bacteria are known as opportunistic pathogens and only cause diseases in a patient with a weakened immune system or another disease or disorder.

Some bacteria function as intracellular pathogens that can grow and reproduce within the cells of the host organism. Such bacteria can be divided into two major categories as either obligate intracellular parasites or facultative intracellular parasites. Obligate intracellular parasites require the host cell in order to reproduce and include such bacteria as but are not limited to *Chlamydophila*, *Rickettsia*, and *Ehrlichia* which are known to cause pneumonia, urinary tract infections, typhus, and Rocky Mountain spotted fever. Facultative intracellular parasites can reproduce either intracellular or extracellular. Some non-limiting examples of facultative intracellular parasites include *Salmonella, Listeria, Legionella, Mycobacterium*, and *Brucella* which are known to cause food poisoning, typhoid fever, sepsis, meningitis, Legionnaire's disease, tuberculosis, leprosy, and brucellosis.

B. Parasitic Infections

In another aspect, the compounds, compositions, and methods disclosed herein may be used to treat parasitic infections, including, for example, *Trypanosoma brucei* or *Trypanosoma cruzi*. African trypanosomiasis is a disease caused by the *Trypanosoma brucei* parasite and generally spread by the tsetse fly. The disease is transmitted when a person is bitten by the tsetse fly and is infected by one of two different subspecies of *Trypanosoma brucei*: a *Trypanosoma brucei rhodesiense* infection or a *Trypanosoma brucei gambiense* infection. The *rhodesiense* infection is typically an acute infection which last for a few weeks to several months while the *gambiense* infection is typically chronic and can last several years including long periods of time when the patient is asymptomatic. Typical symptoms of the disease include headaches, fever, weakness, itchiness, pain in the joints, and stiffness. After time, the disease can spread to the brain and cause damage to the central nervous system leading to such complications as psychiatric disorders, trouble sleeping, tremor, paralysis, seizures, and coma before finally leading causing death. If untreated, the disease is fatal.

Chagas disease is an infection by the parasite *Trypanosoma cruzi* and is spread by the triatomine bugs. The initial infection does not result in significant symptoms but after years, the chronic infection can result in severe symptoms. Some of these severe symptoms include abnormal heart rhythms, heart failures, gastrointestinal issues such as constipation and difficulty swallowing, and death.

C. Cancer and Other Hyperproliferative Diseases

In another aspect, the compounds, compositions, and methods disclosed herein may be used to treat cancer or other hyperproliferative diseases. While hyperproliferative diseases can be associated with any disease which causes a cell to begin to reproduce uncontrollably, the prototypical example is cancer. One of the elements of cancer is that the cell's normal apoptotic cycle is interrupted. As such, agents that interrupt the growth of the cells are important as therapeutic agents for treating these diseases. In this disclosure, the compounds of the present disclosure thereof may be used to lead to decreased cell counts and may be used to treat a variety of types of cancer lines. In some embodiments, the compounds of the present disclosure inhibit enolase and thus glycolysis. In some embodiments, the compounds are efficacious against cancers which contain a mutation or deletion of the one or more enolase genes such as the gene which encodes for enolase 1.

Cancer cells that may be treated with the compounds of the present disclosure include, but are not limited to, bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, and uterus cells.

In certain embodiments regarding methods of treating cancer in a subject, comprising administering to the subject a pharmaceutically effective amount of a compound of the present disclosure, the pharmaceutically effective amount is 0.1-1000 mg/kg. In certain embodiments, the pharmaceutically effective amount is administered in a single dose per day. In certain embodiments, the pharmaceutically effective amount is administered in two or more doses per day. The compound may be administered by contacting a tumor cell during ex vivo purging, for example. The method of treatment may comprise any one or more of the following: a) inducing cytotoxicity in a tumor cell; b) killing a tumor cell; c) inducing apoptosis in a tumor cell; d) inducing differentiation in a tumor cell; or e) inhibiting growth in a tumor cell. The tumor cell may be any type of tumor cell, such as a brain cell. Other types of cells include, for example, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

IV. Pharmaceutical Compositions and Routes of Administration

In another aspect, the present disclosure provides pharmaceutical compositions comprising as an active ingredient a compound of the present disclosure and/or SF2312 and a pharmaceutically acceptable carrier or excipient. In some embodiments, the composition is adapted for administration by a route selected from the group consisting of orally, intraadiposally, intraarterially, intraarticularly, intracranially, intradermally, intralesionally, intramuscularly, intranasally, intraocularally, intrapericardially, intraperitoneally, intrapleurally, intraprostaticaly, intrarectally, intrathecally, intratracheally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, via localized perfusion, bathing target cells directly, and any combinations thereof.

The dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

VII. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "-----" represents an optional bond, which if present is either single or double. The symbol "====" represents a single bond or a double bond. Thus, for example, the formula

includes

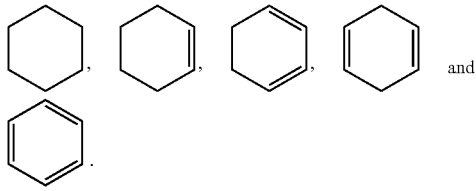

And it is understood that no one such ring atom forms part of more than one double bond. Furthermore, it is noted that the covalent bond symbol "—", when connecting one or two stereogenic atoms, does not indicate any preferred stereochemistry. Instead, it cover all stereoisomers as well as mixtures thereof. The symbol "⌇", when drawn perpendicularly across a bond (e.g.

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⫼" means a single bond where the group attached to the thick end of the wedge is "into the page". The symbol "⌇" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the number of carbon atoms in the group is as indicated as follows: "Cn" defines the exact number (n) of carbon atoms in the group/class. "C≤n" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-C10)}$" designates those alkyl groups having from 2 to 10 carbon atoms. Typically the carbon number indicator follows the group it modifies, is enclosed with parentheses, and is written entirely in subscript; however, the indicator may also precede the group, or be written without parentheses, without signifying any change in meaning. Thus, the terms "C5 olefin", "C5-olefin", "olefin$_{(C5)}$", and "olefin$_{C5}$" are all synonymous.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH₂OH, —CH₂Cl, —CF₃, —CH₂CN, —CH₂C(O)OH, —CH₂C(O)OCH₃, —CH₂C(O)NH₂, —CH₂C(O)CH₃, —CH₂OCH₃, —CH₂OC(O)CH₃, —CH₂NH₂, —CH₂N(CH₃)₂, and —CH₂CH₂Cl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

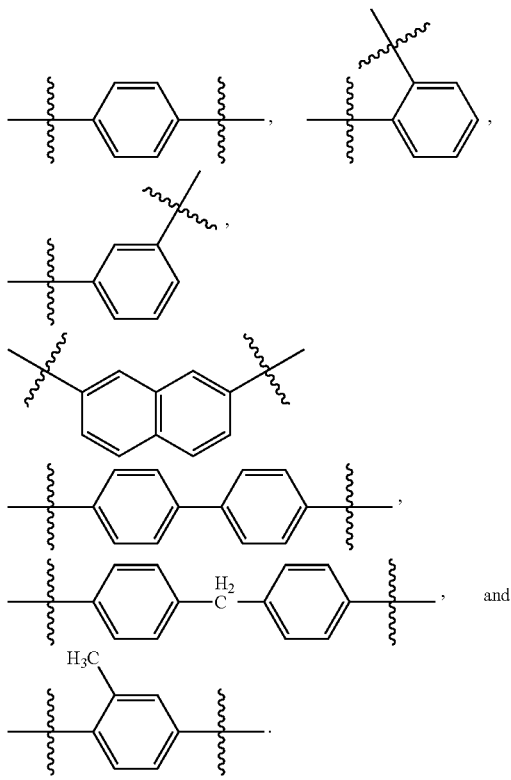

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. Non-limiting examples of substituted aralkyls are: (3-chlorophenyl)-methyl, and 2-chloro-2-phenyl-eth-1-yl.

The term "acyl" when used without the "substituted" modifier refers to the group —C(O)R, in which R is a hydrogen, alkyl, cycloalkyl, alkenyl, aryl, aralkyl or heteroaryl, as those terms are defined herein or if not defined herein based upon standard IUPAC nomenclature. The groups, —CHO, —C(O)CH₃ (acetyl, Ac), —C(O)CH₂CH₃, —C(O)CH₂CH₂CH₃, —C(O)CH(CH₃)₂, —C(O)CH(CH₂)₂, —C(O)C₆H₅, —C(O)C₆H₄CH₃, —C(O)CH₂C₆H₅, —C(O)(imidazolyl) are non-limiting examples of acyl groups. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH₂, —SH, —OCH₃, —OCH₂CH₃, —NHCH₃, —NHCH₂CH₃, —N(CH₃)₂, —OC(O)CH₃, or —S(O)₂NH₂. The groups, —C(O)CH₂CF₃, —CO₂H (carboxyl), —CO₂CH₃ (methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples include: —OCH₃ (methoxy), —OCH₂CH₃ (ethoxy), —OCH₂CH₂CH₃, —OCH(CH₃)₂ (isopropoxy), —OC(CH₃)₃ (tert-butoxy), —OCH(CH₂)₂, —O-cyclopentyl, and —O-cyclohexyl. The terms "aryloxy", "aralkoxy", and "acyloxy", when used without the "substituted" modifier, refers to groups, defined as —OR, in which R is aryl, aralkyl, and acyl, respectively. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "alkylamino" when used without the "substituted" modifier refers to the group —NHR, in which R is an alkyl, as that term is defined above. Non-limiting examples include: —NHCH₃ and —NHCH₂CH₃. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The term "alkylaminodiyl" refers to a divalent group selected from: —NH-alkanediyl-, -alkanediyl-NH—, —NH-alkanediyl-NH—, or -alkanediyl-NH-alkanediyl-, wherein alkanediyl is as defined above. In some particular embodiments, the "alkylaminodiyl" contains only one nitrogen atom. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are openended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, horse, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

In some aspects, the present disclosures uses one or more abbreviations or acronyms. These abbreviations or acronyms include ENO1, enolase 1 as either the gene or the protein; ENO2, enolase 2 as either the gene or the protein; ENO3, enolase 3 as either the gene or the protein. In each of these cases, the enolase is either the gene or the protein depending on the context and as would be obvious to a person of skill in the art. Additional abbreviations or acronyms include ATP, adenosine triphosphate; Bn, benzyl; BPS, 3-bromopropylphenyl sulfone; DCM, dichloromethane; DMAP, 4-dimethylaminopyridine; EDC, 1-ethyl-3-(3'-dimethylaminopropyl)-carbodiimide; Et, ethyl; IC, inhibitory concentration; LiHMDS, lithium hexamethyldisilazide; Me, methyl; MeCN, acetonitrile; MRI, magnetic resonance imaging; NMR, nuclear magnetic resonance; PEP, phosphoenolpyruvate or phosphoenolpyruvic acid; 2-PG, 2-phosphoglycerate or 2-phosphoglyceric acid; PhAH, phosphonoacetohydroxamate; POM, pivaloyloxymethyl; shRNA, short hairpin RNA; T2 MRI, spin-spin relaxation magnetic resonance imaging; THF, tetrahydrofuran; and VHL, Von Hippel-Lindau.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Methods and Materials

A. Spectrafluorimetric Inhibition Determination of ENO1 and ENO2

Human ENO1 and ENO2 were overexpressed in the human D423 cell line and used for enzymatic assays. Inhibitors (PhAH, SF2312 and Deoxy-SF2312, Hex, Hepta, Pom-Hex, and Fosmidomycin) were incubated with the enzyme prior to addition of 5 mM 2-PG substrate. Enzymatic activity was measured by monitoring fluorescence of NADH at 340 nm Exitation/460 nm emission using an Lactate dehydrogenase/Pyruvate kinase linked assay which links the formation of PEP to the oxidation of NADH to NAD+, as we have described in published work (Muller et al., 2012). Enzymatic activity was normalized to that in the absence of the inhibitor (set to 1) and plotted as function of inhibitor concentration.

B. Michaelis-Menten Kinetic Analysis

The Michaelis-Menten Kinetic analysis was performed using standard methods in the field such as those taught by Voet and Voet, 2011. The enzymatic activity of Enolase 1 or 2 v was determine over a concentration range of 10 mM to 0.5 mM 2-PG [S], in the presence of increasing concentrations of inhibitor [I]. These data were plotted as Lineweaver-Burke plots, with 1/[S] in the x-axis and 1/v in the y-axis. The slope of these lines was plotted as a function of inhibitor concentration [I] to yield Dixon plots, whose slope and intercept yielded competitive Ki.

C. NMR and Mass Spec Metabolic Tracing

Glucose labeled with heavy, non-radioactive, $^{13}C$ at carbon C-1 and $^{13}C$ at all carbon atoms were purchased from Cambridge Isotopes (CLM-420-1 and CLM-1396, respectively). Glucose free DMEM media was supplemented with 10 mM $^{13}C$-1 or $^{13}C$-all labeled Glucose. NMR metabolic tracing was performed by substituting conventional DMEM medium with glucose free DMEM medium, to which $^{13}C$-1 glucose (Cambridge Isotopes) was supplemented at 10 mM. The cells were grown in this medium for 4 days with or without the addition of SF2312. After 4 days, conditioned media was extracted with 80% methanol at −80° C., lyophilized and resuspended in $D_2O$. Proton-decoupled $^{13}C$ NMR spectra were acquired using a 500 MHZ Bruker instrument in the M. D. Anderson NMR core facility.

Small-molecule metabolites from cells in culture were extracted with 80% methanol at −80° C. (Yuan, et al., 2012), following our published methodology (Ying, et al., 2012). Methanol extraction recovers polar compounds such as most carboxylic acids, alcohols, sugars but not lipids. After extraction and centrifugation, the samples were dried by speed-vaccuming. Dried samples were analyzed using microcapillary liquid chromatography tandem mass spectrometry (LC-MS/MS) using selected reaction monitoring (SRM) with positive/negative polarity switching on a hybrid 5500 QTRAP mass spectrometer (AB/SCIEX). 300 SRM transitions target >260 polar metabolites (Yuan, et al., 2012) MS-peak quantification was performed using MultiQuant 2.1 software and relative levels of each metabolite in Q3 peak area units across samples.

D. Total Cell Count or Cellular Proliferation and Cellular Apoptosis (Propidium Iodide Positive Cells)

Total cell number was quantified by Hoechst 33342 (Cat# H3570; Invitrogen). Apoptotic cells were counted by staining with propidium iodide. Apoptotic cells become permeable to propidium iodide while live cells are not stained. On the day of apoptosis survey, old media was removed and each well was filled to 100 µl with fresh media. Hoechst and propidium iodide were mixed in 1:100 PBS and 10 µl of the mixture was added in each well gently without touching the cells for a final dilution of 1:1000 from stock. Plates were then incubated at 37° C. for 2 hours. Image capture and quantification was done by High Content Screening System—Operetta (Perkin Elmer).

Cell proliferation of glioma cell lines was assayed either through crystal violet staining or by live-cell confluence measurements with the IncuCyte (Essen BioScience). Growth curves using the IncuCyte were generated by confluence imaging every 4 hours with duplicate replicates with an initial seeding of 1500 cells/well in 96-well plates. At the indicated time point, cells were fixed with 10% formalin and stained with crystal violet. Dye extraction was performed using 10% acetic acid solution, and absorbance was read at 595 nm. Apoptotic cells were counted by staining with YO-PRO®-1 Iodide (491/509, Life Technologies, Y3603). Apoptotic cells become permeable to YO-PRO®-1 while live cells are not stained. Alternatively, Propidium Iodide was employed (Life Technologies) instead of YO-PRO. Total cell number was quantified by Hoechst 33342 (Cat# H3570 Invitrogen). Cells were seeded as $2\times10^3$ cells/well in 96-well plates and treated in the presence or absence of doxycycline. On the day of apoptosis survey, old media was removed and each well was filled to 100 µl with fresh media. Hoechst and YO-PRO®-1 were mixed in 1:100 PBS and 10 µl of the mixture was added in each well gently without touching the cells for a final dilution of 1:1000 from stock. Plates were then incubated at 37° C. for 2 hours. Image capture and quantification was done by High Content Screening System—Operetta (Perkin Elmer). ATP content was measured with the luciferase/luciferin CellTiter-Glo® assay. Briefly, 100 µl of CellTiter-Glo® assay media was added to 96-well plates containing 100 µl of media and cells. Lysis was achieved by the perchloric acid in the buffer and vigorous pipetting, and luminescence was determined using an Omega Luminescence Plate Reader (BMG Labtech). Results were expressed relative to vehicle treated control.

E. Cellular Viability (FIGS. 10A & 10B)

The cellular viability studies of 3-dimensional tumospheres was performed by using the vital dye, tetramethylrhomdamine ethyl ester (TMRE). TMRE was added at 10 nM to the spheres; live cells take up TMRE in response to active ionic gradients, dead cells do not. For reference, a brightfield picture was also taken.

Figure 8:
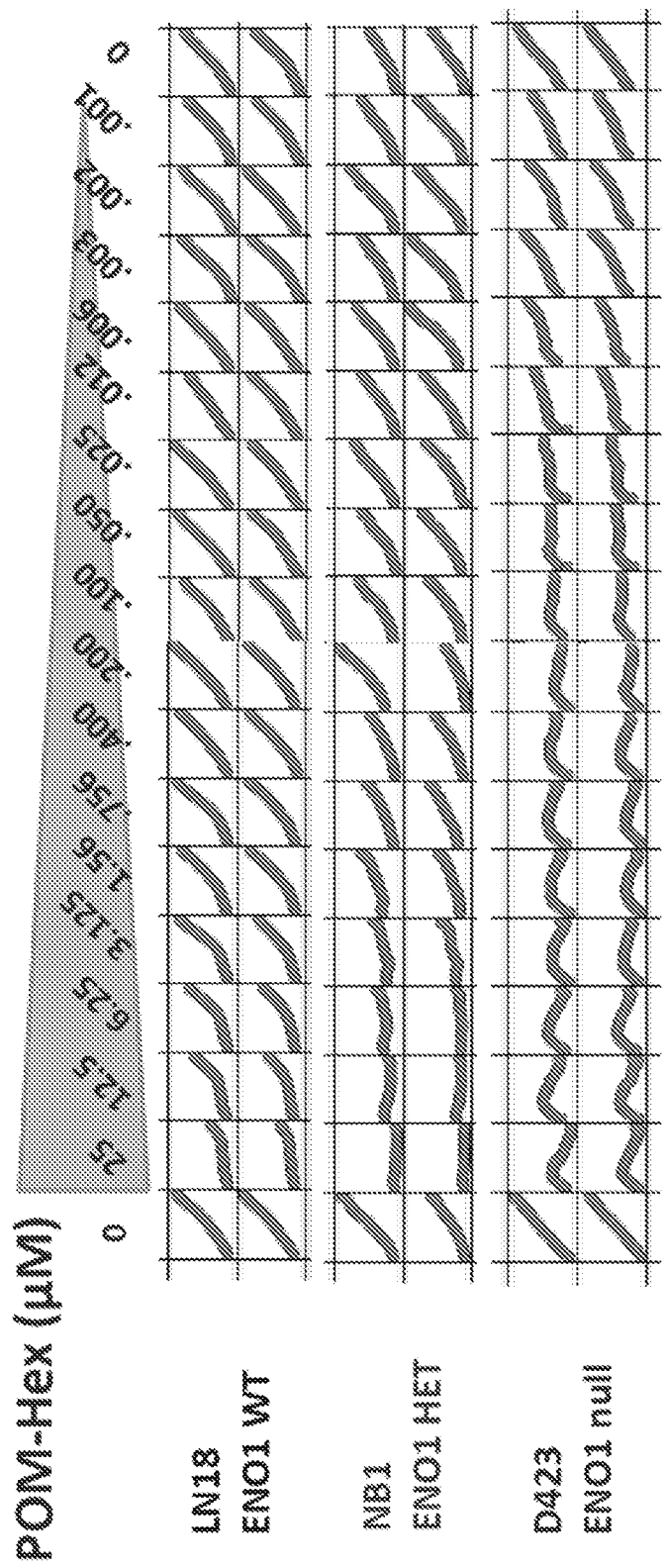
FIG. 8 shows the effect of treating a cell under growth conditions with Pom-Hex using live imaging with Incucyte.

F. Live Imaging with Incucyte (FIG. 8 and FIG. 12)

The inhibitor effects were followed live-cell confluence measurements with the IncuCyte (Essen BioScience) as we described previously (Muller et al., 2012). Growth curves using the IncuCyte were generated by confluence imaging every 2 hours with quadruplicate replicates with and initial seeding of $10^3$ cells/well in 96-well plates.

G. Crystal Violet Staining and Visualization of Tumor Cells (FIG. 9)

At the indicated time point (usually 2 weeks), cells were fixed with 10% formalin and stained with 0.1% crystal violet solution for 1 h as described previously (Muller et al., 2012). Dye extraction was performed using 10% acetic acid solution, and absorbance was read at 595 nm.

H. T2 MRI Tumor Visualization (FIG. 11A-11D)

Nude mice were injected with D423-MG glioma cells which carry the 1p36 deletion spanning ENO1. Tumors formed around 30 days post injection and growth was tracked non-invasively by T2 MRI. In the absence of treatment, tumors grew continuously, ultimately killing the animal. The tumor area (right side of the brain) is distinguished from the normal mouse brain by high contrast. MRI measurements were performed in a 4.7 T Biospec USR47/40 (Bruker Biospin MRI, Billerica, Mass.) at the M. D. Anderson small animal imaging facility (SAIF). Briefly, animals were maintained under deep anesthesia with isoflurane with body temperature maintained by a heating blanket. Anesthetized mice were restrained with the head held in a stereotactic holder. Breathing was monitored and synchronized with the instrument. Routine tumor detection was done by T2-weighed imaging. First, a low resolution axial scan is taken to center the field properly, after which a series of high resolution axial and coronal scans are recorded.

I. Cell Culture

The cell line D423-MG (referred to as to D423 throughout the paper) was kindly provided by Dr. Bigner (Duncan, et al., 2010). The 1p36 homozygous deletion in D423-MG includes the CAMTA1, VAMP3, PER3, UTS2, TNFRSF9, PARK7, ERRFI1, SLC45A1, RERE, ENO1, CA6, SLC2A5, GPR157, MIR34A, H6PD, SPSB1, and SLC25A33 genes. The Gli56 1p36 homozygously deleted cell line was shared by D. Louis, the deletion spans the UTS2, TNFRSF9, PARK7, ERRFI1, SLC45A1, RERE, ENO1, CA6, SLC2A5, GPR157, MIR34A, H6PD, SPSB1, SLC25A33, TMEM201, C1orf200, PIK3CD, CLSTN1, CTNNBIP1, LZIC, NMNAT1, RBP7 and UBE4B genes. The generation of isogenic ENO1 and ENO2 ectopically rescued lines was described previously; (clone pCMV ENO1 5x and clone pCMV ENO2 1x, (Muller, et al., 2012)). D423-MG and its sub-clones as well as Gli56 were deposited in the Dept. of Genomic Medicine/IACS Cell Bank, at M. D. Anderson and authenticated by Short Tandem Repeat (STR) testing. The Gli56 cell line does not have a published STR profile so could not be authenticated, but at the same time, its STR profile did not match any known cell line, confirming lack of contamination. Critically for the experiments, absence of ENO1 was confirmed by western blot (FIGS. 36 & 39). A series of ENO1-intact cell lines was used as controls for western blots, enolase activity and sensitivity to enolase inhibitors. These include D502 (Duncan, et al., 2010), primary human astrocytes (ScienCell), TS543, TS561, TS576 (Cameron Brennan, (Stommel, et al., 2007)), HCC1957, COV504, NB1, U343, LN319, and U373 (Dept. Genomic Medicine/IACS Cell Bank, MDACC). Cell lines were authenticated by STR testing. LN319 is a sub-clone of LN-992 (Bady, et al., 2012), while U373 is a sub-clone of U251 (Torsvik, et al., 2014); for the present work, this is acceptable as the these cell lines were used as non-ENO1-homozygously deleted controls. Their exact identity is irrelevant so long as ENO1 is expressed. The expression of ENO1 was verified by western blot (FIGS. 36 & 39). All cell lines were confirmed as mycoplasma negative by ELISA using the MycoAlert PLUS detection kit (Lonza, Basel, Switzerland). Cells were routinely cultured in Dulbecco's modified Eagle's medium (DMEM) with 10% fetal bovine serum (FBS).

J. Crystallization and X-Ray Structure Acquisition

DNA encoding full length Human Enolase 2 was cloned into pJL-H6 plasmid expression vector using the ligation-independent cloning method (Lee and Kim, 2009) and expressed in 1 L of auto-induction media at 20° C. after transformation into *E. coli* BL21 (DE3). After collecting the *E. coli* cells by centrifugation, the cells were re-suspended in 50 mM HEPES, 300 mM NaCl, 5 mM $MgCl_2$, 5 mM imidazole, 0.5 mM Tris-(carboxyethyl) phosphine, 10% (v/v) glycerol at pH 7.5. 20 µg $mL^{-1}$ DNase and 1 mM phenylmethylsulfonyl fluoride were added to the cell suspension prior to sonication at 4° C. The insoluble cell debris was removed by centrifugation prior to protein purification by His-tag affinity chromatography. The purified enolase 2 protein was further purified using a Superdex75 gel filtration column in 20 mM HEPES, 150 mM NaCl, 5 mM $MgCl_2$, 2 mM 2-mercaptoethanol at pH 7.5.

Apo crystals of Human Enolase 2 were prepared using the hanging drop vapor diffusion method at 20° C., suspending a drop containing 0.5 µL 9.1 mg $mL^{-1}$ Enolase 2 and 0.5 µL reservoir solution above a 500 µL reservoir containing 200 mM ammonium acetate, 100 mM Bis-Tris and 18-22% (w/v) PEG 3350. Streak seeding in the same solution conditions grew larger crystals. The crystals were soaked overnight in 1 µL drops containing 100 mM Bis-Tis, 200 mM ammonium acetate, 32% (w/v) PEG 3350 at pH 65, supplemented with 1-4 mM compound prior to flash freezing in liquid nitrogen. An X-ray diffraction dataset was collected at 100 K using the Advanced Light Source Beamline 8.3.1 equipped with ADSC Q315r detector at a wavelength of 1.11587 Å. For both crystals the MOSFLM strategy algorithm predicted significant overlapping reflections when the detector was positioned sufficiently close to the crystal to collect the highest resolution reflections visible in the diffraction image. The detector was therefore moved further from the crystal to avoid these reflection overlaps.

The diffraction images were indexed and integrated using iMOSFLM (Battye, et al., 2010) and scaled using AIMLESS (Evans and Murshudov, 2013). The X-ray structures were solved by molecular replacement using Phenix 1.9-1692 (Adams, et al., 2010) with the human Enolase 2 protein (PDB code 3UCC) as the search model followed by iterative refinement using Coot (Emsley, et al., 2010) and phenix.refine (Afonine, et al., 2012).

K. Chemicals and Characterization Methods (Examples 2 & 3)

The chemicals used herein were purchased from Sigma-Aldrich. The inhibitors were characterized by NMR and high resolution mass spectroscopy. The $^1H$, $^{13}C$, and $^{31}P$ NMR spectra were collected using a 500 MHZ Bruker NMR at the M. D. Anderson NMR Core facility.

L. Thermal Shift Assay

Thermal shift assays were conducted as described in Martinez Molina, et al. (2013), on lysates of D423 cell line overexpressing ENO1 and ENO2, on recombinant human ENO1 and ENO2 purified from *E. coli* as well as intact D423 ENO2 overexpressing glioma cells. Lysates: The lysates were prepared in 20 mM Tris-HCl, 1 mM EDTA and 1 mM β-mercaptoethanol at pH 7.4 and homogenized using a Polytron homogenizer three times for a period of 10 s followed by sonication, after which the lysates were cleared by centrifugation at 20,000 g for 10 minutes. Lysates were diluted (1:100) in Enolase enzymatic activity buffer as mentioned above. Diluted lysates were treated with SF2312, PhAH or vehicle and heated on a C1000 Thermal cycler (Bio-rad) with a linear temperature gradient (50 to 82.5° C. in 2.5° C. increments) for 3 minutes (FIG. 24). The lysates were then centrifuged at 20,000 g for 10 minutes. Supernatant and pellet were then separated and NuPage LDS Sample buffer (Life Technologies # NP0007) was added. Western Blots were performed as described previously (Muller, et al., 2012). The following antibodies were used: ENO1 (Abcam # ab155102), ENO2 (Dako # M087301-2), Vinculin (EMD Millipore #05-386), pan-ENO (Santa Cruz Biotechnology, sc-7455) and TPI (Proteintech #10713-1-AP). Recombinant human ENO2: The same procedure was carried out on purified recombinant ENO2 from *E. coli*, utilizing the purified protein generated for the X-ray crystallography studies. Stocks of ENO2 recombinant protein were diluted 1:10,000 and treated with PhAH, SF2312, or vehicle in Enolase enzyme activity buffer, followed by thermal denaturation, centrifugation, and immunoblotting as detailed for the lysates. Intact glioma cell lines: D423 glioma cell lines over expressing ENO1 and ENO2 were cultured in 10% DMEM. The cell lines were treated with drugs (100 µM PhaH, 100 µM SF2312) or vehicle and after one day, the cells were trypsinized and washed with PBS. These cells were re-suspended in PBS at the concentration of $0.5 \times 10^6$ cells/mL. Equal volume of re-suspended live cells were heated on a C1000 Thermal cycler (Bio-rad) with a variable temperature gradient (50° C. to 90° C.). Twice the volume of Lysis Buffer (20 mM Tris-HCl, 1 mM EDTA and 1 mM β-mercaptoethanol at pH 7.4) was added to the heat-shocked live cells. These cells were further lysed by a round of freeze-thaw cycle on dry-ice. The lysates were then centrifuged at 20,000 g for 10 minutes. Supernatant was collected and NuPage LDS Sample buffer (Life Technologies # NP0007) was added. Western Blots were performed as described previously (Muller, et al., 2012).

Native lysates of mouse tissues and human cell lines were prepared using 20 mM Tris HCl, 1 mM EDTA, and 1 mM β-mercaptoethanol at pH 7.4 and homogenized using a Polytron homogenizer three times for a period of 10 s followed by sonication, after which the lysates were cleared by centrifugation at 20,000 g for 10 minutes. Enolase activity was measured using two different methods, either by a fluorometric NADH-linked assay or a direct spectrophotometric assay via formation of PEP. In the fluorescent assay, enolase activity was measured via NADH oxidation in a pyruvate kinase-lactate dehydrogenase coupled assay as previously described (Muller, et al., 2012). The assay is conducted in 10 mM KCl, 5 mM $MgSO_4$, 100 mM triethanolamine at pH 7.4, with 400 µM NADH and 2 mM ADP. 2-Phosphoglycerate (2-PGA), pyruvate kinase (PK) and lactate dehydrogenase (LDH) are provided in excess, with conversion of 2-PGA to PEP by enolase being rate limiting. PEP (with ADP) is substrate of PK; pyruvate formed by this reaction is linked to NADH oxidation by LDH. Enolase activity is determined by measuring oxidation of NADH fluorescently by excitation at 340 nm and emission at 460 nm. The substrate concentration, if not otherwise indicated, was 5 mM 2-PGA. Fluorescence was measured using Omega Fluorescence Plate Reader (BMG Labtech). Alternatively, Enolase activity was measured directly by the appearance of PEP from 2-PGA via absorption at 240 nm (Marangos, et al., 1978). The assay medium was the same, except that all the auxiliary reagents (PK/LDH, NADH, ADP) are omitted. Both assays were conducted in a 96-well plated format with the direct assay performed in UV-transmissible plates.

Example 2—Synthesis of Enolase Inhibitors

The compound SF-2312 may be synthesized according to the method described in Scheme 1. Nucleophilic addition of an allyl halide to the starting ethyl diethyl phosphoethan-2-oate under basic conditions resulted in the alkylated intermediate. The ethyl ester was hydrolyzed and the resultant carboxylic acid was reacted with a protected hydroxylamine to obtain the resultant hydroxylamide. The resultant hydroxylamide was subjected to oxidizing conditions to obtain the cyclized product. The phosphate was then deprotected followed by deprotection of the hydroxylamide to obtain the final product, SF-2312.

Scheme 1: Synthesis of SF-2312

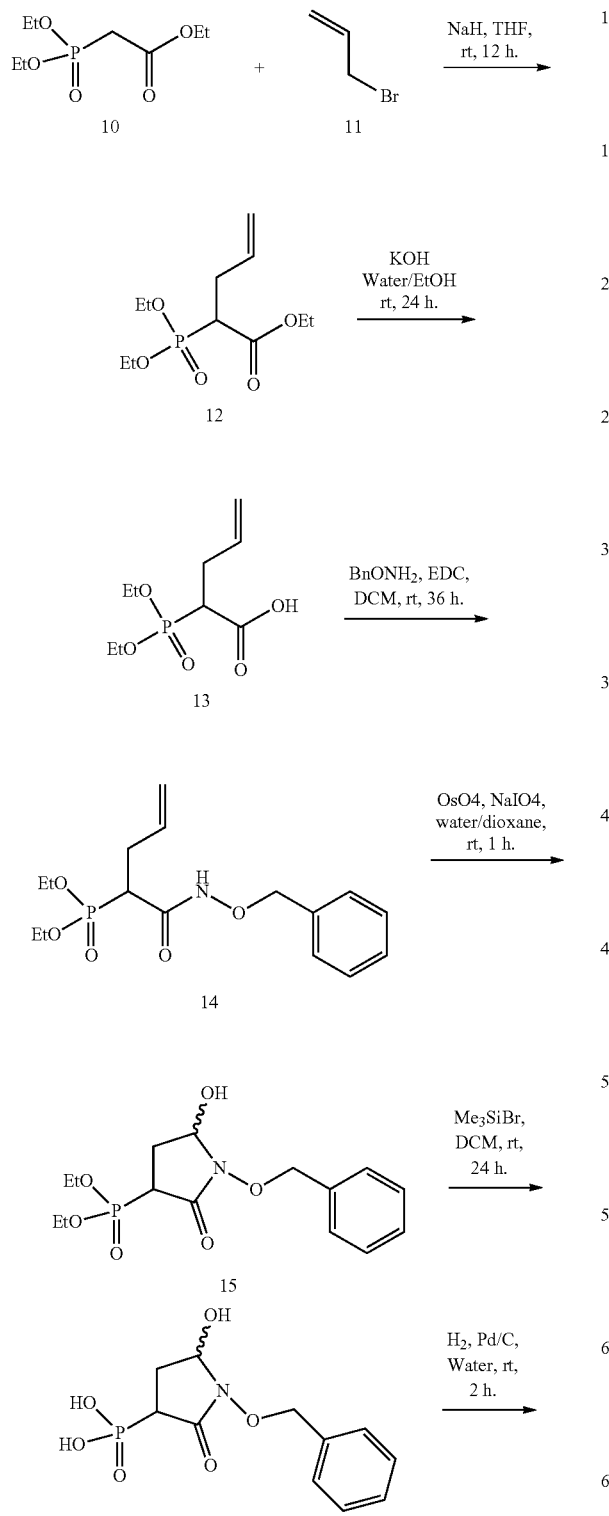

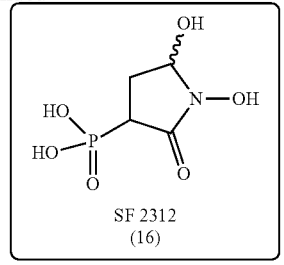

SF2312 was obtained as a racemic mixture of the cis and trans diastereomers (the two stereocenters on the 3 and 5 positions are pointed out in Scheme I). Chiral separation to generate enantiomerically pure SF2312 was conducted by passing through a Phenomenex® (Torrence, Calif.) chiral HPLC column. Yes While SF2312 itself proved impractical to separate due to its high polarity and lack of UV detectable groups, intermediate 15 (Scheme I) was successfully separated into its four enantiopure isomers (FIGS. 21 and 22). However, de-protection reactions (Steps 5 and 6, in Scheme III) carried out on enantiomerically pure intermediates 15 yielded fully racemic SF2312. Indeed, both stereocenters underwent spontaneous epimerization in aqueous solution (FIG. 23). This was unfortunately expected due to the nature of the two stereocenters, with the C-5 being an anomeric center and the 3-H a highly acidic α-proton. As such, these results suggest that the synthesis of enatiomerically pure SF2312 may not be technically feasible.

Similar analysis was carried out with Methyl SF2312. A fully protected Methyl SF2312 racemic mixture was fractionated by chiral HPLC, yielding four peaks whose enantiomeric purity was verified by re-running on the same column. Based on this assessment, Peak 1 showed 99.9% enantiomeric purity, Peak 2 96%, Peak 3 95% and Peak 4 97%. Each Peak was assessed by NMR, which cannot tell absolute stereochemistry, but can readily distinguish cis/trans isomers. Thus, while the racemic starting mix yielded two peaks by $^{31}$P NMR, corresponding to the cis and trans isomers in 1.5:1 ratio, each enantiopure fraction yielded only a single major $^{31}$P NMR peak. Peaks 1 and 2 one the one hand, and peaks 3 and 4 on the other, were identical by NMR. Based on NOESY, Peaks 1+2 correspond to the cis, while 3+4 correspond to the trans isomers (FIG. 43). When enantiopure fractions were extracted with mild basic conditions, single peaks turned into two. Racemization of Peak 1 yielded Peaks 1 and 4 while racemization of Peak 2 yielded Peaks 2 and 3, racemization of Peak 3 yielded peaks 3 and 2, while racemization of Peak 4 yielded Peaks 4 and 1. The simplest interpretation of this result is that mild alkaline treatment racemizes the anomeric hemiaminal at position 5 and that Peaks 1 and 4 have the same stereo chemistry at Position 2 which is the opposite of Peaks 2 and 3, which two in turn have the same stereochemistry at position 2 (FIG. 44). Enantiopure fractions were taken through deprotection reactions to remove the ethyl ester and benzyl protecting groups and subsequently tested for Enolase inhibitory activity. Despite having identical NMR spectra (FIG. 46), Peak 2 showed an $IC_{50}$ of around 3 nM for Enolase inhibition, while Peak 1 was ~1000 times less potent (FIG. 45). Given that chiral purity is less than 100%, without wishing to be bound by any theory, it is believe that the simplest interpretation of these data is that Peak 1 is inactive with respect to Enolase inhibition and that residual inhibitory activity corresponds to enantiomeric impurities from Peaks 2 and 3. Based on the x-ray structures, Peaks 2 and 3 corresponds to the active S-enantiomer at the 3-position, while Peaks 1 and 4 correspond to the relatively inactive R-enantiomer at the 3-position. The chiral center at position 5 is anomeric and readily racemizes in aqueous solvent.

In some embodiments, the deoxy analogs of SF-2312 were prepared as shown in Scheme 2. Triethyl phosphate and a dihaloalkane were reacted at reflux. The resultant haloalkylphosphonate was reacted with ethyl hydroxy-lamino carbamate under basic conditions to generate the target linear compound 6. The compound was reacted with a strong base to obtain the protected cyclic compound. The compound was then deprotected to obtain the desired deoxy analogs of SF-2312.

Scheme 2: Synthesis of Deoxy SF-2312

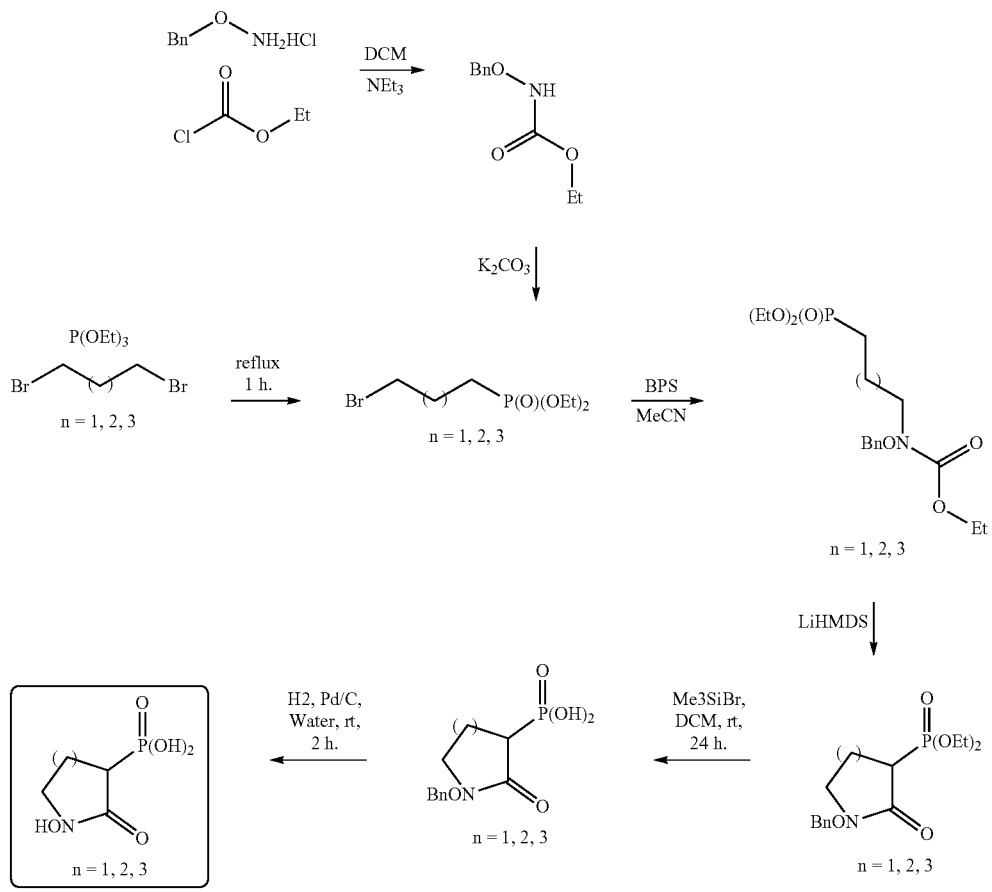

In some embodiments, POM protected versions of the inhibitors were prepared by taking the protected final product and selectively deprotecting the phosphonate. The phosphonate was then reacted with halomethyl pivalate. The hydroxylamine was then deprotected under reducing conditions as shown in Scheme 3.

Scheme 3: Synthesis of POM protected inhibitors

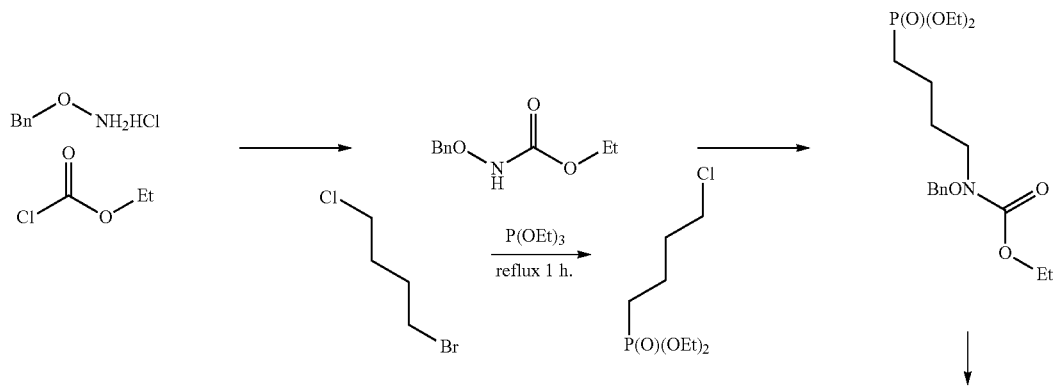

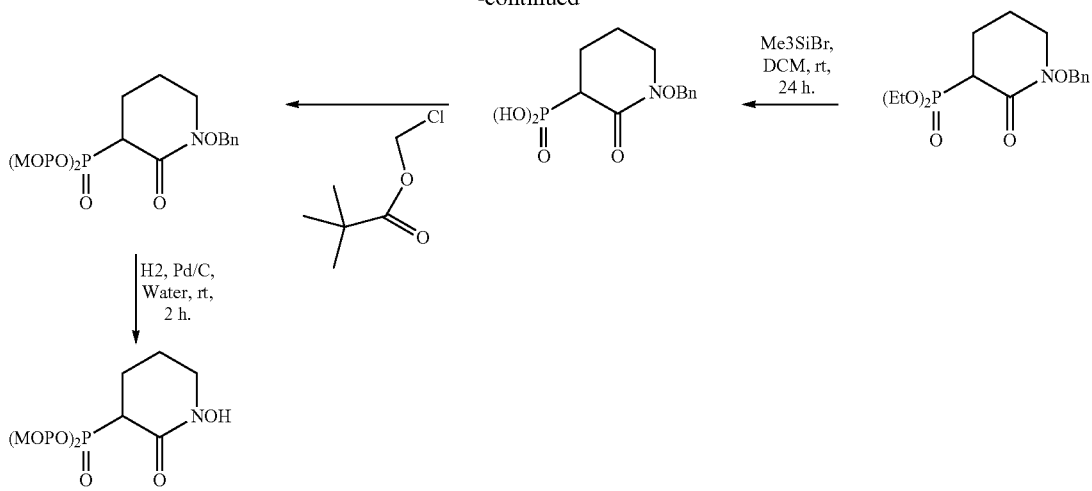

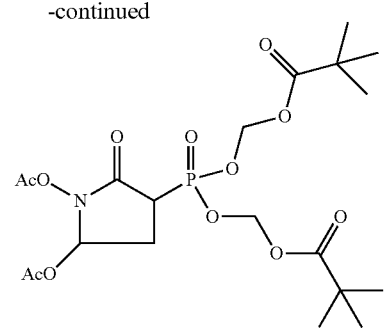

Scheme 4: Preparation of ((1-(benzyloxy)-5-hydroxy-2-oxopyrrolidin-3-yl)phosphoryl)bis(oxy))bis(methylene) bis(2,2-dimethylpropanoate) (POMSF) and ((1,5-diacetoxy-2-oxopyrrolidin-3-yl)phosphoryl)bis(oxy))bis(methylene) bis(2,2-dimethylpropanoate) (DiAcPOMSF)

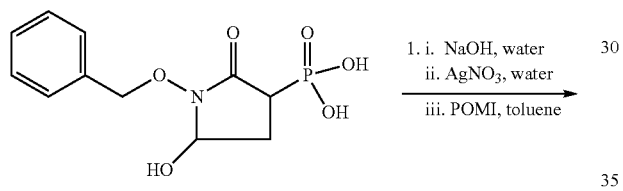

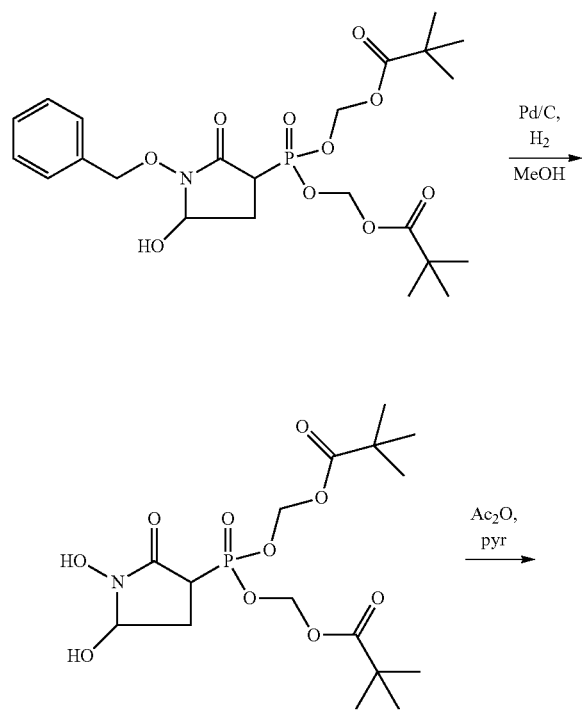

Example 3—Characterization of Enolase Inhibitors

In this example, SF2312 was prepared in a five-step sequence as described by Hanaya and Itoh (2011) with slight modifications. Removal of the benzyl protecting group in the final step provided desired compound SF2312. Ethyl diethoxyphophorylacetate served as the starting material for the preparation of ethyl 2-(diethyoxyphosphory)pent-4-enoate. Thus, ethyl diethoxyphophorylacetate was first deprotonated with sodium hydride at room temperature in THF and then coupled with slight excess amount of allyl bromide over night to give ethyl 2-(diethyoxyphosphory)pent-4-enoate with yield of 58%. The chemoselective hydrolysis of ethyl 2-(diethyoxyphosphory)pent-4-enoate in aqueous ethanol containing KOH provided the corresponding pent-4-enoic acid in a quantitative yield. Condensation of 2-(diethyoxyphosphory)pent-4-enoic acid with O-benzylhydroamine in the presence of 1-ethyl-3-(3'-dimethylaminopropyl)-carbodiimide (EDC) and 4-dimethylaminopyridine (DMAP) afforded N-Benzyloxy-2-(diethoxyphosphoryl)pent-4-enamide in 66% yield. The 1,5-dihydroxy-2-pyrrolidone ring formation of N-Benzyloxy-2-(diethoxyphosphoryl)pent-4-enamide was carried out by the intermolecular hemiacetalization of the hydroxamate with the terminal aldehyde. Namely, the oxidative cleavage of the terminal olefin of N-Benzyloxy-2-(diethoxyphosphoryl)pent-4-enamide with osmium tetraoxide and sodium periodate afforded the aldehyde intermediate, which was immediately cyclized to give a diastereometric mixture (cis/trans=1:1) of 1-Benzyloxy-3-diethoxyphosphoryl-5-hydroxy-2-pyrrolidone (95%). The removal of the ethyl protective group of the phosphoric ester was facilitated by the treatment with trimethylsilyl bromide to give with some unidentified impurities. The benzyl group was removed by hydrogenolysis with Pd/C as a catalyst to give SF-2312 (cis/trans=1:1 by $^1$H NMR). $^1$H NMR (D$_2$O, 600 MHz) δ 5.26 (dd, J=6.8, 2.8 Hz, 1H), 5.10 (d, J=6.2 Hz, 1H), 2.86 (m, 2H), 2.66 (dd, J=17.6, 7.4 Hz, 1H), 2.52 (m, 2H), 2.05 (m, 2H); $^{13}$C NMR (D$_2$O, 500 MHz) δ 171.0, 170.3, 82.4, 81.5, 39.5 (d, 121 MHz), 38.1 (d, 129 MHz), 28.6 (d, 3.3 Hz), 27.7 (d, 2.9 Hz); $^{31}$P NMR (D$_2$O, 500 MHz) δ 15.62, 13.95.

Synthesis and Characterization of Deoxy-SF2312, Hex, and Hepta

The procedures described herein were adapted from those reported in the literature (Hanaya and Itoh, 2011; Liu, et al., 2011). First, diethyl 3-bromopropylphosphonate was synthesized by the Arbuzov reaction. Triethyl phosphite in a tenfold excess of dibromopropane (n=1 for Deoxy-SF2312, n=2 for Hex and n=3 for Hepta) was heated at reflux for 1 h to yield diethyl 3-bromopropylphosphonate in 95% yield after distillation under reduced pressure. A mixture of O-benzylhydroxylamine hydrochloride, chloroformate in pyridine was stirred at room temperature under N$_2$ for 2 h to yield the ethyl ester. Potassium carbonate was added to a solution of 4 and 3-bromopropylphenyl sulfone in MeCN and the mixture was stirred at reflux overnight to yield the linear diethyl phosphate. Cyclization with LiHMDS obtained the cyclized diethylphosphate. Hydrolysis with Me$_3$SiBr in DCM and hydrogenation to remove the benzyl group obtained final deoxy-SF2312 (n=1) or larger ring seizes (n=2 or 3). For deoxy-SF2312 (n=1), $^1$H NMR (MeOD) δ 3.65 (m, 1H), 3.56 (m, 1H), 2.92 (m, 1H), 2.35 (m, 2H). $^{13}$C NMR (MeOD) δ 166.10, 47.73, 38.04 (d, J=141.3 Hz), 16.73 (d, 3.8 Hz). $^{31}$P NMR (MeOD) δ 22.32. HRMS: C$_4$H$_8$NO$_5$P [M+H]$^+$=182.0187 (calculated 182.0214). For Hex (n=2), 1H NMR (MeOD) δ 3.65-3.54 (m, 2H); 2.75 (m, 1H); 2.22 (m, 1H); 2.12-2.03 (m, 2H); 1.82 (m, 1H). MS (ES+) C$_5$H$_{10}$NO$_5$P requires: 195, found 196 [M+H]+. MS (ES−) C$_5$H$_{10}$NO$_5$P requires: 195, found 194 [M−H]$^-$. For Hepta (n=3), 1H NMR (MeOD) δ 4.07 (m, 1H), 3.78 (m, 1H), 2.83 (m, 1H), 2.01-1.97 (m, 2H), 1.80 (m, 1H), 1.62-1.59 (m, 3H), 13C NMR (MeOD) δ 172.7, 63.0, 52.2, 40.7, 26.1, 13.8, 31P NMR (MeOD) δ 15.75 HRMS: C$_4$H$_8$NO$_5$P [M+H]+=182.0187 (calculated 182.0214).

Synthesis and Characterization of Pom-Hex

Hex was synthesized as described in Scheme 2. At the 6th step, the pivoxil ester was added by an SN$_1$ reaction from the chloro-intermediate. $^1$H NMR (500 MHz, CDCl$_3$) δ 5.70 (ddd, J=15.8, 12.0, 5.0, 2H), 5.63 (t, J=9.3, 2H), 3.59 (s, 2H), 3.08 (d, J=26.2, 1H), 2.13 (s, 1H), 2.04 (d, J=7.1, 2H), 1.83 (s, 1H), 1.16 (d, J=2.3, 18H). $^{13}$C NMR (126 MHz, CDCl$_3$) δ 176.94, 176.93, 82.61, 82.56, 81.65, 81.60, 48.90, 41.68, 40.54, 38.74, 26.97, 26.86, 26.84, 26.74, 22.29, 21.55, 21.47. $^{31}$P NMR (202 MHz, CDCl$_3$) δ 22.92. HRMS: [M+H]$^+$ calc. 424.1731 expt. 424.1734.

Synthesis and Characterization of (((1-(benzyloxy)-5-hydroxy-2-oxopyrrolidin-3-yl)phosphoryl)bis (oxy))bis(methylene) bis(2,2-dimethylpropanoate)

To a solution of (1-(benzyloxy)-5-hydroxy-2-oxopyrrolidin-3-yl)phosphonic acid (Hanaya and Itoh, 2011), (650 mg, 2.2 mmol) in water (5.6 mL) was added NaOH (181 mg, 4.5 mmol) and the resulting mixture was stirred at 25° C. for 1 h. To this solution, a solution of AgNO$_3$ (1.1 g, 6.7 mmol) in water (0.8 mL) was added and the resulting mixture was stirred at 25° C. for 2 h. The resulting suspension was stored at 0° C. for 24 h. The solid was collected by vacuum filtration and rinsed with cold water (10 mL) and Et$_2$O (5 mL) and dried under vacuum overnight. The resulting solid was added to a solution of iodomethyl pivalate (753 μl, 4.9 mmol) in toluene (5.6 mL), and the resulting mixture was stirred at 25° C. for 6 h. The solid was filtered off and the filtrant was concentrated. The residue was purified via silica gel chromatography (20-100% EtOAc in hexanes to give (((1-(benzyloxy)-5-hydroxy-2-oxopyrrolidin-3-yl)phosphoryl)bis(oxy))bis(methylene) bis(2,2-dimethylpropanoate) (252 mg, 0.49 mmol, 21% yield) as a colorless liquid. $^1$H NMR (600 MHz, DMSO-d$_6$) δ ppm (mixture of diastereomers): 7.48-7.44 (m, 2H), 7.42-7.36 (m, 3H), 6.79 and 6.69 (2d, J=6.4 Hz, 6.4 Hz, 1H), 5.73-5.56 (m, 4H), 5.2 and 5.1 (2m, 1H), 4.96, 4.92 (2s, 2H) 3.49-3.26 (m, 1H), 2.53-2.24 (m, 1H), 2.00-1.79 (m, 1H), 1.17 (s, 18H). MS (ES+) C$_{23}$H$_{34}$NO$_{10}$P requires: 515.1, found 538.2 [M+Na]$^+$.

Synthesis and Characterization of (((1-(benzyloxy)-5-hydroxy-2-oxopyrrolidin-3-yl)phosphoryl)bis (oxy))bis(methylene) bis(2,2-dimethylpropanoate) (POMSF)

A reaction vessel was charged with (((1-(benzyloxy)-5-hydroxy-2-oxopyrrolidin-3-yl)phosphoryl)bis(oxy))bis (methylene) bis(2,2-dimethylpropanoate) (252 mg, 0.48 mmol), 5% Pd on BaSO$_4$ (104 mg, 0.05 mmol) and MeOH (4.8 mL) under an atmosphere of N$_2$. The suspension was degassed with N$_2$ for 2 minutes and purged with H$_2$ for 2 minutes. The reaction mixture was stirred under an atmosphere of H$_2$ at 50 psi for 4 h. The reaction mixture was purged with N$_2$, and filtered through Celite® and concentrated under reduced pressure to give (((1,5-dihydroxy-2-oxopyrrolidin-3-yl)phosphoryl)bis(oxy))bis(methylene)bis (2,2-dimethylpropanoate) (162 mg, 0.38 mmol, 78% yield) as an orange oil. $^1$H NMR (500 MHz, DMSO-d$_6$) δ ppm (mixture of diastereomers): 9.79 (s, 1H), 6.65, 6.58 (2d, J=5.7 Hz, 6.7 Hz 1H), 5.72-5.52 (m, 4H), 5.0 (m, 1H), 3.42-3.19 (m, 1H), 2.48-2.27 (m, 1H), 1.97-1.68 (m, 1H), 1.17 (s, 18H). $^{31}$P NMR (500 MHz, DMSO-d$_6$) δ ppm 24.81, 24.59. MS (ES+) C$_{16}$H$_{28}$NO$_{10}$P requires: 425.15, found: 448.0 [M+Na]$^+$.

Synthesis and Characterization of (((1,5-diacetoxy-2-oxopyrrolidin-3-yl)phosphoryl)bis(oxy))bis(methylene) bis(2,2-dimethylpropanoate) (DiAcPOMSF)

To a solution of (((1,5-dihydroxy-2-oxopyrrolidin-3-yl) phosphoryl)bis(oxy))bis(methylene) bis(2,2-dimethylpropanoate) (5 mg, 0.012 mmol) in pyridine (0.2 mL) was added Ac$_2$O (6 μl, 0.06 mmol) and the resulting mixture was stirred at room temperature for 18 h. The volatiles were removed under reduced pressure and the residue was dried under reduced pressure for 18 h give (((1,5-diacetoxy-2-oxopyrrolidin-3-yl)phosphoryl)bis(oxy))bis(methylene)bis (2,2-dimethylpropanoate) (5.4 mg, 10.6 μmol, 90% yield) as a brown liquid. $^1$H NMR (500 MHz, CDCl$_3$) δ ppm (mixture of diastereomers): 6.29 (m, 1H) 5.83-5.62 (m, 4H), 3.47-3.13 (m, 1H), 2.91-2.75 (m, 1H), 2.51-1.21 (m, 1H), 2.20, 2.18, 2.13, 2.07 (4s, 6H, diastereomers and rotamers) and 1.24 (s, 18H). $^{31}$P NMR (500 MHz, CDCl$_3$) δ ppm (mixture of diastereomers): 20.03, 19.95. MS (ES+) $C_{20}H_{32}NO_{12}P$ requires: 509.1, found: 532.0 [M+Na]+.

Preparation of (((2-oxo-1,5-bis(propionyloxy)pyrrolidin-3-yl)phosphoryl)bis(oxy))bis(methylene) bis(2,2-dimethylpropanoate) (DiPrPOMSF)

The title compound was prepared by the method described for DiAcPOMSF. $^1$H NMR (500 MHz, CDCl$_3$) δ ppm (mixture of diastereomers): 6.29 (m, 1H) 5.83-5.62 (m, 4H), 3.47-3.13 (m, 1H), 2.91-2.75 (m, 1H), 2.53-2.32 (m, 5H), 2.21-2.12 (4s, 6H, diastereomers and rotamers) and 1.24 (s, 18H). $^{31}$P NMR (500 MHz, CDCl$_3$) δ ppm (mixture of diastereomers): 20.19, 20.06. MS (ES+) $C_{20}H_{32}NO_{12}P$ requires: 537.2, found: 560.3 [M+Na]+.

Preparation of (((5-(isobutyryloxy)-1-((3-methylbutanoyl)oxy)-2-oxopyrrolidin-3-yl)phosphoryl)bis(oxy))bis(methylene) bis(2,2-dimethylpropanoate)

The title compound was prepared by the method described for DiAcPOMSF. $^1$H NMR (500 MHz, CDCl$_3$) δ ppm (mixture of diastereomers): 6.29 (m, 1H) 5.83-5.62 (m, 4H), 3.47-3.13 (m, 1H), 2.91-2.75 (m, 1H), 2.53-2.32 (m, 5H), 2.21-2.12 (m, 6H, diastereomers and rotamers) and 1.24 (s, 18H). $^{31}$P NMR (500 MHz, CDCl$_3$) δ ppm (mixture of diastereomers): 20.19, 20.06. MS (ES+) $C_{20}H_{32}NO_{12}P$ requires: 593.2, found: 616.5 [M+Na]+.

4-(bis((pivaloyloxy)methoxy)phosphoryl)-5-oxopyrrolidine-1,2-diyl bis(3-methylbutanoate)

The title compound was prepared by the method described for DiAcPOMSF. $^1$H NMR (500 MHz, CDCl$_3$) δ ppm (mixture of diastereomers): 6.25 (m, 1H) 5.74-5.59 (m, 4H), 3.36-3.10 (m, 1H), 2.83-2.71 (m, 1H), 2.53-2.32 (m, 5H), 2.26-2.02 (m, 7H), 1.16 (s, 18H), 0.97-0.84 (m, 12H). $^{31}$P NMR (500 MHz, CDCl$_3$) δ ppm (mixture of diastereomers): 20.25, 20.11. MS (ES+) $C_{26}H_{44}NO_{12}P$ requires: 593.26, found: 616.5 [M+Na]+.

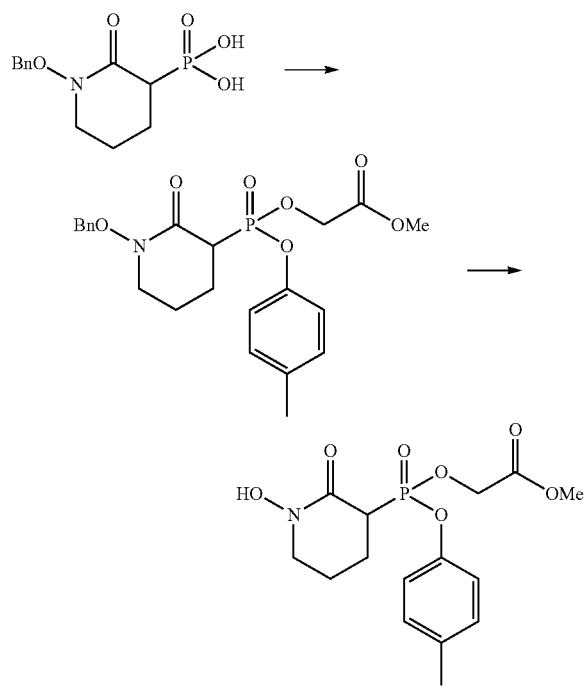

Step 1: (1-(Benzyloxy)-2-oxopiperidin-3-yl)phosphonic dichloride

To a solution of (1-(benzyloxy)-2-oxopiperidin-3-yl) phosphonic acid (150 mg, 0.526 mmol) in DCM (2629 μl) were added COCl$_2$ (921 μl, 10.5 mmol) and N-(chloromethylene)-N-methylmethanaminium chloride (1.3 mg, 10 μmol) and the resulting mixture was stirred at room temperature for 2 h. The mixture was carefully concentrated and dried on the lyophilizer. The crude product was used in the next step without further purification. MS (ES+) $C_{14}H_{20}NO_5P$ requires: 311.1, found: 336.0 [M+H]+ (Methoxy adduct).

Step 2: Methyl 2-(((1-(benzyloxy)-2-oxopiperidin-3-yl)(p-tolyloxy)phosphoryl)oxy)acetate A solution of (1-(benzyloxy)-2-oxopiperidin-3-yl)phosphonic dichloride (25 mg, 0.078 mmol) in DCM (776 μl) was added to a solution of p-cresol (10.07 mg, 0.093 mmol), glycine methyl ester hydrochloride (11 mg, 0.093 mmol) and DIPEA (67 μl, 0.38 mmol) in DCM (776 μl). The resulting mixture was stirred at rt for 18 h. The solvent was evaporated under reduced pressure. The residue was purified via silica gel chromatography (0-100% EtOAc in hexanes to give methyl 2-(((1-(benzyloxy)-2-oxopiperidin-3-yl)(p-tolyloxy)phosphoryl)amino)acetate (6.8 mg, 0.015 mmol, 19.63% yield) as a colorless liquid. (p-Cresol and glycine methyl ester hydrochloride was azeotroped before use.). $^1$H NMR (500 MHz, CDCl$_3$) δ ppm: 7.42-7.35 (m, 2H), 7.31-7.28 (m, 3H), 7.22 (d, 4H, 2.1 Hz) 4.93 (dd, 2H, J=11.4, 12.0), 4.53-4.49 (m, 1H), 3.84-3.69 (m, 1H), 3.69-3.55 (m, 1H), 3.59 (s, 3H), 3.38-3.25 (m, 2H), 2.10 (s, 3H), 2.10-1.92 (m, 2H), 1.74-2.52 (m, 3H). $^{31}$P NMR (500 MHz, CDCl$_3$) δ ppm: 27.61. MS (ES+) $C_{22}H_{27}N_2O_6P$ requires: 446.4, found: 347.4 [M+H].

Step 3: Methyl 2-(((1-hydroxy-2-oxopiperidin-3-yl)(p-tolyloxy)phosphoryl)amino)acetate A reaction vessel was charged with methyl 2-(((1-(benzyloxy)-2-oxopiperidin-3-yl)(p-tolyloxy)phosphoryl) amino)acetate (6.8 mg, 0.015 mmol), 5% Palladium on barium sulfate (3.24 mg, 1.523 μmol) and MeOH (1 mL) under an atmosphere of N$_2$. The suspension was degassed with N$_2$ for 2 minutes and purged with H$_2$ for 2 minutes. The reaction mixture was stirred under an atmosphere of H$_2$ at 50 psi for 4 h. The reaction mixture was purged with N$_2$ and filtered through Celite® and concentrated under reduced pressure to give methyl 2-(((1-hydroxy-2-oxopiperidin-3-yl)(p-tolyloxy)phosphoryl)amino)acetate (3 mg, 8.42 μmol, 55.3% yield) as a colorless oil. $^1$H NMR (500 MHz, CDCl$_3$) δ ppm: 6.98 (dd, 4H, 8.01, 20.0 Hz) 4.44 (m, 1H), 3.94-3.85 (m, 1H), 3.7-3.55 (m, 3H), 3.60 (s, 3H), 3.28 (dd, 1H, J=6.23, 2.27 Hz), 2.23 (s, 3H), 2.14-2.00 (m, 2H), 1.99 (m, 1H), 1.89-1.94 (m, 2H). $^{31}$P NMR (500 MHz, CDCl$_3$) δ ppm: 26.52. MS (ES+) $C_{15}H_{21}N_2O_6P$ requires: 356.11, found: 357.3 [M+H]+.

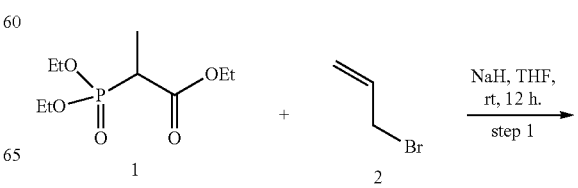

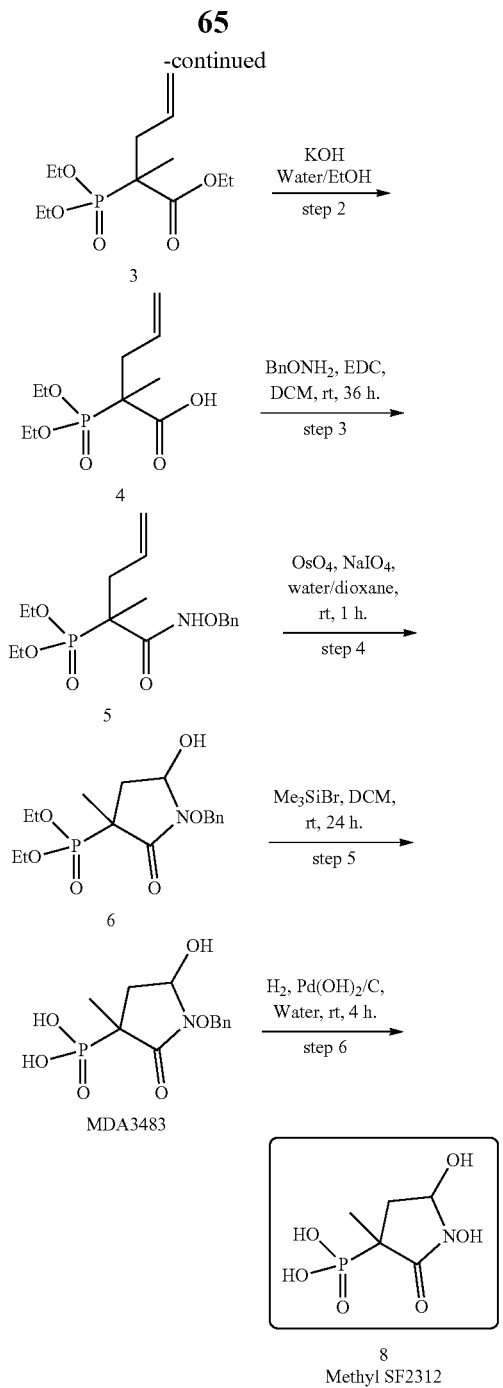

8
Methyl SF2312

Step 1: ethyl 2-(diethoxyphosphoryl)-2-methylpent-4-enoate

To a solution of ethyl 2-(diethoxyphosphoryl)propanoate (10.0 g, 42 mmol) in THF (100 mL) at 0° C. was added NaH (2 g, 50 mmol). The mixture was stirred at 0° C. for 1 h. The 3-bromoprop-1-ene (6.1 g, 50 mmol) was added. The mixture was stirred at RT overnight. Added aq $NH_4Cl$ (50 mL) at 0° C. and the solvent was removed, extracted with DCM (3×200 ml), the combined organic layers were dried over anhydr-$MgSO_4$, filtered and concentrated to give a yellow oil (12 g, crude). MS (ES+) $C_{12}H_{23}O_5P$ requires: 278, found: 279 $[M+H]^+$.

Step 2: 2-(diethoxyphosphoryl)-2-methylpent-4-enoic acid

To a solution of ethyl 2-(diethoxyphosphoryl)-2-methylpent-4-enoate (12 g, 43 mmol) in EtOH (100 mL) was added 10 M aq. KOH (6.5 mL, 65 mmol). The mixture was stirred at RT for 48 h. Then the mixture was heated to 50° C. for 48 h. The solvent was removed, diluted with water (50 mL), extracted by DCM (2×100 mL). Then adjusted pH with 1M HCl, extracted with DCM (3×100 mL), the combined organic layers were dried over anhydr-$MgSO_4$, filtered and concentrated to afford the title compound as a yellow oil (8 g, crude). MS (ES+) $C_{10}H_{19}O_5P$ requires: 250, found: 251 $[M+H]^+$.

Step 3: diethyl 1-(benzyloxyamino)-2-methyl-1-oxopent-4-en-2-ylphosphonate

To a solution of 2-(diethoxyphosphoryl)-2-methylpent-4-enoic acid (8.0 g, 32 mmol) and O-benzylhydroxylamine hydrochloride (4.3 g, 35.2 mmol) in DCM (200 mL) was added DMAP (5.9 g, 48 mmol) and EDC hydrochloride (6.2 g, 48 mmol). After stirring for 36 h at RT, the mixture was washed with 1M HCl (2×50 mL) and brine (50 mL). The organic layer was dried over anhydrous $MgSO_4$ and evaporated in vacuo to obtain a yellow oil (9 g, crude). MS (ES+) $C_{17}H_{26}NO_5P$ requires: 355, found: 356$[M+H]^+$.

Step 4: Diethyl 1-(benzyloxy)-5-hydroxy-3-methyl-2-oxopyrrolidin-3-ylphosphonate To the solution of diethyl diethyl 1-(benzyloxyamino)-2-methyl-1-oxopent-4-en-2-ylphosphonate (5.0 g, 14.1 mmol) in dioxane/$H_2O$ (300 mL/300 mL) was added $OsO_4$ (286 mg, 1.13 mmol). The mixture was stirred at RT for 30 min, then $NaIO_4$ (9 g, 8.42.2 mmol) was added portionwise, the mixture was stirred at RT for 1 h, and diluted with water (1000 mL), extracted with DCM (3×500 mL). The combined organic layers were washed with water (300 mL) and brine (300 mL), dried with anhydrous $MgSO_4$, filtered, and concentrated to afford the title compound as a light yellow oil (5 g, crude). MS (ES+) $C_{16}H_{24}NO_6P$ requires: 357, found: 358$[M+H]^+$.

Step 5: 1-(benzyloxy)-5-hydroxy-3-methyl-2-oxopyrrolidin-3-ylphosphonic acid (Protected Methyl SF2312)

To the solution of diethyl 1-(benzyloxy)-5-hydroxy-3-methyl-2-oxopyrrolidin-3-ylphosphonate (5 g, crude) in DCM (250 mL) was added TMS-I (8.4 g, 42 mmol). The reaction mixture was stirred at RT over night. after the reaction was complete, concentrated and dissolve in DCM (50 ml) and water (20 mL), the water phase was extracted with EA (50 ml×5), then the water phase was purified by reverse phrase column to obtain the title compound as a white solid (1.5 g, 40%). MS (ES+) $C_{12}H_{16}NO_6P$ requires: 301, found: 302 $[M+H]^+$ and 283 $[M-H_2O+H]^+$. $^1H$ NMR (500 MHz, $D_2O$) δ 7.68-6.89 (m, 5H), 5.27-4.80 (m, 3H), 2.20 (dddd, J=224.7, 210.2, 20.7, 9.8 Hz, 2H), 1.46-0.81 (m, 3H).

Step 6: 1,5-dihydroxy-3-methyl-2-oxopyrrolidin-3-ylphosphonic acid (Methyl SF2312)

To a solution of 1-(benzyloxy)-5-hydroxy-3-methyl-2-oxopyrrolidin-3-ylphosphonic acid (100 mg) in water (10 mL), Pd(OH)$_2$ (20 mg) was added, the mixture was stirred under H$_2$ atmosphere for 4 h at RT. After the reaction was completed, filtered and lyophilized to afford pure product as white solid (50 mg, 75%). MS (ES+) C$_5$H$_{10}$NO$_6$P, requires: 211, found: 210[M−H]$^−$. $^1$H NMR-$^{31}$P dec (500 MHz, D$_2$O) δ 5.22 (dd, J=6.9, 4.3 Hz, 1H), 5.10 (dd, J=6.6, 1.8 Hz, 1H), 2.76 (dd, J=14.2, 7.0 Hz, 1H), 2.29 (dd, J=14.4, 1.8 Hz, 1H), 2.19 (dd, J=14.3, 6.6 Hz, 1H), 1.62 (dd, J=14.2, 4.4 Hz, 1H), 1.35 (s, 3H), 1.28 (s, 3H). $^1$H NMR (500 MHz, D$_2$O) δ 5.22 (dd, J=6.9, 4.4 Hz, 1H), 5.10 (dm, J=6.3, 1H), 2.76 (ddd, J=17.5, 14.2, 7.0 Hz, 1H), 2.33-2.14 (m, 2H), 1.62 (td, J=14.4, 4.4 Hz, 1H). $^{31}$P NMR-$^1$H dec (202 MHz, D$_2$O) δ 20.89, 19.81. $^{31}$P NMR (202 MHz, D$_2$O) δ 20.88 (q, J=15.7 Hz), 19.80 (q, J=15.8 Hz).

Synthesis and Characterization of 3-fluoro-1,5-dihydroxy-2-oxopyrrolidin-3-yl)phosphonic acid (FluoroSF2312)

(3-fluoro-1,5-dihydroxy-2-oxopyrrolidin-3-yl)phosphonic acid was prepared in a five-step sequence as described by Hanaya and Itoh (2011) with slight modifications. Ethyl 2-(diethoxyphosphoryl)-2-fluoroacetate was obtained commercially and served as the starting material for the preparation of ethyl 2-(diethoxyphosphoryl)-2-fluoropent-4-enoate. Thus, Ethyl 2-(diethoxyphosphoryl)-2-fluoroacetate was first deprotonated with sodium hydride in THF and then coupled with excess amount of allyl bromide overnight to give ethyl 2-(diethoxyphosphoryl)-2-fluoropent-4-enoate with yield of >80%. The chemoselective hydrolysis of ethyl 2-(diethoxyphosphoryl)-2-fluoropent-4-enoate in aqueous ethanol containing LiOH provided the corresponding pent-4-enoic acid in a quantitative yield. Condensation of 2-(diethoxyphosphoryl)-2-fluoropent-4-enoic acid with O-benzylhydroamine in the presence of 1-ethyl-3-(3'-dimethylaminopropyl)-carbodiimide (EDC) and 4-dimethylaminopyridine (DMAP) afforded diethyl (1-((benzyloxy)amino)-2-fluoro-1-oxopent-4-en-2-yl)phosphonate in 70% yield. The 1,5-dihydroxy-3-fluoro-2-pyrrolidone ring formation of diethyl (1-(benzyloxy)-3-fluoro-5-hydroxy-2-oxopyrrolidin-3-yl)phosphonate was carried out by the intermolecular hemiacetalization of the hydroxamate with the terminal aldehyde. Namely, the oxidative cleavage of the terminal olefin of diethyl (1-((benzyloxy)amino)-2-fluoro-1-oxopent-4-en-2-yl)phosphonate with osmium tetraoxide and sodium periodate afforded the aldehyde intermediate, which was immediately cyclized to give a diastereometric mixture (cis/trans=1:1) of diethyl (1-((benzyloxy)amino)-2-fluoro-1-oxopent-4-en-2-yl)phosphonate (95%). The removal of the ethyl protective group of the phosphoric ester was carried out by the treatment with trimethylsilyl bromide and the benzyl group was removed by hydrogenolysis with Pd/C as a catalyst to give (3-fluoro-1,5-dihydroxy-2-oxopyrrolidin-3-yl)phosphonic acid (Fluoro SF2312) (cis/trans=1:1 by $^1$H NMR). $^1$H NMR (600 MHz, D$_2$O) δ 5.33 (d, J=6.6 Hz, 1H), 5.23 (td, J=6.4, 4.3 Hz, 2H), 3.18-3.05 (m, 2H), 2.79-2.55 (m, 3H), 2.13 (dddd, J=29.9, 15.3, 11.0, 4.3 Hz, 2H). MS (+ c ESI): m/z (%) 216 [MH$^+$] (100) MS (− c ESI): m/z (%) 214 [M−H$^+$] (35).

Figure 1:
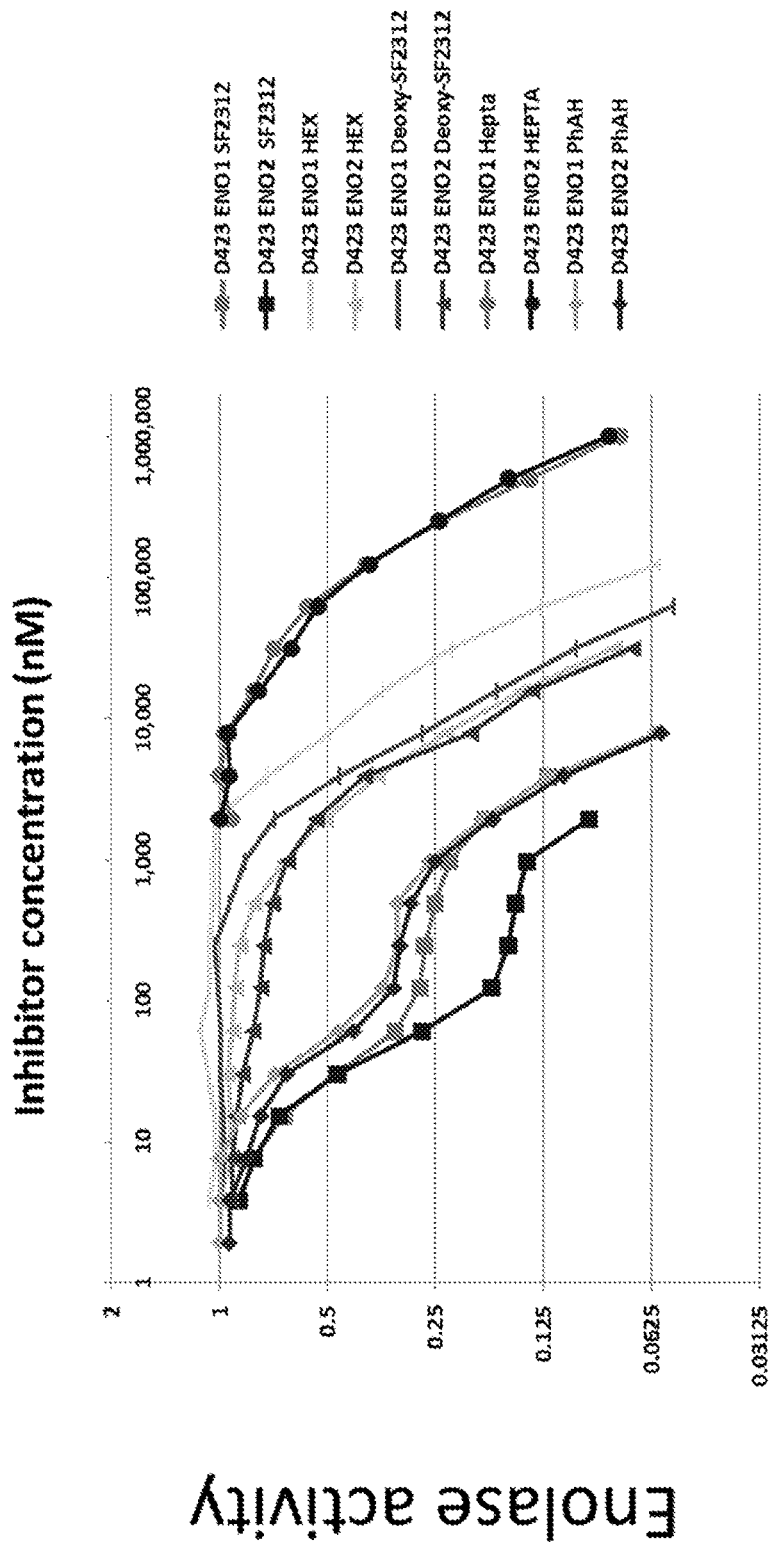
FIG. 1 shows enolase enzymatic activity as measured spectrofluorimetrically in vitro following the conversion of 2-PG to PEP by human ENO1 and ENO2. Human ENO1 and ENO2 were overexpressed in the human D423 cell line and used for enzymatic assays. Inhibitors (PhAH, SF2312 and DeoxySF2312, Hex, Hepta and Fosmidomycin) were incubated with the enzyme prior to addition of 5 mM 2-PG substrate. Enzymatic activity was normalized to that in the absence of the inhibitor (set to 1) and plotted as function of inhibitor concentration.

Example 4—Biological Activity of Compounds and Inhibition of the Enolase Activity As can be seen in FIG. 1, SF2312 was more potent than PhAH against ENO2. The inhibition exhibited a bi-phasic pattern, whereby the main difference between ENO2 and ENO2 occurred after IC$_{50}$ was reached. The hydroxyl group of SF2312 may play a role in this difference as deoxy-SF2312 shows minimal difference in inhibitory effectiveness between ENO2 and ENO1. In dehydroxy-variants of SF2312, increasing the ring size progressively decreased potency but even the seven-membered inhibitor retained inhibitory activity. The six-membered ring, Hex, also showed approximately 6-fold greater activity against ENO2 versus ENO1. The fosmidomycin, which has the same empirical formula as Hex, was found to be completely inactive as an enolase inhibitor, even concentrations of >10,000,000 nM. The effect of SF2312, deoxy-SF2312 and PhAH on the enzymatic activity of enolase in vitro was also determined using an indirect, Pyruvate kinase/Lactate Dehydrogenase linked assay (NADH fluorescence) or directly by measuring the appearance of PEP (absorption at 240 nm). Enolase inhibitory activity was measured in lysates of mouse organs, human cancer cell lines overexpressing ENO1 and ENO2 as well as purified human ENO1 and ENO2 expressed in *E. coli* (Table 3). Depending on the source, the IC$_{50}$ of SF2312 ranged from 10 nM to 50 nM and in side-by-side comparisons was more potent than PhAH (FIG. 23). SF2312 showed similar IC$_{50}$ towards ENO1 and ENO2, but interestingly, IC$_{75}$ and upwards were much lower for ENO2 than for ENO1 (FIG. 23). At IC$_{50}$, SF2312 exhibited non-competitive kinetics with respect to substrate 2-PGA (FIG. 24). The IC$_{50}$ of SF2312 is about 50% lower than that of PhAH and the IC$_{75}$ is much lower still (FIG. 23) in the isolated enzymatic assay. The shape of the inhibitor titration curve is unusual. Without wishing to be bound by any theory, it is believed that the shape of the inhibitor titration curve may be related to the anti-cooperative binding behavior of the enolase dimer, whereby binding of inhibitor to one active site in the dimer decreases the affinity for inhibitor binding at the other active site (Qin, et al., 2012). A number of natural phosphonates and phosphonate substrate analogues were tested for enolase inhibitory activity. The phosphonate antibiotics Fosfomycin and Fosmidomycin as well as the antiviral Foscarnet, showed no enolase inhibitory activity even at 10 mM (FIG. 29) despite having structural similarity to SF2312. Additionally, the last intermediate and the hydrogenated product of 15 were devoid of Enolase inhibitory activity at up to 1 mM.

TABLE 3

| X-ray diffraction data collection and refinement statistics for Inhibitor Bound Enolase 2 | | | | |
|---|---|---|---|---|
| | Enolase 2:PhaH (PDB 4ZA0) | Enolase 2:SF2312 (PDB 4ZCW) | Enolase 2:mSF2312 (PDB 5EU9) | Enolase 2:Hex (PDB 5IDZ) |
| Data Collection | | | | |
| Wavelength (Å) | 1.116 | 1.116 | 1.116 | 1.116 |
| Space group | P2$_1$2$_1$2$_1$ | P2$_1$2$_1$2$_1$ | P 1 2$_1$ 1 | P2$_1$2$_1$2$_1$ |

TABLE 3-continued

X-ray diffraction data collection and refinement statistics for Inhibitor Bound Enolase 2

|  | Enolase 2:PhAH (PDB 4ZA0) | Enolase 2:SF2312 (PDB 4ZCW) | Enolase 2:mSF2312 (PDB 5EU9) | Enolase 2:Hex (PDB 5IDZ) |
|---|---|---|---|---|
| Cell dimensions |  |  |  |  |
| a, b, c (Å) | 67.8, 108.7, 112.2 | 68.3, 109.5, 117.3 | 119.3, 110.3, 136.9 | 68.1, 108.7. 116.5 |
| α, β, γ (°) | 90, 90, 90 | 90, 90, 90 | 90, 90, 90 | 90. 90, 90 |
| No. of unique reflections | 37271 | 60867 | 217213 | 26400 |
| Resolution (Å) | 67.8-2.31 (2.39-2.31) | 80.0-1.99 (2.04-1.99) | 89.9-2.05 (2.12-2.05) | 79.5-2.63 (2.75-2.63) |
| Rmerge (all $I^+$ and $I^-$) | 0.220 (0.840) | 0.092 (0.449) | 0.074 (0.304) | 0.089 (0.314) |
| I/σI | 10.9 (3.1) | 13.3 (3.8) | 6.4 (2.1) | 15.6 (5.1) |
| Completeness (%) | 100.0 (100.0) | 100.0 (99.6) | 97.4 (93.7) | 99.9 (99.3) |
| Redundancy | 12.4 (11.4) | 7.0 (6.6) | 2.0 (2.0) | 6.9 (6.6) |
| Refinement |  |  |  |  |
| Resolution (Å) | 58.0-2.31 | 51.7-1.99 | 89.9-2.05 | 54.4-2.63 |
| σF | 1.34 | 1.35 | 1.34 | 1.34 |
| No. of reflections | 37211 | 60788 | 217011 | 26345 |
| $R_{work}/R_{free}$ | 0.164/0.204 | 0.157/0.202 | 0.154/0.192 | 0.162/0.218 |
| Wilson B | 18.4 | 21.2 | 18.2 | 35.4 |
| No. of atoms |  |  |  |  |
| Protein | 6629 | 6685 | 26693 | 6694 |
| Ligand | 18 | 24 | 164 | 44 |
| $Mg^{2+}$ | 4 | 4 | 18 | 2 |
| Water | 488 | 593 | 2238 | 154 |
| Average B-factors (Å$^2$) |  |  |  |  |
| Protein | 19.6 | 24.6 | 20.8 | 35.8 |
| Ligand | 13.5 | 19.9 | 23.9 | 39.0 |
| $Mg^{2+}$ | 4.9 | 11.9 | 17.5 | 28.0 |
| Water | 25.3 | 32.5 | 28.7 | 31.1 |
| r.m.s.d. |  |  |  |  |
| Bond lengths (Å) | 0.009 | 0.018 | 0.008 | 0.004 |
| Bond angles (°) | 0.638 | 1.396 | 1.04 | 0.692 |

Values in parentheses are for the highest resolution shell.

In some cases, the inhibitory potency of SF2312 against enolase was influenced by whether the inhibitor or the substrate was first added in the assay system. Pre-incubation of PhAH (diamonds) or SF2312 (squares) with either human ENO1 or ENO2 before the addition of the substrate 2-PG resulted in inhibition of enzymatic activity ($IC_{50}$~20 nM); inhibition of ENO2 with SF2312 was more profound and more durable for than ENO1 ($IC_{50}$ for SF2312 is 10-times lower for ENO2 than ENO1) while PhAH caused more or less equal inhibition of ENO1 and ENO2 as can be seen in FIG. 2A. Concomitant addition of SF2312/PhAH and 2-PG resulted in weaker inhibition than if the inhibitors were pre-incubated before addition of substrate as shown in FIG. 2B; this behavior was described previously for PhAH inhibition of yeast enolase (Anderson, et al., 1984), i.e. PhAH acts as a "slow" $k_{on}$ inhibitor. SF2312 was less potent than PhAH when assayed under these conditions, indicating that it shows an even slower $k_{on}$ than PhAH. Since SF2312 is more potent than PhAH when pre-incubated prior to addition of substrate, this observation indicated that SF2312 has a much slower $k_{off}$ than PhAH and that the increased inhibitory potency of SF2312 against ENO2 over ENO1 is due to differences in $k_{off}$ rather than $k_{on}$. The difference between ENO2 and ENO1 was more pronounced for the off-rate, as the differences between the isozymes were pronounced when the inhibitors were pre-incubated with the enzyme (FIG. 23 and FIG. 25A), but were not different when the substrate was added prior to the inhibitors (FIG. 25B). Deoxy-SF2312 was much less potent as an enolase inhibitor, with an $IC_{50}$ of ~2000 nM, which was similar for ENO1 and ENO2. Unlike SF2312, deoxy-SF2312 showed clear competitive kinetics with respect to the substrate 2-PGA (FIG. 24). Without wishing to be bound by any theory, it is believed that the difference in activity between SF2312 and deoxy-SF2312 may be attributed to the hydroxyl group of SF2312, as deoxy-SF2312 shows minimal difference in inhibitory effectiveness between ENO2 and ENO1. SF2312, like PhAH, bound to the di-Mg form of the enzyme. ENO2 showed higher affinity for the second Magnesium ion ($Mg_b$) and overall much greater stability than ENO1 (Marangos and Schmechel, 1980; Marango, et al., 1978; Marango, et al., 1979). Since the $Mg_b$ must first dissociate before the inhibitor can come out of the active site, without wishing to be bound by any theory, the higher affinity of ENO2 for $Mg_b$ may explain the slower $k_{off}$ for SF2312 in ENO2 versus ENO1. Without wishing to be bound by any theory, it is believed that one difference in binding of SF2312 to enolase versus binding of PhAH is due to the additional hydrogen bonds with the active site residues which are involved in the dehydration reaction.

As an additional test of SF2312 binding to the enolase protein, ligand-induced thermal shift assays were performed on cell lysates under the same conditions as we performed the enzymatic assay (Martinez Molina, et al., 2013). The principal of the assay is that heat-denatured proteins precipitate out of solution when their hydrophobic core is exposed. As a result, heat denatured proteins disappear from the lysate after centrifugation, whereas native properly folded proteins remain in solution. The levels of specific proteins in the supernatant, such as non-denatured proteins, are followed by immunoblotting as a function of increasing temperature. Incubation of cell lysates with 1 μM of SF2312, shifted the melting temperature of ENO2 from ~67.5° C. to >75° C., which represents a >7.5° C. shift in the thermal denaturation of ENO2 (FIG. 26). In contrast, the same concentration of PhAH led to a much more modest ~2.5° C. stabilization of the protein. This stabilization issued by SF2312 could be related to hydrogen bonds formed between the 5-OH and the active site (FIG. 27), which may help lock the enzyme in the tighter configuration (de A. S. Navarro, et al., 2007; Brewer and Wampler, 2001; Zhang, et al., 1997). Similar results were obtained for ENO1, except that the protein was overall less thermally stable than ENO2 (Marangos, et al., 1978). Importantly, neither PhAH nor SF2312 had any effect on the thermal stability of the internal controls, Vinculin or Triosephosphate isomerase (FIG. 26). As a further validation, the thermal shift assay was repeated using recombinant human ENO2 protein expressed in *E. coli*. These recombinant proteins were also used in the X-ray crystallography experiments. The results were consistent with the results obtained in cell lysates, with SF2312 causing a ~15° C. stabilization of the protein (FIG. 28), which was much greater than that induced by PhAH (~5° C.).

Figure 3:
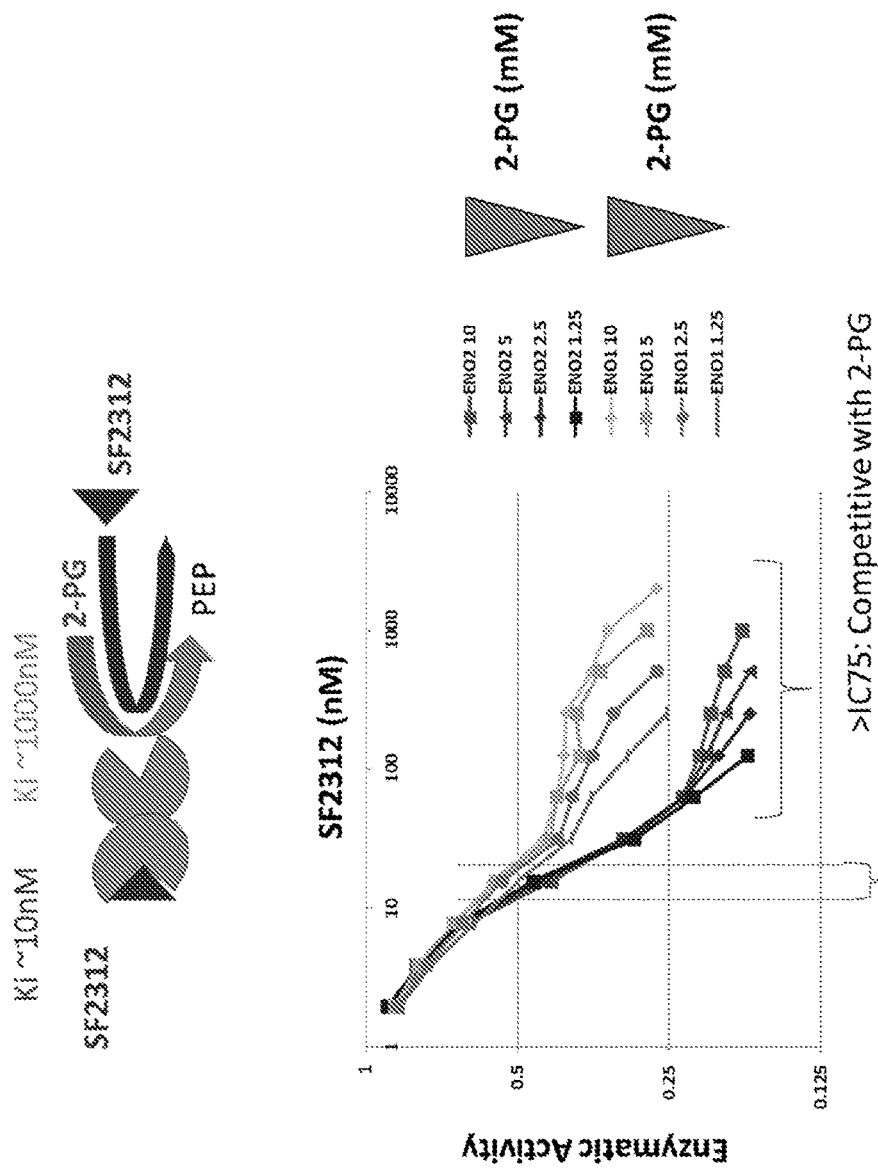
FIG. 3 shows the Michealis-Menten kinetic analysis of SF2312 with ENO1 and ENO2 using various concentrations of the substrate of ENO1 and ENO2, 2-phosphoglycerate. Michealis-Menten kinetic analysis of SF2312 with ENO1 and ENO2, were titrated in the substrate, 2-PG (1.25, 2.5, 5, 10 mM curves being shown for ENO1 and ENO2, as indicated). SF2312 showed highly unusual mixed substrate-dependence inhibition kinetics. Specifically, at 50% inhibition ($IC_{50}$) of enolase activity, SF2312 behaved as a classical non-competitive inhibitor, being essentially unaffected by the concentration of substrate (2-PG). However, at inhibition higher than 75% of initial activity ($IC_{75}$), there was a clear dependence on the concentration of substrate. While ENO1 and ENO2 show essentially the same $IC_{50}$ for SF2312, the compounds differed substantially in $IC_{75}$ and how 2-PG competes with the inhibitor, with the inhibitor being much more difficult to be competed off with substrate in ENO2 than in ENO1.

Michealis-Menten kinetic analysis of SF2312 with ENO1 and ENO2 was performed, titrating the substrate, 2-PG (1.25, 2.5, 5, 10 mM curves being shown for ENO1 and ENO2, as indicated) as shown in FIG. 3. SF2312 showed highly unusual mixed substrate-dependence inhibition kinetics. Specifically, at 50% inhibition ($IC_{50}$) of enolase activity, SF2312 behaved as a classical non-competitive inhibitor, being essentially unaffected by the concentration of substrate (2-PG). However, at inhibition higher than 75% of initial activity ($IC_{75}$), there was a clear dependence on the concentration of substrate. This mixed inhibition is highly unusual and may be related to the known interactions between the monomers of the enolase dimer, whereby binding of one inhibitor molecule to one dimer, alters the conformation and binding affinity of the other dimer. While ENO1 and ENO2 showed essentially the same $IC_{50}$ for SF2312, the two enzymes differed substantially in $IC_{75}$ and how 2-PG competes with the inhibitor, with the inhibitor being much more difficult to be competed off with substrate in ENO2 than in ENO1.

Figure 4A:
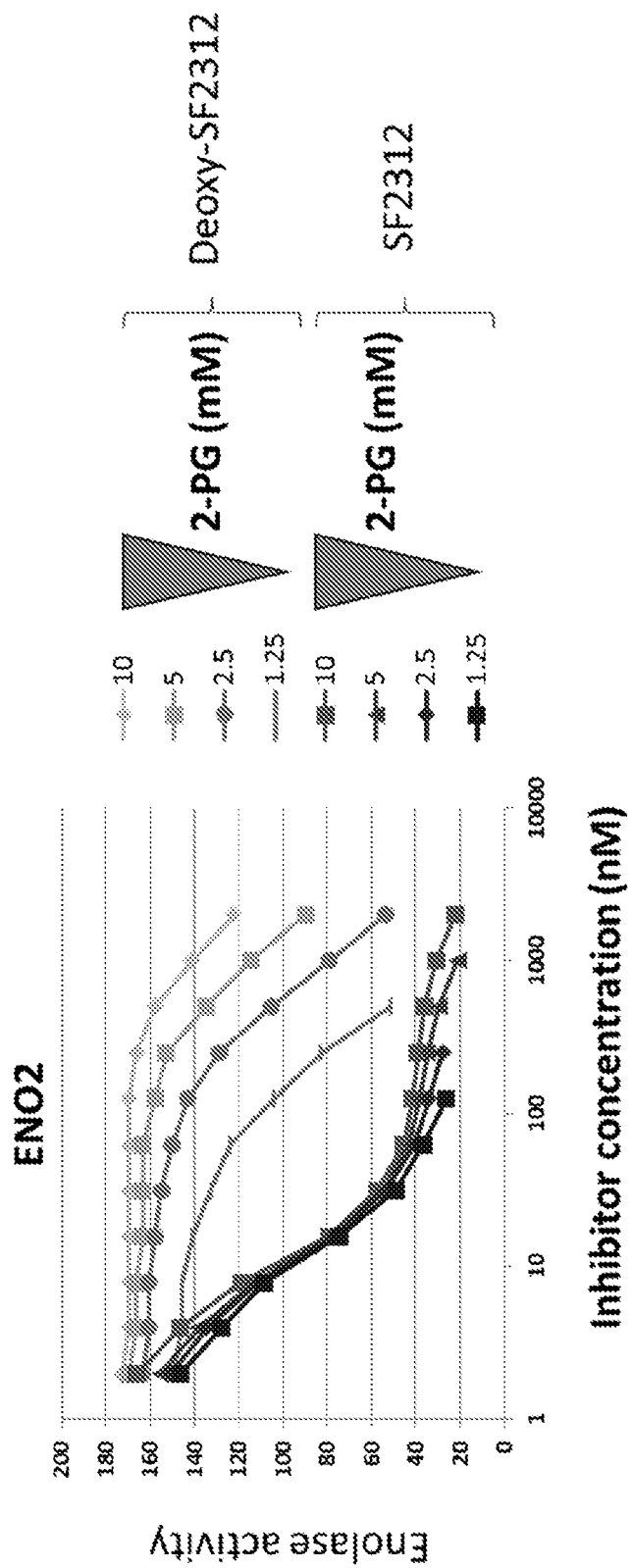
FIGS. 4A-4D show the removal of the 5-OH group results in an inhibitor with substantially higher $IC_{50}$. In addition, while SF2312 shows mixed inhibition kinetics, deoxy-SF2312 and its larger ringed derivatives all show typical competitive Michaelis-Menten kinetics. The enzymatic activity of SF2312 and deoxy-SF2312 is shown as a function of concentration of the compound in FIG. 4A. Lineweaver-Burke for ENO1 (FIG. 4B) and for ENO2 (FIG. 4C) and the Lineweaver-Burke plots were used to derive slopes used in the double reciprocal (Dixon) plot and Dixon plots (FIG. 4D) used to calculate the $K_i$ for the inhibitors and are shown here for Hex. Hex displayed a considerably lower $K_i$ for ENO2 than ENO1.
Figure 4B:
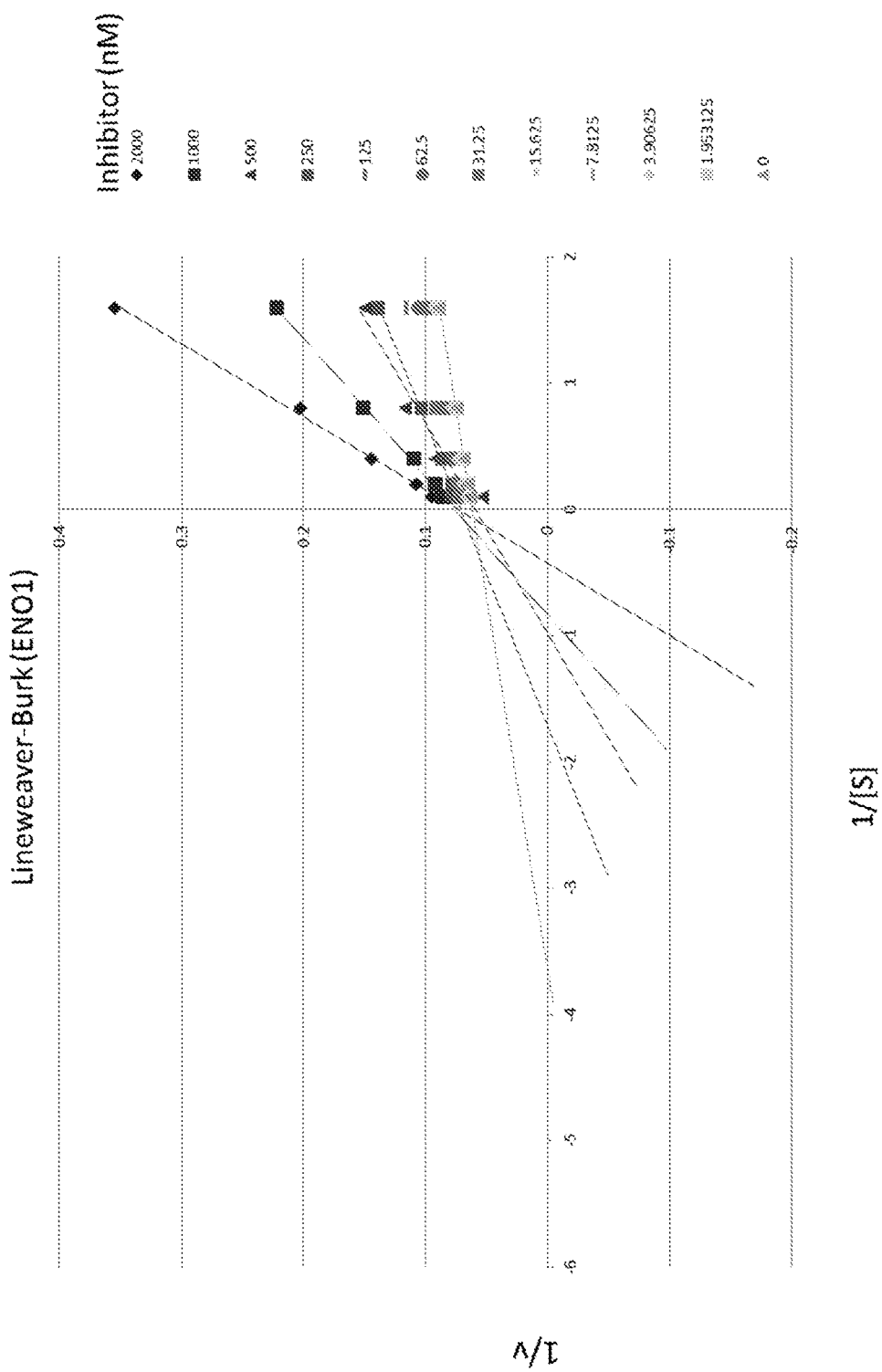
Figure 4C:
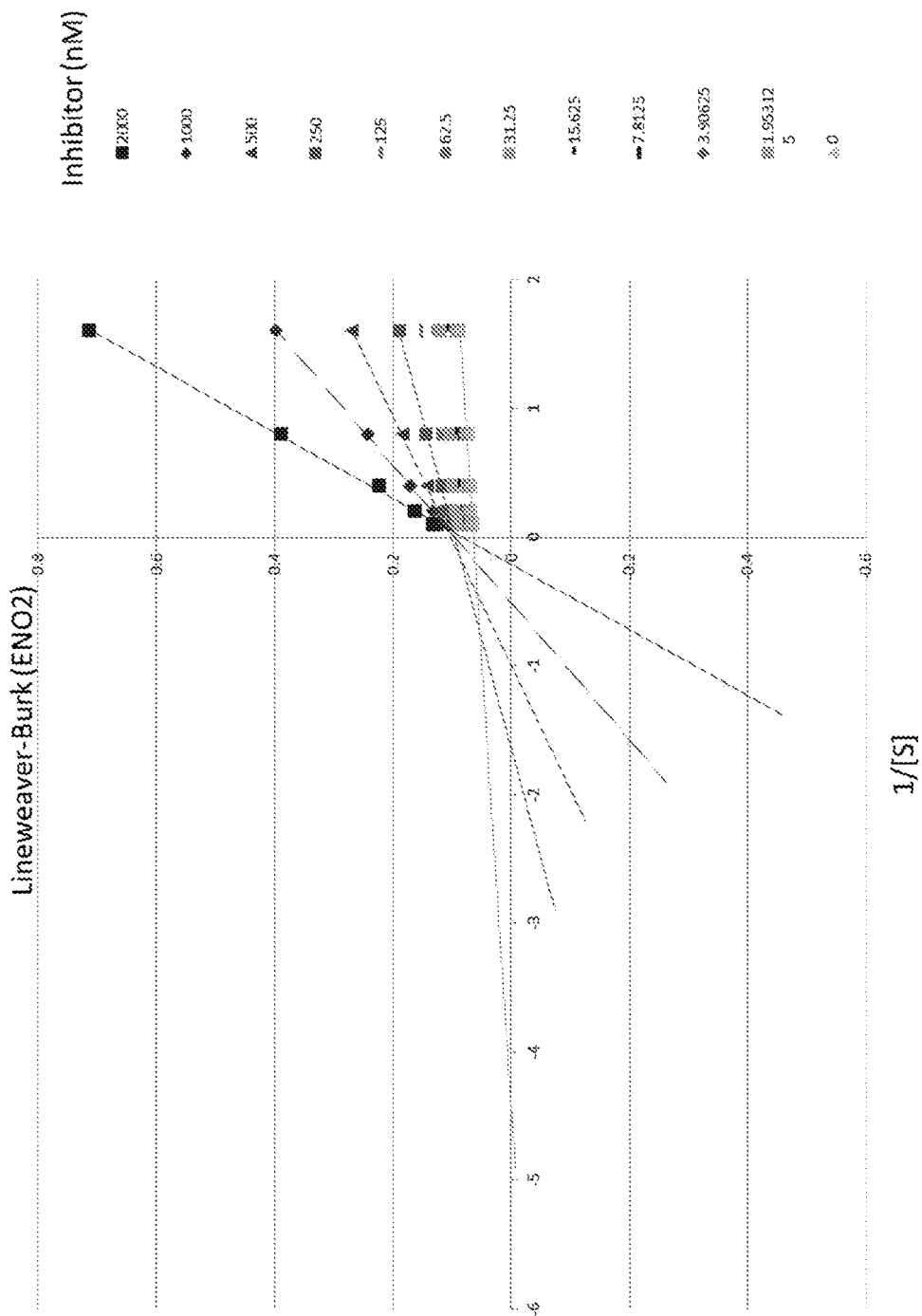
Figure 4D:
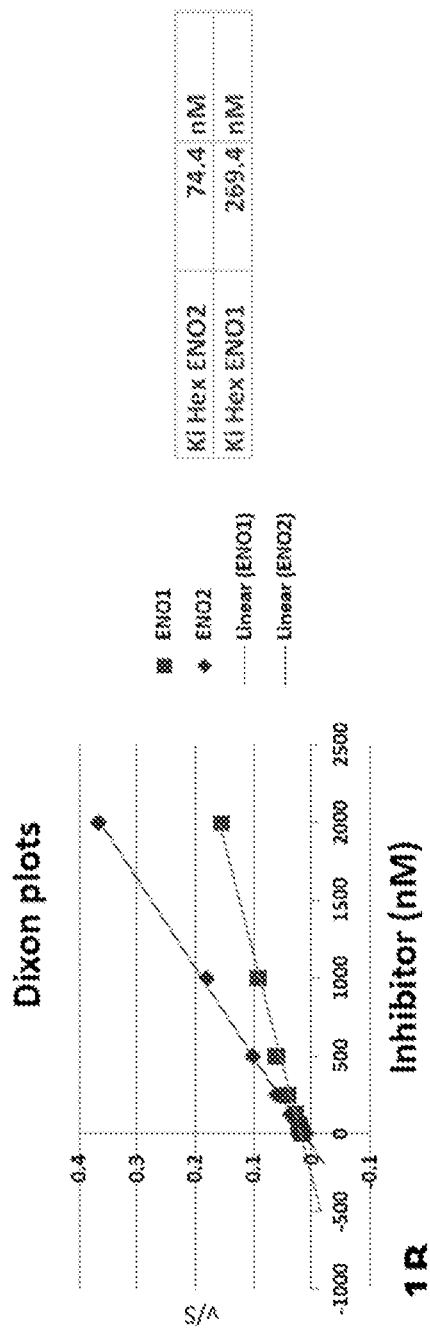

Removal of the 5-OH group results in an inhibitor with substantially higher $IC_{50}$ which is shown in FIG. 4A. In addition, while SF2312 shows mixed inhibition kinetics, deoxy-SF2312 and its larger ringed derivatives all show typical competitive Michaelis-Menten kinetics. As such, the relative difference in $IC_{50}$ between SF2312 and deoxy-SF2312 was greater with greater concentrations of substrate 2-PG. In FIGS. 4B & 4C, Lineweaver-Burke plots were used to derive slopes used in the double reciprocal (Dixon) plot (FIG. 4D), the slope and intercept of which were used to calculate the $K_i$ (shown in the figure for Hex). Hex displayed a considerably lower $K_i$ for ENO2 than ENO1.

Figures 5A, 5B:
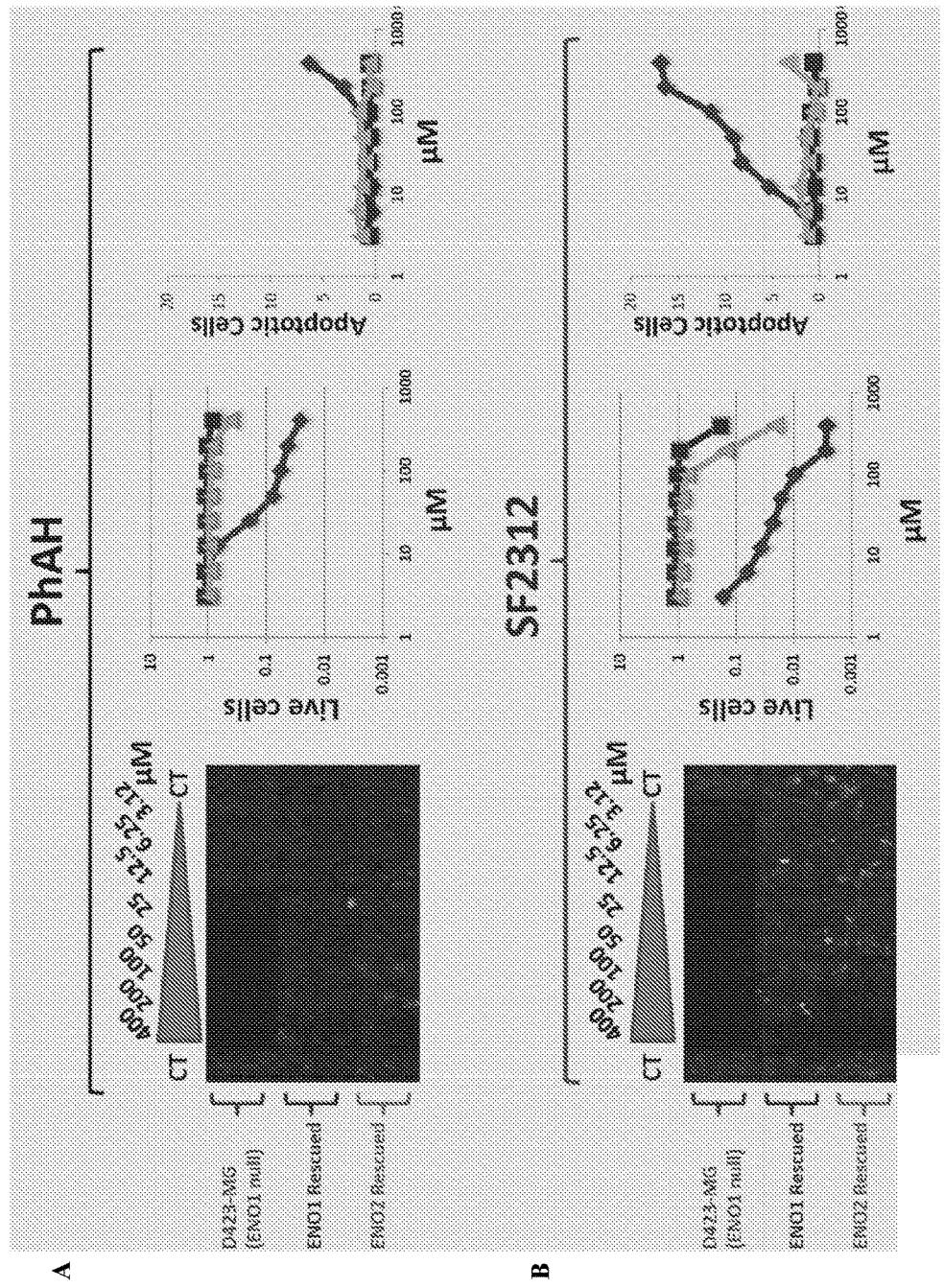
FIGS. 5A & 5B shows a head to head comparison of PhAH and SF2312 in killing ENO1 deleted glioma cells. SF2312 was compared head-to-head with PhAH for its effect on cell proliferation (total cell number, Hoechst 33342) and apoptosis (propidium iodide positive cells) after 2-weeks of treatment. Both PhAH and SF2312 show preferential toxicity to ENO1 deleted (light gray) as compared to isogenic ENO1-rescued (black symbols). However, SF2312 (FIG. 5B) was shown to be about 6 times more potent than PhAH (FIG. 5A) at inhibiting the growth of ENO1-deleted cells (light gray) and 10 times more potent at inducing cell death. Re-expression of ENO2 restored resistance to enolase inhibitor (medium gray), but residual sensitivity to SF2312 was at least 4-times greater than that of PhAH, consistent with SF2312 showing preference for ENO2 over ENO1.

PhAH had been shown to selectively inhibit the proliferation of D423 ENO1-deleted glioma cells to a much greater extent than isogenic rescued controls (Muller, et al., 2012). SF2312 was compared head-to-head with PhAH for its effect on cell proliferation (total cell number, Hoechst 33342) and apoptosis (propidium iodide positive cells) after 2-weeks of treatment and is shown in FIGS. 5A & 5B. SF2312 was approximately 8-fold more potent at inhibiting the proliferation of ENO1-deleted glioma cells as compared to PhAH (FIG. 30). The effect on cell death induction was more accentuated: SF2312 was at least 16-fold more potent than PhAH at inducing cell death in ENO1-deleted glioma cells (FIG. 30). SF2312 may be up to 4-fold more potent than these data would suggest as the X-ray structure suggests only one isomer of SF2312 out of a mixture of four is likely to be active. The sensitivity to SF2312 of ENO1-deleted glioma cells was fully reversed by ectopic re-expression of ENO1 and to a lesser extent, by overexpression of ENO2 expression (FIG. 30), a finding consistent with SF2312 having a preference for inhibiting ENO2 (FIG. 23; FIG. 24), at least above $IC_{75}$. SF2312 was also more potent than PhAH in another ENO1-deleted glioma cell line, Gli56 (FIG. 31). SF2312 was up 128-fold more potent at inhibiting the proliferation of Gli56 ENO1-deleted glioma cells as compared to ENO1-intact glioma lines (FIG. 31). Without wishing to be bound by any theory, it is believed that the increase in selective toxicity to ENO1-deleted glioma cells derives from the inhibitory preference that SF2312 shows for ENO2 over ENO1 (FIG. 23). One reason for increased sensitivity of ENO1-deleted cells to enolase inhibitors is that these cells only retain 10% of the normal enzymatic activity as ENO1 being the major isoform, such that even low levels of a pan-enolase inhibitor are sufficient to inhibit the remaining enzymatic activity below toxic threshold (FIG. 38, FIG. 36, and FIG. 39) (Muller, et al., 2012). As such, restoration of ENO1 expression or overexpression of ENO2 is able to restore resistance to PhAH and SF2312 (FIG. 30) (Muller, et al., 2012). Based upon these results, ENO1 is more effective than ENO2 at restoring resistance to SF2312 (FIG. 30), consistent with preference of that inhibitor for ENO2. Thus, while not strictly required for selective killing, an inhibitor with preference for ENO2 over ENO1 will result in even further selectivity to ENO1-deleted cells as its toxicity to ENO1-intact cells would be reduced. While the $IC_{50}$ of SF2312 did not markedly differ between ENO1 and ENO2 in the in vitro enzymatic assay (FIG. 23), the $IC_{75}$ of SF2312 was lower for ENO2. Without wishing to be bound by any theory, it is believed that the data indicate that the inhibitor-enzyme complex is more stable for ENO2 than for ENO1.

Figure 6A:
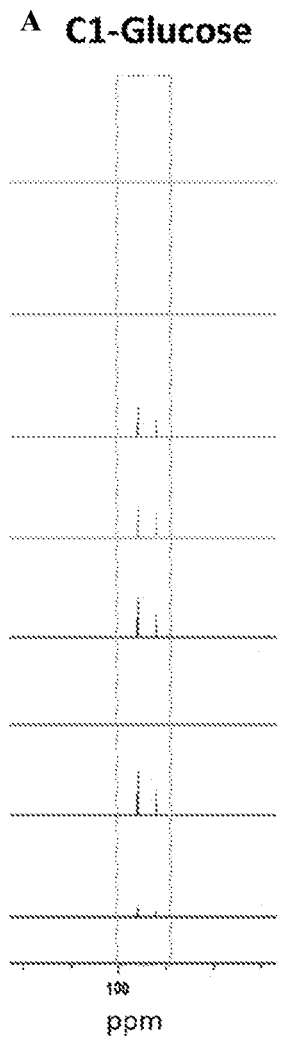
FIGS. 6A-6C show the quantification of intermediates and products through $^{13}C$ NMR after treatment of cells with inhibitors PhAH and SF2312. Metabolic tracing using $^{13}C$ NMR with $^{13}C$-glucose singly labeled at carbon atom 1 (C-1) was performed in cell lines homozygously deleted or genomically intact for ENO1 in the presence or absence of 10 µM SF2312. Media was collected after four days, and metabolites quantified by NMR. In the ENO1 deleted cell lines (Gli56, D423), SF2312 treatment caused a dramatic decrease in the conversions of $^{13}C$-1 glucose to $^{13}C$-3 lactate, indicating an interruption of flow through glycolysis. Similar the interruption of the production of $^{13}C$-3 glycerate also highlights the interruption in glycolysis (FIG. 6C).
Figure 6B:
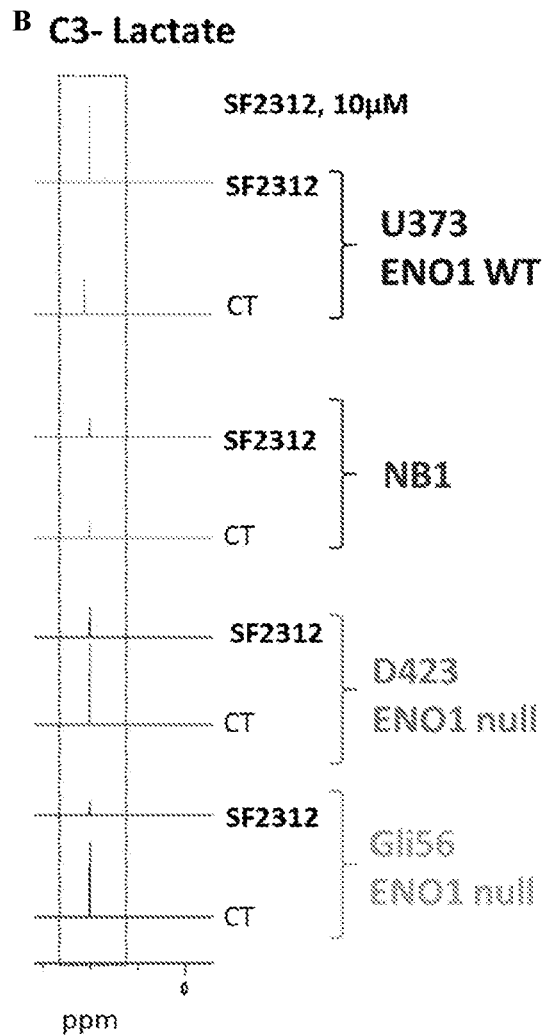
Figure 6C:
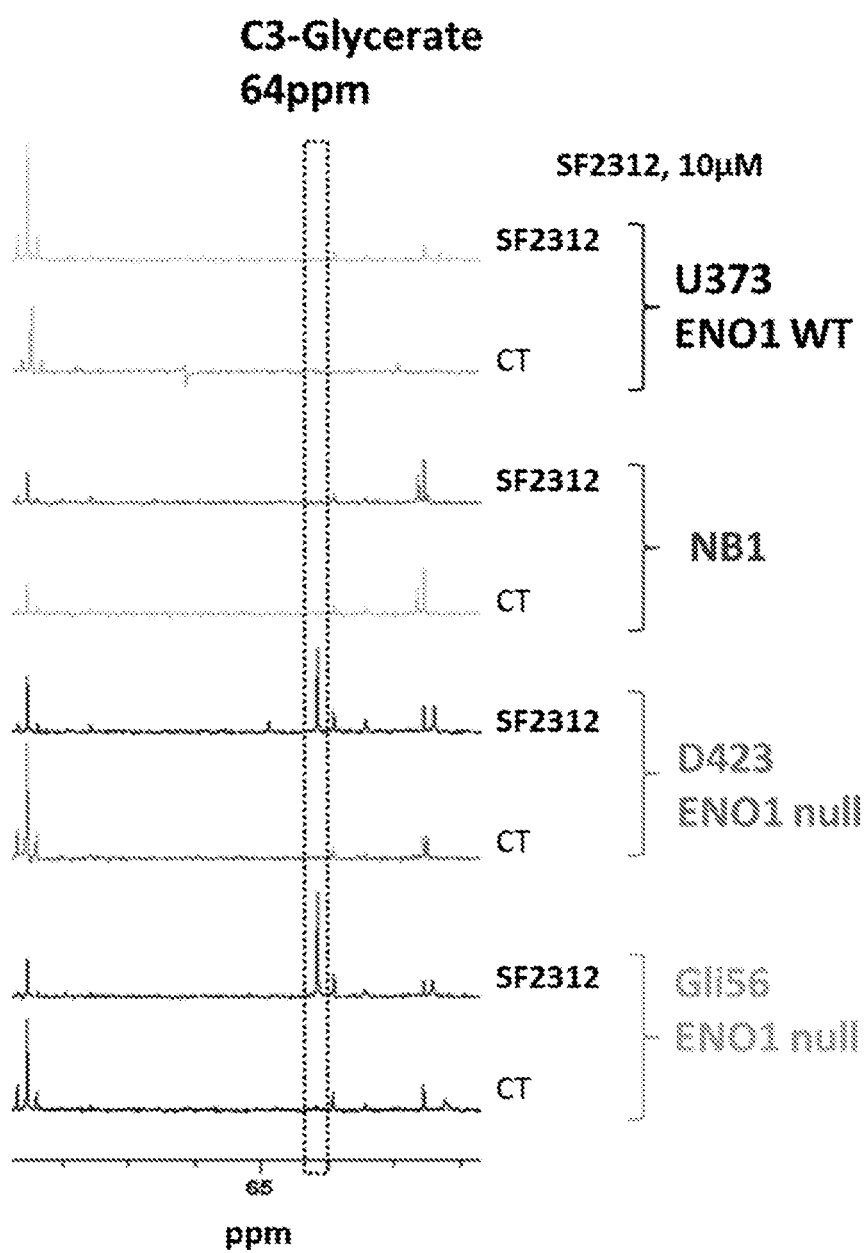

Research has shown that PhAH and shRNA against ENO2 can selectively inhibit glycolysis and lead to a build-up of intermediates upstream of blocked enolase in ENO1-deleted glioma cells (Muller, et al., 2012; US 2014/0378529; WO 2013/0909732). In FIGS. 6A & 6B, metabolic tracing using $^{13}C$ NMR with $^{13}C$-glucose singly labeled at carbon atom 1 (C-1) was performed in cell lines homozygously deleted or genomically intact for ENO1 in the presence or absence of 10 μM SF2312. Media was collected after four days, and metabolites quantified by NMR. In the ENO1 deleted cell lines (Gli56, D423), SF2312 treatment caused a dramatic decrease in the conversions of $^{13}C$-1 glucose to $^{13}C$-3 lactate, indicating an interruption of flow through glycolysis. SF2312 dose-dependently reduced the conversion of $^{13}C$ glucose to $^{13}C$ lactate in a manner selective for ENO1-deleted over ENO1-rescued or otherwise ENO1-intact glioma cells (FIG. 32; FIG. 33); this held true regardless of whether $^{13}C$-1 (FIG. 32; FIG. 33) or $^{13}C$ uniformly labeled glucose was employed (FIG. 34). Similar trends were observed with PhAH, but of more modest magnitude. Supporting that SF2312 treatment caused this interruption at the enolase step, there was a profound accumulation of glycerate shown in FIG. 6C when the residual enolase in ENO1 deleted cell is inhibited by shRNA against ENO2 or 25 μM of PhAH (US 2014/0378529; WO 2013/0909732).

ATP levels and cell death were measured as a function of time and concentration of SF2312 and PhAH in ENO1-deleted and isogenically rescued controls (FIGS. 35 & 36). As early as 8 hours after initiating of treatment, both PhAH and SF2312 were found to dose-dependently decreased ATP levels in ENO1-deleted but not ENO1-rescued glioma cells (FIG. 35). SF2312 was ~8-fold more potent than PhAH, with concentration of SF2312 as low as 12.5 µM reducing ATP levels by >40% in ENO1-deleted cells while concentrations of PhAH in excess of 100 µM were required to achieve the same level of ATP depletion. ATP alterations were not caused by cell death or changes in cell numbers, as these parameters did not change until 24 hours of treatment (FIG. 36). In a related set of experiments, SF2312 (as well as PhAH to a lesser extent) treatment of ENO1-deleted cells was also found to lead to a dramatic decrease of the ratio of phosphocreatine to creatine (FIG. 37B), indicating a severe depletion of high-energy phosphate reserve fully concordant with the depletion of ATP.

Mass spectroscopy measurements were performed of the levels of 3-PGA (2-PGA is below detection limit) and PEP, the metabolites immediately upstream and downstream of the enolase reaction in response to SF2312 in both ENO1-intact and ENO1-deleted glioma cells (FIG. 37A). Consistent with specific inhibition of enolase, a dramatic increase in the ratio of 3-PGA/PEP was observed in response to SF2312 treatment (FIG. 37A); while both ENO1-deleted and ENO1-rescued cells experienced an elevation in the 3-PGA/PEP ratio, this ratio was higher in ENO1-deleted cells, as compared to isogenic rescued controls, consistent with the ~90% decreased enolase activity in deleted versus rescued glioma cells (FIGS. 38-40).

Figures 32A, 32B, 32C, 32D:
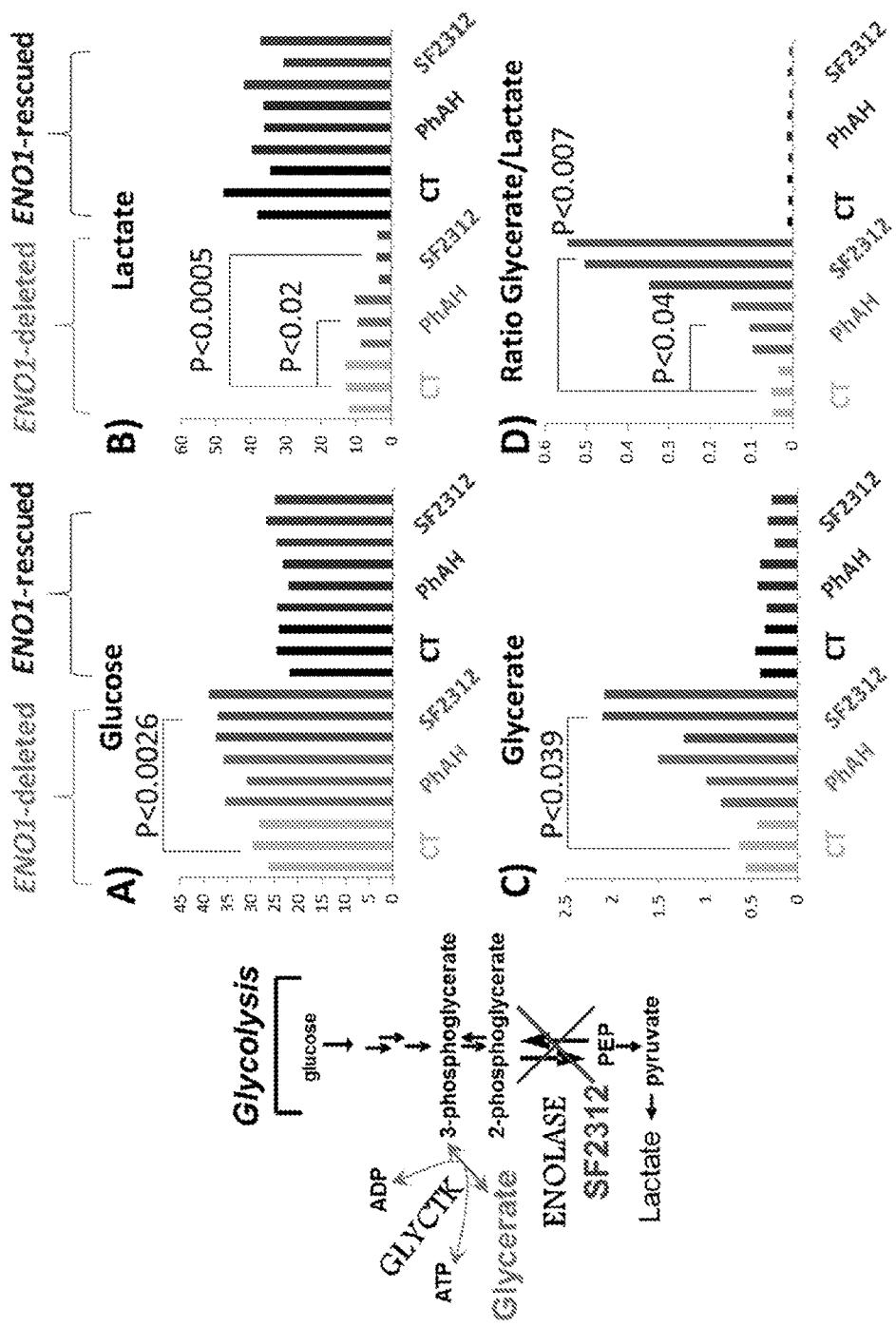

$^{13}$C-1 glucose tracing by NMR treatment was performed with a concentration of SF2312 (10 µM) that is non-toxic to ENO1-intact glioma cells for four days, led to profound inhibition of glucose consumption (isomeric peaks at 97 and 93 ppm) and lactate production (single peak at 20 ppm) in the media of D423 and Gli56 ENO1 deleted but not ENO1-intact glioma cells (FIG. 33). At the same time, a single peak at 64 ppm became visible in the D423 and Gli56 ENO1-deleted cells treated with SF2312. The most likely origin of this peak is the C-3 atom glycerate, which has a reported $^{13}$C peak of 64 ppm (Spectral Database of Organic Compounds, SDBS No. 18695) and is the atom on which the $^{13}$C label derived from the C-1 atom on glucose is expected. Mass spec based metabolomics demonstrated that glycerate accumulates both intracellularly and in media in response to enolase inhibition by pharmacological (PhAH) as well as genetic (shRNA against ENO2) means in D423 ENO1-deleted cells (WO 2013/090732 or US 2012/069767). Glycerate likely forms in response to enolase inhibition as 2-PGA or 3-PGA accumulate and (the substrates of the enzyme) spontaneously hydrolyze, or alternatively, are dephosphorylated by the action of glycerate kinase (GLYCTK, FIG. 41). These experiments were repeated with D423 ENO1-deleted and isogenic ENO1-rescued control glioma cells with both PhAH and SF2312 (FIGS. 32C & 32D). First, SF2312 treatment was found to (and to a lesser extent, PhAH) dramatically increase conversion of $^{13}$C-glucose to $^{13}$C-glycerate (FIG. 32C). This effect is especially noticeable when expressed as a ratio of $^{13}$C-glycerate to $^{13}$C-lactate, metabolites upstream and downstream of the enolase reaction, respectively (FIG. 32D). Importantly, the production of glycerate was completely abrogated by restoration of ENO1 (D423 ENO1 in FIG. 32), showing strict dependence on deleted ENO1.

Finally, thermal shift assays were utilized to demonstrate direct binding of SF2312 and PhAH to enolase 2, in the setting of intact glioma cells (Martinez Molina, et al., 2013). To facilitate this assay, glioma cells overexpressing ENO2 were utilized (D423 ENO2); as ENO1-deleted cells are too easily killed by inhibitor treatments. Similar to the results obtained in cell lysates, in the absence of inhibitors, ENO2 experienced thermal denaturation in intact glioma cells at ~65° C. (FIG. 42). Treatment with 100 µM of SF2312 resulted in a shift of the thermal melting curve of ~15° C., while the treatment with the same concentration of PhAH resulted in a much more modest shift, of ~5° C. These results are fully consistent with those obtained in cell lysates (FIG. 26) and provide direct evidence of inhibitor binding to the enzyme in the setting of intact cells.

Figures 7A, 7B:
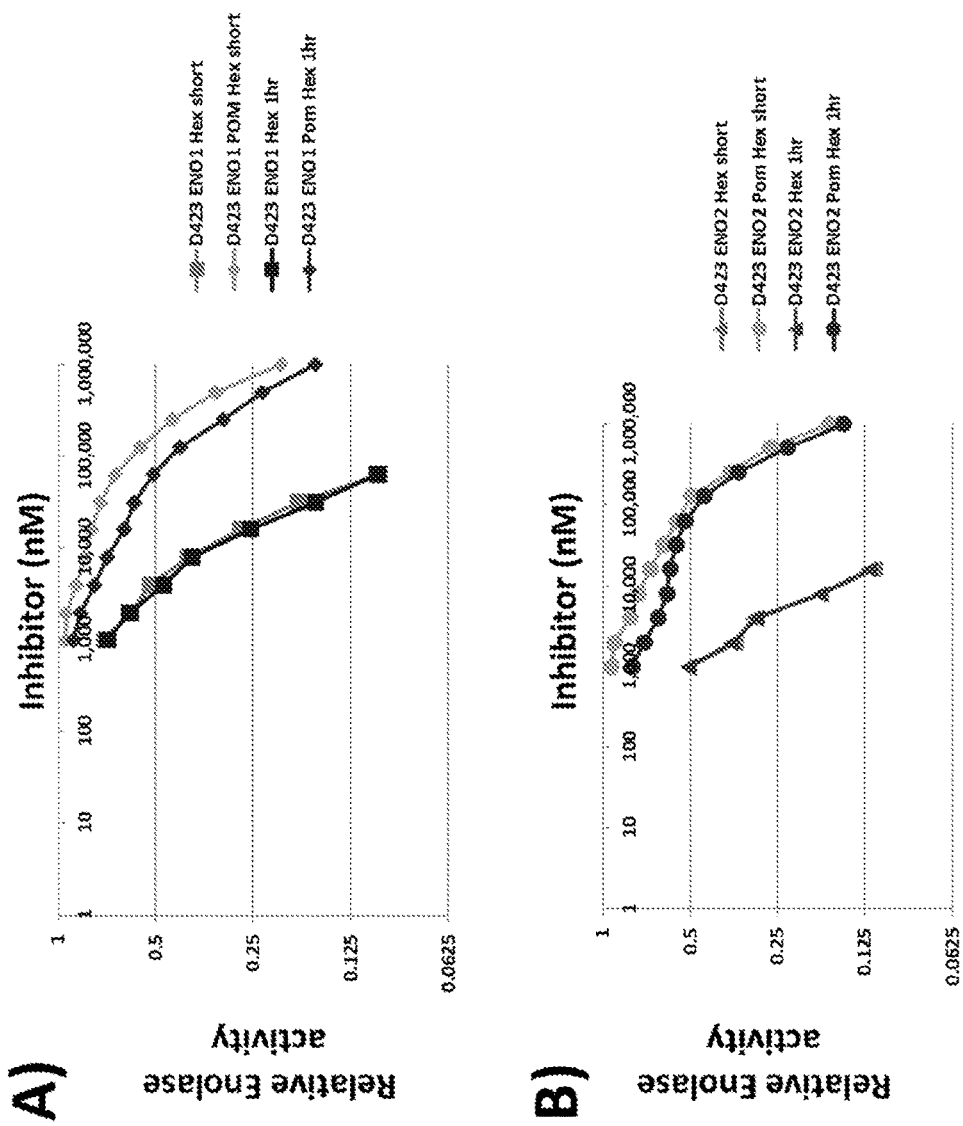
FIGS. 7A & 7B show the effect of protecting the phosphate with pivaloyloxymethyl protecting groups on its inhibition activity in ENO1 (FIG. 7A) and ENO2 (FIG. 7B). The direct inhibitory activity of Pom-Hex against ENO1 and ENO2 in comparison to its parent compound, Hex, was determined in vitro. As described in FIG. 2, the data was obtained by using human ENO1 and ENO2 that was overexpressed in the human D423 cell line and used for enzymatic assays. Inhibitors (Hex and Pom-Hex) were incubated with the enzyme prior to addition of 5 mM 2-PG substrate. Enzymatic activity was normalized to that in the absence of the inhibitor (set to 1) and plotted as function of inhibitor concentration. Pom-Hex was found to be a much weaker enolase inhibitor than its parent compound, Hex. Yet, Pom-Hex still retains some enolase inhibitory activity (~100 µM $IC_{50}$)

The direct inhibitory activity of Pom-Hex against ENO1 and ENO2 in comparison to its parent compound, Hex, was determined in vitro using the same methods as described in FIGS. 7A & 7B. In the presence of cellular esterases, the Pom-Hex compound was covered into the active parent compound, Hex. Pom-Hex was found to be a much weaker enolase inhibitor than its parent compound, Hex. Yet, Pom-Hex still retained some enolase inhibitory activity (~100 µM $IC_{50}$). However, it is difficult to rule out contaminations of <5% of unreacted Hex, therefore, it remains unclear whether the residual inhibition is in fact due to the intact Pom-Hex molecule or contaminant Hex. In one hypothesis, spontaneous hydrolysis of Pom-Hex to liberated Hex was responsible for the inhibition. However, increasing the incubation time to 1 hr, only marginally increased the inhibition by Pom-Hex, suggesting that the intact pro-drugged molecule exerted some inhibitory activity.

Several glioma cell lines, including ENO1-deleted D423-MG were tested for sensitivity to Pom-Hex under conventional growth conditions. Cell proliferation was followed using live imaging with the Incucyte (FIG. 8) or by terminal fixation and staining by crystal violet (FIG. 9). There was a clear hierarchy of sensitivity, with the normal human astrocytes being highly resistant whereas the ENO1 deleted D423 glioma cells being sensitive to even low nM levels of the inhibitor. Cell lines that were heterozygously deleted for ENO1, which has previously been shown to have intermediate sensitivity to PhAH (Muller, et al., 2012), also showed intermediate sensitivity to Pom-Hex.

To more accurately model tumors, glioma cells were grown in 3 dimensional neurosphere conditions. The surface to volume ratio of the neurosphere was considerably smaller than in convention cell culture conditions and as such, compounds with poor cell penetration such as phosphonates have considerably lower efficacy than in conventional cell culture. Thus, under these conditions, even ENO1 deleted cells were only mildly sensitive to the parental free phosphonate, Hex (FIG. 10A). However, under the same conditions, the cell permeable pro-drug, Pom-Hex, was highly toxic to ENO1 deleted glioma cells (FIG. 10B). Cell viability in spheres was monitored using 100 nM of tetramethylrhodamine, which is actively taken up by live but not dead cells.

Nude mice were injected with D423-MG glioma cells which carry the 1p36 deletion spanning ENO1. Tumors formed around 30 days post injection and growth was tracked non-invasively by T2 MRI. In the absence of treatment, tumors grew continuously, ultimately killing the animal. The tumor area (right side of the brain) was distinguished from the normal mouse brain by high contrast. Note the continuous growth (from FIGS. 11A & 11B) was observed in the absence of treatment. Intravenous injection of 10 mg/kg of Pom-Hex for 11 days (FIG. 11C) not only stopped tumor grow but completely eradicated the tumor (disappearance of high contrast area). The animal remained healthy and tumor free for at least 3 months after discontinuation of treatment (FIG. 11D).

VHL is a common event in renal clear cell carcinoma. Deletion of VHL activates the HIF pathway, suppressing respiration and rendering cancer cells highly dependent on glycolysis. As such, efforts have been made to target glycolysis to achieve selective toxicity to VHL deficient kidney cancer. As such, the enolase inhibitor Pom-Hex was tested in VHL deteted kidney cancer cell lines. In two independent VHL deleted kidney cancer cell lines, RCC4 (bottom) and 786-O (top panel), the enolase inhibitor, Pom-Hex, was 4-8 times more toxic to the VHL deleted (upper), compared to isogenic rescued controls, expressing VHL from an ectopic locus (lower panels, italics). As in FIG. 12, growth in response to increasing doses of Pom-Hex was measured by live growth imaging using the Incucyte.

The stability of Pom-SF2312 in cell culture media (DMEM with 10% fetal bovine serum) was measured by proton-decoupled $^{31}$P NMR on a Brucker 500 MHZ at the M. D. Anderson NMR core (FIG. 14). Pom-SF2312, Hemi-Pom-SF2312 and SF2312 appears doublets reflecting the cis-trans isomers. Within 12 hours, more than half of Pom-SF2312 hydrolyzed to Hemi-Pom-SF2312. However, Hemi-Pom-SF2312 did not appreciably hydrolyze to SF2312 within 24 hours.

Furthermore, POMHEX shows considerably greater stability than Pom-SF2312 in media (FIGS. 15A & 15B). 1.5 mM Pom-Hex and 1.5 mM Pom-SF2312 were dissolved in standard cell culture media (DMEM media containing 10% FBS with the addition of 10% $D_2O$ for locking of the NMR signal). Proton-decoupled $^{31}$P NMR scans were taken at repeated intervals. The experiment was performed at room temperature. While over half of Pom-SF2312 had hydrolyzed by 12 hours, it took more than 24 hours for half of the initial Pom-Hex to hydrolyze. Estimated half-lives are 8 hours for Pom-SF2312 and 36 hours for Pom-Hex. The hydrolysis did not proceed further, and neither SF2312, nor Hex, were detectable even after 72 hours of incubation.

Pom-SF2312 and Diacetyl-Pom-SF2312 are selectively toxic to ENO1-deleted glioma cells (FIGS. 16A & 16B). The x axis shows time (3 days total) plotted against confluence. The slopes represent growth rates. Flat slope indicate inhibited growth, negative slope indicate cells dying. The approximate $IC_{50}$'s for growth inhibition of ENO1 null glioma cells are <75 nM for Pom-Hex and ~150 nM for Diacetyl-Pom-SF2312. These $IC_{50}$'s are somewhat less potent than Pom-Hex, with an $IC_{50}$ of about 35 nM.

Animals (NUDE immunocompromised mice) injected intracranially with the ENO1 deleted Glioblastoma cell line, Gli56. After 30 days, tumors became readily visible by MRI (T2, the white hyperintense regions are tumor on the background grey of the normal brain). In the absence of treatment, Gli56 tumors grow continuously (Mouse #1, and Mouse #3, from Day 30 to Day 40). The treatment with Pom-SF2312 did not significantly slow tumor growth (Mouse #2), even at 4 MPK (mg/kg), which was the maximum tolerated dose (FIG. 17). However, Pom-Hex treatment not only stopped tumor growth, but actually led to a profound tumor regression, and eventual disappearance. The tumors have not recurred after discontinuation of treatment.

The X-ray structure of the enolase has been solved with SF2312, Hex, and Hepta bound into the active site (FIG. 18A-18D). Crystals of human ENO2 were generated using recombinant protein expressed in E. coli. They were then co-crystallized with PhAH and SF2312 by soaking for 16 hours in cryoprotectant containing a 2 mM solution of PhAH or a 4 mM solution of SF2312 respectively. The structure of dimeric ENO2:PhAH (4ZA0; Table 4) and ENO2:SF2312 (4ZCW; Table 5) complexes were analyzed by X-ray crystallography and solved at 2.31 Å and 1.99 Å resolution, with $R_{free}$ for the refined structures of 0.195 and 0.202 respectively (Tables 4 & 5 for the PhAH and SF2312 structures, respectively). PhAH binds to human ENO2 in a similar mode to what had been reported previously in yeast and trypanosome enolase (de A. S. Navarro, et al., 2007; Wedekind, et al., 1994; Zhang, et al., 1994), with the ligand interacting with two magnesium ions in the active site pocket. The SF2312 bound structure revealed the preferential binding of the S,S stereoisomer with the compound adopting a binding mode similar to PhAH. For both PhAH and SF2312, the phosphono group coordinates the catalytic magnesium, $Mg_{(B)}$, and forms salt bridged interactions with R371 (FIG. 27). The carbonyl of PhAH and SF2312 interacts with both $Mg_{(A)}$ and $Mg_{(B)}$ to complete the octahedral coordination of these ions and the hydrogen bonding of the hydroxylamine group is conserved for both inhibitors. In the PhAH bound structure, the hydroxylamine hydrogen binds via a buried water molecule to E209, E166 and H370. E209, E166 and H370 act in concert to remove the hydroxyl from the substrate 2-PGA during the catalytic cycle and are critical for enolase activity (Qin, et al., 2012). In the SF2312 bound structure, the 5'-hydroxyl group of SF2312 replaces the water molecule and binds directly to E166 and H370. SF2312 binds to E209 via a water mediated hydrogen bond and to the backbone of N151 and G396 through a second water molecule. The position of these two water molecules is conserved in the ENO2:PhAH complex where these molecules play an indirect role in the binding of PhAH by stabilizing the position and orientation of E209, E167 and H370 (FIG. 27). The crystallization parameters for the PhAH and SF2312 bound to enolase 2 are shown in Tables 4 and 5, respectively.

X-ray structures of human ENO2 with PhAH (PDB ID:4ZA0), SF2312 (PDB ID:4ZA0), Methyl SF2312 (PDB ID: 5EU9), Hex (PDB: 5IDZ) were resolved. All chiral inhibitors (SF2312, Methyl SF2312, Hex) only bound in the S enantiomer at the 3-position, and S-enantiomer at the 5 position (for SF2312 and Methyl SF2312). PhAH, SF2312 and Methyl SF2312 bind the enzyme with two magnesium atoms with the phosphonohydroxamate moiety forming a di-oxo bridge (FIG. 47). In addition, these inhibitors form strong interactions with conserved, catalytic residues, directly for SF2312 and Methyl SF2312, and indirectly, for PhAH. Hex binds quite differently from the latter with a single Mg atom and has essentially no H-bonds with the active site residues, explaining why it is a competitive inhibitor, unlike PhAH and SF2312 which are non-competitive with 2-PG (FIG. 48).

TABLE 4

Crystallization Data Collection and Refinement Statistics for PhAH Bound to Enolase 2

| | Enolase 2:PhaH (PDB 4ZA0) |
|---|---|
| Data Collection | |
| Space group | $P2_1 2_1 2_1$ |
| Cell dimensions | |
| a, b, c (Å) | 67.8, 108.7, 112.2 |
| α, β, γ (°) | 90, 90, 90 |
| No. of unique reflections | 37271 |
| Resolution (Å) | 67.8-2.31 (2.39-2.31) |
| Rmerge (all I$^+$ and I$^-$) | 0.220 (0.840) |
| I/σI | 10.9 (3.1) |

TABLE 4-continued

Crystallization Data Collection and Refinement Statistics for PhAH Bound to Enolase 2

| | Enolase 2:PhaH (PDB 4ZA0) |
|---|---|
| Completeness (%) | 100.0 (100.0) |
| Redundancy | 12.4 (11.4) |
| Refinement | |
| Resolution (Å) | 58.0-2.31 |
| σF | 1.34 |
| No. of reflections | 37211 |
| $R_{work}/R_{free}$ | 0.164/0.204 |
| Wilson B | 18.4 |
| No. of atoms | |
| Protein | 6629 |
| Ligand | 18 |
| $Mg^{2+}$ | 4 |
| Water | 488 |
| Average B-factors ($Å^2$) | |
| Protein | 19.6 |
| Ligand | 13.5 |
| $Mg^{2+}$ | 4.9 |
| Water | 25.3 |
| r.m.s.d. | |
| Bond lengths (Å) | 0.009 |
| Bond angles (°) | 0.638 |

Values in parentheses are for the highest resolution shell.

TABLE 5

Crystallization Parameters and Properties for SF2312 Bound to Enolase 2

| Parameter | Enolase 2:SF2312 |
|---|---|
| Data Collection Statistics | |
| Space group | $P2_1 2_1 2_1$ |
| Unit Cell Dimensions | |
| a, b, c, (Å) | 68.30, 109.46, 117.27 |
| α, β, γ (°) | 90.0, 90.0, 90.0 |
| Resolution (Å) | 80.02-1.99 (2.04-1.99) |
| Rmerge (all I+ & I−) | 0.092 (0.449) |
| Rpim (all I+ & I−) | 0.038 (0.189) |
| Total unique reflections | 60867 |
| I/σ(I) | 13.3 (3.8) |
| Completeness (%) | 100.0 (99.6) |
| Redundancy | 7.0 (6.6) |
| Refinement Statistics | |
| Resolution (Å) | 51.69-1.99 |
| No. of reflections | 60788 |
| $R_{work}/R_{free}$ | 0.160/0.203 |
| No. of atoms per asymmetric unit | |
| Protein | 7314 |
| Water | 601 |
| Magnesium | 4 |
| SF2312 | 24 |
| Average B factor ($Å^2$) | |
| Protein | 25.0 |
| Water | 11.6 |
| Magnesium | 21.3 |
| SF2312 | 33.3 |
| R.M.S.D. from ideality | |
| Bond lengths (Å) | 0.010 |
| Bond angles (°) | 1.135 |

All of the compounds, compositions and methods disclosed and claimed herein can be made and executed without undue experimentation in light of the present disclosure. While the disclosure may have only been described in terms of certain embodiments, it will be apparent to those of skill in the art that variations may be applied to the compounds, compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

US 2014/0378529
WO 2013/0909732
Adams, et al., "PHENIX: a comprehensive Python-based system for macromolecular structure solution," Acta Cryst Sect. D D66:213-221, 2010.
Afonine, et al., "Towards automated crystallographic structure refinement with phenix.refine," D68, 353-367, 2012.
Anderson, et al., "Reaction intermediate analogues for enolase," Biochemistry, 23(12):2779-2789, 1984
Battye et al., "iMOSFLM: a new graphical interface for diffraction-image processing with MOSFLM," Acta Cryst. Sect. D, D67(4):271-281, 2010.
Bady, et al., "DNA fingerprinting of glioma cell lines and considerations on similarity measurements," Neuro-oncology, 14:701-711, 2012.
Brewer and Wampler, "A differential scanning calorimetric study of the effects of metal ions, substrate/product, substrate analogues and chaotropic anions on the thermal denaturation of yeast enolase 1," International journal of biological macromolecules 28, 213-218,
Capello, et al., "α-enolase: a promising therapeutic and diagnostic tumor target," FEBS Journal, 278(7): 1064-1074
de A. S. Navarro, et al., "Structural flexibility in Trypanosoma brucei enolase revealed by X-ray crystallography and molecular dynamics," The FEBS journal 274:5077-5089, 2007.
Duncan, et al., "Integrated genomic analyses identify ERRFI1 and TACC3 as glioblastoma-targeted genes," Oncotarget, 1:265-277, 2010.
Emsley et al., "Features and development of Coot," Acta Cryst. Sect. D, D66:486-501, 2010.
Evans and Murshudov, "How good are my data and what is the resolution?," Acta Cryst Sect. D. D69:1204-1214, 2013.
Hanaya and Itoh, "An effective synthesis of antibiotic SF-2312 (3-dihydroxyphosphoryl-1,5-dihydroxy-2-pyrolidone," Heterocycles, 82(2): 1675-1683, 2011
Handbook of Pharmaceutical Salts: Properties, and Use, (Stahl and Wermuth Eds.), Verlag Helvetica Chimica Acta, 2002.
Lee and Kim, "High-throughput T7 LIC vector for introducing C-terminus poly-histidine tags with variable lengths without extra sequences," Protein Exp. Purify., 63(1):58-61, 2009

Liu, et al., "A new approach to cyclic hydroxamic acids: intramolecular cyclization of N-benzyloxy carbamates with carbon nucleophiles," *Tetrahedron*, 67(12):2206-2214, 2011

Marangos and Schmechel, "The neurobiology of the brain enolase," *Essays Neurochem. Neuropharmacol.*, 4:211-247, 1980

Marango, et al., "Functional properties of neuronal and glial isoenzymes of brain enolase," *J. Neurochem.*, 31(3):727-732, 1978

Marango, et al., "The existence and neurobiological significance of neuronal and glial forms of the glycolytic enzyme enolase," *Biol. Psychiatry*, 17(4):563-579, 1979

*March's Advanced Organic Chemistry: Reactions, Mechanisms, and Structure*, 2007.

Martinez Molina, et al., Monitoring drug target engagement in cells and tissues using the cellular thermal shift assay. *Science* 341:84-87, 2013.

Muller, et al., "Passenger deletions generate therapeutic vulnerabilities in cancer," *Nature*, 488(7411):337-342, 2012

Poyner, et al., "Toward identification of acid/base catalysts in the active site of enolase: comparison of the properties of K345A, E168Q, and E211Q variants," *Biochemistry*, 35(5):1692-1699, 1996

Qin, et al., "Structures of asymmetric complexes of human neuron specific enolase with resolved substrate and product and an analogous complex with two inhibitors indicate subunit interaction and inhibitor cooperativity,". *Journal of Inorganic Biochemistry*, 111:187-194, 2012.

Schultz, "Prodrugs of biologically active phosphate esters," *Bioorg. Med. Chem.*, 11(6):885-898, 2003

Stommel, et al., "Coactivation of receptor tyrosine kinases affects the response of tumor cells to targeted therapies," *Science*, 318:287-290, 2007.

Torsvik, et al., "U-251 revisited: genetic drift and phenotypic consequences of long-term cultures of glioblastoma cells," *Cancer Medicine*, 3:812-824, 2014.

Voet and Voet, *Biochemistry*, 4th Ed., John Wiley & Sons, 2011

Watanabe et al., *Science Reports of Meiji Seika Kaisha*, 25:12-17, 1986

Wedekind, et al., "Chelation of serine 39 to $Mg^{2+}$ latches a gate at the active site of enolase: structure of the bis ($Mg^{2+}$) complex of yeast enolase and the intermediate analog phosphonoacetohydroxamate at 2.1-A resolution," *Biochemistry* 33:9333-9342, 1994.

Wuts, *Greene's Protecting Groups in Organic Synthesis*, 5th Ed., Wiley-Interscience, 2014

Ying, et al., "Oncogenic Kras maintains pancreatic tumors through regulation of anabolic glucose metabolism," *Cell*, 149, 2012.

Yuan, et al., "A positive/negative ion-switching, targeted mass spectrometry-based metabolomics platform for bodily fluids, cells, and fresh and fixed tissue," *Nature Protocols*, 7:872-881, 2012.

Zhang, et al., "Catalytic metal ion binding in enolase: the crystal structure of an enolase-$Mn^{2+}$-phosphonoacetohydroxamate complex at 2.4-A resolution," *Biochemistry* 33, 6295-6300, 1994.

What is claimed is:

1. A compound of the formula:

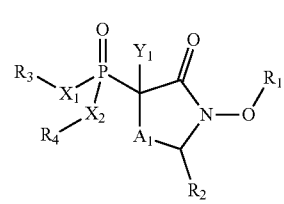

(I)

or a pharmaceutically acceptable salt, wherein:
$R_1$ is hydrogen, $acyl_{(C\leq12)}$ or substituted $acyl_{(C\leq12)}$;
$R_2$ is hydrogen, $acyloxy_{(C\leq12)}$, or substituted $acyloxy_{(C\leq12)}$;
$X_1$ and $X_2$ are each independently O, S, or $NR_a$, wherein:
$R_a$ is hydrogen, $alkyl_{(C\leq6)}$, or substituted $alkyl_{(C\leq6)}$;
$R_3$ and $R_4$ are each independently hydrogen or $alkyl_{(C\leq12)}$, $aryl_{(C\leq12)}$, $aralkyl_{(C\leq12)}$, $heteroaryl_{(C\leq12)}$, $heteroaralkyl_{(C\leq12)}$, or a substituted version of these groups; or a phosphate protecting group; or $R_3$ and $R_4$ are taken together and are $alkanediyl_{(C\leq8)}$ or substituted $alkanediyl_{(C\leq8)}$; or —$X_3$—$R_5$; wherein:
$X_3$ is a covalent bond, $alkanediyl_{(C\leq8)}$, or substituted $alkanediyl_{(C\leq8)}$; and
$R_5$ is $acyl_{(C\leq18)}$, $alkoxy_{(C\leq18)}$, —C(O)-$alkoxy_{(C\leq18)}$, $acyloxy_{(C\leq18)}$, or a substituted version of any of these groups;
$A_1$ is $alkanediyl_{(C1-3)}$; and
$Y_1$ is hydrogen, amino, halo, hydroxy, phosphate, $alkyl_{(C\leq12)}$, or substituted $alkyl_{(C\leq12)}$.

2. The compound of claim 1 further defined as:

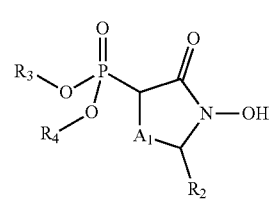

(II)

wherein:
$R_2$ is hydrogen, $acyloxy_{(C\leq12)}$, or substituted $acyloxy_{(C\leq12)}$;
$R_3$ and $R_4$ are each independently hydrogen, $alkyl_{(C\leq12)}$, substituted $alkyl_{(C\leq12)}$, or a phosphate protecting group; and
$A_1$ is $alkanediyl_{(C1-3)}$; or

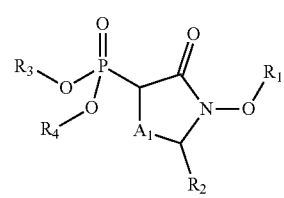

(III)

wherein:
R₁ is acyl$_{(C≤12)}$ or substituted acyl$_{(C≤12)}$;
R₂ is acyloxy$_{(C≤12)}$, or substituted acyloxy$_{(C≤12)}$;
R₃ is alkyl$_{(C≤12)}$, substituted alkyl$_{(C≤12)}$, or a phosphate protecting group;
R₄ is hydrogen, alkyl$_{(C≤12)}$, substituted alkyl$_{(C≤12)}$, or a phosphate protecting group; and
A₁ is alkanediyl$_{(C1-3)}$;
or a pharmaceutically acceptable salt of either formula.

3. The compound of claim 2 further defined as:

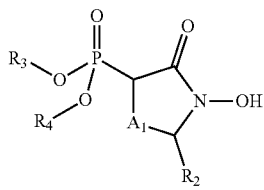
(II)

wherein:
R₂ is hydrogen;
R₃ and R₄ are each independently hydrogen, alkyl$_{(C≤12)}$, substituted alkyl$_{(C≤12)}$, or a phosphate protecting group; and
A₁ is alkanediyl$_{(C1-3)}$;
or a pharmaceutically acceptable salt thereof.

4. The compound of claim 1, wherein R₁ is hydrogen.
5. The compound of claim 1, wherein R₂ is acyloxy$_{(C≤8)}$ or substituted acyloxy$_{(C≤8)}$.
6. The compound of claim 1, wherein R₂ is hydrogen.
7. The compound of claim 1, wherein R₃ is a phosphate protecting group.
8. The compound of claim 7, wherein R₃ is a phosphate protecting group of the formula: -alkanediyl$_{(C≤6)}$-acyloxy$_{(C≤12)}$ or substituted -alkanediyl$_{(C≤6)}$-acyloxy$_{(C≤12)}$.
9. The compound of claim 8, wherein R₃ is pivaloyloxymethyl.
10. The compound of claim 1, wherein X₁ and X₂ are each O.
11. The compound of claim 1, wherein R₄ is a phosphate protecting group.
12. The compound of claim 11, wherein R₄ is a phosphate protecting group of the formula: -alkanediyl$_{(C≤6)}$-acyloxy$_{(C≤12)}$ or substituted -alkanediyl$_{(C≤6)}$-acyloxy$_{(C≤12)}$.
13. The compound of claim 11, wherein R₄ is pivaloyloxymethyl.
14. The compound of claim 1, wherein A₁ is —CH₂—, —CH₂CH₂—, or —CH₂CH₂CH₂—.
15. The compound of claim 1, wherein Y₁ is hydrogen.
16. The compound of claim 1, wherein the compound is further defined as:

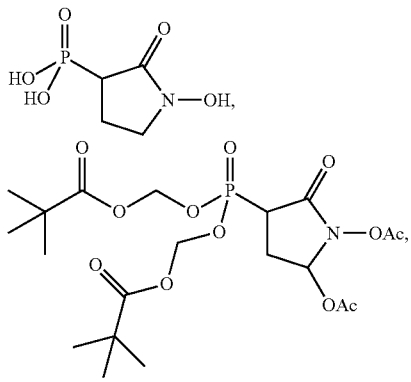

-continued

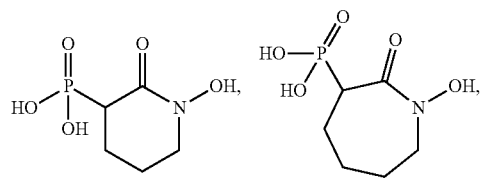

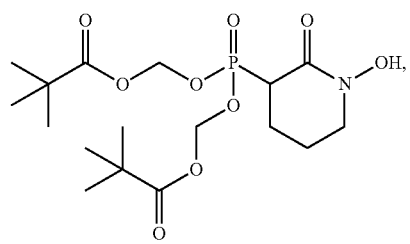

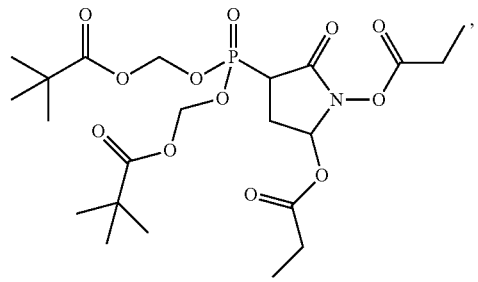

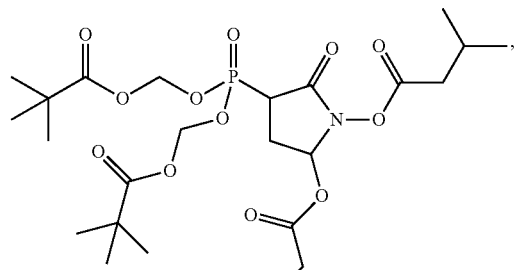

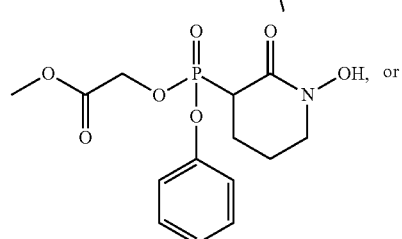

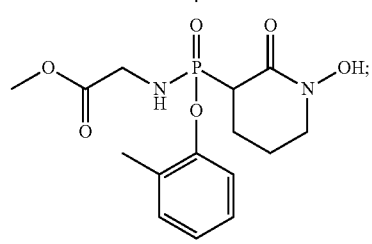

or a pharmaceutically acceptable salt of any of these formulas.

17. The compound of claim 16, wherein the compound is further defined as:

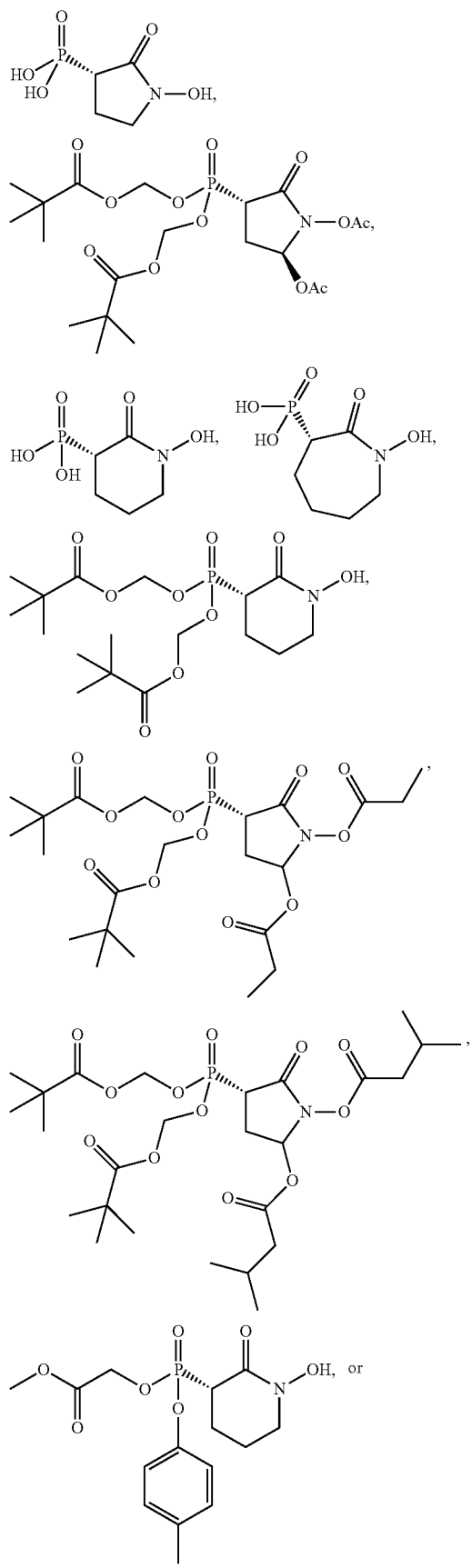

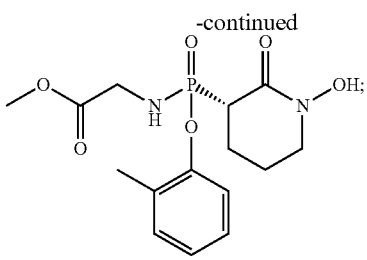

or a pharmaceutically acceptable salt of any of these formulas.

18. A method of treating a glioma, a melanoma, lung cancer and/or a kidney cancer comprising administering to a patient in need thereof a therapeutically effective amount of a compound of the formula:

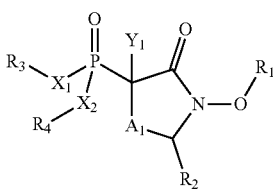

(I)

wherein:

$R_1$ is hydrogen, acyl$_{(C\leq 12)}$ or substituted acyl$_{(C\leq 12)}$;

$R_2$ is hydrogen, hydroxy, alkoxy$_{(C\leq 12)}$, substituted alkoxy$_{(C\leq 12)}$, acyloxy$_{(C\leq 12)}$, or substituted acyloxy$_{(C\leq 12)}$;

$X_1$ and $X_2$ are each independently O, S, or $NR_a$, wherein:

$R_a$ is hydrogen, alkyl$_{(C\leq 6)}$, or substituted alkyl$_{(C\leq 6)}$;

$R_3$ and $R_4$ are each independently hydrogen or alkyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, or a substituted version of these groups; or a phosphate protecting group; or $R_3$ and $R_4$ are taken together and are alkanediyl$_{(C\leq 8)}$ or substituted alkanediyl$_{(C\leq 8)}$; or —$X_3$—$R_5$; wherein:

$X_3$ is a covalent bond, alkanediyl$_{(C\leq 8)}$, or substituted alkanediyl$_{(C\leq 8)}$; and $R_5$ is acyl$_{(C\leq 18)}$, alkoxy$_{(C\leq 18)}$, —C(O)-alkoxy$_{(C\leq 18)}$, acyloxy$_{(C\leq 18)}$, or a substituted version of any of these groups;

$A_1$ is alkanediyl$_{(C1-3)}$; and $Y_1$ is hydrogen, amino, halo, hydroxy, phosphate, alkyl$_{(C\leq 12)}$, or substituted alkyl$_{(C\leq 12)}$;

or a pharmaceutically acceptable salt thereof.

19. A compound of the formula:

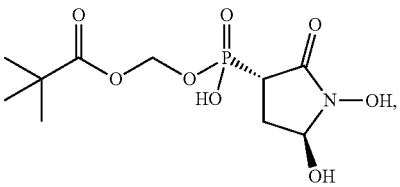

-continued
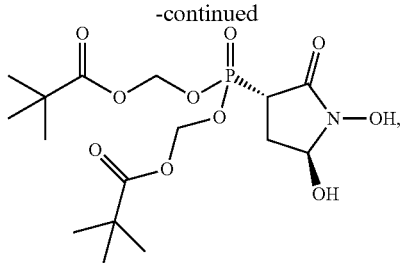
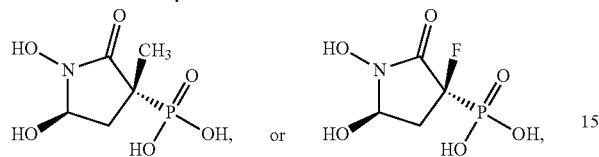
or a pharmaceutically acceptable salt of any of these formulas.
* * * * *